(12) United States Patent
Haining et al.

(10) Patent No.: US 9,164,094 B2
(45) Date of Patent: Oct. 20, 2015

(54) BIOMARKERS TO IDENTIFY HIV-SPECIFIC T-CELL SUBSETS

(75) Inventors: W. Nicholas Haining, Newton, MA (US); Benjamin Ebert, Brookline, MA (US); Bruce Walker, Nahant, MA (US)

(73) Assignees: Dana-Farber Cancer Institute, Boston, MA (US); Brigham and Women's Hospital, Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 13/452,344

(22) Filed: Apr. 20, 2012

(65) Prior Publication Data

US 2013/0005792 A1 Jan. 3, 2013

Related U.S. Application Data

(63) Continuation of application No. PCT/US2010/002662, filed on Oct. 1, 2010.

(60) Provisional application No. 61/279,587, filed on Oct. 22, 2009.

(51) Int. Cl.
*A61K 31/7105* (2006.01)
*C12Q 1/70* (2006.01)
*G01N 33/569* (2006.01)

(52) U.S. Cl.
CPC ...... *G01N 33/56988* (2013.01); *G01N 2333/16* (2013.01); *G01N 2800/52* (2013.01); *G01N 2800/56* (2013.01)

(58) Field of Classification Search
USPC ............ 435/4, 6, 91.1, 5, 6.1, 6.11; 536/23.1, 536/24.32; 935/77; 506/9, 16; 514/44
See application file for complete search history.

(56) References Cited

U.S. PATENT DOCUMENTS

| | | | |
|---|---|---|---|
| 2004/0034209 A1 | 2/2004 | Ho et al. | |
| 2009/0010908 A1* | 1/2009 | Gow et al. | 424/94.1 |
| 2009/0047662 A1 | 2/2009 | Philpott et al. | |
| 2012/0041687 A1* | 2/2012 | Bevilacqua et al. | 702/21 |
| 2012/0289418 A1* | 11/2012 | Willard-Gallo et al. | 506/9 |
| 2013/0116305 A1* | 5/2013 | Wahl et al. | 514/44 A |

OTHER PUBLICATIONS

Haining et al., J. Immunol., vol. 181, pp. 1859-1868 (2008).*
Betts et al., Blood, vol. 107, No. 12, pp. 4781-4789 (2006).*
Zajac et al, J. Exp'l. Med., vol. 188, No. 12, pp. 2205-2213 (1998).*
Petrovas et al., J. Exp'l. Med., vol. 203, No. 10, pp. 2281-2292 (2006).*
International Search Report for PCT/US10/02662, mailed on Mar. 25, 2011.
International Preliminary Report on Patentability dated May 3, 2012 from corresponding International Application No. PCT/US2010/002662.
Precopio, et al. "Immunization with Vaccinia Virus Induces polyfunctional and phenotypically distinctive CD8+ T cell responses", The Journal of Experimental Medicine vol. 204, No. 6, Jun. 11, 2001, pp. 1405-1416.
Haining, et al. "Identification of an Evolutionarily Conserved Transcriptional Signature of CD8 Memory Differentiation that is Shared by T and B Cells" The Journal of Immunology, 2008, pp. 1879-1868.
Written Opinion of the International Searching Authority dated Mar. 25, 2011.

* cited by examiner

*Primary Examiner* — Jane Zara
(74) *Attorney, Agent, or Firm* — Mintz Levin Cohn Ferris Glovsky and Popeo, P.C.; Peter F. Corless, Esq.

(57) ABSTRACT

The invention relates to expression profiles of HIV-specific T-cells and their methods of use, including but not limited to treatment of HIV, increasing T-cell function and/or survival in HIV infected subjects, monitoring HIV disease progression and classifying HIV infected subjects as controllers or chronic progressors.

13 Claims, 137 Drawing Sheets d

|  | Actual Controller | Actual Progressor |
|---|---|---|
| Predicted Controller | 17 | 1 |
| Predicted Progressor | 7 | 17 |

Accuracy          81.0%

| ProbeSetID | GeneSymbol | GeneDescription | SelectionFrequency |
|---|---|---|---|
| 213060_s_at | CHI3L2 | chitinase 3-like 2 | 1 |
| 202270_at | GBP1 | guanylate binding protein 1, interferon-inducible, 67kDa | 1 |
| 205488_at | GZMA | granzyme A (granzyme 1, cytotoxic T-lymphocyte-associated serine esterase 3) | 1 |
| 208965_s_at | IFI16 | interferon, gamma-inducible protein 16 | 1 |
| 209417_s_at | IFI35 | interferon-induced protein 35 | 1 |
| 204415_at | IFI6 | interferon, alpha-inducible protein 6 | 1 |
| 205798_at | IL7R | interleukin 7 receptor | 1 |
| 203882_at | IRF9 | interferon regulatory factor 9 | 1 |
| 201762_s_at | PSME2 | proteasome (prosome, macropain) activator subunit 2 (PA28 beta) | 1 |
| 203307_s_at | TAP1 | transporter 1, ATP-binding cassette, sub-family B (MDR/TAP) | 1 |
| 216920_s_at | TARP | TCR gamma alternate reading frame protein | 1 |
| 215806_x_at | TRGC2 | T cell receptor gamma constant 2 | 1 |
| 209813_at | TRGV9 | T cell receptor gamma variable 9 | 1 |
| 201649_at | UBE2L6 | ubiquitin-conjugating enzyme E2L 6 | 0.976190476 |
| 219326_s_at | B3GNT2 | UDP-GlcNAc:betaGal beta-1,3-N-acetylglucosaminyltransferase 2 | 0.976190476 |
| 204747_at | IFIT3 | interferon-induced protein with tetratricopeptide repeats 3 | 0.976190476 |
| 220021_at | TMC7 | transmembrane channel-like 7 | 0.976190476 |
| 209670_at | TRAC | T cell receptor alpha constant | 0.952380952 |
| 219717_at | C4orf30 | chromosome 4 open reading frame 30 | 0.952380952 |
| 205907_at | CD1C | CD1c molecule | 0.952380952 |
| 208872_at | S100A10 | S100 calcium binding protein A10 | 0.904761905 |
| 208769_s_at | GP1BB | glycoprotein Ib (platelet), beta polypeptide | 0.880952381 |
| 210164_at | GZMB | granzyme B (granzyme 2, cytotoxic T-lymphocyte-associated serine esterase 1) | 0.880952381 |
| 200904_at | HLA-E | major histocompatibility complex, class I, E | 0.857142857 |
| 221419_s_at | 221419_s_at | | 0.857142857 |
| 209732_at | CLEC2B | C-type lectin domain family 2, member B | 0.857142857 |
| 212249_at | PIK3R1 | phosphoinositide-3-kinase, regulatory subunit 1 (alpha) | 0.857142857 |
| 202687_s_at | TNFSF10 | tumor necrosis factor (ligand) superfamily, member 10 | 0.833333333 |
| 214717_at | DKFZp434H1419 | hypothetical protein DKFZp434H1419 | 0.833333333 |
| 209140_x_at | HLA-B | major histocompatibility complex, class I, B | 0.833333333 |
| 205768_s_at | SLC27A2 | solute carrier family 27 (fatty acid transporter), member 2 | 0.809523801 |
| 221269_s_at | SH3BGRL3 | SH3 domain binding glutamic acid-rich protein like 3 | 0.809523801 |
| 210946_at | PPAP2A | phosphatidic acid phosphatase type 2A | 0.785714286 |
| 209667_at | CES2 | carboxylesterase 2 (intestine, liver) | 0.761904762 |
| 215082_at | ELOVL5 | ELOVL family member 5, elongation of long chain fatty acids (FEN1/Elo2, SUR4/Elo3-like, yeast) | 0.595047619 |
| 204661_at | CD52 | CD52 molecule | 0.666666667 |
| 209040_s_at | PSMB8 | proteasome (prosome, macropain) subunit, beta type, 8 (large multifunctional peptidase 7) | 0.619047619 |
| 217773_s_at | NDUFA4 | NADH dehydrogenase (ubiquinone) 1 alpha subcomplex, 4, 9kDa | 0.595238095 |
| 214757_at | MSH2L2 | postmeiotic segregation increased 2-like 2 pseudogene | 0.595238095 |
| 205406_s_at | SPA17 | sperm autoantigenic protein 17 | 0.547619048 |
| 202156_s_at | CUGBP2 | CUG triplet repeat, RNA binding protein 2 | 0.380952381 |

FIGURE 11 (CONTINUED)

| ProbeSetID | GeneSymbol | GeneDescription | SelectionFrequency |
|---|---|---|---|
| 203695_s_at | DFNA5 | deafness, autosomal dominant 5 | 0.380952381 |
| 220358_at | BATF3 | basic leucine zipper transcription factor, ATF-like 3 | 0.30952381 |
| 204698_at | ISG20 | interferon stimulated exonuclease gene 20kDa | 0.30952381 |
| 203761_at | SLA | Src-like-adaptor | 0.30952381 |
| 201858_s_at | SRGN | serglycin | 0.30952381 |
| 202975_s_at | RHOBTB3 | Rho-related BTB domain containing 3 | 0.261904762 |
| 201105_at | LGALS1 | lectin, galactoside-binding, soluble, 1 | 0.238095238 |
| 203939_at | NT5E | 5'-nucleotidase, ecto (CD73) | 0.238095238 |
| 210140_at | CST7 | cystatin F (leukocystatin) | 0.214285714 |
| 204279_at | PSMB9 | proteasome (prosome, macropain) subunit, beta type, 9 (large multifunctional peptidase 2) | 0.19047619 |
| 202712_s_at | CKMT1B | creatine kinase, mitochondrial 1B | 0.166666667 |
| 211434_s_at | CCRL2 | chemokine (C-C motif) receptor-like 2 | 0.142857143 |
| 209355_s_at | ECM1 | extracellular matrix protein 1 | 0.142857143 |
| 212570_at | ENDOD1 | endonuclease domain containing 1 | 0.119047619 |
| 206584_at | LY96 | lymphocyte antigen 96 | 0.119047619 |
| 200887_s_at | STAT1 | signal transducer and activator of transcription 1, 91kDa | 0.119047619 |
| 205891_at | ADORA2B | adenosine A2b receptor | 0.095238095 |
| 211005_at | LAT | linker for activation of T cells | 0.071428571 |
| 205856_s_at | SLC14A1 | solute carrier family 14 (urea transporter), member 1 (Kidd blood group) | 0.047619048 |
| 210397_at | DEFB1 | defensin, beta 1 | 0.047619048 |
| 212998_x_at | HLA-DQB1 | major histocompatibility complex, class II, DQ beta 1 | 0.047619048 |
| 202531_at | IRF1 | interferon regulatory factor 1 | 0.047619048 |
| 202659_at | PSMB10 | proteasome (prosome, macropain) subunit, beta type, 10 | 0.047619048 |
| 206118_at | STAT4 | signal transducer and activator of transcription 4 | 0.047619048 |
| 204637_at | CGA | glycoprotein hormones, alpha polypeptide | 0.023809524 |
| 205065_at | ENPP1 | ectonucleotide pyrophosphatase/phosphodiesterase 1 | 0.023809524 |
| 211165_x_at | EPHB2 | EPH receptor B2 | 0.023809524 |
| 210915_x_at | IL23A | interleukin 23, alpha subunit p19 | 0.023809524 |
| 208581_x_at | MT1X | metallothionein 1X | 0.023809524 |
| 207351_s_at | SH2D2A | SH2 domain protein 2A | 0.023809524 |

A.
1 caagagagag agagagcgtg caagccccaa agcgagcgac atgtcccttt ggggagcagt
61 ccctctgcac cccagagtga ggaggacgca ggggtcagag gtggctacag ggcaggcaga 121 ggaggcacct
gtaggggtg gtgggctggt ggcccaggag aagtcaggaa gggagcccag 181 ctggtgacaa gagagcccag
aggtgcctgg ggctgagtgt gagagcccgg aagatttcag 241 ccatgcctca cagctccgac agcagtgact
ccagcttcag ccgctctcct cccctggca 301 aacaggactc atctgatgat gtgagaagag ttcagaggag
ggagaaaaat cgtattgccg 361 cccagaagag ccgacagagg cagacacaga aggccgacac cctgcacctg
gagagcgaag 421 acctggagaa acagaacgcg gctctacgca aggagatcaa gcagctcaca gaggaactga 481
agtacttcac gtcggtgctg aacagccacg agccctgtg ctcggtgctg gccgccagca 541 cgccctcgcc
ccccgaggtg gtgtacagcg cccacgcatt ccaccaacct catgtcagct 601 ccccgcgctt ccagccctga
gcttccgatg cggggagagc agagcctcgg gaggggcaca 661 cagactgtgg cagagctgcg cccatcccgc
agaggcccct gtccacctgg agacccggag 721 acagaggcct ggacaaggag tgaacacggg aactgtcacg
actgaaggg cgtgaggcct 781 cccagcagtg ccgcagcgtt tcgagggcg tgtgctggac ccaccactg
tgggttgcag 841 gcccaatgca gaagagtatt aagaaagatg ctcaagtccc atggcacaga gcaaggcggg 901
cagggaacgg ttatttttct aaataaatgc tttaaaagaa aaaaaaaaa aaa

SEQ ID NO: 2

B.
1 mphssdssds sfsrspppgk qdssddvrry qrreknriaa qksrqrqtqk adtlhlesed 61 lekqnaalrk
eikglteelk yftsvinshe plcsvlaast psppevvysa hafhqphvss 121 prfqp

SEQ ID NO: 3

| probeset_id | GeneTitle | GeneSymbol | GeneID | t | q |
|---|---|---|---|---|---|
| 210621_s_at | RAS p21 protein activator (GTPase activating protein) 1 | RASA1 | 5921 | 6.102845 | 0.007526 |
| 202524_s_at | sparc/osteonectin, cwcv and kazal-like domains proteoglycan (testican) 2 | SPOCK2 | 9806 | 4.358444 | 0.358674 |
| 202677_at | RAS p21 protein activator (GTPase activating protein) 1 | RASA1 | 5921 | 4.019843 | 0.421399 |
| 205288_at | CDC14 cell division cycle 14 homolog A (S. cerevisiae) | CDC14A | 8556 | 3.954898 | 0.421399 |
| 216668_at | --- | --- | --- | 3.938437 | 0.421399 |
| 216042_at | tumor necrosis factor receptor superfamily, member 25 | TNFRSF25 | 8718 | 3.893672 | 0.421399 |
| 204897_at | prostaglandin E receptor 4 (subtype EP4) | PTGER4 | 5734 | 3.878922 | 0.421399 |
| 212594_at | programmed cell death 4 (neoplastic transformation inhibitor) | PDCD4 | 27250 | 3.870662 | 0.421399 |
| 202643_s_at | tumor necrosis factor, alpha-induced protein 3 | TNFAIP3 | 7128 | 3.86239 | 0.421399 |
| 203725_at | growth arrest and DNA-damage-inducible, alpha | GADD45A | 1647 | 3.860574 | 0.421399 |
| 216834_at | regulator of G-protein signaling 1 | RGS1 | 5996 | 3.838977 | 0.421399 |
| 210538_s_at | baculoviral IAP repeat-containing 3 | BIRC3 | 330 | 3.78425 | 0.421399 |
| 201195_s_at | solute carrier family 7 (cationic amino acid transporter, y+ system), member 5 | SLC7A5 | 8140 | 3.77992 | 0.421399 |
| 203708_at | phosphodiesterase 4B, cAMP-specific (phosphodiesterase E4 dunce homolog, Drosophila) | PDE4B | 5142 | 3.736681 | 0.421399 |
| 203413_at | NEL-like 2 (chicken) | NELL2 | 4753 | 3.736636 | 0.421399 |
| 211426_x_at | guanine nucleotide binding protein (G protein), q polypeptide | GNAQ | 2776 | 3.718252 | 0.421399 |
| 202644_s_at | tumor necrosis factor, alpha-induced protein 3 | TNFAIP3 | 7128 | 3.699406 | 0.421399 |
| 208744_x_at | heat shock 105kDa/110kDa protein 1 | HSPH1 | 10808 | 3.685959 | 0.421399 |
| 221618_s_at | TAF9B RNA polymerase II, TATA box binding protein (TBP)-associated factor, 31kDa /// similar to transcription associated factor 9B | LOC728198 /// TAF9B | 51616 /// 728198 | 3.685703 | 0.421399 |
| 202988_s_at | regulator of G-protein signaling 1 | RGS1 | 5996 | 3.681003 | 0.421399 |
| 218346_s_at | sestrin 1 | SESN1 | 27244 | 3.675679 | 0.421399 |
| 204093_at | cyclin H | CCNH | 902 | 3.665929 | 0.421399 |
| 202147_s_at | interferon-related developmental regulator 1 | IFRD1 | 3475 | 3.663846 | 0.421399 |
| 202612_s_at | mediator complex subunit 14 | MED14 | 9282 | 3.642599 | 0.428654 |
| 219220_x_at | mitochondrial ribosomal protein S22 | MRPS22 | 56945 | 3.6085 | 0.433373 |
| 217434_at | melanocortin 2 receptor (adrenocorticotropic hormone) | MC2R | 4158 | 3.603807 | 0.433373 |
| 213198_at | activin A receptor, type IB | ACVR1B | 91 | 3.54465 | 0.471311 |
| 215671_at | phosphodiesterase 4B, cAMP-specific (phosphodiesterase E4 dunce homolog, Drosophila) | PDE4B | 5142 | 3.535287 | 0.4723 |
| 212828_at | synaptojanin 2 | SYNJ2 | 8871 | 3.52019 | 0.47591 |
| 205567_at | Werner syndrome | WRN | 7486 | 3.445721 | 0.524274 |
| 212774_at | zinc finger protein 238 | ZNF238 | 10472 | 3.429588 | 0.524274 |
| 212652_s_at | sorting nexin 4 | SNX4 | 8723 | 3.427343 | 0.524274 |
| 210440_s_at | CDC14 cell division cycle 14 homolog A (S. cerevisiae) | CDC14A | 8556 | 3.409686 | 0.524274 |
| 222366_at | Transcribed locus | --- | --- | 3.408979 | 0.524274 |
| 212842_x_at | RANBP2-like and GRIP domain containing 5 /// RANBP2-like and GRIP domain containing 4 /// RANBP2-like and GRIP domain containing 8 /// RANBP2-like and GRIP domain containing 6 | RGPD4 /// RGPD5 /// RGPD6 /// RGPD8 | 285190 /// 727851 /// 729540 /// 84220 | 3.404826 | 0.524274 |
| 221756_at | phosphoinositide-3-kinase interacting protein 1 | PIK3IP1 | 113791 | 3.393236 | 0.524274 |

FIGURE 14 (CONTINUED)

| | | | | |
|---|---|---|---|---|
| 211856_x_at | CD28 molecule | CD28 | 940 | 3.377707 | 0.524274 |
| 212723_at | jumonji domain containing 6 | JMJD6 | 23210 | 3.36603 | 0.524274 |
| 204155_s_at | KIAA0999 protein | KIAA0999 | 23387 | 3.360743 | 0.524274 |
| 200911_s_at | transforming, acidic coiled-coil containing protein 1 | TACC1 | 6867 | 3.359818 | 0.524274 |
| 201260_s_at | synaptophysin-like 1 | SYPL1 | 6856 | 3.356806 | 0.524274 |
| 213161_at | chromosome 9 open reading frame 97 | C9orf97 | 158427 | 3.316162 | 0.562181 |
| 208113_x_at | poly(A) binding protein, cytoplasmic 3 | PABPC3 | 5042 | 3.309036 | 0.562181 |
| 204567_s_at | ATP-binding cassette, sub-family G (WHITE), member 1 | ABCG1 | 9619 | 3.301306 | 0.562181 |
| 216507_at | transmembrane anterior posterior transformation 1 | TAPT1 | 202018 | 3.298073 | 0.562181 |
| 217783_s_at | yippee-like 5 (Drosophila) | YPEL5 | 51646 | 3.278703 | 0.569778 |
| 222149_x_at | golgi autoantigen, golgin subfamily a. 8G /// golgi autoantigen, golgin subfamily a. 8E /// golgin-like hypothetical protein LOC440321 | FLJ32679 /// GOLGA8E /// GOLGA8G | 283768 /// 390535 /// 440321 | 3.261185 | 0.572938 |
| 207785_s_at | recombination signal binding protein for immunoglobulin kappa J region | RBPJ | 3516 | 3.254771 | 0.572938 |
| 206240_s_at | zinc finger protein 136 | ZNF136 | 7695 | 3.242229 | 0.578032 |
| 211302_s_at | phosphodiesterase 4B, cAMP-specific (phosphodiesterase E4 dunce homolog, Drosophila) | PDE4B | 5142 | 3.240741 | 0.578032 |
| 217936_at | Rho GTPase activating protein 5 | ARHGAP5 | 394 | 3.238402 | 0.578032 |
| 213097_at | zuotin related factor 1 | ZRF1 | 27000 | 3.230394 | 0.584702 |
| 211956_s_at | eukaryotic translation initiation factor 1 | EIF1 | 10209 | 3.218113 | 0.592547 |
| 220009_at | LON peptidase N-terminal domain and ring finger 3 | LONRF3 | 79836 | 3.217957 | 0.592547 |
| 205239_at | amphiregulin (schwannoma-derived growth factor) /// similar to Amphiregulin precursor (AR) (Colorectum cell-derived growth factor) (CRDGF) | AREG /// LOC727738 | 374 /// 727738 | 3.193815 | 0.620402 |
| 203758_at | cathepsin O | CTSO | 1519 | 3.157571 | 0.65843 |
| 207041_at | mannan-binding lectin serine peptidase 2 | MASP2 | 10747 | 3.152405 | 0.659793 |
| 202027_at | transmembrane protein 184B | TMEM184B | 25829 | 3.149718 | 0.659793 |
| 204015_s_at | dual specificity phosphatase 4 | DUSP4 | 1846 | 3.133074 | 0.665781 |
| 209267_s_at | solute carrier family 39 (zinc transporter), member 8 | SLC39A8 | 64116 | 3.132592 | 0.665781 |
| 214081_at | plexin domain containing 1 | PLXDC1 | 57125 | 3.116051 | 0.668264 |
| 203053_at | breast carcinoma amplified sequence 2 | BCAS2 | 10286 | 3.114933 | 0.668264 |
| 218311_at | mitogen-activated protein kinase kinase kinase kinase 3 | MAP4K3 | 8491 | 3.109655 | 0.668264 |
| 217843_s_at | mediator complex subunit 4 | MED4 | 29079 | 3.107119 | 0.668264 |
| 214700_x_at | RAP1 interacting factor homolog (yeast) | RIF1 | 55183 | 3.104424 | 0.668264 |
| 219700_at | plexin domain containing 1 | PLXDC1 | 57125 | 3.098819 | 0.668264 |
| 219312_s_at | zinc finger and BTB domain containing 10 | ZBTB10 | 65986 | 3.077987 | 0.679372 |
| 217142_at | similar to Elongation FacTor family member (eft-4) | LOC442215 | 442215 | 3.077047 | 0.679372 |
| 204433_s_at | spermatogenesis associated 2 | SPATA2 | 9825 | 3.074281 | 0.679372 |
| 204995_at | cyclin-dependent kinase 5, regulatory subunit 1 (p35) | CDK5R1 | 8851 | 3.062 | 0.686712 |
| 211596_s_at | leucine-rich repeats and immunoglobulin-like domains 1 | LRIG1 | 26018 | 3.060855 | 0.688712 |
| 212400_at | family with sequence similarity 102, member A | FAM102A | 399665 | 3.020866 | 0.707388 |
| 212561_at | RAB6 interacting protein 1 | RAB6IP1 | 23258 | 3.016257 | 0.707388 |
| 202866_at | DnaJ (Hsp40) homolog, subfamily B, member 12 | DNAJB12 | 54788 | 3.01409 | 0.707388 |

FIGURE 14 (CONTINUED)

| | | | | | |
|---|---|---|---|---|---|
| 206621_s_at | eukaryotic translation initiation factor 4H | EIF4H | | 7458 | 3.013139 | 0.707388 |
| 216056_at | CD44 molecule (Indian blood group) | CD44 | | 960 | 3.007286 | 0.707388 |
| 201800_s_at | oxysterol binding protein | OSBP | | 5007 | 2.989052 | 0.707388 |
| 222308_x_at | Transcribed locus | --- | | | 2.988094 | 0.707388 |
| 208881_x_at | isopentenyl-diphosphate delta isomerase 1 | IDI1 | | 3422 | 2.977631 | 0.707388 |
| 216823_at | ribosomal protein S3A /// similar to ribosomal protein S3a /// similar to 40S ribosomal protein S3a (V-fos transformation effector protein) /// similar to 40S ribosomal protein S3a /// 40S ribosomal protein S3a pseudogene | LOC146053 /// LOC391168 /// LOC391706 /// LOC400652 /// LOC439992 /// LOC643932 /// LOC644972 /// LOC646216 /// LOC646527 /// RPS3A | 146053 /// 391168 /// 391706 /// 400652 /// 439992 /// 6189 /// 643932 /// 644972 /// 646216 /// 646527 | 2.97665 | 0.707388 |
| 202371_at | transcription elongation factor A (SII)-like 4 | TCEAL4 | | 79921 | 2.968666 | 0.707388 |
| 218149_s_at | zinc finger protein 395 | ZNF395 | | 55893 | 2.968342 | 0.707388 |
| 220657_at | kelch-like 11 (Drosophila) | KLHL11 | | 55175 | 2.967117 | 0.707388 |
| 209682_at | Cas-Br-M (murine) ecotropic retroviral transforming sequence b | CBLB | | 868 | 2.965748 | 0.707388 |
| 205798_at | interleukin 7 receptor | IL7R | | 3575 | 2.956947 | 0.710946 |
| 221423_s_at | Yip1 domain family, member 5 | YIPF5 | | 81555 | 2.953985 | 0.710946 |
| 214177_s_at | pre-B-cell leukemia homeobox interacting protein 1 | PBXIP1 | | 57326 | 2.952906 | 0.710946 |
| 215915_at | GULP, engulfment adaptor PTB domain containing 1 | GULP1 | | 51454 | 2.937958 | 0.729414 |
| 220671_at | CCR4 carbon catabolite repression 4-like (S. cerevisiae) | CCRN4L | | 25819 | 2.934848 | 0.729414 |
| 212439_at | inositol hexaphosphate kinase 1 | IHPK1 | | 9807 | 2.91777 | 0.744465 |
| 214910_s_at | apolipoprotein M | APOM | | 55937 | 2.917463 | 0.744465 |
| 209871_s_at | amyloid beta (A4) precursor protein-binding, family A, member 2 (X11-like) | APBA2 | | 321 | 2.901997 | 0.74575 |
| 56919_at | WD repeat domain 48 | WDR48 | | 57599 | 2.900309 | 0.74575 |
| 212479_s_at | required for meiotic nuclear division 5 homolog A (S. cerevisiae) | RMND5A | | 64795 | 2.893239 | 0.74575 |
| 214480_at | ets variant gene 3 | ETV3 | | 2117 | 2.871235 | 0.763884 |
| 210281_s_at | zinc finger, MYM-type 2 | ZMYM2 | | 7750 | 2.865801 | 0.763884 |
| 212098_at | hypothetical protein LOC151162 | LOC151162 | | 151162 | 2.862768 | 0.763884 |
| 213737_x_at | golgi autoantigen, golgin subfamily a, 8G /// golgi autoantigen, golgin subfamily a, 8E /// golgin-like hypothetical protein LOC440321 | FLJ32679 /// GOLGA8E /// GOLGA8G | 283768 /// 390535 /// 440321 | | 2.859986 | 0.763884 |
| 202731_at | programmed cell death 4 (neoplastic transformation inhibitor) | PDCD4 | | 27250 | 2.859792 | 0.763884 |
| 204064_at | THO complex 1 | THOC1 | | 9984 | 2.854056 | 0.769097 |
| 209824_s_at | aryl hydrocarbon receptor nuclear translocator-like | ARNTL | | 406 | 2.852889 | 0.769097 |
| 215592_at | CDNA FLJ12232 fis, clone MAMMA1001206 | --- | | | 2.851328 | 0.769097 |
| 221821_s_at | chromosome 12 open reading frame 41 | C12orf41 | | 54934 | 2.840881 | 0.778228 |
| 207113_s_at | tumor necrosis factor (TNF superfamily, member 2) | TNF | | 7124 | 2.833033 | 0.782863 |
| 213285_at | transmembrane protein 30B | TMEM30B | | 161291 | 2.829208 | 0.786818 |

FIGURE 14 (CONTINUED)

| | | | | |
|---|---|---|---|---|
| 213615_at | Membrane bound O-acyltransferase domain containing 5 | MBOAT5 | 10162 | 2.809843 | 0.813 |
| 220814_at | — | — | — | 2.807338 | 0.813 |
| 207184_at | solute carrier family 6 (neurotransmitter transporter, GABA), member 13 | SLC6A13 | 6540 | 2.80416 | 0.813 |
| 208122_x_at | killer cell immunoglobulin-like receptor, two domains, short cytoplasmic tail, 3 | KIR2DS3 | 3808 | 2.803959 | 0.814269 |
| 204568_at | KIAA0831 | KIAA0831 | 22863 | 2.797555 | 0.818641 |
| 208910_s_at | complement component 1, q subcomponent binding protein | C1QBP | 708 | 2.79368 | 0.824301 |
| 208624_s_at | eukaryotic translation initiation factor 4 gamma, 1 | EIF4G1 | 1981 | 2.786457 | 0.824301 |
| 211449_at | mutS homolog 6 (E. coli) | MSH6 | 2956 | 2.783996 | 0.824301 |
| 221127_s_at | regulated in glioma | RIG | 10530 | 2.783884 | 0.824301 |
| 214775_at | Nedd4 binding protein 3 | N4BP3 | 23138 | 2.77957 | 0.826033 |
| 217191_x_at | — | — | — | 2.774094 | 0.830816 |
| 204135_at | filamin A interacting protein 1-like | FILIP1L | 11259 | 2.772083 | 0.830816 |
| 216248_s_at | nuclear receptor subfamily 4, group A, member 2 | NR4A2 | 4929 | 2.768435 | 0.83379 |
| 204615_x_at | isopentenyl-diphosphate delta isomerase 1 | IDI1 | 3422 | 2.767244 | 0.83379 |
| 203543_s_at | Kruppel-like factor 9 | KLF9 | 687 | 2.757837 | 0.843005 |
| 218784_s_at | chromosome 6 open reading frame 64 | C6orf64 | 55776 | 2.746884 | 0.848523 |
| 218472_s_at | pelota homolog (Drosophila) | PELO | 53918 | 2.739202 | 0.852106 |
| 204992_s_at | profilin 2 | PFN2 | 5217 | 2.734342 | 0.852106 |
| 203313_s_at | TGFB-induced factor homeobox 1 | TGIF1 | 7050 | 2.731691 | 0.852106 |
| 214176_s_at | Transcribed locus | — | | 2.728847 | 0.852106 |
| 209181_s_at | Rab geranylgeranyltransferase, beta subunit | RABGGTB | 5876 | 2.718975 | 0.852106 |
| 213547_at | cullin-associated and neddylation-dissociated 2 (putative) | CAND2 | 23066 | 2.716758 | 0.852106 |
| 202193_at | LIM domain kinase 2 | LIMK2 | 3985 | 2.715031 | 0.852106 |
| 213555_at | RWD domain containing 2A | RWDD2A | 112611 | 2.714331 | 0.852106 |
| 214247_s_at | dickkopf homolog 3 (Xenopus laevis) | DKK3 | 27122 | 2.71381 | 0.852106 |
| 207735_at | ring finger protein 125 | RNF125 | 54941 | 2.712912 | 0.852106 |
| 219132_at | pellino homolog 2 (Drosophila) | PELI2 | 57161 | 2.712876 | 0.852106 |
| 218399_s_at | cell division cycle associated 4 | CDCA4 | 55038 | 2.710363 | 0.852106 |
| 213518_at | protein kinase C, iota | PRKCI | 5584 | 2.708574 | 0.852106 |
| 215716_s_at | ATPase, Ca++ transporting, plasma membrane 1 | ATP2B1 | 490 | 2.703858 | 0.853874 |
| 209535_s_at | — | — | | 2.702875 | 0.853874 |
| 208673_s_at | splicing factor, arginine/serine-rich 3 | SFRS3 | 6428 | 2.700417 | 0.853874 |
| 202595_s_at | leptin receptor overlapping transcript-like 1 | LEPROTL1 | 23484 | 2.69904 | 0.853874 |
| 202165_at | protein phosphatase 1, regulatory (inhibitor) subunit 2 | PPP1R2 | 5504 | 2.69716 | 0.853874 |
| 201259_s_at | synaptophysin-like 1 | SYPL1 | 6856 | 2.694686 | 0.853874 |
| 220643_s_at | Fas apoptotic inhibitory molecule | FAIM | 55179 | 2.693547 | 0.853874 |
| 212063_at | CD44 molecule (Indian blood group) | CD44 | 960 | 2.693352 | 0.853874 |
| 213970_at | RAB, member of RAS oncogene family-like 3 /// similar to RAB, member of RAS oncogene family-like 3 | LOC653256 /// RABL3 | 285282 /// 653256 | 2.687393 | 0.853874 |
| 217579_x_at | Transcribed locus | — | | 2.678399 | 0.853874 |
| 218577_at | leucine rich repeat containing 40 | LRRC40 | 55631 | 2.673808 | 0.853874 |
| 207681_at | chemokine (C-X-C motif) receptor 3 | CXCR3 | 2833 | 2.670851 | 0.853874 |

FIGURE 14 (CONTINUED)

| | | | | | |
|---|---|---|---|---|---|
| 204622_x_at | nuclear receptor subfamily 4, group A, member 2 | NR4A2 | 4929 | 2.668807 | 0.853874 |
| 214871_x_at | CDNA clone IMAGE:3347954 | | | 2.664172 | 0.853874 |
| 203408_s_at | SATB homeobox 1 | SATB1 | 6304 | 2.659846 | 0.853874 |
| 205836_s_at | YTH domain containing 2 | YTHDC2 | 64848 | 2.658214 | 0.853874 |
| 206587_at | chaperonin containing TCP1, subunit 6B (zeta 2) | CCT6B | 10693 | 2.656478 | 0.853874 |
| 218252_at | cytoskeleton associated protein 2 | CKAP2 | 26586 | 2.655766 | 0.853874 |
| 215157_x_at | poly(A) binding protein, cytoplasmic 1 | PABPC1 | 26986 | 2.65513 | 0.853874 |
| 217709_at | | | | 2.649384 | 0.859457 |
| 202381_at | ADAM metallopeptidase domain 9 (meltrin gamma) | ADAM9 | 8754 | 2.645573 | 0.860415 |
| 204334_at | Kruppel-like factor 7 (ubiquitous) | KLF7 | 8609 | 2.642512 | 0.860415 |
| 216962_at | RPA interacting protein | RPAIN | 84268 | 2.638828 | 0.862215 |
| 206055_s_at | small nuclear ribonucleoprotein polypeptide A' | SNRPA1 | 6627 | 2.629298 | 0.866649 |
| 65591_at | WD repeat domain 48 | WDR48 | 57599 | 2.629056 | 0.866649 |
| 208144_s_at | | | | 2.628945 | 0.866649 |
| 212648_at | DEAH (Asp-Glu-Ala-His) box polypeptide 29 | DHX29 | 54505 | 2.621064 | 0.873794 |
| 214801_at | CDNA FLJ11392 fis, clone HEMBA1000575 | | | 2.618272 | 0.874998 |
| 210871_x_at | synovial sarcoma, X breakpoint 2 interacting protein | SSX2IP | 117178 | 2.612874 | 0.880393 |
| 208989_s_at | F-box and leucine-rich repeat protein 11 | FBXL11 | 22992 | 2.594543 | 0.890175 |
| 201408_at | protein phosphatase 1, catalytic subunit, beta isoform | PPP1CB | 5500 | 2.59275 | 0.890891 |
| 207877_s_at | nuclear VCP-like | NVL | 4931 | 2.588869 | 0.892861 |
| 201181_at | guanine nucleotide binding protein (G protein), alpha inhibiting activity polypeptide 3 | GNAI3 | 2773 | 2.602662 | 0.888013 |
| 214332_s_at | Ts translation elongation factor, mitochondrial | TSFM | 10102 | 2.601444 | 0.888013 |
| 200004_at | eukaryotic translation initiation factor 4 gamma, 2 | EIF4G2 | 1982 | 2.583782 | 0.900002 |
| 203006_at | inositol polyphosphate-5-phosphatase, 40kDa | INPP5A | 3632 | 2.581643 | 0.902077 |
| 209609_s_at | mitochondrial ribosomal protein L9 | MRPL9 | 65005 | 2.572996 | 0.913069 |
| 209149_s_at | transmembrane 9 superfamily member 1 | TM9SF1 | 10548 | 2.572861 | 0.913069 |
| 213224_at | hypothetical protein LOC92482 | LOC92482 | 92482 | 2.563975 | 0.919927 |
| 209273_s_at | Iron-sulfur cluster assembly 1 homolog (S. cerevisiae) | ISCA1 | 81689 | 2.563248 | 0.919927 |
| 212177_at | splicing factor, arginine/serine-rich 18 | SFRS18 | 25957 | 2.554404 | 0.919927 |
| 53987_at | RAN binding protein 10 | RANBP10 | 57610 | 2.549391 | 0.919927 |
| 218203_at | asparagine-linked glycosylation 5 homolog (S. cerevisiae, dolichyl-phosphate beta-glucosyltransferase) | ALG5 | 29880 | 2.543379 | 0.919927 |
| 219117_s_at | FK506 binding protein 11, 19 kDa | FKBP11 | 51303 | 2.541763 | 0.919927 |
| 201504_s_at | translin | TSN | 7247 | 2.541723 | 0.919927 |
| 212782_x_at | polymerase (RNA) II (DNA directed) polypeptide J, 13.3kDa | POLR2J | 5439 | 2.541173 | 0.919927 |
| 206147_x_at | sex comb on midleg-like 2 (Drosophila) | SCML2 | 10389 | 2.540181 | 0.919927 |
| 216062_at | Transcribed locus | | | 2.539996 | 0.919927 |
| 208798_x_at | golgi autoantigen, golgin subfamily a, 8A | GOLGA8A | 23015 | 2.534337 | 0.930224 |
| 201070_x_at | splicing factor 3b, subunit 1, 155kDa | SF3B1 | 23451 | 2.52693 | 0.934755 |

FIGURE 14 (CONTINUED)

| | | | | |
|---|---|---|---|---|
| 203580_s_at | solute carrier family 7 (cationic amino acid transporter, y+ system), member 6 | SLC7A6 | 9057 | 2.526793 | 0.934755 |
| 220386_s_at | echinoderm microtubule associated protein like 4 | EML4 | 27436 | 2.523807 | 0.934755 |
| 209898_x_at | intersectin 2 | ITSN2 | 50618 | 2.523776 | 0.934755 |
| 218017_s_at | heparan-alpha-glucosaminide N-acetyltransferase | HGSNAT | 138050 | 2.520065 | 0.934878 |
| 212508_at | modulator of apoptosis 1 | MOAP1 | 64112 | 2.519008 | 0.934878 |
| 217028_at | chemokine (C-X-C motif) receptor 4 | CXCR4 | 7852 | 2.518981 | 0.934878 |
| 215167_at | mediator complex subunit 14 | MED14 | 9282 | 2.517989 | 0.934878 |
| 208190_s_at | lipolysis stimulated lipoprotein receptor | LSR | 51599 | 2.51541 | 0.9383 |
| 218587_s_at | KTEL (Lys-Tyr-Glu-Leu) containing 1 | KTELC1 | 56983 | 2.512075 | 0.940768 |
| 215951_at | TBC1 domain family, member 2B | TBC1D2B | 23102 | 2.509793 | 0.940768 |
| 214446_at | elongation factor, RNA polymerase II, 2 | ELL2 | 22936 | 2.508233 | 0.940768 |
| 219361_s_at | interferon stimulated exonuclease gene 20kDa-like 1 | ISG20L1 | 64782 | 2.506478 | 0.941568 |
| 203775_at | solute carrier family 25, member 13 (citrin) | SLC25A13 | 10165 | 2.504291 | 0.944149 |
| 221986_s_at | kelch-like 24 (Drosophila) | KLHL24 | 54800 | 2.503127 | 0.944387 |
| 214327_x_at | tumor protein, translationally-controlled 1 | TPT1 | 7178 | 2.494126 | 0.945644 |
| 208968_s_at | cytokine induced apoptosis inhibitor 1 | CIAPIN1 | 57019 | 2.492988 | 0.94564 |
| 221894_at | aarF domain containing kinase 2 | ADCK2 | 90956 | 2.492683 | 0.94564 |
| 211955_at | RAN binding protein 5 | RANBP5 | 3843 | 2.491585 | 0.94564 |
| 204270_at | v-ski sarcoma viral oncogene homolog (avian) | SKI | 6497 | 2.491374 | 0.945644 |
| 203865_s_at | adenosine deaminase, RNA-specific, B1 (RED1 homolog rat) | ADARB1 | 104 | 2.48929 | 0.94564 |
| 215053_at | Snf2-related CREBBP activator protein | SRCAP | 10847 | 2.486605 | 0.94564 |
| 202181_at | KIAA0247 | KIAA0247 | 9766 | 2.485502 | 0.94564 |
| 212284_x_at | tumor protein, translationally-controlled 1 | TPT1 | 7178 | 2.485277 | 0.94564 |
| 219717_at | chromosome 4 open reading frame 30 | C4orf30 | 54876 | 2.485262 | 0.94564 |
| 202523_s_at | sparc/osteonectin, cwcv and kazal-like domains proteoglycan (testican) 2 | SPOCK2 | 9806 | 2.48326 | 0.94564 |
| 205540_s_at | Ras-related GTP binding B | RRAGB | 10325 | 2.48273 | 0.94564 |
| 201389_at | integrin, alpha 5 (fibronectin receptor, alpha polypeptide) | ITGA5 | 3678 | 2.477595 | 0.945648 |
| 202843_at | DnaJ (Hsp40) homolog, subfamily B, member 9 | DNAJB9 | 4189 | 2.47685 | 0.945989 |
| 218579_s_at | DEAH (Asp-Glu-Ala-His) box polypeptide 35 | DHX35 | 60625 | 2.475459 | 0.945989 |
| 214683_s_at | CDC-like kinase 1 | CLK1 | 1195 | 2.473706 | 0.945989 |
| 212434_at | GrpE-like 1, mitochondrial (E. coli) | GRPEL1 | 80273 | 2.472534 | 0.945989 |
| 211893_x_at | CD6 molecule | CD6 | 923 | 2.470514 | 0.945989 |
| 205966_at | TAF13 RNA polymerase II, TATA box binding protein (TBP)-associated factor, 18kDa | TAF13 | 6884 | 2.46959 | 0.945989 |
| 207079_s_at | mediator complex subunit 6 | MED6 | 10001 | 2.464536 | 0.945989 |
| 218386_x_at | ubiquitin specific peptidase 16 | USP16 | 10600 | 2.46445 | 0.945989 |
| 202146_at | interferon-related developmental regulator 1 | IFRD1 | 3475 | 2.462514 | 0.945989 |
| 202436_s_at | cytochrome P450, family 1, subfamily B, polypeptide 1 | CYP1B1 | 1545 | 2.456843 | 0.953221 |
| 203380_x_at | splicing factor, arginine/serine-rich 5 | SFRS5 | 6430 | 2.455063 | 0.955096 |
| 201417_at | SRY (sex determining region Y)-box 4 | SOX4 | 6659 | 2.453488 | 0.955994 |
| 200921_s_at | B-cell translocation gene 1, anti-proliferative | BTG1 | 694 | 2.451227 | 0.955994 |
| 204790_at | SMAD family member 7 | SMAD7 | 4092 | 2.4503 | 0.955994 |

FIGURE 14 (CONTINUED)

| | | | | |
|---|---|---|---|---|
| 206976_s_at | heat shock 105kDa/110kDa protein 1 | HSPH1 | 10808 | 2.446554 | 0.955994 |
| 212722_s_at | jumonji domain containing 6 | JMJD6 | 23210 | 2.444481 | 0.955994 |
| 210017_at | mucosa associated lymphoid tissue lymphoma translocation gene 1 | MALT1 | 10892 | 2.443662 | 0.955994 |
| 205259_at | nuclear receptor subfamily 3, group C, member 2 | NR3C2 | 4306 | 2.440498 | 0.955994 |
| 215823_x_at | poly(A) binding protein, cytoplasmic 3 /// poly(A) binding protein, cytoplasmic 1 /// hypothetical LOC341315 /// similar to Polyadenylate-binding protein 1 (Poly(A)-binding protein 1) (PABP 1) | LOC341315 /// LOC652607 /// PABPC1 /// PABPC3 | 26986 /// 341315 /// 5042 /// 652607 | 2.439228 | 0.955994 |
| 212089_at | lamin A/C | LMNA | 4000 | 2.436625 | 0.956222 |
| 212014_x_at | CD44 molecule (Indian blood group) | CD44 | 960 | 2.435005 | 0.95725 |
| 208724_s_at | RAB1A, member RAS oncogene family | RAB1A | 5861 | 2.429922 | 0.963147 |
| 200082_s_at | ribosomal protein S7 /// similar to 40S ribosomal protein S7 (S8) | LOC644315 /// RPS7 | 6201 /// 644315 | 2.421208 | 0.965103 |
| 210054_at | chromosome 4 open reading frame 15 | C4orf15 | 79441 | 2.420858 | 0.965103 |
| 219028_at | homeodomain interacting protein kinase 2 | HIPK2 | 28996 | 2.415199 | 0.965103 |
| 218218_at | adaptor protein, phosphotyrosine interaction, PH domain and leucine zipper containing 2 | APPL2 | 55198 | 2.415134 | 0.965103 |
| 213310_at | Eukaryotic translation initiation factor 2C, 2 | EIF2C2 | 27161 | 2.4133 | 0.965103 |
| 221773_at | ELK3, ETS-domain protein (SRF accessory protein 2) | ELK3 | 2004 | 2.413153 | 0.965103 |
| 212447_at | kelch repeat and BTB (POZ) domain containing 2 | KBTBD2 | 25948 | 2.412631 | 0.965103 |
| 206404_at | fibroblast growth factor 9 (glia-activating factor) | FGF9 | 2254 | 2.412065 | 0.965103 |
| 201513_at | translin | TSN | 7247 | 2.410556 | 0.965103 |
| 217998_at | pleckstrin homology-like domain, family A, member 1 /// hypothetical LOC652993 | LOC652993 /// PHLDA1 | 22822 /// 652993 | 2.410412 | 0.965103 |
| 214125_s_at | Neuron derived neurotrophic factor | NENF | 29937 | 2.410151 | 0.965103 |
| 209185_s_at | insulin receptor substrate 2 | IRS2 | 8660 | 2.40643 | 0.965484 |
| 208160_at | hypothetical protein FLJ10232 | FLJ10232 | 55099 | 2.404512 | 0.965484 |
| 209712_at | solute carrier family 35 (UDP-glucuronic acid/UDP-N-acetylgalactosamine dual transporter), member D1 | SLC35D1 | 23169 | 2.403846 | 0.965484 |
| 216044_x_at | family with sequence similarity 69, member A | FAM69A | 388650 | 2.395344 | 0.968985 |
| 37433_at | protein inhibitor of activated STAT, 2 | PIAS2 | 9063 | 2.394352 | 0.968985 |
| 209993_at | ATP-binding cassette, sub-family B (MDR/TAP), member 1 | ABCB1 | 5243 | 2.393495 | 0.968985 |
| 206337_at | chemokine (C-C motif) receptor 7 | CCR7 | 1236 | 2.391027 | 0.968985 |
| 206114_at | EPH receptor A4 | EPHA4 | 2043 | 2.390647 | 0.968985 |
| 2008804_s_at | splicing factor, arginine/serine-rich 6 | SFRS6 | 6431 | 2.389085 | 0.968985 |
| 221768_at | Splicing factor proline/glutamine-rich (polypyrimidine tract binding protein associated) | SFPQ | 6421 | 2.388672 | 0.968985 |
| 206156_at | gap junction protein, beta 5, 31.1kDa | GJB5 | 2709 | 2.387915 | 0.968985 |
| 202565_s_at | supervillin | SVIL | 6840 | 2.387738 | 0.968985 |
| 214879_x_at | upstream transcription factor 2, c-fos interacting | USF2 | 7392 | 2.38314 | 0.973168 |
| 214124_x_at | Transcribed locus | --- | --- | 2.382812 | 0.973168 |
| 222326_at | Transcribed locus | --- | --- | 2.382554 | 0.973168 |
| 216945_x_at | PAS domain containing serine/threonine kinase | PASK | 23178 | 2.378087 | 0.97962 |
| 201917_s_at | solute carrier family 25, member 36 | SLC25A36 | 55186 | 2.376248 | 0.981949 |

FIGURE 14 (CONTINUED)

| Probe ID | Description | Gene Symbol | Col4 | Col5 | Col6 |
|---|---|---|---|---|---|
| 216282_x_at | polymerase (RNA) II (DNA directed) polypeptide C, 33kDa | POLR2C | | 5432 | 2.375281 | 0.982256 |
| 220271_x_at | EF-hand calcium binding domain 6 | EFCAB6 | | 64800 | 2.370658 | 0.982963 |
| 60815_at | polymerase (RNA) II (DNA directed) polypeptide J, 13.3kDa pseudogene | POLR2J4 | | 84820 | 2.37039 | 0.982963 |
| 214129_at | similar to phosphodiesterase 4D interacting protein isoform 2 | LOC727942 | | 727942 | 2.370315 | 0.982963 |
| 221425_s_at | iron-sulfur cluster assembly 1 homolog (S. cerevisiae) | ISCA1 | | 81689 | 2.368778 | 0.982963 |
| 201690_s_at | tumor protein D52 | TPD52 | | 7163 | 2.365403 | 0.982963 |
| 213538_at | SON DNA binding protein | SON | | 6651 | 2.364927 | 0.982963 |
| 219826_at | zinc finger protein 419 | ZNF419 | | 79744 | 2.363416 | 0.982963 |
| 205100_at | glutamine-fructose-6-phosphate transaminase 2 | GFPT2 | | 9945 | 2.362071 | 0.982963 |
| 206618_at | interleukin 18 receptor 1 | IL18R1 | | 8809 | 2.36182 | 0.982963 |
| 202733_at | procollagen-proline, 2-oxoglutarate 4-dioxygenase (proline 4-hydroxylase), alpha polypeptide II | P4HA2 | | 8974 | 2.359704 | 0.983708 |
| 218935_s_at | coiled-coil domain containing 59 | CCDC59 | | 29080 | 2.353506 | 0.983708 |
| 217790_s_at | signal sequence receptor, gamma (translocon-associated protein gamma) | SSR3 | | 6747 | 2.349436 | 0.983708 |
| 212154_at | syndecan 2 | SDC2 | | 6383 | 2.346603 | 0.983708 |
| 202055_at | karyopherin alpha 1 (importin alpha 5) | KPNA1 | | 3836 | 2.345873 | 0.983708 |
| 208602_x_at | CD6 molecule | CD6 | | 923 | 2.344537 | 0.983708 |
| 202673_at | dolichyl-phosphate mannosyltransferase polypeptide 1, catalytic subunit | DPM1 | | 8813 | 2.344374 | 0.983708 |
| 217798_at | CCR4-NOT transcription complex, subunit 2 | CNOT2 | | 4848 | 2.343613 | 0.983708 |
| 201711_x_at | RAN binding protein 2 | RANBP2 | | 5903 | 2.343207 | 0.983708 |
| 217242_at | zinc finger protein 154 | ZNF154 | | 7710 | 2.339597 | 0.985797 |
| 208313_s_at | splicing factor 1 | SF1 | | 7536 | 2.339157 | 0.985797 |
| 211861_x_at | CD28 molecule | CD28 | | 940 | 2.338931 | 0.985797 |
| 201300_s_at | prion protein (p27-30) (Creutzfeldt-Jakob disease, Gerstmann-Strausler-Scheinker syndrome, fatal familial insomnia) | PRNP | | 5621 | 2.33728 | 0.985797 |
| 218606_at | zinc finger, DHHC-type containing 7 | ZDHHC7 | | 55625 | 2.331543 | 0.985797 |
| 200705_s_at | eukaryotic translation elongation factor 1 beta 2 /// hCG1983058 | EEF1B2 /// hCG_1983058 | 1933 /// 644820 | | 2.329986 | 0.985797 |
| 203068_at | kelch-like 21 (Drosophila) | KLHL21 | | 9903 | 2.325087 | 0.987521 |
| 221871_s_at | TRK-fused gene | TFG | | 10342 | 2.324693 | 0.987521 |
| 215545_at | — | — | | | 2.322949 | 0.989811 |
| 222101_s_at | dachsous 1 (Drosophila) | DCHS1 | | 8642 | 2.319277 | 0.990446 |
| 203357_s_at | calpain 7 | CAPN7 | | 23473 | 2.318887 | 0.990446 |
| 212521_s_at | phosphodiesterase 8A | PDE8A | | 5151 | 2.318399 | 0.990446 |
| 207339_s_at | lymphotoxin beta (TNF superfamily, member 3) | LTB | | 4050 | 2.314409 | 0.990482 |
| 210117_at | sperm associated antigen 1 | SPAG1 | | 6674 | 2.312762 | 0.990482 |
| 208632_at | ring finger protein 10 | RNF10 | | 9921 | 2.312234 | 0.990482 |
| 202496_at | enhancer of mRNA decapping 4 | EDC4 | | 23644 | 2.311507 | 0.990482 |
| 212869_x_at | tumor protein, translationally-controlled 1 | TPT1 | | 7178 | 2.308857 | 0.991589 |
| 201257_x_at | ribosomal protein S3A | RPS3A | | 6189 | 2.307594 | 0.991589 |
| 216342_x_at | similar to 40S ribosomal protein S4, X isoform | LOC390183 /// LOC442162 | 390183 /// 442162 | | 2.307366 | 0.991589 |

FIGURE 14 (CONTINUED)

| | | | | |
|---|---|---|---|---|
| 209363_s_at | mediator complex subunit 21 | MED21 | 9412 | 2.30657 | 0.991744 |
| 208263_at | — | — | — | 2.304408 | 0.992138 |
| 211113_s_at | ATP-binding cassette, sub-family G (WHITE), member 1 | ABCG1 | 9619 | 2.301922 | 0.992432 |
| 215889_at | SKI-like oncogene | SKIL | 6498 | 2.300162 | 0.993134 |
| 209674_at | cryptochrome 1 (photolyase-like) | CRY1 | 1407 | 2.295257 | 0.995336 |
| 207310_s_at | nitric oxide synthase 1 (neuronal) | NOS1 | 4842 | 2.294198 | 0.995336 |
| 207937_x_at | fibroblast growth factor receptor 1 (fms-related tyrosine kinase 2, Pfeiffer syndrome) | FGFR1 | 2260 | 2.293767 | 0.995336 |
| 204203_at | CCAAT/enhancer binding protein (C/EBP), gamma | CEBPG | 1054 | 2.293108 | 0.995336 |
| 210995_s_at | tripartite motif-containing 23 | TRIM23 | 373 | 2.292316 | 0.995336 |
| 200719_at | S-phase kinase-associated protein 1 | SKP1 | 6500 | 2.289812 | 0.995336 |
| 219423_x_at | tumor necrosis factor receptor superfamily, member 25 | TNFRSF25 | 8718 | 2.287152 | 0.995336 |
| 202160_at | CREB binding protein (Rubinstein-Taybi syndrome) | CREBBP | 1387 | 2.286371 | 0.995336 |
| 221617_at | TAF9B RNA polymerase II, TATA box binding protein (TBP)-associated factor, 31kDa | TAF9B | 51616 | 2.285063 | 0.995336 |
| 217822_at | WW domain binding protein 11 | WBP11 | 51729 | 2.284145 | 0.995786 |
| 216947_at | desmin | DES | 1674 | 2.28285 | 0.997165 |
| 216297_at | MRNA; cDNA DKFZp564C156 (from clone DKFZp564C156) | — | — | 2.280524 | 0.999842 |
| 206545_at | CD28 molecule | CD28 | 940 | 2.279083 | 0.999842 |
| 200893_at | splicing factor, arginine/serine-rich 10 (transformer 2 homolog, Drosophila) | SFRS10 | 6434 | 2.277612 | 0.999842 |
| 205042_at | glucosamine (UDP-N-acetyl)-2-epimerase/N-acetylmannosamine kinase | GNE | 10020 | 2.275836 | 0.999842 |
| 221976_s_at | Hepatoma-derived growth factor, related protein 3 | HDGFRP3 | 50810 | 2.273036 | 0.999842 |
| 205388_at | RCAN family member 3 | RCAN3 | 11123 | 2.272653 | 0.999842 |
| 205388_at | troponin C type 2 (fast) | TNNC2 | 7125 | 2.270959 | 0.999842 |
| 208828_at | polymerase (DNA directed), epsilon 3 (p17 subunit) | POLE3 | 54107 | 2.270571 | 0.999842 |
| 209501_at | cerebellar degeneration-related protein 2, 62kDa | CDR2 | 1039 | 2.270007 | 0.999842 |
| 202689_at | RNA binding motif protein 15B | RBM15B | 29990 | 2.268699 | 0.999842 |
| 217824_at | ubiquitin-conjugating enzyme E2, J1 (UBC6 homolog, yeast) | UBE2J1 | 51465 | 2.267532 | 0.999842 |
| 215737_x_at | upstream transcription factor 2, c-fos interacting | USF2 | 7392 | 2.266026 | 0.999842 |
| 204202_at | IQ motif containing E | IQCE | 23288 | 2.265529 | 0.999842 |
| 209994_s_at | ATP-binding cassette, sub-family B (MDR/TAP), member 1 /// ATP-binding cassette, sub-family B (MDR/TAP), member 4 | ABCB1 /// ABCB4 | 5243 /// 5244 | 2.264393 | 0.999842 |
| 201185_at | HtrA serine peptidase 1 | HTRA1 | 5654 | 2.262879 | 0.999842 |
| 215640_at | TBC1 domain family, member 2B | TBC1D2B | 23102 | 2.257998 | 0.999842 |
| 221834_at | Seven in absentia homolog 1 (Drosophila) | SIAH1 | 6477 | 2.257215 | 0.999842 |
| 221478_at | BCL2/adenovirus E1B 19kDa interacting protein 3-like | BNIP3L | 665 | 2.256252 | 0.999842 |
| 212237_at | additional sex combs like 1 (Drosophila) | ASXL1 | 171023 | 2.254407 | 0.999842 |
| 222177_s_at | SCAN domain containing 2 | SCAND2 | 54581 | 2.253338 | 0.999842 |
| 219927_at | FCF1 small subunit (SSU) processome component homolog (S. cerevisiae) | FCF1 | 51077 | 2.252937 | 0.999842 |
| 200738_s_at | phosphoglycerate kinase 1 | PGK1 | 5230 | 2.252717 | 0.999842 |
| 212309_at | cytoplasmic linker associated protein 2 | CLASP2 | 23122 | 2.25031 | 0.999842 |
| 220486_x_at | transmembrane protein 164 | TMEM164 | 84187 | 2.250191 | 0.999842 |

FIGURE 14 (CONTINUED)

| | | | | | |
|---|---|---|---|---|---|
| 216497_at | heterogeneous nuclear ribonucleoprotein A1 /// similar to Heterogeneous nuclear ribonucleoprotein A1 (Helix-destabilizing protein) (Single-strand binding protein) (hnRNP core protein A1) (HDP-1) (Topoisomerase-inhibitor suppressed) /// heterogeneous nuclear ribonucleoprotein A1-like /// heterogeneous nuclear ribonucleoprotein A1 pseudogene 4 /// similar to Heterogeneous nuclear ribonucleoprotein A1 (Helix-destabilizing protein) (Single-strand RNA-binding protein) (hnRNP core protein A1) (HDP) /// heterogeneous nuclear ribonucleoprotein A1 pseudogene /// hypothetical LOC642817 /// heterogeneous nuclear ribonucleoprotein A1 pseudogene 5 | hCG_2023776 /// HNRNPA1 /// HNRPA1L-2 /// HNRPA1P4 /// HNRPA1P5 /// LOC120364 /// LOC344741 /// LOC391670 /// LOC400769 /// LOC402112 /// LOC440125 /// LOC642817 /// LOC644037 /// LOC645001 /// LOC645347 /// LOC645691 /// LOC648210 /// LOC728170 /// LOC728643 /// LOC728732 /// LOC729102 /// LOC729366 /// LOC730246 /// LOC731363 /// LOC732014 /// RP11-78J21.1 | 120364 /// 144983 /// 3178 /// 344741 /// 389674 /// 391670 /// 400769 /// 402112 /// 402562 /// 440125 /// 642817 /// 644037 /// 645001 /// 645347 /// 645691 /// 648210 /// 664709 /// 664721 /// 728170 /// 728643 /// 728732 /// 729102 /// 729366 /// 730246 /// 731363 /// 732014 | | 2.247925 | 0.999842 |
| 221847_at | Full-length cDNA clone CS0DE005YD08 of Placenta of Homo sapiens (human) | | | | 2.24739 | 0.999842 |
| 211927_x_at | eukaryotic translation elongation factor 1 gamma /// elongation factor 1 gamma pseudogene | EEF1G /// LOC729998 | 1937 /// 729998 | | 2.247272 | 0.999842 |
| 209686_at | S100 calcium binding protein B | S100B | 6285 | | 2.245669 | 0.999842 |
| 219343_at | cell division cycle 37 homolog (S. cerevisiae)-like 1 | CDC37L1 | 55664 | | 2.2454 | 0.999842 |
| 202930_s_at | succinate-CoA ligase, ADP-forming, beta subunit | SUCLA2 | 8803 | | 2.236365 | 0.999842 |
| 222309_at | Chromosome 6 open reading frame 62 | C6orf62 | 81688 | | 2.233855 | 0.999842 |
| 206406_at | sperm mitochondria-associated cysteine-rich protein | SMCP | 4184 | | 2.233241 | 0.999842 |
| 217682_at | CDNA FLJ37032 fis, clone BRACE2011265 | | | | 2.227829 | 0.999842 |
| 212764_at | | | | | 2.227796 | 0.999842 |
| 201324_at | epithelial membrane protein 1 | EMP1 | 2012 | | 2.227739 | 0.999842 |
| 207515_s_at | polymerase (RNA) I polypeptide C, 30kDa | POLR1C | 9533 | | 2.226737 | 0.999842 |
| 215707_s_at | prion protein (p27-30) (Creutzfeldt-Jakob disease, Gerstmann-Strausler-Scheinker syndrome, fatal familial insomnia) | PRNP | 5621 | | 2.22629 | 0.999842 |
| 215512_at | membrane-associated ring finger (C3HC4) 6 | | 10299 | 6-Mar | 2.225775 | 0.999842 |
| 206592_s_at | adaptor-related protein complex 3, delta 1 subunit | AP3D1 | 8943 | | 2.225278 | 0.999842 |
| 211720_x_at | ribosomal protein, large, P0 | RPLP0 | 6175 | | 2.222868 | 0.999842 |

FIGURE 14 (CONTINUED)

| | | | | | |
|---|---|---|---|---|---|
| 204566_at | protein phosphatase 1D magnesium-dependent, delta isoform | PPM1D | | 8493 | 2.221209 | 0.999842 |
| 222373_at | --- | --- | | | 2.220988 | 0.999842 |
| 217591_at | Transcribed locus | --- | | | 2.219113 | 0.999842 |
| 216035_x_at | transcription factor 7-like 2 (T-cell specific, HMG-box) | TCF7L2 | | 6934 | 2.218585 | 0.999842 |
| 218296_x_at | misato homolog 1 (Drosophila) /// similar to misato | LOC731059 /// MSTO1 | 55154 /// 731059 | | 2.218276 | 0.999842 |
| 218923_at | chitobiase, di-N-acetyl- | CTBS | | 1486 | 2.215965 | 0.999842 |
| 37005_at | neuroblastoma, suppression of tumorigenicity 1 | NBL1 | | 4681 | 2.215959 | 0.999842 |
| 201528_at | replication protein A1, 70kDa | RPA1 | | 6117 | 2.21572 | 0.999842 |
| 222311_s_at | splicing factor, arginine/serine-rich 15 | SFRS15 | | 57466 | 2.214884 | 0.999842 |
| 202611_s_at | mediator complex subunit 14 | MED14 | | 9282 | 2.211491 | 0.999842 |
| 213612_x_at | neuroblastoma breakpoint family, member 15 /// neuroblastoma breakpoint family, member 10 /// neuroblastoma breakpoint family, member 8 /// neuroblastoma breakpoint family, member 16 /// hypothetical protein LOC728980 | LOC728980 /// NBPF10 /// NBPF15 /// NBPF16 /// NBPF8 | 284565 /// 440673 /// 641559 /// 728936 /// 728980 | | 2.209781 | 0.999842 |
| 200099_s_at | ribosomal protein S3A /// similar to ribosomal protein S3a | LOC439992 /// RPS3A | 439992 /// 6189 | | 2.209133 | 0.999842 |
| 218372_at | mediator complex subunit 9 | MED9 | | 55090 | 2.208667 | 0.999842 |
| 210676_x_at | RANBP2-like and GRIP domain containing 5 /// RANBP2-like and GRIP domain containing 8 /// RANBP2-like and GRIP domain containing 6 | RGPD5 /// RGPD6 /// RGPD8 | 727851 /// 729540 /// 84220 | | 2.20714 | 0.999842 |
| 217607_x_at | eukaryotic translation initiation factor 4 gamma, 2 | EIF4G2 | | 1982 | 2.204431 | 0.999842 |
| 219543_at | phenazine biosynthesis-like protein domain containing | PBLD | | 64081 | 2.204246 | 0.999842 |
| 200892_s_at | splicing factor, arginine/serine-rich 10 (transformer 2 homolog, Drosophila) | SFRS10 | | 6434 | 2.203327 | 0.999842 |
| 200668_s_at | ubiquitin-conjugating enzyme E2D 3 (UBC4/5 homolog, yeast) | UBE2D3 | | 7323 | 2.201794 | 0.999842 |
| 221687_s_at | family with sequence similarity 125, member B | FAM125B | | 89853 | 2.19819 | 0.999842 |
| 212391_x_at | ribosomal protein S3A | RPS3A | | 6189 | 2.197912 | 0.999842 |
| 213282_at | CDNA FLJ39590 fis, clone SKNMC1000079 | --- | | | 2.19722 | 0.999842 |
| 204023_at | replication factor C (activator 1) 4, 37kDa | RFC4 | | 5984 | 2.196373 | 0.999842 |
| 218091_at | HIV-1 Rev binding protein | HRB | | 3267 | 2.195946 | 0.999842 |
| 202981_x_at | seven in absentia homolog 1 (Drosophila) | SIAH1 | | 6477 | 2.195529 | 0.999842 |
| 204458_at | lysophospholipase 3 (lysosomal phospholipase A2) | LYPLA3 | | 23659 | 2.194908 | 0.999842 |
| 222035_s_at | poly(A) polymerase alpha | PAPOLA | | 10914 | 2.194582 | 0.999842 |
| 204593_s_at | Smith-Magenis syndrome chromosome region, candidate 7-like | SMCR7L | | 54471 | 2.192288 | 0.999842 |
| 209980_s_at | serine hydroxymethyltransferase 1 (soluble) | SHMT1 | | 6470 | 2.190352 | 0.999842 |
| 211973_at | AF034176 Human mRNA (Tripodis and Ragoussis) Homo sapiens cDNA clone ntcon5 contig | --- | | | 2.190082 | 0.999842 |
| 209406_at | BCL2-associated athanogene 2 | BAG2 | | 9532 | 2.189011 | 0.999842 |
| 209024_s_at | synaptotagmin binding, cytoplasmic RNA interacting protein | SYNCRIP | | 10492 | 2.188887 | 0.999842 |
| 204642_at | endothelial differentiation, sphingolipid G-protein-coupled receptor, 1 | EDG1 | | 1901 | 2.18445 | 0.999842 |
| 202537_s_at | chromatin modifying protein 2B | CHMP2B | | 25978 | 2.182319 | 0.999842 |
| 213346_at | chromosome 13 open reading frame 27 | C13orf27 | | 93081 | 2.18125 | 0.999842 |

FIGURE 14 (CONTINUED)

| | | | | |
|---|---|---|---|---|
| 212684_at | zinc finger protein 3 | ZNF3 | 7551 | 2.180183 | 0.999842 |
| 217252_at | sequestosome 1 | SQSTM1 | 8878 | 2.179627 | 0.999842 |
| 203466_at | MpV17 mitochondrial inner membrane protein | MPV17 | 4358 | 2.179359 | 0.999842 |
| 208275_x_at | undifferentiated embryonic cell transcription factor 1 | UTF1 | 8433 | 2.179327 | 0.999842 |
| 212787_at | YLP motif containing 1 | YLPM1 | 56252 | 2.178219 | 0.999842 |
| 201033_x_at | ribosomal protein, large, P0 | RPLP0 | 6175 | 2.178118 | 0.999842 |
| 216479_at | ribosomal protein L21 /// similar to 60S ribosomal protein L21 /// similar to ribosomal protein L21 /// ribosomal protein L21 pseudogene /// similar to ribosomal protein L21 isoform 1 /// 60S ribosomal protein L21 pseudogene | LOC387753 /// LOC388621 /// LOC389156 /// LOC440487 /// LOC440575 /// LOC442160 /// LOC442738 /// LOC641293 /// LOC645157 /// LOC645174 /// LOC646279 /// LOC650059 /// LOC652328 /// LOC653079 /// LOC653156 /// LOC653665 /// LOC653737 /// LOC727810 /// LOC727821 /// LOC728501 /// LOC728693 /// LOC728782 /// LOC729208 /// LOC729241 /// LOC729402 /// LOC729484 /// LOC731567 /// LOC732301 /// RPL21 | 387753 /// 388621 /// 389156 /// 440487 /// 440575 /// 442160 /// 6144 /// 641293 /// 642738 /// 645157 /// 645174 /// 646279 /// 650059 /// 652328 /// 653079 /// 653156 /// 653665 /// 653737 /// 727810 /// 727821 /// 728501 /// 728693 /// 728782 /// 729208 /// 729241 /// 729402 /// 729484 /// 731567 /// 732301 | 2.176185 | 0.999842 |
| 214553_s_at | cyclic AMP phosphoprotein, 19 kD | ARPP-19 | 10776 | 2.174524 | 0.999842 |
| 212933_x_at | ribosomal protein L13 | RPL13 | 6137 | 2.173498 | 0.999842 |
| 204142_at | enolase superfamily member 1 | ENOSF1 | 55556 | 2.1705 | 0.999842 |
| 215490_at | chromosome 1 open reading frame 69 | C1orf69 | 200205 | 2.167572 | 0.999842 |
| 211202_s_at | jumonji, AT rich interactive domain 1B | JARID1B | 10765 | 2.166096 | 0.999842 |
| 217748_at | adiponectin receptor 1 | ADIPOR1 | 51094 | 2.166035 | 0.999842 |
| 201359_at | coatomer protein complex, subunit beta 1 | COPB1 | 1315 | 2.165479 | 0.999842 |
| 200949_x_at | ribosomal protein S20 | RPS20 | 6224 | 2.163448 | 0.999842 |

FIGURE 14 (CONTINUED)

| Probe ID | Description | Gene | Ref | Value | P |
|---|---|---|---|---|---|
| 214785_at | vacuolar protein sorting 13 homolog A (S. cerevisiae) | VPS13A | | 23230 | 2.158774 | 0.999842 |
| 213227_at | progesterone receptor membrane component 2 | PGRMC2 | | 10424 | 2.158444 | 0.999842 |
| 208868_s_at | GABA(A) receptor-associated protein like 1 | GABARAPL1 | | 23710 | 2.157821 | 0.999842 |
| 213172_at | tetratricopeptide repeat domain 9 | TTC9 | | 23508 | 2.155316 | 0.999842 |
| 202646_s_at | cold shock domain containing E1, RNA-binding | CSDE1 | | 7812 | 2.155085 | 0.999842 |
| 214305_s_at | splicing factor 3b, subunit 1, 155kDa | SF3B1 | | 23451 | 2.154989 | 0.999842 |
| 203847_s_at | A kinase (PRKA) anchor protein 8 | AKAP8 | | 10270 | 2.154964 | 0.999842 |
| 211751_at | phosphodiesterase 4D interacting protein (myomegalin) | PDE4DIP | | 9659 | 2.154377 | 0.999842 |
| 210426_x_at | RAR-related orphan receptor A | RORA | | 6095 | 2.153926 | 0.999842 |
| 215233_at | jumonji domain containing 6 | JMJD6 | | 23210 | 2.151668 | 0.999842 |
| 201919_at | solute carrier family 25, member 36 | SLC25A36 | | 55186 | 2.151462 | 0.999842 |
| 221493_at | TSPY-like 1 | TSPYL1 | | 7259 | 2.15084 | 0.999842 |
| 208856_x_at | ribosomal protein, large, P0 | RPLP0 | | 6175 | 2.150626 | 0.999842 |
| 206559_x_at | eukaryotic translation elongation factor 1 alpha 1 | EEF1A1 | | 1915 | 2.150424 | 0.999842 |
| 204080_at | target of EGR1, member 1 (nuclear) | TOE1 | | 114034 | 2.150146 | 0.999842 |
| 214245_at | ribosomal protein S14 | RPS14 | | 6208 | 2.14823 | 0.999842 |
| 212101_at | karyopherin alpha 6 (importin alpha 7) | KPNA6 | | 23633 | 2.145419 | 0.999842 |
| 221842_s_at | zinc finger protein 131 | ZNF131 | | 7690 | 2.145166 | 0.999842 |
| 217356_s_at | phosphoglycerate kinase 1 | PGK1 | | 5230 | 2.143442 | 0.999842 |
| 217807_s_at | glioma tumor suppressor candidate region gene 2 | GLTSCR2 | | 29997 | 2.143058 | 0.999842 |
| 209845_at | makorin, ring finger protein, 1 | MKRN1 | | 23608 | 2.142511 | 0.999842 |
| 204856_at | UDP-GlcNAc:betaGal beta-1,3-N-acetylglucosaminyltransferase 3 | B3GNT3 | | 10331 | 2.138608 | 0.999842 |
| 212813_at | junctional adhesion molecule 3 | JAM3 | | 83700 | 2.13849 | 0.999842 |
| 214834_at | small nuclear ribonucleoprotein polypeptide N /// Prader-Willi/Angelman syndrome-5 /// small nucleolar RNA, C/D box 108 /// small nucleolar RNA, C/D box 64 /// paternally expressed transcript PAR-SN | PAR-SN /// PAR5 /// SNORD108 /// SNORD64 /// SNRPN | 338427 /// 347686 /// 347746 /// 6638 /// 8123 | | 2.137113 | 0.999842 |
| 206044_s_at | v-raf murine sarcoma viral oncogene homolog B1 | BRAF | | 673 | 2.135943 | 0.999842 |
| 200650_s_at | lactate dehydrogenase A | LDHA | | 3939 | 2.135006 | 0.999842 |
| 215528_at | MRNA; cDNA DKFZp586O1318 (from clone DKFZp586O1318) | --- | --- | | 2.132419 | 0.999842 |
| 221657_s_at | ankyrin repeat and SOCS box-containing 6 | ASB6 | | 140459 | 2.130539 | 0.999842 |
| 214658_at | transmembrane emp24 protein transport domain containing 7 | TMED7 | | 51014 | 2.128668 | 0.999842 |
| 218168_s_at | chaperone, ABC1 activity of bc1 complex homolog (S. pombe) | CABC1 | | 56997 | 2.128069 | 0.999842 |
| 217850_at | guanine nucleotide binding protein-like 3 (nucleolar) | GNL3 | | 26354 | 2.127825 | 0.999842 |
| 215575_at | phosphodiesterase 4D interacting protein (myomegalin) | PDE4DIP | | 9659 | 2.12757 | 0.999842 |
| 218829_s_at | chromodomain helicase DNA binding protein 7 | CHD7 | | 55636 | 2.126938 | 0.999842 |
| 214947_at | CDNA FLJ43660 fis, clone SYNOV4004823 | --- | --- | | 2.126398 | 0.999842 |
| 211439_at | splicing factor, arginine/serine-rich 7, 35kDa | SFRS7 | | 6432 | 2.125496 | 0.999842 |
| 202730_s_at | programmed cell death 4 (neoplastic transformation inhibitor) | PDCD4 | | 27250 | 2.124808 | 0.999842 |
| 218478_s_at | zinc finger, CCHC domain containing 8 | ZCCHC8 | | 55596 | 2.124477 | 0.999842 |
| 216350_at | zinc finger protein 10 | ZNF10 | | 7556 | 2.122403 | 0.999842 |
| 213864_s_at | nucleosome assembly protein 1-like 1 | NAP1L1 | | 4673 | 2.122277 | 0.999842 |

FIGURE 14 (CONTINUED)

| | | | | | |
|---|---|---|---|---|---|
| 209412_at | transmembrane protein 1 | TMEM1 | | 7109 | 2.121527 | 0.999842 |
| 219449_s_at | transmembrane protein 70 | TMEM70 | | 54968 | 2.121243 | 0.999842 |
| 210671_x_at | mitogen-activated protein kinase 8 | MAPK8 | | 5599 | 2.117429 | 0.999842 |
| 202021_x_at | eukaryotic translation initiation factor 1 | EIF1 | | 10209 | 2.117223 | 0.999842 |
| 204612_at | protein kinase (cAMP-dependent, catalytic) inhibitor alpha | PKIA | | 5569 | 2.117206 | 0.999842 |
| 212655_at | zinc finger, CCHC domain containing 14 | ZCCHC14 | | 23174 | 2.11646 | 0.999842 |
| 212635_at | transportin 1 | TNPO1 | | 3842 | 2.115769 | 0.999842 |
| 219359_at | ATH1, acid trehalase-like 1 (yeast) | ATH1 | | 80162 | 2.114544 | 0.999842 |
| 209524_at | hepatoma-derived growth factor, related protein 3 | HDGFRP3 | | 50810 | 2.114294 | 0.999842 |
| 209655_s_at | transmembrane protein 47 | TMEM47 | | 83604 | 2.114111 | 0.999842 |
| 211943_x_at | tumor protein, translationally-controlled 1 | TPT1 | | 7178 | 2.113465 | 0.999842 |
| 200061_s_at | ribosomal protein S24 | RPS24 | | 6229 | 2.11251 | 0.999842 |
| 211598_x_at | vasoactive intestinal peptide receptor 2 | VIPR2 | | 7434 | 2.110932 | 0.999842 |
| 218886_at | PAK1 interacting protein 1 | PAK1IP1 | | 55003 | 2.110751 | 0.999842 |
| 210178_x_at | FUS interacting protein (serine/arginine-rich) 1 /// similar to FUS-interacting serine-arginine-rich protein 1 (TLS-associated protein with Ser-Arg repeats) (TLS-associated protein with SR repeats) (TASR) (TLS-associated serine-arginine protein) (TLS-associated SR protein) (Neural-specific SR protein... | FUSIP1 /// LOC727922 | 10772 /// 727922 | | 2.110265 | 0.999842 |
| 212392_s_at | phosphodiesterase 4D interacting protein (myomegalin) /// similar to phosphodiesterase 4D interacting protein isoform 2 | LOC652526 /// LOC727927 /// PDE4DIP | 652526 /// 727927 /// 9659 | | 2.110079 | 0.999842 |
| 215509_s_at | BUB1 budding uninhibited by benzimidazoles 1 homolog (yeast) | BUB1 | | 699 | 2.108765 | 0.999842 |
| 210284_s_at | mitogen-activated protein kinase kinase kinase 7 interacting protein 2 | MAP3K7IP2 | | 23118 | 2.107827 | 0.999842 |
| 218852_at | protein phosphatase 2 (formerly 2A), regulatory subunit B", gamma | PPP2R3C | | 55012 | 2.10757 | 0.999842 |
| 204651_at | nuclear respiratory factor 1 | NRF1 | | 4899 | 2.107524 | 0.999842 |
| 211808_s_at | CREB binding protein (Rubinstein-Taybi syndrome) | CREBBP | | 1387 | 2.106633 | 0.999842 |
| 201328_at | v-ets erythroblastosis virus E26 oncogene homolog 2 (avian) | ETS2 | | 2114 | 2.10658 | 0.999842 |
| 204817_at | extra spindle pole bodies homolog 1 (S. cerevisiae) | ESPL1 | | 9700 | 2.106148 | 0.999842 |
| 216430_x_at | isovaleryl Coenzyme A dehydrogenase | IVD | | 3712 | 2.102387 | 0.999842 |
| 214280_x_at | heterogeneous nuclear ribonucleoprotein A1 | HNRNPA1 | | 3178 | 2.101729 | 0.999842 |
| 58367_s_at | zinc finger protein 419 | ZNF419 | | 79744 | 2.100589 | 0.999842 |
| 207016_s_at | aldehyde dehydrogenase 1 family, member A2 | ALDH1A2 | | 8854 | 2.098652 | 0.999842 |
| 217576_x_at | son of sevenless homolog 2 (Drosophila) | SOS2 | | 6655 | 2.096924 | 0.999842 |
| 212515_s_at | DEAD (Asp-Glu-Ala-Asp) box polypeptide 3, X-linked | DDX3X | | 1654 | 2.095366 | 0.999842 |
| 201548_s_at | jumonji, AT rich interactive domain 1B | JARID1B | | 10765 | 2.095061 | 0.999842 |
| 211913_s_at | c-mer proto-oncogene tyrosine kinase | MERTK | | 10461 | 2.093882 | 0.999842 |
| 209733_at | hypothetical protein LOC286440 | LOC286440 | | 286440 | 2.093813 | 0.999842 |
| 209841_s_at | leucine rich repeat neuronal 3 | LRRN3 | | 54674 | 2.093564 | 0.999842 |
| 208184_s_at | transmembrane protein 1 | TMEM1 | | 7109 | 2.093338 | 0.999842 |
| 208752_x_at | nucleosome assembly protein 1-like 1 | NAP1L1 | | 4673 | 2.093069 | 0.999842 |
| 209163_at | cytochrome b-561 | CYB561 | | 1534 | 2.092255 | 0.999842 |

FIGURE 14 (CONTINUED)

| | | | | | |
|---|---|---|---|---|---|
| 210047_at | solute carrier family 11 (proton-coupled divalent metal ion transporters), member 2 | SLC11A2 | | 4891 | 2.09167 | 0.999842 |
| 208044_s_at | peroxisome proliferator-activated receptor delta | PPARD | | 5467 | 2.091135 | 0.999842 |
| 219471_at | chromosome 13 open reading frame 18 | C13orf18 | | 80183 | 2.091007 | 0.999842 |
| 208274_at | oculomedin | OCLM | | 10896 | 2.090496 | 0.999842 |
| 208290_s_at | eukaryotic translation initiation factor 5 | EIF5 | | 1983 | 2.088403 | 0.999842 |
| 201210_at | DEAD (Asp-Glu-Ala-Asp) box polypeptide 3, X-linked | DDX3X | | 1654 | 2.088047 | 0.999842 |
| 208567_s_at | potassium inwardly-rectifying channel, subfamily J, member 12 | KCNJ12 | | 3768 | 2.087219 | 0.999842 |
| 209838_at | COP9 constitutive photomorphogenic homolog subunit 2 (Arabidopsis) | COPS2 | | 9318 | 2.086468 | 0.999842 |
| 209870_s_at | amyloid beta (A4) precursor protein-binding, family A, member 2 (X11-like) | APBA2 | | 321 | 2.082192 | 0.999842 |
| 50277_at | golgi associated, gamma adaptin ear containing, ARF binding protein 1 | GGA1 | | 26088 | 2.081811 | 0.999842 |
| 44146_at | glucocorticoid modulatory element binding protein 2 | GMEB2 | | 26205 | 2.080694 | 0.999842 |
| 218683_at | polypyrimidine tract binding protein 2 | PTBP2 | | 58155 | 2.08031 | 0.999842 |
| 203346_at | methylenetetrahydrofolate dehydrogenase (NADP+ dependent) 2-like | MTHFD2L | | 441024 | 2.078247 | 0.999842 |
| 203375_s_at | tripeptidyl peptidase II | TPP2 | | 7174 | 2.077853 | 0.999842 |
| 216347_s_at | protein phosphatase 1, regulatory (inhibitor) subunit 13B | PPP1R13B | | 23368 | 2.077437 | 0.999842 |
| 203636_at | midline 1 (Opitz/BBB syndrome) | MID1 | | 4281 | 2.075067 | 0.999842 |
| 213019_at | RAN binding protein 6 | RANBP6 | | 26953 | 2.074864 | 0.999842 |
| 202352_s_at | proteasome (prosome, macropain) 26S subunit, non-ATPase, 12 | PSMD12 | | 5718 | 2.074244 | 0.999842 |
| 217120_s_at | mediator complex subunit 14 | MED14 | | 9282 | 2.074153 | 0.999842 |
| 214863_at | Full length insert cDNA clone ZC35F11 | --- | | | 2.07363 | 0.999842 |
| 213763_at | homeodomain interacting protein kinase 2 | HIPK2 | | 28996 | 2.073523 | 0.999842 |
| 210778_s_at | MAX dimerization protein 4 | MXD4 | | 10608 | 2.071656 | 0.999842 |
| 221675_s_at | choline phosphotransferase 1 | CHPT1 | | 56994 | 2.070737 | 0.999842 |
| 220576_at | GPI deacylase | PGAP1 | | 80055 | 2.065053 | 0.999842 |
| 207984_s_at | membrane protein, palmitoylated 2 (MAGUK p55 subfamily member 2) | MPP2 | | 4355 | 2.064386 | 0.999842 |
| 214354_x_at | surfactant, pulmonary-associated protein B | SFTPB | | 6439 | 2.063379 | 0.999842 |
| 221919_at | heterogeneous nuclear ribonucleoprotein A1 /// hypothetical protein LOC728844 | HNRNPA1 /// LOC728844 | 3178 /// 728844 | | 2.062624 | 0.999842 |
| 210691_s_at | calcyclin binding protein | CACYBP | | 27101 | 2.062483 | 0.999842 |
| 216548_x_at | high-mobility group (nonhistone chromosomal) protein 4-like | HMG4L | | 128872 | 2.062217 | 0.999842 |
| 219321_at | membrane protein, palmitoylated 5 (MAGUK p55 subfamily member 5) | MPP5 | | 64398 | 2.062179 | 0.999842 |
| 219248_at | THUMP domain containing 2 | THUMPD2 | | 80745 | 2.061558 | 0.999842 |
| 205198_s_at | ATPase, Cu++ transporting, alpha polypeptide (Menkes syndrome) /// similar to ATPase, Cu++ transporting, alpha polypeptide | ATP7A /// LOC644732 | 538 /// 644732 | | 2.061512 | 0.999842 |
| 210429_at | Rh blood group, D antigen | RHD | | 6007 | 2.060246 | 0.999842 |
| 218856_at | tumor necrosis factor receptor superfamily, member 21 | TNFRSF21 | | 27242 | 2.058949 | 0.999842 |
| 217719_at | eukaryotic translation initiation factor 3, subunit E interacting protein | EIF3EIP | | 51386 | 2.058583 | 0.999842 |
| 206095_s_at | FUS interacting protein (serine/arginine-rich) 1 /// similar to FUS-interacting serine-arginine-rich protein 1 (TLS-associated protein with Ser-Arg repeats) (TLS-associated protein with SR repeats) (TASR) (TLS-associated serine-arginine protein) (TLS-associated SR protein) (Neural-specific SR protein)... | FUSIP1 /// LOC727922 | 10772 /// 727922 | | 2.058476 | 0.999842 |

FIGURE 14 (CONTINUED)

| | | | | |
|---|---|---|---|---|
| 205981_s_at | inhibitor of growth family, member 2 | ING2 | 3622 | 2.055621 | 0.999842 |
| 215734_at | chromosome 19 open reading frame 36 | C19orf36 | 113177 | 2.054489 | 0.999842 |
| 214449_s_at | ras homolog gene family, member Q | RHOQ | 23433 | 2.054307 | 0.999842 |
| 51176_at | mediator complex subunit 27 | MED27 | 9442 | 2.052362 | 0.999842 |
| 208198_x_at | killer cell immunoglobulin-like receptor, two domains, short cytoplasmic tail, 1 | KIR2DS1 | 3806 | 2.047843 | 0.999842 |
| 212805_at | prune homolog 2 (Drosophila) | PRUNE2 | 158471 | 2.047256 | 0.999842 |
| 217367_s_at | zinc fingers and homeoboxes 3 | ZHX3 | 23051 | 2.044521 | 0.999842 |
| 204621_s_at | nuclear receptor subfamily 4, group A, member 2 | NR4A2 | 4929 | 2.044483 | 0.999842 |
| 219562_at | RAB26, member RAS oncogene family | RAB26 | 25837 | 2.042244 | 0.999842 |
| 215630_at | cDNA FLJ14102 fis, clone MAMMA1000940 | | | 2.041621 | 0.999842 |
| 200737_at | phosphoglycerate kinase 1 | PGK1 | 5230 | 2.041303 | 0.999842 |
| 214008_at | Twinfilin, actin-binding protein, homolog 1 (Drosophila) | TWF1 | 5756 | 2.041221 | 0.999842 |
| 211345_x_at | eukaryotic translation elongation factor 1 gamma /// elongation factor 1 gamma pseudogene | EEF1G /// LOC729998 | 1937 /// 729998 | 2.041174 | 0.999842 |
| 213725_x_at | xylosyltransferase I | XYLT1 | 64131 | 2.038204 | 0.999842 |
| 216979_at | nuclear receptor subfamily 4, group A, member 3 | NR4A3 | 8013 | 2.037575 | 0.999842 |
| 208384_s_at | midline 2 | MID2 | 11043 | 2.036539 | 0.999842 |
| 212558_at | sprouty homolog 1, antagonist of FGF signaling (Drosophila) | SPRY1 | 10252 | 2.035056 | 0.999842 |
| 203321_s_at | ADNP homeobox 2 | ADNP2 | 22850 | 2.034107 | 0.999842 |
| 217655_at | FXYD domain containing ion transport regulator 5 | FXYD5 | 53827 | 2.029777 | 0.999842 |
| 89948_at | chromosome 20 open reading frame 67 | C20orf67 | 63935 | 2.027922 | 0.999842 |
| 212628_at | protein kinase N2 | PKN2 | 5586 | 2.027843 | 0.999842 |
| 219182_at | hypothetical protein FLJ22167 | FLJ22167 | 79583 | 2.027446 | 0.999842 |
| 212176_at | splicing factor, arginine/serine-rich 18 | SFRS18 | 25957 | 2.027393 | 0.999842 |
| 205892_s_at | fatty acid binding protein 1, liver | FABP1 | 2168 | 2.027061 | 0.999842 |
| 208410_x_at | amelogenin (amelogenesis imperfecta 1, X-linked) | AMELX | 265 | 2.025715 | 0.999842 |
| 46256_at | splA/ryanodine receptor domain and SOCS box containing 3 | SPSB3 | 90864 | 2.023653 | 0.999842 |
| 222247_at | putative X-linked retinopathy protein | DXS542 | 57825 | 2.023276 | 0.999842 |
| 211555_s_at | guanylate cyclase 1, soluble, beta 3 | GUCY1B3 | 2983 | 2.021895 | 0.999842 |
| 213281_at | Jun oncogene | JUN | 3725 | 2.020379 | 0.999842 |
| 208051_s_at | poly(A) binding protein interacting protein 1 | PAIP1 | 10605 | 2.020016 | 0.999842 |
| 207128_s_at | zinc finger protein 223 | ZNF223 | 7766 | 2.016375 | 0.999842 |
| 221971_x_at | centaurin, gamma-like family, member 2 | CTGLF2 | 729092 | 2.012843 | 0.999842 |
| 218406_x_at | neuron derived neurotrophic factor | NENF | 29937 | 2.012699 | 0.999842 |
| 220212_s_at | thyroid adenoma associated | THADA | 63892 | 2.010788 | 0.999842 |
| 214016_s_at | splicing factor proline/glutamine-rich (polypyrimidine tract binding protein associated) | SFPQ | 6421 | 2.009902 | 0.999842 |
| 212279_at | transmembrane protein 97 | TMEM97 | 27346 | 2.008972 | 0.999842 |
| 36711_at | v-maf musculoaponeurotic fibrosarcoma oncogene homolog F (avian) | MAFF | 23764 | 2.008811 | 0.999842 |
| 213958_at | CD6 molecule | CD6 | 923 | 2.00796 | 0.999842 |
| 215135_s_at | aspartyl aminopeptidase | DNPEP | 23549 | 2.007805 | 0.999842 |
| 210346_s_at | CDC-like kinase 4 | CLK4 | 57396 | 2.00762 | 0.999842 |

FIGURE 14 (CONTINUED)

| | | | | |
|---|---|---|---|---|
| 211979_at | G protein-coupled receptor 107 | GPR107 | 57720 | 2.004594 | 0.999842 |
| 212607_at | v-akt murine thymoma viral oncogene homolog 3 (protein kinase B, gamma) | AKT3 | 10000 | 2.00203 | 0.999842 |
| 203362_s_at | MAD2 mitotic arrest deficient-like 1 (yeast) | MAD2L1 | 4085 | 2.001594 | 0.999842 |
| 212017_at | | LOC130074 | 130074 | 2.001472 | 0.999842 |
| 206799_at | secretoglobin, family 1D, member 2 | SCGB1D2 | 10647 | 2.000709 | 0.999842 |
| 208713_at | heterogeneous nuclear ribonucleoprotein U-like 1 | HNRPUL1 | 11100 | 2.000289 | 0.999842 |
| 218739_at | abhydrolase domain containing 5 | ABHD5 | 51099 | 2.000006 | 0.999842 |
| 201387_s_at | ubiquitin carboxyl-terminal esterase L1 (ubiquitin thiolesterase) | UCHL1 | 7345 | -2.000432 | 0.999842 |
| 214123_s_at | chromosome 4 open reading frame 10 | C4orf10 | 317648 | -2.000534 | 0.999842 |
| 37424_at | coiled-coil alpha-helical rod protein 1 | CCHCR1 | 54535 | -2.00116 | 0.999842 |
| 210427_x_at | annexin A2 | ANXA2 | 302 | -2.002025 | 0.999842 |
| 203311_s_at | ADP-ribosylation factor 6 | ARF6 | 382 | -2.002828 | 0.999842 |
| 201572_x_at | dCMP deaminase | DCTD | 1635 | -2.002974 | 0.999842 |
| 202307_s_at | transporter 1, ATP-binding cassette, sub-family B (MDR/TAP) | TAP1 | 6890 | -2.004624 | 0.999842 |
| 216004_s_at | PBX/knotted 1 homeobox 1 | PKNOX1 | 5316 | -2.005241 | 0.999842 |
| 222139_at | KIAA1466 gene | KIAA1466 | 57612 | -2.005652 | 0.999842 |
| 222180_at | CDNA FLJ14122 fis, clone MAMMA1002033 | | | -2.006673 | 0.999842 |
| 203825_at | bromodomain containing 3 | BRD3 | 8019 | -2.008574 | 0.999842 |
| 206795_at | coagulation factor II (thrombin) receptor-like 2 | F2RL2 | 2151 | -2.011262 | 0.999842 |
| 201762_s_at | proteasome (prosome, macropain) activator subunit 2 (PA28 beta) | PSME2 | 5721 | -2.012016 | 0.999842 |
| 216991_at | zinc finger protein 224 | ZNF224 | 7767 | -2.012839 | 0.999842 |
| 221771_s_at | M-phase phosphoprotein 8 | MPHOSPH8 | 54737 | -2.012947 | 0.999842 |
| 204279_at | proteasome (prosome, macropain) subunit, beta type, 9 (large multifunctional peptidase 2) | PSMB9 | 5698 | -2.013904 | 0.999842 |
| 202205_at | vasodilator-stimulated phosphoprotein | VASP | 7408 | -2.014419 | 0.999842 |
| 222225_at | 60S ribosomal pseudogene | FLJ45055 | 644128 | -2.014512 | 0.999842 |
| 215193_x_at | major histocompatibility complex, class II, DR beta 1 /// major histocompatibility complex, class II, DR beta 3 /// major histocompatibility complex, class II, DR beta 4 /// hypothetical protein LOC730415 | HLA-DRB1 /// HLA-DRB3 /// HLA-DRB4 /// LOC730415 | 3123 /// 3125 /// 3126 /// 730415 | -2.015716 | 0.999842 |
| 208678_at | ATPase, H+ transporting, lysosomal 31kDa, V1 subunit E1 | ATP6V1E1 | 529 | -2.01657 | 0.999842 |
| 201633_s_at | cytochrome b5 type B (outer mitochondrial membrane) | CYB5B | 80777 | -2.0168 | 0.999842 |
| 205231_s_at | epilepsy, progressive myoclonus type 2A, Lafora disease (laforin) | EPM2A | 7957 | -2.016821 | 0.999842 |
| 203249_at | enhancer of zeste homolog 1 (Drosophila) | EZH1 | 2145 | -2.017039 | 0.999842 |
| 212607_at | ring finger protein 167 | RNF167 | 26001 | -2.019783 | 0.999842 |
| 219450_at | chromosome 4 open reading frame 19 | C4orf19 | 55286 | -2.02243 | 0.999842 |
| 212678_at | neurofibromin 1 (neurofibromatosis, von Recklinghausen disease, Watson disease) | NF1 | 4763 | -2.022693 | 0.999842 |
| 207181_s_at | caspase 7, apoptosis-related cysteine peptidase | CASP7 | 840 | -2.024013 | 0.999842 |
| 208997_s_at | uncoupling protein 2 (mitochondrial, proton carrier) | UCP2 | 7351 | -2.025785 | 0.999842 |
| 201040_at | guanine nucleotide binding protein (G protein), alpha inhibiting activity polypeptide 2 | GNAI2 | 2771 | -2.026031 | 0.999842 |
| 219920_s_at | GDP-mannose pyrophosphorylase B | GMPPB | 29925 | -2.026423 | 0.999842 |

FIGURE 14 (CONTINUED)

| | | | | | |
|---|---|---|---|---|---|
| 215746_at | (clone B3B3E13) chromosome 4p16.3 DNA fragment | | | | |
| 201614_s_at | RuvB-like 1 (E. coli) | RUVBL1 | | 8607 | -2.027182 | 0.999842 |
| 221080_s_at | DENN/MADD domain containing 1C | DENND1C | | 79958 | -2.027701 | 0.999842 |
| 211644_x_at | immunoglobulin kappa constant /// netrin 2-like (chicken) /// immunoglobulin kappa locus | IGK@ /// IGKC /// NTN2L | 3514 /// 4917 /// 50802 | | -2.028539 | 0.999842 |
| 221936_x_at | Mitochondrial ribosomal protein L41 | MRPL41 | | 64975 | -2.031678 | 0.999842 |
| 201863_at | family with sequence similarity 32, member A | FAM32A | | 26017 | -2.032229 | 0.999842 |
| 201216_at | endoplasmic reticulum protein 29 | ERP29 | | 10961 | -2.032426 | 0.999842 |
| 218700_s_at | RAB7, member RAS oncogene family-like 1 | RAB7L1 | | 8934 | -2.032913 | 0.999842 |
| 213062_at | N-terminal asparagine amidase | NTAN1 | | 123803 | -2.034548 | 0.999842 |
| 201267_s_at | proteasome (prosome, macropain) 26S subunit, ATPase, 3 | PSMC3 | | 5702 | -2.034967 | 0.999842 |
| 220085_at | helicase, lymphoid-specific | HELLS | | 3070 | -2.034989 | 0.999842 |
| 201127_s_at | ATP citrate lyase | ACLY | | 47 | -2.035038 | 0.999842 |
| 217381_s_at | T cell receptor gamma variable 5 /// hypothetical protein LOC648852 | LOC648852 /// TRGV5 | 648852 /// 6978 | | -2.038535 | 0.999842 |
| 202577_s_at | DEAD (Asp-Glu-Ala-As) box polypeptide 19A | DDX19A | | 55308 | -2.038913 | 0.999842 |
| 207391_s_at | phosphatidylinositol-4-phosphate 5-kinase, type I, alpha | PIP5K1A | | 8394 | -2.04079 | 0.999842 |
| 214883_at | thyroid hormone receptor, alpha (erythroblastic leukemia viral (v-erb-a) oncogene homolog, avian) | THRA | | 7067 | -2.041488 | 0.999842 |
| 218734_at | N-acetyltransferase 11 | NAT11 | | 79829 | -2.042525 | 0.999842 |
| 214377_s_at | chymotrypsin-like | CTRL | | 1506 | -2.044525 | 0.999842 |
| 221997_s_at | Mitochondrial ribosomal protein L52 | MRPL52 | | 122704 | -2.045597 | 0.999842 |
| 206150_at | CD27 molecule | CD27 | | 939 | -2.046959 | 0.999842 |
| 202270_at | guanylate binding protein 1, interferon-inducible, 67kDa | GBP1 | | 2633 | -2.051925 | 0.999842 |
| 219031_s_at | nuclear import 7 homolog (S. cerevisiae) | NIP7 | | 51388 | -2.052094 | 0.999842 |
| 205229_s_at | coagulation factor C homolog, cochlin (Limulus polyphemus) | COCH | | 1690 | -2.053791 | 0.999842 |
| 208000_at | GPI anchored molecule like protein | GML | | 2765 | -2.053924 | 0.999842 |
| 215236_s_at | phosphatidylinositol binding clathrin assembly protein | PICALM | | 8301 | -2.054524 | 0.999842 |
| 202323_s_at | acyl-Coenzyme A binding domain containing 3 | ACBD3 | | 64746 | -2.054985 | 0.999842 |
| 201308_s_at | septin 11 | | 11-Sep | 55752 | -2.055677 | 0.999842 |
| 212082_s_at | myosin, light chain 6, alkali, smooth muscle and non-muscle | MYL6 | | 4637 | -2.055771 | 0.999842 |
| 219807_x_at | RAB4B, member RAS oncogene family | RAB4B | | 53916 | -2.05898 | 0.999842 |
| 214342_at | ataxin 7-like 1 | ATXN7L1 | | 222255 | -2.060414 | 0.999842 |
| 206441_s_at | COMM domain containing 4 | COMMD4 | | 54939 | -2.061628 | 0.999842 |
| 215071_s_at | histone cluster 1, H2ac | HIST1H2AC | | 8334 | -2.061937 | 0.999842 |
| 213446_s_at | IQ motif containing GTPase activating protein 1 | IQGAP1 | | 8826 | -2.062222 | 0.999842 |
| 213280_at | GTPase activating Rap/RanGAP domain-like 4 | GARNL4 | | 23108 | -2.062227 | 0.999842 |
| 208815_x_at | annexin A2 pseudogene 2 | ANXA2P2 | | 304 | -2.065256 | 0.999842 |
| 209446_s_at | chromosome 7 open reading frame 44 | C7orf44 | | 55744 | -2.066757 | 0.999842 |
| 211742_s_at | ecotropic viral integration site 2B | EVI2B | | 2124 | -2.069932 | 0.999842 |

FIGURE 14 (CONTINUED)

| Probe ID | Description | Gene | ID | Value | P-value |
|---|---|---|---|---|---|
| 210972_x_at | T cell receptor alpha locus /// T cell receptor delta variable 2 /// T cell receptor alpha variable 20 /// T cell receptor alpha joining 17 /// T cell receptor alpha constant | TRA@ /// TRAC /// TRAJ17 /// TRAV20 /// TRDV2 | 28517 /// 28663 /// 28738 /// 28755 /// 6955 | -2.071463 | 0.999842 |
| 203160_s_at | ring finger protein 8 | RNF8 | 9025 | -2.073032 | 0.999842 |
| 218811_at | ORAI calcium release-activated calcium modulator 2 | ORAI2 | 80228 | -2.073336 | 0.999842 |
| 218774_at | decapping enzyme, scavenger | DCPS | 28960 | -2.073863 | 0.999842 |
| 211139_s_at | NGFI-A binding protein 1 (EGR1 binding protein 1) | NAB1 | 4664 | -2.074392 | 0.999842 |
| 215287_at | ELISC-1 | --- | --- | -2.074413 | 0.999842 |
| 213521_at | protein tyrosine phosphatase, non-receptor type 18 (brain-derived) | PTPN18 | 26469 | -2.07455 | 0.999842 |
| 202269_x_at | guanylate binding protein 1, interferon-inducible, 67kDa | GBP1 | 2633 | -2.074827 | 0.999842 |
| 205572_at | angiopoietin 2 | ANGPT2 | 285 | -2.076672 | 0.999842 |
| 209685_s_at | protein kinase C, beta 1 | PRKCB1 | 5579 | -2.077604 | 0.999842 |
| 203103_s_at | PRP19/PSO4 pre-mRNA processing factor 19 homolog (S. cerevisiae) | PRPF19 | 27339 | -2.080886 | 0.999842 |
| 200814_at | proteasome (prosome, macropain) activator subunit 1 (PA28 alpha) | PSME1 | 5720 | -2.081854 | 0.999842 |
| 200787_s_at | phosphoprotein enriched in astrocytes 15 | PEA15 | 8682 | -2.08508 | 0.999842 |
| 206306_at | ryanodine receptor 3 | RYR3 | 6263 | -2.088117 | 0.999842 |
| 213349_at | transmembrane and coiled-coil domain family 1 | TMCC1 | 23023 | -2.089437 | 0.999842 |
| 214995_s_at | apolipoprotein B mRNA editing enzyme, catalytic polypeptide-like 3G /// apolipoprotein B mRNA editing enzyme, catalytic polypeptide-like 3F | APOBEC3F /// APOBEC3G | 200316 /// 60489 | -2.089937 | 0.999842 |
| 217126_at | Kpni repeat mrna (cdna clone pcd-kpni-8), 3' end | --- | --- | -2.090014 | 0.999842 |
| 209424_at | alpha-methylacyl-CoA racemase | AMACR | 23600 | -2.090059 | 0.999842 |
| 213730_x_at | transcription factor 3 (E2A immunoglobulin enhancer binding factors E12/E47) | TCF3 | 6929 | -2.090391 | 0.999842 |
| 220124_at | giant axonal neuropathy (gigaxonin) | GAN | 8139 | -2.093448 | 0.999842 |
| 214970_s_at | ST6 beta-galactosamide alpha-2,6-sialyltranferase 1 | ST6GAL1 | 6480 | -2.095149 | 0.999842 |
| 219308_s_at | adenylate kinase 5 | AK5 | 26289 | -2.095852 | 0.999842 |
| 212748_at | megakaryoblastic leukemia (translocation) 1 | MKL1 | 57591 | -2.097535 | 0.999842 |
| 204160_s_at | ectonucleotide pyrophosphatase/phosphodiesterase 4 (putative function) | ENPP4 | 22875 | -2.098283 | 0.999842 |
| 201735_s_at | chloride channel 3 | CLCN3 | 1182 | -2.098285 | 0.999842 |
| 205114_s_at | chemokine (C-C motif) ligand 3 /// chemokine (C-C motif) ligand 3-like 1 /// chemokine (C-C motif) ligand 3-like 3 /// similar to Small inducible cytokine A3-like 1 precursor (Tonsillar lymphocyte LD78 beta protein) (LD78-beta(1-70)) (G0/G1 switch regulatory protein 19-2) (GOS19-2 protein) (PAT 464.2) /// similar to chemokine (C-C motif) ligand 3-like 3 | CCL3 /// CCL3L1 /// CCL3L3 /// LOC728830 /// LOC730422 | 414062 /// 6348 /// 6349 /// 728830 /// 730422 | -2.098934 | 0.999842 |
| 207419_s_at | ras-related C3 botulinum toxin substrate 2 (rho family, small GTP binding protein Rac2) | RAC2 | 5880 | -2.102638 | 0.999842 |
| 214735_at | phosphoinositide-binding protein PIP3-E | PIP3-E | 26034 | -2.102814 | 0.999842 |
| 57539_at | zinc finger, CCCH-type with G patch domain | ZGPAT | 84619 | -2.103581 | 0.999842 |
| 205703_at | --- | --- | --- | -2.106786 | 0.999842 |
| 204226_at | staufen, RNA binding protein, homolog 2 (Drosophila) | STAU2 | 27067 | -2.10817 | 0.999842 |
| 205396_at | SMAD family member 3 | SMAD3 | 4088 | -2.108608 | 0.999842 |
| 207870_at | A kinase (PRKA) anchor protein (yotiao) 9 | AKAP9 | 10142 | -2.109249 | 0.999842 |
| 212784_at | capicua homolog (Drosophila) | CIC | 23152 | -2.109293 | 0.999842 |

FIGURE 14 (CONTINUED)

| | | | | | |
|---|---|---|---|---|---|
| 220990_s_at | transmembrane protein 49 /// microRNA 21 | MIRN21 /// TMEM49 | 406991 /// 81671 | -2.111163 | 0.999842 |
| 215541_s_at | diaphanous homolog 1 (Drosophila) | DIAPH1 | 1729 | -2.111547 | 0.999842 |
| 218409_s_at | DnaJ (Hsp40) homolog, subfamily C, member 1 | DNAJC1 | 64215 | -2.111661 | 0.999842 |
| 216528_at | mRNA; cDNA DKFZp564C163 (from clone DKFZp564C163) | | | -2.111825 | 0.999842 |
| 203595_s_at | interferon-induced protein with tetratricopeptide repeats 5 | IFIT5 | 24138 | -2.11479 | 0.999842 |
| 210807_s_at | solute carrier family 16, member 7 (monocarboxylic acid transporter 2) | SLC16A7 | 9194 | -2.115275 | 0.999842 |
| 201275_at | farnesyl diphosphate synthase (farnesyl pyrophosphate synthetase, dimethylallyltranstransferase, geranyltranstransferase) | FDPS | 2224 | -2.116677 | 0.999842 |
| 203227_s_at | tetraspanin 31 | TSPAN31 | 6302 | -2.118554 | 0.999842 |
| 214137_at | Protein tyrosine phosphatase, receptor type, J | PTPRJ | 5795 | -2.118709 | 0.999842 |
| 211178_s_at | proline-serine-threonine phosphatase interacting protein 1 | PSTPIP1 | 9051 | -2.11889 | 0.999842 |
| 221864_at | ORAI calcium release-activated calcium modulator 3 | ORAI3 | 93129 | -2.121945 | 0.999842 |
| 201021_s_at | destrin (actin depolymerizing factor) | DSTN | 11034 | -2.124301 | 0.999842 |
| 220947_s_at | TBC1 domain family, member 10B | TBC1D10B | 26000 | -2.125496 | 0.999842 |
| 206484_s_at | X-prolyl aminopeptidase (aminopeptidase P) 2, membrane-bound | XPNPEP2 | 7512 | -2.125971 | 0.999842 |
| 221542_s_at | ER lipid raft associated 2 | ERLIN2 | 11160 | -2.12849 | 0.999842 |
| 222217_s_at | solute carrier family 27 (fatty acid transporter), member 3 | SLC27A3 | 11000 | -2.129071 | 0.999842 |
| 219994_at | amyloid beta (A4) precursor protein-binding, family B, member 1 interacting protein | APBB1IP | 54518 | -2.129079 | 0.999842 |
| 215379_x_at | immunoglobulin lambda locus /// immunoglobulin lambda variable 3-25 /// immunoglobulin lambda variable 2-14 /// immunoglobulin lambda joining 3 | IGL@ /// IGLJ3 /// IGLV2-14 /// IGLV3-25 | 28793 /// 28815 /// 28831 /// 3535 | -2.129778 | 0.999842 |
| 209671_x_at | T cell receptor alpha locus /// T cell receptor alpha constant | TRA@ /// TRAC | 28755 /// 6955 | -2.129991 | 0.999842 |
| 208649_s_at | valosin-containing protein | VCP | 7415 | -2.130846 | 0.999842 |
| 1405_i_at | chemokine (C-C motif) ligand 5 | CCL5 | 6352 | -2.130885 | 0.999842 |
| 212116_at | tripartite motif-containing 27 | TRIM27 | 5987 | -2.131953 | 0.999842 |
| 205426_s_at | huntingtin interacting protein 1 | HIP1 | 3092 | -2.132452 | 0.999842 |
| 212663_at | FK506 binding protein 15, 133kDa | FKBP15 | 23307 | -2.132801 | 0.999842 |
| 210812_at | X-ray repair complementing defective repair in Chinese hamster cells 4 | XRCC4 | 7518 | -2.135329 | 0.999842 |
| 209825_s_at | uridine-cytidine kinase 2 | UCK2 | 7371 | -2.135386 | 0.999842 |
| 214545_s_at | proline synthetase co-transcribed homolog (bacterial) | PROSC | 11212 | -2.137106 | 0.999842 |
| 201756_at | replication protein A2, 32kDa | RPA2 | 6118 | -2.137819 | 0.999842 |
| 215843_s_at | tolloid-like 2 | TLL2 | 7093 | -2.138123 | 0.999842 |
| 221744_at | WD repeat domain 68 | WDR68 | 10238 | -2.140478 | 0.999842 |
| 217770_at | phosphatidylinositol glycan anchor biosynthesis, class T | PIGT | 51604 | -2.140963 | 0.999842 |
| 35254_at | TRAF-type zinc finger domain containing 1 | TRAFD1 | 10906 | -2.141184 | 0.999842 |
| 42361_g_at | coiled-coil alpha-helical rod protein 1 | CCHCR1 | 54535 | -2.143308 | 0.999842 |
| 213589_s_at | UDP-GlcNAc:betaGal beta-1,3-N-acetylglucosaminyltransferase-like 1 | B3GNTL1 | 146712 | -2.143421 | 0.999842 |
| 209198_s_at | synaptotagmin XI | SYT11 | 23208 | -2.143766 | 0.999842 |
| 203515_s_at | phosphomevalonate kinase | PMVK | 10654 | -2.14437 | 0.999842 |
| 47069_at | proline rich 5 (renal) | PRR5 | 55615 | -2.145005 | 0.999842 |
| 201700_at | cyclin D3 | CCND3 | 896 | -2.145947 | 0.999842 |

FIGURE 14 (CONTINUED)

| | | | | | |
|---|---|---|---|---|---|
| 209762_x_at | SP110 nuclear body protein | SP110 | | 3431 | -2.146903 | 0.999842 |
| 216835_s_at | docking protein 1, 62kDa (downstream of tyrosine kinase 1) | DOK1 | | 1796 | -2.149075 | 0.999842 |
| 215121_x_at | immunoglobulin lambda locus /// immunoglobulin lambda variable 4-3 /// immunoglobulin lambda variable 3-25 /// immunoglobulin lambda variable 2-14 | IGL@ /// IGLV2-14 /// IGLV3-25 /// IGLV4-3 | 28786 /// 28793 /// 28815 /// 3535 | | -2.149809 | 0.999842 |
| 205241_at | SCO cytochrome oxidase deficient homolog 2 (yeast) | SCO2 | | 9997 | -2.150315 | 0.999842 |
| 209482_at | processing of precursor 7, ribonuclease P/MRP subunit (S. cerevisiae) | POP7 | | 10248 | -2.152565 | 0.999842 |
| 218270_at | mitochondrial ribosomal protein L24 | MRPL24 | | 79590 | -2.152597 | 0.999842 |
| 57163_at | elongation of very long chain fatty acids (FEN1/Elo2, SUR4/Elo3, yeast)-like 1 | ELOVL1 | | 64834 | -2.153494 | 0.999842 |
| 219193_at | WD repeat domain 70 | WDR70 | | 55100 | -2.154374 | 0.999842 |
| 219205_at | serine racemase | SRR | | 63826 | -2.154459 | 0.999842 |
| 204882_at | Rho GTPase activating protein 25 | ARHGAP25 | | 9938 | -2.155266 | 0.999842 |
| 201954_at | actin related protein 2/3 complex, subunit 1B, 41kDa /// similar to Actin-related protein 2/3 complex, subunit 1B (ARP2/3 complex 41 kDa subunit) (p41-ARC) | ARPC1B /// LOC653888 | 10095 /// 653888 | | -2.155304 | 0.999842 |
| 209679_s_at | small trans-membrane and glycosylated protein | LOC57228 | | 57228 | -2.15585 | 0.999842 |
| 78383_at | Topoisomerase I binding, arginine/serine-rich | TOPORS | | 10210 | -2.158688 | 0.999842 |
| 202121_s_at | chromatin modifying protein 2A | CHMP2A | | 27243 | -2.159458 | 0.999842 |
| 218913_s_at | GEM interacting protein | GMIP | | 51291 | -2.160334 | 0.999842 |
| 209155_s_at | 5'-nucleotidase, cytosolic II | NT5C2 | | 22978 | -2.170779 | 0.999842 |
| 214340_at | arachidonate 12-lipoxygenase pseudogene 2 | ALOX12P2 | | 245 | -2.172329 | 0.999842 |
| 213060_s_at | chitinase 3-like 2 | CHI3L2 | | 1117 | -2.175725 | 0.999842 |
| 213046_at | poly(A) binding protein, nuclear 1 | PABPN1 | | 8106 | -2.176327 | 0.999842 |
| 206066_s_at | RAD51 homolog C (S. cerevisiae) | RAD51C | | 5889 | -2.178267 | 0.999842 |
| 200996_at | ARP3 actin-related protein 3 homolog (yeast) | ACTR3 | | 10096 | -2.181321 | 0.999842 |
| 2011194_at | selenoprotein W, 1 | SEPW1 | | 6415 | -2.181792 | 0.999842 |
| 210892_s_at | general transcription factor II, i | GTF2I | | 2969 | -2.182621 | 0.999842 |
| 210568_s_at | RecQ protein-like (DNA helicase Q1-like) | RECQL | | 5965 | -2.191442 | 0.999842 |
| 219003_s_at | mannosidase, endo-alpha | MANEA | | 79694 | -2.192031 | 0.999842 |
| 209514_s_at | RAB27A, member RAS oncogene family | RAB27A | | 5873 | -2.192759 | 0.999842 |
| 217962_at | nucleolar protein family A, member 3 (H/ACA small nucleolar RNPs) | NOLA3 | | 55505 | -2.193999 | 0.999842 |
| 217776_at | retinol dehydrogenase 11 (all-trans/9-cis/11-cis) | RDH11 | | 51109 | -2.197094 | 0.999842 |
| 203226_s_at | tetraspanin 31 | TSPAN31 | | 6302 | -2.198671 | 0.999842 |
| 219690_at | transmembrane protein 149 | TMEM149 | | 79713 | -2.202343 | 0.999842 |
| 207416_s_at | nuclear factor of activated T-cells, cytoplasmic, calcineurin-dependent 3 | NFATC3 | | 4775 | -2.204823 | 0.999842 |
| 218504_at | fumarylacetoacetate hydrolase domain containing 2A | FAHD2A | | 51011 | -2.205066 | 0.999842 |
| 212252_at | calcium/calmodulin-dependent protein kinase kinase 2, beta | CAMKK2 | | 10645 | -2.206291 | 0.999842 |
| 210164_at | granzyme B (granzyme 2, cytotoxic T-lymphocyte-associated serine esterase 1) | GZMB | | 3002 | -2.212516 | 0.999842 |
| 203143_s_at | KIAA0040 | KIAA0040 | | 9674 | -2.213193 | 0.999842 |
| 203405_at | proteasome (prosome, macropain) assembly chaperone 1 | PSMG1 | | 8624 | -2.213451 | 0.999842 |
| 200982_s_at | annexin A6 | ANXA6 | | 309 | -2.214011 | 0.999842 |
| 218163_at | malignant T cell amplified sequence 1 | MCTS1 | | 28985 | -2.214785 | 0.999842 |
| 202747_s_at | integral membrane protein 2A | ITM2A | | 9452 | -2.214827 | 0.999842 |

FIGURE 14 (CONTINUED)

| Probe ID | Description | Gene Symbol | Gene ID | Value | P-value |
|---|---|---|---|---|---|
| 211804_s_at | cyclin-dependent kinase 2 | CDK2 | 1017 | -2.21587 | 0.999842 |
| 221374_at | fibroblast growth factor 16 | FGF16 | 8823 | -2.217071 | 0.999842 |
| 211804_s_at | family with sequence similarity 45, member B /// family with sequence similarity 45, member A /// similar to family with sequence similarity 45, member A | FAM45A /// FAM45B /// LOC731832 | 404636 /// 55855 /// 731832 | -2.217733 | 0.999842 |
| 209808_x_at | inhibitor of growth family, member 1 | ING1 | 3621 | -2.217818 | 0.999842 |
| 219549_s_at | reticulon 3 | RTN3 | 10313 | -2.218935 | 0.999842 |
| 213867_x_at | actin, beta | ACTB | 60 | -2.222052 | 0.999842 |
| 218520_at | TANK-binding kinase 1 | TBK1 | 29110 | -2.224399 | 0.999842 |
| 217508_s_at | chromosome 18 open reading frame 25 | C18orf25 | 147339 | -2.224458 | 0.999842 |
| 207057_at | solute carrier family 16, member 7 (monocarboxylic acid transporter 2) | SLC16A7 | 9194 | -2.227306 | 0.999842 |
| 215672_s_at | adenosylhomocysteinase 3 | KIAA0828 | 23382 | -2.229487 | 0.999842 |
| 209503_s_at | proteasome (prosome, macropain) 26S subunit, ATPase, 5 | PSMC5 | 5705 | -2.230395 | 0.999842 |
| 208972_s_at | ATP synthase, H+ transporting, mitochondrial F0 complex, subunit C1 (subunit 9) | ATP5G1 | 516 | -2.232452 | 0.999842 |
| 200617_at | KIAA0152 | KIAA0152 | 9761 | -2.234502 | 0.999842 |
| 217183_at | low density lipoprotein receptor (familial hypercholesterolemia) | LDLR | 3949 | -2.23891 | 0.999842 |
| 207622_s_at | ATP-binding cassette, sub-family F (GCN20), member 2 | ABCF2 | 10061 | -2.238971 | 0.999842 |
| 209133_s_at | tripartite motif-containing 22 | TRIM22 | 10346 | -2.244567 | 0.999842 |
| 207795_s_at | killer cell lectin-like receptor subfamily D, member 1 | KLRD1 | 3824 | -2.245444 | 0.999842 |
| 222369_at | N-acetyltransferase 11 | NAT11 | 79829 | -2.246198 | 0.999842 |
| 217309_s_at | Down syndrome critical region gene 3 | DSCR3 | 10311 | -2.247293 | 0.999842 |
| 210951_x_at | RAB27A, member RAS oncogene family | RAB27A | 5873 | -2.248046 | 0.999842 |
| 214293_at | Septin 11 | | 11-Sep | -2.248806 | 0.999842 |
| 216980_s_at | sialophorin (leukosialin, CD43) | SPN | 6693 | -2.252631 | 0.999842 |
| 208677_s_at | basigin (Ok blood group) | BSG | 682 | -2.255795 | 0.999842 |
| 212811_x_at | solute carrier family 1 (glutamate/neutral amino acid transporter), member 4 | SLC1A4 | 6509 | -2.257732 | 0.999842 |
| 205484_at | signaling threshold regulating transmembrane adaptor 1 | SIT1 | 27240 | -2.260847 | 0.999842 |
| 218388_at | 6-phosphogluconolactonase | PGLS | 25796 | -2.262343 | 0.999842 |
| 211796_s_at | T cell receptor beta variable 19 /// T cell receptor beta variable 5-4 /// T cell receptor beta variable 3-1 /// T cell receptor beta variable 7-2 /// T cell receptor beta constant 1 | TRBC1 /// TRBV19 /// TRBV3-1 /// TRBV5-4 /// TRBV7-2 | 28568 /// 28596 /// 28611 /// 28619 /// 28639 | -2.262811 | 0.999842 |
| 200913_at | protein phosphatase 1G (formerly 2C), magnesium-dependent, gamma isoform | PPM1G | 5496 | -2.264556 | 0.999842 |
| 215342_s_at | RAB GTPase activating protein 1-like | RABGAP1L | 9910 | -2.265079 | 0.999842 |
| 212025_s_at | flightless I homolog (Drosophila) | FLII | 2314 | -2.265235 | 0.999842 |
| 212596_at | caspase 4, apoptosis-related cysteine peptidase | CASP4 | 837 | -2.266037 | 0.999842 |
| 204128_s_at | replication factor C (activator 1) 3, 38kDa | RFC3 | 5983 | -2.268727 | 0.999842 |
| 203773_x_at | biliverdin reductase A | BLVRA | 644 | -2.273153 | 0.999842 |
| 209389_x_at | diazepam binding inhibitor (GABA receptor modulator, acyl-Coenzyme A binding protein) | DBI | 1622 | -2.274519 | 0.999842 |
| 90265_at | centaurin, alpha 1 | CENTA1 | 11033 | -2.274589 | 0.999842 |
| 218397_at | Fanconi anemia, complementation group L | FANCL | 55120 | -2.276529 | 0.999842 |
| 202546_at | vesicle-associated membrane protein 8 (endobrevin) | VAMP8 | 8673 | -2.278573 | 0.999842 |
| 218112_at | mitochondrial ribosomal protein S34 | MRPS34 | 65993 | -2.285039 | 0.995336 |

FIGURE 14 (CONTINUED)

| Probe ID | Description | Symbol | | Value | Score |
|---|---|---|---|---|---|
| 202848_s_at | G protein-coupled receptor kinase 6 | GRK6 | | 2870 | -2.285218 | 0.995336 |
| 213023_at | utrophin | UTRN | | 7402 | -2.285846 | 0.995336 |
| 209933_s_at | CD300a molecule | CD300A | | 11314 | -2.286991 | 0.995336 |
| 202555_s_at | myosin, light chain kinase | MYLK | | 4638 | -2.287423 | 0.995336 |
| 214731_at | CTTNBP2 N-terminal like | CTTNBP2NL | | 55917 | -2.2881 | 0.995336 |
| 202446_s_at | phospholipid scramblase 1 | PLSCR1 | | 5359 | -2.288756 | 0.994105 |
| 215209_at | SEC24 related gene family, member D (S. cerevisiae) | SEC24D | | 9871 | -2.296886 | 0.994105 |
| 202339_at | symplekin | SYMPK | | 8189 | -2.296936 | 0.994105 |
| 208965_s_at | interferon, gamma-inducible protein 16 | IFI16 | | 3428 | -2.298739 | 0.993134 |
| 222065_s_at | flightless I homolog (Drosophila) | FLII | | 2314 | -2.298779 | 0.993134 |
| 209127_s_at | squamous cell carcinoma antigen recognized by T cells 3 | SART3 | | 9733 | -2.300519 | 0.993134 |
| 219821_s_at | glucose-fructose oxidoreductase domain containing 1 | GFOD1 | | 54438 | -2.302577 | 0.992432 |
| 216748_at | pyrin and HIN domain family, member 1 | PYHIN1 | | 149628 | -2.303495 | 0.992138 |
| 212517_at | attractin | ATRN | | 8455 | -2.303933 | 0.992138 |
| 203243_s_at | PDZ and LIM domain 5 | PDLIM5 | | 10611 | -2.305576 | 0.992138 |
| 212136_at | ATPase, Ca++ transporting, plasma membrane 4 | ATP2B4 | | 493 | -2.307716 | 0.991589 |
| 204003_s_at | nucleoporin like 2 | NUPL2 | | 11097 | -2.3096 | 0.991589 |
| 31826_at | FK506 binding protein 15, 133kDa | FKBP15 | | 23307 | -2.311638 | 0.990482 |
| 220603_s_at | multiple C2 domains, transmembrane 2 | MCTP2 | | 55784 | -2.313553 | 0.990482 |
| 202645_s_at | multiple endocrine neoplasia I | MEN1 | | 4221 | -2.315952 | 0.990446 |
| 202430_s_at | phospholipid scramblase 1 | PLSCR1 | | 5359 | -2.316283 | 0.990446 |
| 210824_at | --- | --- | | | -2.317314 | 0.990446 |
| 205642_at | centrosomal protein 110kDa | CEP110 | | 11064 | -2.318111 | 0.990446 |
| 205599_at | TNF receptor-associated factor 1 | TRAF1 | | 7185 | -2.318147 | 0.990446 |
| 221666_s_at | PYD and CARD domain containing | PYCARD | | 29108 | -2.321191 | 0.990446 |
| 211791_s_at | potassium voltage-gated channel, shaker-related subfamily, beta member 2 | KCNAB2 | | 8514 | -2.326949 | 0.985797 |
| 218294_s_at | nucleoporin 50kDa | NUP50 | | 10762 | -2.327504 | 0.985797 |
| 213888_s_at | TRAF3 interacting protein 3 | TRAF3IP3 | | 80342 | -2.328011 | 0.985797 |
| 201823_s_at | ring finger protein 14 | RNF14 | | 9604 | -2.328307 | 0.985797 |
| 205345_at | BRCA1 associated RING domain 1 | BARD1 | | 580 | -2.329218 | 0.985797 |
| 202358_s_at | sorting nexin 19 | SNX19 | | 399979 | -2.33007 | 0.985797 |
| 209670_at | T cell receptor alpha constant | TRAC | | 28755 | -2.330755 | 0.985797 |
| 208438_s_at | Gardner-Rasheed feline sarcoma viral (v-fgr) oncogene homolog | FGR | | 2268 | -2.330904 | 0.985797 |
| 204079_at | tyrosylprotein sulfotransferase 2 | TPST2 | | 8459 | -2.333184 | 0.985797 |
| 203612_at | bystin-like | BYSL | | 705 | -2.333648 | 0.985797 |
| 206332_s_at | interferon, gamma-inducible protein 16 | IFI16 | | 3428 | -2.334376 | 0.985797 |
| 207332_s_at | transferrin receptor (p90, CD71) | TFRC | | 7037 | -2.334941 | 0.985797 |
| 206486_at | lymphocyte-activation gene 3 | LAG3 | | 3902 | -2.335934 | 0.985797 |
| 205272_s_at | proline-rich protein HaeIII subfamily 1 /// proline-rich protein HaeIII subfamily 2 | PRH1 /// PRH2 | 5554 /// 5555 | | -2.340475 | 0.985797 |
| 215176_x_at | Netrin 2-like (chicken) | NTN2L | | 4917 | -2.34512 | 0.983708 |
| 209196_at | WD repeat domain 46 | WDR46 | | 9277 | -2.345284 | 0.983708 |
| 220096_at | ribonuclease T2 | RNASET2 | | 8635 | -2.345308 | 0.983708 |

FIGURE 14 (CONTINUED)

| | | | | | |
|---|---|---|---|---|---|
| 217103_at | low density lipoprotein receptor (familial hypercholesterolemia) | LDLR | | 3949 | -2.347621 | 0.983708 |
| 218507_at | hypoxia-inducible protein 2 | HIG2 | | 29923 | -2.34774 | 0.983708 |
| 203030_s_at | protein tyrosine phosphatase, receptor type, N polypeptide 2 | PTPRN2 | | 5799 | -2.348458 | 0.983708 |
| 213603_s_at | ras-related C3 botulinum toxin substrate 2 (rho family, small GTP binding protein Rac2) | RAC2 | | 5880 | -2.349372 | 0.983708 |
| 221669_s_at | acyl-Coenzyme A dehydrogenase family, member 8 | ACAD8 | | 27034 | -2.350417 | 0.983708 |
| 217223_s_at | breakpoint cluster region | BCR | | 613 | -2.352349 | 0.983708 |
| 201230_s_at | ariadne homolog 2 (Drosophila) | ARIH2 | | 10425 | -2.352848 | 0.983708 |
| 205126_at | vaccinia related kinase 2 | VRK2 | | 7444 | -2.355216 | 0.983708 |
| 209553_at | vacuolar protein sorting 8 homolog (S. cerevisiae) | VPS8 | | 23355 | -2.355407 | 0.983708 |
| 214096_s_at | serine hydroxymethyltransferase 2 (mitochondrial) | SHMT2 | | 6472 | -2.357866 | 0.983708 |
| 207629_s_at | rho/rac guanine nucleotide exchange factor (GEF) 2 | ARHGEF2 | | 9181 | -2.36097 | 0.983057 |
| 215057_at | Hypothetical protein FLJ44451 | FLJ44451 | | 100101122 | -2.363465 | 0.982963 |
| 210606_x_at | killer cell lectin-like receptor subfamily D, member 1 | KLRD1 | | 3824 | -2.364968 | 0.982963 |
| 202369_s_at | translocation associated membrane protein 2 | TRAM2 | | 9697 | -2.365521 | 0.982963 |
| 219861_at | DnaJ (Hsp40) homolog, subfamily C, member 17 | DNAJC17 | | 55192 | -2.36604 | 0.982963 |
| 213418_at | heat shock 70kDa protein 6 (HSP70B') | HSPA6 | | 3310 | -2.366397 | 0.982963 |
| 220558_x_at | tetraspanin 32 | TSPAN32 | | 10077 | -2.367895 | 0.982963 |
| 204655_at | chemokine (C-C motif) ligand 5 | CCL5 | | 6352 | -2.368428 | 0.982963 |
| 219473_at | ectonucleoside triphosphate diphosphohydrolase 1 | ENTPD1 | | 953 | -2.380552 | 0.975852 |
| 218670_at | pseudouridylate synthase 1 | PUS1 | | 80324 | -2.38687 | 0.969041 |
| 212863_x_at | C-terminal binding protein 1 | CTBP1 | | 1487 | -2.390791 | 0.968985 |
| 203729_at | epithelial membrane protein 3 | EMP3 | | 2014 | -2.391383 | 0.968985 |
| 202330_s_at | uracil-DNA glycosylase | UNG | | 7374 | -2.392323 | 0.968985 |
| 213863_s_at | ornithine decarboxylase antizyme 3 | OAZ3 | | 51686 | -2.396142 | 0.968985 |
| 209890_at | tetraspanin 5 | TSPAN5 | | 10098 | -2.397432 | 0.968985 |
| 218783_at | integrator complex subunit 7 | INTS7 | | 25896 | -2.399517 | 0.968985 |
| 212342_at | Yip1 domain family, member 6 | YIPF6 | | 286451 | -2.401605 | 0.966636 |
| 214677_x_at | immunoglobulin lambda locus /// immunoglobulin lambda variable 4-3 /// immunoglobulin lambda variable 3-25 /// immunoglobulin lambda variable 2-14 /// immunoglobulin lambda joining 3 | IGL@ /// IGLJ3 /// IGLV2-14 /// IGLV3-25 /// IGLV4-3 | 28786 /// 28793 /// 28815 /// 28831 /// 3535 | | -2.402143 | 0.966636 |
| 209734_at | NCK-associated protein 1-like | NCKAP1L | | 3071 | -2.404151 | 0.965484 |
| 205449_at | SAC3 domain containing 1 | SAC3D1 | | 29901 | -2.404316 | 0.965484 |
| 50374_at | chromosome 17 open reading frame 90 | C17orf90 | | 339229 | -2.405973 | 0.965484 |
| 219846_at | gon-4-like (C. elegans) | GON4L | | 54856 | -2.406746 | 0.965484 |
| 219843_at | intracisternal A particle-promoted polypeptide | IPP | | 3652 | -2.411438 | 0.965103 |
| 203252_at | CDK2-associated protein 2 | CDK2AP2 | | 10263 | -2.413337 | 0.965103 |
| 201339_s_at | sterol carrier protein 2 | SCP2 | | 6342 | -2.414247 | 0.965103 |
| 209611_s_at | solute carrier family 1 (glutamate/neutral amino acid transporter), member 4 | SLC1A4 | | 6509 | -2.414601 | 0.965103 |
| 201804_x_at | parathymosin | PTMS | | 5763 | -2.420425 | 0.965103 |
| 36004_at | inhibitor of kappa light polypeptide gene enhancer in B-cells, kinase gamma | IKBKG | | 8517 | -2.421728 | 0.965103 |
| 219519_s_at | sialic acid binding Ig-like lectin 1, sialoadhesin | SIGLEC1 | | 6614 | -2.42246 | 0.965103 |

FIGURE 14 (CONTINUED)

| Probe | Description | Gene | ID | Value | Value2 |
|---|---|---|---|---|---|
| 204747_at | interferon-induced protein with tetratricopeptide repeats 3 | IFIT3 | 3437 | -2.422839 | 0.965103 |
| 213045_at | microtubule associated serine/threonine kinase 3 | MAST3 | 23031 | -2.423957 | 0.965103 |
| 206558_at | single-minded homolog 2 (Drosophila) | SIM2 | 6493 | -2.425833 | 0.965103 |
| 209403_at | TBC1 domain family, member 3 /// TBC1 domain family, member 3B /// TBC1 domain family, member 3C /// similar to USP6 N-terminal like /// TBC1 domain family, member 3F /// TBC1 domain family, member 3H /// TBC1 domain family, member 3F /// TBC1 domain family, member 3E | LOC653380 /// LOC653498 /// LOC729837 /// TBC1D3 /// TBC1D3B /// TBC1D3C /// TBC1D3E /// TBC1D3F /// TBC1D3H | 414059 /// 414060 /// 653380 /// 653498 /// 727735 /// 729837 /// 729873 /// 729877 /// 84218 | -2.43324 | 0.957631 |
| 202101_s_at | v-ral simian leukemia viral oncogene homolog B (ras related; GTP binding protein) | RALB | 5899 | -2.434327 | 0.95725 |
| 203153_at | interferon-induced protein with tetratricopeptide repeats 1 | IFIT1 | 3434 | -2.437652 | 0.955994 |
| 217457_s_at | RAP1, GTP-GDP dissociation stimulator 1 | RAP1GDS1 | 5910 | -2.438018 | 0.955994 |
| 203401_at | phosphoribosyl pyrophosphate synthetase 2 | PRPS2 | 5634 | -2.43916 | 0.955994 |
| 221797_at | chromosome 17 open reading frame 90 | C17orf90 | 339229 | -2.439745 | 0.955994 |
| 220073_s_at | pleckstrin homology domain containing, family G (with RhoGef domain) member 6 | PLEKHG6 | 55200 | -2.440486 | 0.955994 |
| 215409_at | 1-acylglycerol-3-phosphate O-acyltransferase 7 (lysophosphatidic acid acyltransferase, eta) | AGPAT7 | 254531 | -2.440614 | 0.955994 |
| 205483_s_at | ISG15 ubiquitin-like modifier | ISG15 | 9636 | -2.44086 | 0.955994 |
| 217755_at | hematological and neurological expressed 1 | HN1 | 51155 | -2.442135 | 0.955994 |
| 203016_s_at | synovial sarcoma, X breakpoint 2 interacting protein | SSX2IP | 117178 | -2.44516 | 0.955994 |
| 57715_at | family with sequence similarity 26, member B | FAM26B | 51063 | -2.452142 | 0.955994 |
| 202592_at | biogenesis of lysosome-related organelles complex-1, subunit 1 | BLOC1S1 | 2647 | -2.460968 | 0.945989 |
| 218543_s_at | poly (ADP-ribose) polymerase family, member 12 | PARP12 | 64761 | -2.461486 | 0.945989 |
| 203882_at | interferon regulatory factor 9 | IRF9 | 10379 | -2.463635 | 0.945989 |
| 202402_s_at | cysteinyl-tRNA synthetase | CARS | 833 | -2.463806 | 0.945989 |
| 52159_at | HemK methyltransferase family member 1 | HEMK1 | 51409 | -2.467389 | 0.945989 |
| 206687_s_at | protein tyrosine phosphatase, non-receptor type 6 | PTPN6 | 5777 | -2.467811 | 0.945989 |
| 208647_at | farnesyl-diphosphate farnesyltransferase 1 | FDFT1 | 2222 | -2.46951 | 0.945989 |
| 205081_at | cysteine-rich protein 1 (intestinal) | CRIP1 | 1396 | -2.474319 | 0.945989 |
| 206513_at | absent in melanoma 2 | AIM2 | 9447 | -2.478787 | 0.945648 |
| 208659_at | chloride intracellular channel 1 | CLIC1 | 1192 | -2.479185 | 0.945648 |
| 200862_at | 24-dehydrocholesterol reductase | DHCR24 | 1718 | -2.480873 | 0.94564 |
| 202748_at | guanylate binding protein 2, interferon-inducible | GBP2 | 2634 | -2.48152 | 0.94564 |
| 210007_s_at | glycerol-3-phosphate dehydrogenase 2 (mitochondrial) | GPD2 | 2820 | -2.482177 | 0.94564 |
| 201848_s_at | BCL2/adenovirus E1B 19kDa interacting protein 3 | BNIP3 | 664 | -2.487797 | 0.94564 |
| 215999_at | CMT1A duplicated region transcript 1 | CDRT1 | 374286 | -2.488423 | 0.94564 |
| 212804_s_at | GTPase activating protein and VPS9 domains 1 | GAPVD1 | 26130 | -2.489935 | 0.94564 |
| 204006_s_at | Fc fragment of IgG, low affinity IIIa, receptor (CD16a) /// Fc fragment of IgG, low affinity IIIb, receptor (CD16b) | FCGR3A /// FCGR3B | 2214 /// 2215 | -2.494078 | 0.94564 |
| 210140_at | cystatin F (leukocystatin) | CST7 | 8530 | -2.498432 | 0.94564 |

FIGURE 14 (CONTINUED)

| | | | | | |
|---|---|---|---|---|---|
| 220771_at | melanoma antigen | LOC51152 | | 51152 | -2.500688 | 0.945564 |
| 210893_at | --- | --- | | | -2.507891 | 0.940768 |
| 213733_at | myosin IF | MYO1F | | 4542 | -2.509095 | 0.940768 |
| 204252_at | cyclin-dependent kinase 2 | CDK2 | | 1017 | -2.509392 | 0.940768 |
| 209813_x_at | T cell receptor gamma constant 2 /// T cell receptor gamma variable 9 /// TCR gamma alternate reading frame protein | TARP /// TRGC2 /// TRGV9 | 445347 /// 6967 /// 6983 | | -2.522398 | 0.934755 |
| 221876_at | zinc finger protein 783 | ZNF783 | | 155060 | -2.522887 | 0.934755 |
| 37012_at | capping protein (actin filament) muscle Z-line, beta | CAPZB | | 832 | -2.523261 | 0.934755 |
| 204398_s_at | echinoderm microtubule associated protein like 2 | EML2 | | 24139 | -2.527401 | 0.934755 |
| 202145_at | lymphocyte antigen 6 complex, locus E | LY6E | | 4061 | -2.532151 | 0.932664 |
| 220586_at | chromodomain helicase DNA binding protein 9 | CHD9 | | 80205 | -2.540493 | 0.919927 |
| 216920_s_at | T cell receptor gamma constant 2 /// T cell receptor gamma variable 9 /// TCR gamma alternate reading frame protein | TARP /// TRGC2 /// TRGV9 | 445347 /// 6967 /// 6983 | | -2.542233 | 0.919927 |
| 218197_s_at | oxidation resistance 1 | OXR1 | | 55074 | -2.543601 | 0.919927 |
| 206615_s_at | ADAM metallopeptidase domain 22 | ADAM22 | | 53616 | -2.545701 | 0.919927 |
| 215084_s_at | leucine rich repeat containing 42 | LRRC42 | | 115353 | -2.545709 | 0.919927 |
| 214657_s_at | Trophoblast-derived noncoding RNA | TncRNA | | 283131 | -2.546708 | 0.919927 |
| 215806_x_at | T cell receptor gamma constant 2 /// T cell receptor gamma variable 9 /// TCR gamma alternate reading frame protein | TARP /// TRGC2 /// TRGV9 | 445347 /// 6967 /// 6983 | | -2.548486 | 0.919927 |
| 215713_at | CDNA: FLJ23125 fis, clone LNG08217 | --- | | | -2.549053 | 0.919927 |
| 215797_at | T cell receptor alpha variable 8-3 | TRAV8-3 | | 28683 | -2.55185 | 0.919927 |
| 209138_x_at | Immunoglobulin lambda locus | IGL@ | | 3535 | -2.554937 | 0.919927 |
| 204959_at | myeloid cell nuclear differentiation antigen | MNDA | | 4332 | -2.559718 | 0.919927 |
| 214895_s_at | ADAM metallopeptidase domain 10 | ADAM10 | | 102 | -2.560982 | 0.919927 |
| 211786_at | tumor necrosis factor receptor superfamily, member 9 | TNFRSF9 | | 3604 | -2.561003 | 0.919927 |
| 200800_s_at | heat shock 70kDa protein 1A /// heat shock 70kDa protein 1B | HSPA1A /// HSPA1B | 3303 /// 3304 | | -2.567499 | 0.917727 |
| 213374_x_at | 3-hydroxyisobutyryl-Coenzyme A hydrolase | HIBCH | | 26275 | -2.56778 | 0.917727 |
| 213915_at | natural killer cell group 7 sequence | NKG7 | | 4818 | -2.571943 | 0.913069 |
| 221514_at | UTP14, U3 small nucleolar ribonucleoprotein, homolog A (yeast) | UTP14A | | 10813 | -2.574838 | 0.913069 |
| 208670_s_at | EP300 interacting inhibitor of differentiation 1 | EID1 | | 23741 | -2.588208 | 0.892861 |
| 203169_at | RGP1 retrograde golgi transport homolog (S. cerevisiae) | RGP1 | | 9827 | -2.58995 | 0.892861 |
| 215443_at | thyroid stimulating hormone receptor | TSHR | | 7253 | -2.594297 | 0.890175 |
| 202837_at | TRAF-type zinc finger domain containing 1 | TRAFD1 | | 10906 | -2.595966 | 0.890175 |
| 207667_s_at | mitogen-activated protein kinase kinase 3 | MAP2K3 | | 5606 | -2.597547 | 0.890175 |
| 215611_at | transcription factor 12 (HTF4, helix-loop-helix transcription factors 4) | TCF12 | | 6938 | -2.598297 | 0.890175 |
| 218335_x_at | TNFAIP3 interacting protein 2 | TNIP2 | | 79155 | -2.60439 | 0.887011 |
| 204441_s_at | polymerase (DNA directed), alpha 2 (70kD subunit) | POLA2 | | 23649 | -2.610632 | 0.881556 |
| 212099_at | ras homolog gene family, member B | RHOB | | 388 | -2.612423 | 0.880393 |
| 201233_at | proteasome (prosome, macropain) 26S subunit, non-ATPase, 13 | PSMD13 | | 5719 | -2.617423 | 0.874998 |
| 213507_s_at | karyopherin (importin) beta 1 | KPNB1 | | 3837 | -2.620521 | 0.873794 |
| 203814_s_at | NAD(P)H dehydrogenase, quinone 2 | NQO2 | | 4835 | -2.623466 | 0.872958 |
| 201639_s_at | cleavage and polyadenylation specific factor 1, 160kDa | CPSF1 | | 29894 | -2.623673 | 0.872958 |

FIGURE 14 (CONTINUED)

| | | | | |
|---|---|---|---|---|
| 220788_s_at | ring finger protein 31 | RNF31 | 55072 | -2.631476 | 0.866649 |
| 200850_s_at | S-adenosylhomocysteine hydrolase-like 1 | AHCYL1 | 10768 | -2.633959 | 0.866649 |
| 211070_x_at | diazepam binding inhibitor (GABA receptor modulator, acyl-Coenzyme A binding protein) | DBI | 1622 | -2.637035 | 0.863216 |
| 220049_at | hypothetical protein MGC5566 | MGC5566 | 79015 | -2.638811 | 0.862215 |
| 218681_s_at | stromal cell-derived factor 2-like 1 | SDF2L1 | 23753 | -2.642281 | 0.860415 |
| 211504_x_at | Rho-associated, coiled-coil containing protein kinase 2 | ROCK2 | 9475 | -2.644899 | 0.860415 |
| 221873_at | zinc finger protein 143 | ZNF143 | 7702 | -2.645331 | 0.860415 |
| 217497_at | endothelial cell growth factor 1 (platelet-derived) | ECGF1 | 1890 | -2.653325 | 0.853874 |
| 202760_s_at | A kinase (PRKA) anchor protein 2 /// PALM2-AKAP2 | AKAP2 /// PALM2-AKAP2 | 11217 /// 445815 | -2.653912 | 0.853874 |
| 218593_at | RNA binding motif protein 28 | RBM28 | 55131 | -2.656287 | 0.853874 |
| 201541_s_at | zinc finger, HIT type 1 | ZNHIT1 | 10467 | -2.658826 | 0.853874 |
| 200812_at | chaperonin containing TCP1, subunit 7 (eta) | CCT7 | 10574 | -2.661078 | 0.853874 |
| 217173_s_at | low density lipoprotein receptor (familial hypercholesterolemia) | LDLR | 3949 | -2.664139 | 0.853874 |
| 208097_s_at | thioredoxin domain containing 1 | TXNDC1 | 81542 | -2.664249 | 0.853874 |
| 204162_at | NDC80 homolog, kinetochore complex component (S. cerevisiae) | NDC80 | 10403 | -2.665556 | 0.853874 |
| 219159_s_at | SLAM family member 7 | SLAMF7 | 57823 | -2.66699 | 0.853874 |
| 217857_s_at | RNA binding motif protein 8A | RBM8A | 9939 | -2.667241 | 0.853874 |
| 202086_at | myxovirus (influenza virus) resistance 1, interferon-inducible protein p78 (mouse) | MX1 | 4599 | -2.667578 | 0.853874 |
| 37425_g_at | coiled-coil alpha-helical rod protein 1 | CCHCR1 | 54535 | -2.671183 | 0.853874 |
| 206589_at | growth factor independent 1 transcription repressor | GFI1 | 2672 | -2.675827 | 0.853874 |
| 203150_at | Rab9 effector protein with kelch motifs | RABEPK | 10244 | -2.67629 | 0.853874 |
| 221079_s_at | methyltransferase like 2B /// methyltransferase like 2A | METTL2A /// METTL2B | 339175 /// 55798 | -2.681647 | 0.853874 |
| 206092_x_at | regulator of telomere elongation helicase 1 | RTEL1 | 51750 | -2.68586 | 0.853874 |
| 204661_at | CD52 molecule | CD52 | 1043 | -2.687852 | 0.853874 |
| 217292_at | myotubularin related protein 7 | MTMR7 | 9108 | -2.691707 | 0.853874 |
| 202869_at | 2',5'-oligoadenylate synthetase 1, 40/46kDa | OAS1 | 4938 | -2.700101 | 0.853874 |
| 214004_s_at | vestigial like 4 (Drosophila) | VGLL4 | 9686 | -2.708912 | 0.852106 |
| 214059_at | Interferon-induced protein 44 | IFI44 | 10561 | -2.709346 | 0.852106 |
| 220307_at | CD244 molecule, natural killer cell receptor 2B4 | CD244 | 51744 | -2.711134 | 0.852106 |
| 212567_s_at | microtubule-associated protein 4 | MAP4 | 4134 | -2.713028 | 0.852106 |
| 201061_s_at | stomatin | STOM | 2040 | -2.715958 | 0.852106 |
| 203931_s_at | mitochondrial ribosomal protein L12 | MRPL12 | 6182 | -2.723132 | 0.852106 |
| 211144_x_at | T cell receptor gamma constant 2 /// T cell receptor gamma variable 9 /// TCR gamma alternate reading frame protein | TARP /// TRGC2 /// TRGV9 | 445347 /// 6967 /// 6983 | -2.724738 | 0.852106 |
| 214340_at | transmembrane protein 187 | TMEM187 | 8269 | -2.727179 | 0.852106 |
| 215105_at | hypothetical gene CG030 | CG030 | 116828 | -2.731114 | 0.852106 |
| 202198_s_at | myotubularin related protein 3 | MTMR3 | 8897 | -2.734718 | 0.852106 |
| 214926_at | spectrin, alpha, non-erythrocytic 1 (alpha-fodrin) | SPTAN1 | 6709 | -2.748293 | 0.848523 |
| 201580_s_at | thioredoxin domain containing 13 | TXNDC13 | 56255 | -2.749566 | 0.848523 |
| 202411_at | interferon, alpha-inducible protein 27 | IFI27 | 3429 | -2.752903 | 0.846362 |

FIGURE 14 (CONTINUED)

| Probe ID | Description | Gene Symbol | Value1 | Value2 | Value3 |
|---|---|---|---|---|---|
| 216298_at | hypothetical protein LOC648852 | LOC648852 | 648852 | -2.755525 | 0.844341 |
| 33850_at | microtubule-associated protein 4 | MAP4 | 4134 | -2.758097 | 0.843005 |
| 203109_at | ubiquitin-conjugating enzyme E2M (UBC12 homolog, yeast) | UBE2M | 9040 | -2.765071 | 0.834774 |
| 204994_at | myxovirus (influenza virus) resistance 2 (mouse) | MX2 | 4600 | -2.772816 | 0.830816 |
| 218986_s_at | hypothetical protein FLJ20035 | FLJ20035 | 55601 | -2.779552 | 0.826033 |
| 200863_s_at | RAB11A, member RAS oncogene family | RAB11A | 8766 | -2.785379 | 0.824301 |
| 222154_s_at | viral DNA polymerase-transactivated protein 6 | LOC26010 | 26010 | -2.799965 | 0.813 |
| 213433_at | ADP-ribosylation factor-like 3 | ARL3 | 403 | -2.80017 | 0.813 |
| 221708_s_at | unc-45 homolog A (C. elegans) | UNC45A | 55898 | -2.801569 | 0.813 |
| 200675_at | CD81 molecule | CD81 | 975 | -2.802487 | 0.813 |
| 204073_s_at | chromosome 11 open reading frame 9 | C11orf9 | 745 | -2.81372 | 0.782863 |
| 32402_s_at | symplekin | SYMPK | 8189 | -2.833536 | 0.778228 |
| 200623_s_at | calmodulin 3 (phosphorylase kinase, delta) | CALM3 | 808 | -2.839109 | 0.777545 |
| 201601_x_at | interferon induced transmembrane protein 1 (9-27) | IFITM1 | 8519 | -2.843273 | |
| 202428_x_at | diazepam binding inhibitor (GABA receptor modulator, acyl-Coenzyme A binding protein) | DBI | 1622 | -2.846548 | 0.774818 |
| 205904_at | MHC class I polypeptide-related sequence A | MICA | 4276 | -2.862126 | 0.763884 |
| 214836_x_at | immunoglobulin kappa constant /// immunoglobulin kappa variable 1-5 | IGKC /// IGKV1-5 | 28299 /// 3514 | -2.863496 | 0.763884 |
| 44673_at | sialic acid binding Ig-like lectin 1, sialoadhesin | SIGLEC1 | 6614 | -2.864676 | 0.763884 |
| 220631_at | O-sialoglycoprotein endopeptidase-like 1 | OSGEPL1 | 64172 | -2.865379 | 0.763884 |
| 218367_x_at | ubiquitin specific peptidase 21 | USP21 | 27005 | -2.866218 | 0.763884 |
| 218999_at | transmembrane protein 140 | TMEM140 | 55281 | -2.868119 | 0.763884 |
| 216519_s_at | proline synthetase co-transcribed homolog (bacterial) | PROSC | 11212 | -2.884539 | 0.758815 |
| 202659_at | proteasome (prosome, macropain) subunit, beta type, 10 | PSMB10 | 5699 | -2.894005 | 0.74575 |
| 215719_x_at | Fas (TNF receptor superfamily, member 6) | FAS | 355 | -2.894768 | 0.74575 |
| 219211_at | ubiquitin specific peptidase 18 | USP18 | 11274 | -2.895115 | 0.74575 |
| 221513_s_at | UTP14, U3 small nucleolar ribonucleoprotein, homolog C (yeast) /// UTP14, U3 small nucleolar ribonucleoprotein, homolog A (yeast) | UTP14A /// UTP14C | 10813 /// 9724 | -2.896457 | 0.74575 |
| 206746_at | beaded filament structural protein 1, filensin | BFSP1 | 631 | -2.897094 | 0.74575 |
| 2133294_at | Full-length cDNA clone CS0DK002YF13 of HeLa cells Cot 25-normalized of Homo sapiens (human) | | | -2.8981 | 0.74575 |
| 34210_at | CD52 molecule | CD52 | 1043 | -2.901647 | 0.74575 |
| 117_at | heat shock 70kDa protein 6 (HSP70B') | HSPA6 | 3310 | -2.909103 | 0.74575 |
| 221143_at | replication protein A4, 34kDa | RPA4 | 29935 | -2.921265 | 0.744465 |
| 202604_x_at | ADAM metallopeptidase domain 10 | ADAM10 | 102 | -2.931555 | 0.730023 |
| 204853_at | origin recognition complex, subunit 2-like (yeast) | ORC2L | 4999 | -2.934116 | 0.729414 |
| 214343_s_at | ataxin 7-like 1 | ATXN7L1 | 222255 | -2.946185 | 0.719337 |
| 208492_at | regulatory factor X-associated protein | RFXAP | 5994 | -2.953293 | 0.710946 |
| 210321_at | granzyme H (cathepsin G-like 2, protein h-CCPX) | GZMH | 2999 | -2.964101 | 0.707388 |
| 212166_at | exportin 7 | XPO7 | 23039 | -2.96494 | 0.707388 |
| 200643_at | high density lipoprotein binding protein (vigilin) | HDLBP | 3069 | -2.965827 | 0.707388 |
| 218620_s_at | HemK methyltransferase family member 1 | HEMK1 | 51409 | -2.972887 | 0.707388 |

FIGURE 14 (CONTINUED)

| | | | | |
|---|---|---|---|---|
| 216197_at | activating transcription factor 7 interacting protein | ATF7IP | 55729 | -2.976676 | 0.707388 |
| 216883_x_at | phosphodiesterase 6D, cGMP-specific, rod, delta | PDE6D | 5147 | -2.979193 | 0.707388 |
| 216540_at | T cell receptor alpha locus | TRA@ | 6955 | -2.979247 | 0.707388 |
| 207761_s_at | methyltransferase like 7A | METTL7A | 25840 | -2.981419 | 0.707388 |
| 207492_at | N-glycanase 1 | NGLY1 | 55768 | -2.987963 | 0.707388 |
| 217138_x_at | Immunoglobulin lambda locus | IGL@ | 3535 | -2.992135 | 0.707388 |
| 222002_at | Chromosome 7 open reading frame 26 | C7orf26 | 79034 | -2.995426 | 0.707388 |
| 201315_x_at | interferon induced transmembrane protein 2 (1-8D) | IFITM2 | 10581 | -3.006596 | 0.707388 |
| 202942_at | electron-transfer-flavoprotein, beta polypeptide | ETFB | 2109 | -3.021587 | 0.707388 |
| 208003_s_at | nuclear factor of activated T-cells 5, tonicity-responsive | NFAT5 | 10725 | -3.0318 | 0.704919 |
| 202480_s_at | death effector domain containing | DEDD | 9191 | -3.040346 | 0.694092 |
| 213617_s_at | chromosome 18 open reading frame 10 | C18orf10 | 25941 | -3.040592 | 0.694092 |
| 205702_at | putative homeodomain transcription factor 1 | PHTF1 | 10745 | -3.041724 | 0.694092 |
| 207509_s_at | leukocyte-associated immunoglobulin-like receptor 2 | LAIR2 | 3904 | -3.045286 | 0.694092 |
| 210156_s_at | protein-L-isoaspartate (D-aspartate) O-methyltransferase | PCMT1 | 5110 | -3.054953 | 0.688018 |
| 216565_x_at | interferon induced transmembrane protein pseudogene | LOC391020 | 391020 | -3.058544 | 0.686712 |
| 209732_at | C-type lectin domain family 2, member B | CLEC2B | 9976 | -3.059706 | 0.686712 |
| 205552_s_at | 2,5'-oligoadenylate synthetase 1, 40/46kDa | OAS1 | 4938 | -3.083134 | 0.679372 |
| 200900_s_at | mannose-6-phosphate receptor (cation dependent) | M6PR | 4074 | -3.087961 | 0.6765 |
| 216958_s_at | isovaleryl Coenzyme A dehydrogenase | IVD | 3712 | -3.095566 | 0.668264 |
| 203471_s_at | pleckstrin | PLEK | 5341 | -3.095829 | 0.668264 |
| 203392_s_at | C-terminal binding protein 1 | CTBP1 | 1487 | -3.098844 | 0.668264 |
| 210137_s_at | dCMP deaminase | DCTD | 1635 | -3.118266 | 0.668264 |
| 216237_s_at | minichromosome maintenance complex component 5 | MCM5 | 4174 | -3.125737 | 0.668264 |
| 209044_x_at | splicing factor 3b, subunit 4, 49kDa | SF3B4 | 10262 | -3.133064 | 0.665781 |
| 205718_at | integrin, beta 7 | ITGB7 | 3695 | -3.13477 | 0.665781 |
| 221879_at | calmodulin-like 4 | CALML4 | 91860 | -3.16149 | 0.65785 |
| 200760_s_at | ADP-ribosylation-like factor 6 interacting protein 5 | ARL6IP5 | 10550 | -3.163834 | 0.65785 |
| 205842_s_at | Janus kinase 2 (a protein tyrosine kinase) | JAK2 | 3717 | -3.188324 | 0.623484 |
| 212162_at | kinase D-interacting substrate of 220 kDa | KIDINS220 | 57498 | -3.208084 | 0.602636 |
| 218272_at | hypothetical protein FLJ20699 | FLJ20699 | 55020 | -3.253421 | 0.572938 |
| 216252_x_at | Fas (TNF receptor superfamily, member 6) | FAS | 355 | -3.258874 | 0.572938 |
| 212203_x_at | interferon induced transmembrane protein 3 (1-8U) | IFITM3 | 10410 | -3.258878 | 0.572938 |
| 204103_at | chemokine (C-C motif) ligand 4 | CCL4 | 6351 | -3.275972 | 0.569778 |
| 218927_s_at | carbohydrate (chondroitin 4) sulfotransferase 12 | CHST12 | 55501 | -3.280979 | 0.569778 |
| 201263_at | threonyl-tRNA synthetase | TARS | 6897 | -3.293493 | 0.562471 |
| 203941_at | integrator complex subunit 9 | INTS9 | 55756 | -3.306854 | 0.562181 |
| 206133_at | XIAP associated factor-1 | XAF1 | 54739 | -3.326924 | 0.5527 |
| 209449_at | LSM2 homolog, U6 small nuclear RNA associated (S. cerevisiae) | LSM2 | 57819 | -3.332443 | 0.551467 |
| 64408_s_at | calmodulin-like 4 | CALML4 | 91860 | -3.35522 | 0.524274 |
| 209969_s_at | signal transducer and activator of transcription 1, 91kDa | STAT1 | 6772 | -3.367198 | 0.524274 |
| 202305_s_at | fasciculation and elongation protein zeta 2 (zygin II) | FEZ2 | 9637 | -3.378249 | 0.524274 |

FIGURE 14 (CONTINUED)

| | | | | | |
|---|---|---|---|---|---|
| 215864_at | cDNA: FLJ21424 fis, clone COL04157 | | | -3.392941 | -0.524274 |
| 213403_at | Clone 23908 mRNA sequence | | | -3.395549 | 0.524274 |
| 212729_at | discs, large homolog 3 (neuroendocrine-dlg, Drosophila) | DLG3 | 1741 | -3.436891 | 0.524274 |
| 214195_at | tripeptidyl peptidase I | TPP1 | 1200 | -3.45291 | 0.524274 |
| 221651_x_at | immunoglobulin kappa constant /// immunoglobulin kappa variable 1-5 /// immunoglobulin kappa variable 2-24 /// immunoglobulin kappa locus | IGK@ /// IGKC /// IGKV1-5 /// IGKV2-24 | 28299 /// 28923 /// 3514 /// 50802 | -3.46206 | 0.521169 |
| 201886_at | WD repeat domain 23 | WDR23 | 80344 | -3.479719 | 0.504724 |
| 201641_at | bone marrow stromal cell antigen 2 | BST2 | 684 | -3.484017 | 0.504724 |
| 203470_s_at | pleckstrin | PLEK | 5341 | -3.49573 | 0.500671 |
| 218400_at | 2'-5'-oligoadenylate synthetase 3, 100kDa | OAS3 | 4940 | -3.529733 | 0.4723 |
| 206553_at | 2'-5'-oligoadenylate synthetase 2, 69/71kDa | OAS2 | 4939 | -3.547919 | 0.471311 |
| 213797_at | radical S-adenosyl methionine domain containing 2 | RSAD2 | 91543 | -3.569007 | 0.458443 |
| 204415_at | interferon, alpha-inducible protein 6 | IFI6 | 2537 | -3.586851 | 0.445071 |
| 203790_s_at | heat-responsive protein 12 | HRSP12 | 10247 | -3.615157 | 0.433373 |
| 205965_at | basic leucine zipper transcription factor, ATF-like | BATF | 10538 | -3.630572 | 0.430313 |
| 215345_x_at | T cell receptor gamma variable 7 | TRGV7 | 6981 | -3.640388 | 0.428654 |
| 208741_at | Sin3A-associated protein, 18kDa | SAP18 | 10284 | -3.664203 | 0.421399 |
| 221671_x_at | immunoglobulin kappa constant /// immunoglobulin kappa variable 1-5 /// immunoglobulin kappa variable 2-24 /// immunoglobulin kappa locus | IGK@ /// IGKC /// IGKV1-5 /// IGKV2-24 | 28299 /// 28923 /// 3514 /// 50802 | -3.703389 | 0.421399 |
| 202417_at | kelch-like ECH-associated protein 1 | KEAP1 | 9817 | -3.712357 | 0.421399 |
| 207229_at | killer cell lectin-like receptor subfamily A, member 1 | KLRA1 | 10748 | -3.74285 | 0.421399 |
| 214669_x_at | immunoglobulin kappa locus | IGK@ | 50802 | -3.797643 | 0.421399 |
| 201484_at | suppressor of Ty 4 homolog 1 (S. cerevisiae) | SUPT4H1 | 6827 | -3.81015 | 0.421399 |
| 201949_x_at | G protein-coupled receptor 56 | GPR56 | 9289 | -3.915727 | 0.421399 |
| 214617_at | capping protein (actin filament) muscle Z-line, beta | CAPZB | 832 | -3.983587 | 0.421399 |
| 204968_at | perforin 1 (pore forming protein) | PRF1 | 5551 | -3.994811 | 0.421399 |
| 202458_at | chromosome 6 open reading frame 47 | C6orf47 | 57827 | -4.054763 | 0.421399 |
| 204439_at | protease, serine, 23 | PRSS23 | 11098 | -4.133224 | 0.421399 |
| 206582_s_at | interferon-induced protein 44-like | IFI44L | 10964 | -4.330995 | 0.358674 |
| 209417_s_at | G protein-coupled receptor 56 | GPR56 | 9289 | -4.572991 | 0.253543 |
| 214453_s_at | interferon-induced protein 35 | IFI35 | 3430 | -5.028481 | 0.080065 |
| | interferon-induced protein 44 | IFI44 | 10561 | -5.110811 | 0.080065 |

FIGURE 15

| probeset_id | GeneTitle | GeneSymbol | GeneID | t | q |
|---|---|---|---|---|---|
| 210164_at | granzyme B (granzyme 2, cytotoxic T-lymphocyte-associated serine esterase 1) | GZMB | 3002 | 18.227709 | 0.001874 |
| 209969_s_at | signal transducer and activator of transcription 1, 91kDa | STAT1 | 6772 | 14.929347 | 0.00444 |
| 202269_x_at | guanylate binding protein 1, interferon-inducible, 67kDa | GBP1 | 2633 | 10.838547 | 0.034349 |
| 205066_s_at | ectonucleotide pyrophosphatase/phosphodiesterase 1 | ENPP1 | 5167 | 10.210011 | 0.040357 |
| 200887_s_at | signal transducer and activator of transcription 1, 91kDa | STAT1 | 6772 | 9.269462 | 0.066247 |
| 201105_at | lectin, galactoside-binding, soluble, 1 (galectin 1) | LGALS1 | 3956 | 8.888005 | 0.075221 |
| 209417_s_at | interferon-induced protein 35 | IFI35 | 3430 | 8.664381 | 0.077699 |
| 205488_at | granzyme A (granzyme 1, cytotoxic T-lymphocyte-associated serine esterase 3) | GZMA | 3001 | 8.343608 | 0.089478 |
| 202688_at | tumor necrosis factor (ligand) superfamily, member 10 | TNFSF10 | 8743 | 7.975849 | 0.105387 |
| 217997_at | pleckstrin homology-like domain, family A, member 1 | PHLDA1 | 22822 | 7.794043 | 0.106351 |
| 201649_at | ubiquitin-conjugating enzyme E2L 6 | UBE2L6 | 9246 | 7.128327 | 0.183614 |
| 217996_at | pleckstrin homology-like domain, family A, member 1 | PHLDA1 | 22822 | 6.857691 | 0.222102 |
| 201666_at | TIMP metallopeptidase inhibitor 1 | TIMP1 | 7076 | 6.69877 | 0.227814 |
| 204279_at | proteasome (prosome, macropain) subunit, beta type, 9 (large multifunctional peptidase 2) | PSMB9 | 5698 | 6.66554 | 0.227814 |
| 207351_s_at | SH2 domain protein 2A | SH2D2A | 9047 | 6.547141 | 0.227814 |
| 202307_s_at | transporter 1, ATP-binding cassette, sub-family B (MDR/TAP) | TAP1 | 6890 | 6.491677 | 0.227814 |
| 203939_at | 5'-nucleotidase, ecto (CD73) | NT5E | 4907 | 6.478622 | 0.227814 |
| 216231_s_at | beta-2-microglobulin | B2M | 567 | 6.466658 | 0.227814 |
| 200905_x_at | major histocompatibility complex, class I, E | HLA-E | 3133 | 6.240698 | 0.263103 |
| 202659_at | proteasome (prosome, macropain) subunit, beta type, 10 | PSMB10 | 5699 | 6.238794 | 0.263103 |
| 203882_at | interferon regulatory factor 9 | IRF9 | 10379 | 6.143691 | 0.278594 |
| 202270_at | guanylate binding protein 1, interferon-inducible, 67kDa | GBP1 | 2633 | 6.071515 | 0.288521 |
| 202531_at | interferon regulatory factor 1 | IRF1 | 3659 | 5.737293 | 0.368172 |
| 203695_s_at | deafness, autosomal dominant 5 | DFNA5 | 1687 | 5.725111 | 0.368172 |
| 204804_at | tripartite motif-containing 21 | TRIM21 | 6737 | 5.683695 | 0.368172 |
| 202975_s_at | Rho-related BTB domain containing 3 | RHOBTB3 | 22836 | 5.643445 | 0.368172 |
| 206118_at | signal transducer and activator of transcription 4 | STAT4 | 6775 | 5.495037 | 0.368172 |
| 210140_at | cystatin F (leukocystatin) | CST7 | 8530 | 5.487539 | 0.368172 |
| 210948_s_at | lymphoid enhancer-binding factor 1 | LEF1 | 51176 | 5.451529 | 0.368172 |
| 201858_s_at | serglycin | SRGN | 5552 | 5.449523 | 0.368172 |
| 203760_s_at | Src-like-adaptor | SLA | 6503 | 5.448234 | 0.368172 |
| 209670_at | T cell receptor alpha constant | TRAC | 28755 | 5.435559 | 0.368172 |
| 209365_s_at | extracellular matrix protein 1 | ECM1 | 1893 | 5.423926 | 0.368172 |
| 211005_at | linker for activation of T cells | LAT | 27040 | 5.42136 | 0.366172 |
| 204070_at | retinoic acid receptor responder (tazarotene induced) 3 | RARRES3 | 5920 | 5.385485 | 0.374415 |
| 203729_at | epithelial membrane protein 3 | EMP3 | 2014 | 5.358671 | 0.376963 |
| 217456_x_at | major histocompatibility complex, class I, E | HLA-E | 3133 | 5.324484 | 0.383186 |
| 204415_at | interferon, alpha-inducible protein 6 | IFI6 | 2537 | 5.300603 | 0.384986 |
| 205065_at | ectonucleotide pyrophosphatase/phosphodiesterase 1 | ENPP1 | 5167 | 5.272298 | 0.389122 |
| 34210_at | CD52 molecule | CD52 | 1043 | 5.222255 | 0.395123 |
| 209667_at | carboxylesterase 2 (intestine, liver) | CES2 | 8824 | 5.133136 | 0.42509 |
| 209813_x_at | T cell receptor gamma constant 2 /// T cell receptor gamma variable 9 /// TCR gamma alternate reading frame protein | TARP /// TRGC2 /// TRGV9 | 445347 /// 6967 /// 6983 | 5.127041 | 0.42509 |
| 208581_x_at | metallothionein 1X | MT1X | 4501 | 5.075682 | 0.443485 |

FIGURE 15 (CONTINUED)

| | | | | |
|---|---|---|---|---|
| 209040_s_at | proteasome (prosome, macropain) subunit, beta type. 8 (large multifunctional peptidase 7) | PSMB8 | 5696 | 5.058703 | 0.443676 |
| 33304_at | interferon stimulated exonuclease gene 20kDa | ISG20 | 3669 | 4.959533 | 0.482434 |
| 221269_s_at | SH3 domain binding glutamic acid-rich protein like 3 | SH3BGRL3 | 83442 | 4.920797 | 0.487407 |
| 213193_x_at | T cell receptor beta variable 19 /// T cell receptor beta constant 1 | TRBC1 /// TRBV19 | 28568 /// 28639 | 4.664671 | 0.623444 |
| 204637_at | glycoprotein hormones, alpha polypeptide | CGA | 1081 | 4.647779 | 0.623444 |
| 208899_x_at | ATPase, H+ transporting, lysosomal 34kDa, V1 subunit D | ATP6V1D | 51382 | 4.61805 | 0.623444 |
| 205856_at | solute carrier family 14 (urea transporter), member 1 (Kidd blood group) | SLC14A1 | 6563 | 4.617547 | 0.623444 |
| 210397_at | defensin, beta 1 | DEFB1 | 1672 | 4.597083 | 0.623444 |
| 211165_x_at | EPH receptor B2 | EPHB2 | 2048 | 4.52819 | 0.643373 |
| 219716_at | apolipoprotein L, 6 | APOL6 | 80830 | 4.483015 | 0.658014 |
| 213220_at | hypothetical protein LOC92482 | LOC92482 | 92482 | 4.474231 | 0.658014 |
| 204698_at | interferon stimulated exonuclease gene 20kDa | ISG20 | 3669 | 4.460427 | 0.659838 |
| 201762_s_at | proteasome (prosome, macropain) activator subunit 2 (PA28 beta) | PSME2 | 5721 | 4.448891 | 0.659838 |
| 204747_at | interferon-induced protein with tetratricopeptide repeats 3 | IFIT3 | 3437 | 4.400184 | 0.659838 |
| 209140_x_at | major histocompatibility complex, class I, B | HLA-B | 3106 | 4.368345 | 0.659838 |
| 209732_at | C-type lectin domain family 2, member B | CLEC2B | 9976 | 4.357969 | 0.659838 |
| 203761_at | Src-like-adaptor | SLA | 6503 | 4.336402 | 0.659838 |
| 200904_at | major histocompatibility complex, class I, E | HLA-E | 3133 | 4.331984 | 0.659838 |
| 205406_s_at | sperm autoantigenic protein 17 | SPA17 | 53340 | 4.297531 | 0.659838 |
| 206584_at | lymphocyte antigen 96 | LY96 | 23643 | 4.269787 | 0.659838 |
| 219326_s_at | UDP-GlcNAc:betaGal beta-1,3-N-acetylglucosaminyltransferase 2 | B3GNT2 | 10678 | 4.249119 | 0.659838 |
| 205987_at | CD1c molecule | CD1C | 911 | 4.226312 | 0.659838 |
| 200872_at | S100 calcium binding protein A10 | S100A10 | 6281 | 4.224039 | 0.659838 |
| 203298_s_at | jumonji, AT rich interactive domain 2 | JARID2 | 3720 | 4.219837 | 0.659838 |
| 210915_x_at | T cell receptor beta variable 19 /// T cell receptor beta constant 1 | TRBC1 /// TRBV19 | 28568 /// 28639 | 4.212395 | 0.659838 |
| 214757_at | CDNA clone IMAGE:3456494 | | | 4.204413 | 0.659838 |
| 202712_s_at | creatine kinase, mitochondrial 1B /// creatine kinase, mitochondrial 1A | CKMT1A /// CKMT1B | 1159 /// 548596 | 4.160303 | 0.659838 |
| 207288_at | chromosome X and Y open reading frame 2 | CXYorf2 | 80161 | 4.159694 | 0.659838 |
| 204661_at | CD52 molecule | CD52 | 1043 | 4.15591 | 0.659838 |
| 221139_s_at | cysteine sulfinic acid decarboxylase | CSAD | 51380 | 4.128038 | 0.659838 |
| 202687_s_at | tumor necrosis factor (ligand) superfamily, member 10 | TNFSF10 | 8743 | 4.12724 | 0.659838 |
| 215806_x_at | T cell receptor gamma constant 2 /// T cell receptor gamma variable 9 /// TCR gamma alternate reading frame protein | TARP /// TRGC2 /// TRGV9 | 445347 /// 6967 /// 6983 | 4.120661 | 0.659838 |
| 209515_s_at | RAB27A, member RAS oncogene family | RAB27A | 5873 | 4.088021 | 0.659838 |
| 215082_at | ELOVL family member 5, elongation of long chain fatty acids (FEN1/Elo2, SUR4/Elo3-like, yeast) | ELOVL5 | 60481 | 4.074971 | 0.659838 |
| 219209_at | interferon induced with helicase C domain 1 | IFIH1 | 64135 | 4.062895 | 0.659838 |
| 219717_at | chromosome 4 open reading frame 30 | C4orf30 | 54876 | 4.06228 | 0.659838 |
| 212573_at | endonuclease domain containing 1 | ENDOD1 | 23052 | 4.045748 | 0.659838 |
| 220021_at | transmembrane channel-like 7 | TMC7 | 79905 | 4.039762 | 0.659838 |
| 212570_at | endonuclease domain containing 1 | ENDOD1 | 23052 | 4.031653 | 0.659838 |

FIGURE 15 (CONTINUED)

| | | TARP /// TRGC2 /// TRGV9 | 445347 /// 6967 /// 6983 | | |
|---|---|---|---|---|---|
| 216920_s_at | T cell receptor gamma constant 2 /// T cell receptor gamma variable 9 /// TCR gamma alternate reading frame protein | | | 4.028937 | 0.659838 |
| 205798_at | interleukin 7 receptor | IL7R | 3575 | 4.010822 | 0.659838 |
| 221419_s_at | | | | 3.997943 | 0.659838 |
| 212998_x_at | major histocompatibility complex, class II, DQ beta 1 | HLA-DQB1 | 3119 | 3.980246 | 0.659838 |
| 214717_at | hypothetical protein DKFZp434H1419 | DKFZp434H1419 | 150967 | 3.958514 | 0.659838 |
| 212249_at | phosphoinositide-3-kinase, regulatory subunit 1 (p85 alpha) | PIK3R1 | 5295 | 3.957294 | 0.659838 |
| 220704_at | IKAROS family zinc finger 1 (Ikaros) | IKZF1 | 10320 | 3.947866 | 0.659838 |
| 213060_s_at | chitinase 3-like 2 | CHI3L2 | 1117 | 3.942297 | 0.659838 |
| 220358_at | basic leucine zipper transcription factor, ATF-like 3 | BATF3 | 55509 | 3.933133 | 0.659838 |
| 210946_at | phosphatidic acid phosphatase type 2A | PPAP2A | 8611 | 3.929366 | 0.659838 |
| 209769_s_at | glycoprotein Ib (platelet), beta polypeptide | GP1BB | 2812 | 3.90943 | 0.659838 |
| 211600_at | | | | 3.909174 | 0.659838 |
| 205768_s_at | solute carrier family 27 (fatty acid transporter), member 2 | SLC27A2 | 11001 | 3.907836 | 0.659838 |
| 202156_s_at | CUG triplet repeat, RNA binding protein 2 | CUGBP2 | 10659 | 3.893065 | 0.659838 |
| 217773_s_at | NADH dehydrogenase (ubiquinone) 1 alpha subcomplex, 4, 9kDa | NDUFA4 | 4697 | 3.872607 | 0.659838 |
| 211434_s_at | chemokine (C-C motif) receptor-like 2 /// similar to chemokine (C-C motif) receptor-like 2 | CCRL2 /// LOC727811 | 727811 /// 9034 | 3.865089 | 0.659838 |
| 208965_s_at | interferon, gamma-inducible protein 16 | IFI16 | 3428 | 3.859984 | 0.659838 |
| 205891_at | adenosine A2b receptor | ADORA2B | 136 | 3.842007 | 0.659838 |
| 215537_x_at | dimethylarginine dimethylaminohydrolase 2 | DDAH2 | 23564 | 3.833539 | 0.659838 |
| 201426_s_at | vimentin | VIM | 7431 | 3.830078 | 0.659838 |
| 219296_at | zinc finger, DHHC-type containing 13 | ZDHHC13 | 54503 | 3.826049 | 0.659838 |
| 201564_s_at | fascin homolog 1, actin-bundling protein (Strongylocentrotus purpuratus) | FSCN1 | 6624 | 3.802566 | 0.659838 |
| 200848_at | S-adenosylhomocysteine hydrolase-like 1 | AHCYL1 | 10768 | 3.795461 | 0.659838 |
| 201329_s_at | v-ets erythroblastosis virus E26 oncogene homolog 2 (avian) | ETS2 | 2114 | 3.775619 | 0.659838 |
| 212185_x_at | metallothionein 2A | MT2A | 4502 | 3.772668 | 0.659838 |
| 215949_x_at | immunoglobulin heavy constant mu | IGHM | 3507 | 3.74507 | 0.659838 |
| 217065_at | T cell receptor alpha locus | TRA@ | 6955 | 3.742999 | 0.659838 |
| 202110_at | cytochrome c oxidase subunit VIIb | COX7B | 1349 | 3.735991 | 0.659838 |
| 216538_at | mRNA; cDNA DKFZp566C093 (from clone DKFZp566C093) | | | 3.718778 | 0.659838 |
| 206248_at | protein kinase C, epsilon | PRKCE | 5581 | 3.704881 | 0.659838 |
| 205267_at | POU class 2 associating factor 1 | POU2AF1 | 5450 | 3.70105 | 0.659838 |
| 207734_at | lymphocyte transmembrane adaptor 1 | LAX1 | 54900 | 3.690583 | 0.659838 |
| 204138_s_at | myeloid zinc finger 1 | MZF1 | 7593 | 3.684846 | 0.659838 |
| 218751_s_at | F-box and WD repeat domain containing 7 | FBXW7 | 55294 | 3.673787 | 0.659838 |
| 210279_at | G protein-coupled receptor 18 | GPR18 | 2841 | 3.668422 | 0.659838 |
| 210951_x_at | RAB27A, member RAS oncogene family | RAB27A | 5873 | 3.667693 | 0.659838 |
| 221309_at | RNA binding motif protein 17 | RBM17 | 84991 | 3.667668 | 0.659838 |
| 217622_at | rhomboid domain containing 3 | RHBDD3 | 25807 | 3.646813 | 0.659838 |
| 204220_at | glia maturation factor, gamma | GMFG | 9535 | 3.641916 | 0.659838 |
| 205173_x_at | CD58 molecule | CD58 | 965 | 3.638125 | 0.659838 |
| 218193_s_at | golgi transport 1 homolog B (S. cerevisiae) | GOLT1B | 51026 | 3.62911 | 0.659838 |
| 213996_at | yippee-like 1 (Drosophila) | YPEL1 | 29799 | 3.621062 | 0.659838 |

FIGURE 15 (CONTINUED)

| | | | | |
|---|---|---|---|---|
| 208522_s_at | patched homolog 1 (Drosophila) | PTCH1 | 5727 | 3.610641 | 0.659838 |
| 214459_x_at | major histocompatibility complex, class I, C | HLA-C | 3107 | 3.609019 | 0.659838 |
| 217371_s_at | interleukin 15 | IL15 | 3600 | 3.593537 | 0.659838 |
| 219600_s_at | transmembrane protein 50B | TMEM50B | 757 | 3.59194 | 0.659838 |
| 206458_s_at | wingless-type MMTV integration site family, member 2B | WNT2B | 7482 | 3.579152 | 0.659838 |
| 202652_x_at | dimethylarginine dimethylaminohydrolase 2 | DDAH2 | 23564 | 3.57425 | 0.659838 |
| 206824_at | carboxylesterase 1 (monocyte/macrophage serine esterase 1) /// carboxylesterase 4-like | CES1 /// CES4 | 1066 /// 51716 | 3.574053 | 0.659838 |
| 219070_s_at | motile sperm domain containing 3 | MOSPD3 | 64598 | 3.568675 | 0.659838 |
| 212956_at | TBC1 domain family, member 9 (with GRAM domain) | TBC1D9 | 23158 | 3.565038 | 0.659838 |
| 205966_at | TAF13 RNA polymerase II, TATA box binding protein (TBP)-associated factor, 18kDa | TAF13 | 6884 | 3.557187 | 0.659838 |
| 221927_s_at | abhydrolase domain containing 11 | ABHD11 | 83451 | 3.557071 | 0.659838 |
| 203763_at | dynein, cytoplasmic 2, light intermediate chain 1 | DYNC2LI1 | 51626 | 3.549701 | 0.659838 |
| 209761_s_at | SP110 nuclear body protein | SP110 | 3431 | 3.52679 | 0.659838 |
| 214244_s_at | ATPase, H+ transporting, lysosomal 9kDa, V0 subunit e1 | ATP6V0E1 | 8992 | 3.518142 | 0.659838 |
| 207191_s_at | immunoglobulin superfamily containing leucine-rich repeat | ISLR | 3671 | 3.517028 | 0.659838 |
| 208791_at | clusterin | CLU | 1191 | 3.516989 | 0.659838 |
| 205992_s_at | interleukin 15 | IL15 | 3600 | 3.516398 | 0.659838 |
| 218747_s_at | TAP binding protein-like | TAPBPL | 55080 | 3.513271 | 0.659838 |
| 217993_s_at | methionine adenosyltransferase II, beta | MAT2B | 27430 | 3.512097 | 0.659838 |
| 221474_at | myosin regulatory light chain MRLC2 | MRLC2 | 103910 | 3.510823 | 0.659838 |
| 203297_s_at | jumonji, AT rich interactive domain 2 | JARID2 | 3720 | 3.505619 | 0.659838 |
| 203002_at | angiomotin like 2 | AMOTL2 | 51421 | 3.488415 | 0.659838 |
| 207955_at | chemokine (C-C motif) ligand 27 | CCL27 | 10850 | 3.484061 | 0.659838 |
| 204234_s_at | zinc finger protein 195 | ZNF195 | 7748 | 3.479671 | 0.659838 |
| 203581_at | RAB4A, member RAS oncogene family | RAB4A | 5867 | 3.453963 | 0.659838 |
| 214329_x_at | tumor necrosis factor (ligand) superfamily, member 10 | TNFSF10 | 8743 | 3.449907 | 0.659838 |
| 220952_s_at | pleckstrin homology domain containing, family A member 5 | PLEKHA5 | 54477 | 3.44818 | 0.659838 |
| 203233_at | interleukin 4 receptor | IL4R | 3566 | 3.431601 | 0.659838 |
| 222256_s_at | phospholipase A2, group IVB (cytosolic) | PLA2G4B | 8681 | 3.429655 | 0.659838 |
| 219201_s_at | twisted gastrulation homolog 1 (Drosophila) | TWSG1 | 57045 | 3.429153 | 0.659838 |
| 221838_at | kelch-like 22 (Drosophila) | KLHL22 | 84861 | 3.419488 | 0.659838 |
| 215669_at | major histocompatibility complex, class II, DR beta 4 | HLA-DRB4 | 3126 | 3.418962 | 0.659838 |
| 205731_s_at | nuclear receptor coactivator 2 | NCOA2 | 10499 | 3.417031 | 0.659838 |
| 204035_at | secretogranin II (chromogranin C) | SCG2 | 7857 | 3.416442 | 0.659838 |
| 202158_s_at | CUG triplet repeat, RNA binding protein 2 | CUGBP2 | 10659 | 3.4148 | 0.659838 |
| 212419_at | chromosome 10 open reading frame 56 | C10orf56 | 219654 | 3.404936 | 0.659838 |
| 204951_at | ras homolog gene family, member H | RHOH | 399 | 3.399886 | 0.659838 |
| 217097_s_at | putative homeodomain transcription factor 2 | PHTF2 | 57157 | 3.38868 | 0.659838 |
| 220092_s_at | anthrax toxin receptor 1 | ANTXR1 | 84168 | 3.373963 | 0.659838 |
| 200968_s_at | peptidylprolyl isomerase B (cyclophilin B) | PPIB | 5479 | 3.368793 | 0.659838 |
| 221968_s_at | zinc finger protein 771 | ZNF771 | 51333 | 3.361364 | 0.659838 |
| 221577_x_at | growth differentiation factor 15 | GDF15 | 9518 | 3.358331 | 0.659838 |
| 205750_at | biphenyl hydrolase-like (serine hydrolase; breast epithelial mucin-associated antigen) | BPHL | 670 | 3.357068 | 0.659838 |
| 215142_at | chromosome X open reading frame 27 | CXorf27 | 25763 | 3.356985 | 0.659838 |

FIGURE 15 (CONTINUED)

| | | | | | |
|---|---|---|---|---|---|
| 211996_s_at | KIAA0220-like protein /// hypothetical gene LOC283846 /// hypothetical protein LOC440345 /// nuclear pore complex interacting protein pseudogene /// similar to Protein KIAA0220 | DKFZp547E087 /// LOC23117 /// LOC440345 /// LOC440353 /// LOC613037 /// LOC728888 | 23117 /// 283846 /// 440345 /// 440353 /// 613037 /// 728888 | 3.355306 | 0.659838 |
| 209349_at | RAD50 homolog (S. cerevisiae) | RAD50 | 10111 | 3.352697 | 0.659838 |
| 208812_x_at | major histocompatibility complex, class I, C /// similar to major histocompatibility complex, class I, C | HLA-C /// LOC732037 | 3107 /// 732037 | 3.352429 | 0.659838 |
| 204833_at | ATG12 autophagy related 12 homolog (S. cerevisiae) | ATG12 | 9140 | 3.349624 | 0.659838 |
| 211211_x_at | SH2 domain protein 1A, Duncan's disease (lymphoproliferative syndrome) | SH2D1A | 4068 | 3.349475 | 0.659838 |
| 203140_at | B-cell CLL/lymphoma 6 (zinc finger protein 51) | BCL6 | 604 | 3.347008 | 0.659838 |
| 210325_at | CD1a molecule | CD1A | 909 | 3.341012 | 0.659838 |
| 213303_x_at | zinc finger and BTB domain containing 7A | ZBTB7A | 51341 | 3.338424 | 0.659838 |
| 202499_s_at | solute carrier family 2 (facilitated glucose transporter), member 3 | SLC2A3 | 6515 | 3.337949 | 0.659838 |
| 213295_at | cylindromatosis (turban tumor syndrome) | CYLD | 1540 | 3.334121 | 0.659838 |
| 211025_x_at | cytochrome c oxidase subunit Vb | COX5B | 1329 | 3.330707 | 0.659838 |
| 204030_s_at | schwannomin interacting protein 1 | SCHIP1 | 29970 | 3.329693 | 0.659838 |
| 208305_at | progesterone receptor | PGR | 5241 | 3.326261 | 0.659838 |
| 214303_x_at | mucin 5AC, oligomeric mucus/gel-forming | MUC5AC | 4586 | 3.322572 | 0.659838 |
| 201470_at | glutathione S-transferase omega 1 | GSTO1 | 9446 | 3.321774 | 0.659838 |
| 216526_x_at | major histocompatibility complex, class I, C | HLA-C | 3107 | 3.319907 | 0.659838 |
| 200760_s_at | ADP-ribosylation-like factor 6 interacting protein 5 | ARL6IP5 | 10550 | 3.319819 | 0.659838 |
| 221750_at | 3-hydroxy-3-methylglutaryl-Coenzyme A synthase 1 (soluble) | HMGCS1 | 3157 | 3.318456 | 0.659838 |
| 208729_x_at | major histocompatibility complex, class I, B | HLA-B | 3106 | 3.31338 | 0.659838 |
| 215685_s_at | distal-less homeobox 2 | DLX2 | 1746 | 3.311145 | 0.659838 |
| 216986_s_at | interferon regulatory factor 4 | IRF4 | 3662 | 3.310301 | 0.659838 |
| 209514_s_at | RAB27A, member RAS oncogene family | RAB27A | 5873 | 3.284745 | 0.659838 |
| 205069_s_at | Rho GTPase activating protein 26 | ARHGAP26 | 23092 | 3.280985 | 0.659838 |
| 51200_at | chromosome 19 open reading frame 60 | C19orf60 | 55049 | 3.280458 | 0.659838 |
| 209575_at | interleukin 10 receptor, beta | IL10RB | 3588 | 3.276532 | 0.659838 |
| 202996_at | polymerase (DNA-directed), delta 4 | POLD4 | 57804 | 3.274484 | 0.659838 |
| 209381_x_at | splicing factor 3a, subunit 2, 66kDa | SF3A2 | 8175 | 3.273434 | 0.659838 |
| 209463_s_at | TAF12 RNA polymerase II, TATA box binding protein (TBP)-associated factor, 20kDa | TAF12 | 6883 | 3.273109 | 0.659838 |
| 209331_s_at | MYC associated factor X | MAX | 4149 | 3.272007 | 0.659838 |
| 205379_at | carbonyl reductase 3 | CBR3 | 874 | 3.269499 | 0.659838 |
| 212451_at | KIAA0256 gene product | KIAA0256 | 9728 | 3.266836 | 0.659838 |
| 207742_s_at | nuclear receptor subfamily 6, group A, member 1 | NR6A1 | 2649 | 3.25911 | 0.659838 |
| 211856_x_at | CD28 molecule | CD28 | 940 | 3.252538 | 0.659838 |
| 200814_at | proteasome (prosome, macropain) activator subunit 1 (PA28 alpha) | PSME1 | 5720 | 3.242506 | 0.659838 |
| 212613_at | butyrophilin, subfamily 3, member A2 | BTN3A2 | 11118 | 3.241053 | 0.659838 |
| 217165_x_at | metallothionein 1F | MT1F | 4494 | 3.236414 | 0.659838 |
| 203842_s_at | microtubule-associated protein, RP/EB family, member 3 | MAPRE3 | 22924 | 3.230593 | 0.659838 |
| 217329_x_at | --- | --- | --- | 3.229426 | 0.659838 |
| 215313_x_at | major histocompatibility complex, class I, A | HLA-A | 3105 | 3.228022 | 0.659838 |

FIGURE 15 (CONTINUED)

| | | | | |
|---|---|---|---|---|
| 217422_s_at | CD22 molecule | CD22 | 933 | 3.225762 | 0.659838 |
| 211796_s_at | T cell receptor beta variable 19 /// T cell receptor beta variable 7-2 /// T cell receptor beta variable 3-1 /// T cell receptor beta variable 5-4 /// T cell receptor beta constant 1 | TRBC1 /// TRBV19 /// TRBV3-1 /// TRBV5-4 /// TRBV7-2 | 28568 /// 28596 /// 28611 /// 28619 /// 28629 | 3.22505 | 0.659838 |
| 216055_at | platelet-derived growth factor beta polypeptide (simian sarcoma viral (v-sis) oncogene homolog) | PDGFB | 5155 | 3.214513 | 0.659838 |
| 202709_at | fibromodulin | FMOD | 2331 | 3.211581 | 0.659838 |
| 202343_x_at | cytochrome c oxidase subunit Vb | COX5B | 1329 | 3.211032 | 0.659838 |
| 212509_s_at | matrix-remodelling associated 7 | MXRA7 | 439921 | 3.201045 | 0.659838 |
| 210123_s_at | cholinergic receptor, nicotinic, alpha 7 /// CHRNA7 (cholinergic receptor, nicotinic, alpha 7, exons 5-10) and FAM7A (family with sequence similarity 7A, exons A-E) fusion | CHRFAM7A /// CHRNA7 | 1139 /// 89832 | 3.200541 | 0.659838 |
| 204571_x_at | protein (peptidylprolyl cis/trans isomerase) NIMA-interacting, 4 (parvulin) | PIN4 | 5303 | 3.200555 | 0.659838 |
| 202101_s_at | v-ral simian leukemia viral oncogene homolog B (ras related; GTP binding protein) | RALB | 5899 | 3.195971 | 0.659838 |
| 216448_at | CDNA FLJ12624 fis, clone NT2RM4001754 | | | 3.195322 | 0.659838 |
| 214669_x_at | immunoglobulin kappa locus | IGK@ | 50802 | 3.191469 | 0.659838 |
| 208465_at | glutamate receptor, metabotropic 2 | GRM2 | 2912 | 3.184808 | 0.659838 |
| 215075_s_at | growth factor receptor-bound protein 2 | GRB2 | 2885 | 3.182688 | 0.659838 |
| 207132_x_at | prefoldin subunit 5 | PFDN5 | 5204 | 3.175111 | 0.659838 |
| 203831_at | R3H domain containing 2 | R3HDM2 | 22864 | 3.173792 | 0.659838 |
| 206337_at | chemokine (C-C motif) receptor 7 | CCR7 | 1236 | 3.172548 | 0.659838 |
| 218922_s_at | LAG1 homolog, ceramide synthase 4 | LASS4 | 79603 | 3.165543 | 0.659838 |
| 208040_s_at | myosin binding protein C, cardiac | MYBPC3 | 4607 | 3.164944 | 0.659838 |
| 208187_s_at | | | | 3.163819 | 0.659838 |
| 222294_s_at | CDNA clone IMAGE:5745639 | | | 3.163475 | 0.659838 |
| 219451_at | methionine sulfoxide reductase B2 | MSRB2 | 22921 | 3.158655 | 0.659838 |
| 202206_at | ADP-ribosylation factor-like 4C | ARL4C | 10123 | 3.145435 | 0.659838 |
| 203758_at | cathepsin O | CTSO | 1519 | 3.145395 | 0.659838 |
| 221912_s_at | coiled-coil domain containing 28B | CCDC28B | 79140 | 3.143915 | 0.659838 |
| 205163_at | fast skeletal myosin light chain 2 | MYLPF | 29895 | 3.142725 | 0.659838 |
| 200046_at | defender against cell death 1 | DAD1 | 1603 | 3.127426 | 0.659838 |
| 218380_at | NLR family, pyrin domain containing 1 | NLRP1 | 22861 | 3.127069 | 0.659838 |
| 203595_s_at | interferon-induced protein with tetratricopeptide repeats 5 | IFIT5 | 24138 | 3.125097 | 0.659838 |
| 203313_s_at | TGFB-induced factor homeobox 1 | TGIF1 | 7050 | 3.123613 | 0.659838 |
| 202822_at | LIM domain containing preferred translocation partner in lipoma | LPP | 4026 | 3.123101 | 0.659838 |
| 214358_at | acetyl-Coenzyme A carboxylase alpha | ACACA | 31 | 3.117105 | 0.659838 |
| 206821_x_at | HIV-1 Rev binding protein-like | HRBL | 3268 | 3.108878 | 0.659838 |
| 215412_x_at | postmeiotic segregation increased 2-like 2 | PMS2L2 | 5380 | 3.108382 | 0.659838 |
| 200616_s_at | KIAA0152 | KIAA0152 | 9761 | 3.108375 | 0.659838 |
| 214069_at | acyl-CoA synthetase medium-chain family member 2A /// acyl-CoA synthetase medium-chain family member 2B | ACSM2A /// ACSM2B | 123876 /// 348158 | 3.107276 | 0.659838 |
| 209846_s_at | butyrophilin, subfamily 3, member A2 | BTN3A2 | 11118 | 3.104637 | 0.659838 |
| 218600_at | LIM domain containing 2 | LIMD2 | 80774 | 3.103956 | 0.659838 |
| 218589_at | purinergic receptor P2Y, G-protein coupled, 5 | P2RY5 | 10161 | 3.100489 | 0.659838 |
| 215211_at | RRN3 RNA polymerase I transcription factor homolog (S. cerevisiae) pseudogene | LOC730092 | 730092 | 3.097573 | 0.659838 |
| 208403_x_at | MYC associated factor X | MAX | 4149 | 3.097516 | 0.659838 |

FIGURE 15 (CONTINUED)

| | | | | | |
|---|---|---|---|---|---|
| 204867_at | GTP cyclohydrolase I feedback regulator | GCHFR | | 2644 | 3.095074 | 0.659838 |
| 219724_s_at | KIAA0748 | KIAA0748 | | 9840 | 3.092041 | 0.659838 |
| 214054_at | docking protein 2, 56kDa | DOK2 | | 9046 | 3.088263 | 0.659838 |
| 203964_at | N-myc (and STAT) interactor | NMI | | 9111 | 3.078189 | 0.659838 |
| 219759_at | endoplasmic reticulum aminopeptidase 2 | ERAP2 | | 64167 | 3.076226 | 0.659838 |
| 204174_at | arachidonate 5-lipoxygenase-activating protein | ALOX5AP | | 241 | 3.074033 | 0.659838 |
| 202296_s_at | RER1 retention in endoplasmic reticulum 1 homolog (S. cerevisiae) | RER1 | | 11079 | 3.074005 | 0.659838 |
| 202207_at | ADP-ribosylation factor-like 4C | ARL4C | | 10123 | 3.071935 | 0.659838 |
| 213915_at | natural killer cell group 7 sequence | NKG7 | | 4818 | 3.071858 | 0.659838 |
| 200604_s_at | protein kinase, cAMP-dependent, regulatory, type I, alpha (tissue specific extinguisher 1) | PRKAR1A | | 5573 | 3.071435 | 0.659838 |
| 219066_at | phosphopantothenoylcysteine decarboxylase | PPCDC | | 60490 | 3.070842 | 0.659838 |
| 212853_at | DCN1, defective in cullin neddylation 1, domain containing 4 (S. cerevisiae) | DCUN1D4 | | 23142 | 3.065712 | 0.659838 |
| 207677_s_at | neutrophil cytosolic factor 4, 40kDa | NCF4 | | 4689 | 3.062292 | 0.659838 |
| 218610_s_at | hypothetical protein FLJ11151 | FLJ11151 | | 55313 | 3.059331 | 0.659838 |
| 212452_x_at | MYST histone acetyltransferase (monocytic leukemia) 4 | MYST4 | | 23522 | 3.056358 | 0.659838 |
| 221044_s_at | tripartite motif-containing 34 /// TRIM6-TRIM34 | TRIM34 /// TRIM6-TRIM34 | 445372 /// 53840 | 3.052578 | 0.659838 |
| 49679_s_at | Metallothionein 1 pseudogene 3 | MT1P3 | | 140851 | 3.050689 | 0.659838 |
| 213357_at | general transcription factor IIH, polypeptide 5 | GTF2H5 | | 404672 | 3.050053 | 0.659838 |
| 214512_s_at | SUB1 homolog (S. cerevisiae) | SUB1 | | 10923 | 3.049781 | 0.659838 |
| 201328_at | v-ets erythroblastosis virus E26 oncogene homolog 2 (avian) | ETS2 | | 2114 | 3.045932 | 0.659838 |
| 209201_x_at | chemokine (C-X-C motif) receptor 4 | CXCR4 | | 7852 | 3.044945 | 0.659838 |
| 218992_at | chromosome 9 open reading frame 46 | C9orf46 | | 55848 | 3.043275 | 0.659838 |
| 218559_s_at | v-maf musculoaponeurotic fibrosarcoma oncogene homolog B (avian) | MAFB | | 9935 | 3.039409 | 0.659838 |
| 201045_s_at | RAB6A, member RAS oncogene family /// RAB6C-like | LOC150786 /// RAB6A | 150786 /// 5870 | 3.038122 | 0.659838 |
| 217888_s_at | ADP-ribosylation factor GTPase activating protein 1 | ARFGAP1 | | 55738 | 3.035113 | 0.659838 |
| 212954_at | dual-specificity tyrosine-(Y)-phosphorylation regulated kinase 4 | DYRK4 | | 8798 | 3.035098 | 0.659838 |
| 215173_at | leucine rich repeat containing 50 | LRRC50 | | 123872 | 3.033865 | 0.659838 |
| 202393_s_at | Kruppel-like factor 10 | KLF10 | | 7071 | 3.029521 | 0.659838 |
| 215223_s_at | superoxide dismutase 2, mitochondrial | SOD2 | | 6648 | 3.026709 | 0.659838 |
| 209147_s_at | phosphatidic acid phosphatase type 2A | PPAP2A | | 8611 | 3.024863 | 0.659838 |
| 205910_s_at | carboxyl ester lipase (bile salt-stimulated lipase) | CEL | | 1056 | 3.023574 | 0.659838 |
| 214144_at | Polymerase (RNA) II (DNA directed) polypeptide D | POLR2D | | 5433 | 3.01744 | 0.659838 |
| 220160_s_at | kaptin (actin binding protein) | KPTN | | 11133 | 3.016844 | 0.659838 |
| 211456_x_at | metallothionein 1 pseudogene 2 | MT1P2 | | 645745 | 3.012768 | 0.659838 |
| 217981_s_at | fracture callus 1 homolog (rat) | FXC1 | | 26515 | 3.010512 | 0.659838 |
| 207179_at | T-cell leukemia homeobox 1 | TLX1 | | 3195 | 3.008433 | 0.659838 |
| 214841_at | cornichon homolog 3 (Drosophila) | CNIH3 | | 149111 | 3.008379 | 0.659838 |
| 217751_at | glutathione S-transferase kappa 1 | GSTK1 | | 373156 | 3.008181 | 0.659838 |
| 216470_x_at | protease, serine, 1 (trypsin 1) /// protease, serine, 2 (trypsin 2) /// protease, serine, 3 (mesotrypsin) /// trypsinogen C | PRSS1 /// PRSS2 /// PRSS3 /// TRY6 | 154754 /// 5645 /// 5646 /// 5644 | 3.007066 | 0.659838 |
| 209344_at | tropomyosin 4 | TPM4 | | 7171 | 3.005798 | 0.659838 |
| 220492_s_at | otoferlin | OTOF | | 9381 | 3.004706 | 0.659838 |

FIGURE 15 (CONTINUED)

| Probe ID | Description | Symbol | Value1 | Value2 | Value3 |
|---|---|---|---|---|---|
| 216859_x_at | --- | --- | --- | 3.00434 | 0.659838 |
| 221693_s_at | mitochondrial ribosomal protein S18A | MRPS18A | 55168 | 3.003459 | 0.659838 |
| 208012_x_at | SP110 nuclear body protein | SP110 | 3431 | 2.991967 | 0.659838 |
| 209292_at | Inhibitor of DNA binding 4, dominant negative helix-loop-helix protein | ID4 | 3400 | 2.991604 | 0.659838 |
| 219534_x_at | cyclin-dependent kinase inhibitor 1C (p57, Kip2) | CDKN1C | 1028 | 2.989513 | 0.659838 |
| 218400_at | 2'-5'-oligoadenylate synthetase 3, 100kDa | OAS3 | 4940 | 2.98878 | 0.659838 |
| 201295_s_at | --- | --- | --- | 2.987276 | 0.659838 |
| 218250_s_at | CCR4-NOT transcription complex, subunit 7 | CNOT7 | 29883 | 2.984043 | 0.659838 |
| 220769_s_at | WD repeat domain 78 | WDR78 | 79819 | 2.983825 | 0.659838 |
| 221277_s_at | pseudouridylate synthase 3 | PUS3 | 83480 | 2.978688 | 0.659838 |
| 205198_s_at | ATPase, Cu++ transporting, alpha polypeptide (Menkes syndrome) /// similar to ATPase, Cu++ transporting, alpha polypeptide | ATP7A /// LOC644732 | 538 /// 644732 | 2.976605 | 0.659838 |
| 200849_s_at | S-adenosylhomocysteine hydrolase-like 1 | AHCYL1 | 10768 | 2.975782 | 0.659838 |
| 206508_at | CD70 molecule | CD70 | 970 | 2.972228 | 0.659838 |
| 221200_at | --- | --- | --- | 2.966979 | 0.659838 |
| 212587_s_at | protein tyrosine phosphatase, receptor type, C | PTPRC | 5788 | 2.958381 | 0.659838 |
| 205692_s_at | CD38 molecule | CD38 | 952 | 2.957133 | 0.659838 |
| 204326_x_at | metallothionein 1X | MT1X | 4501 | 2.953085 | 0.659838 |
| 207238_s_at | protein tyrosine phosphatase, receptor type, C | PTPRC | 5788 | 2.952252 | 0.659838 |
| 212851_at | solute carrier family 25 (mitochondrial carrier; glutamate), member 22 | SLC25A22 | 79751 | 2.951625 | 0.659838 |
| 207766_at | DCN1, defective in cullin neddylation 1, domain containing 4 (S. cerevisiae) | DCUN1D4 | 23142 | 2.950332 | 0.659838 |
| 206751_s_at | cyclin-dependent kinase-like 1 (CDC2-related kinase) | CDKL1 | 8814 | 2.948535 | 0.659838 |
| 222275_at | phosphate cytidylyltransferase 1, choline, beta | PCYT1B | 9468 | 2.940486 | 0.659838 |
| 200878_at | Full-length cDNA clone CS0DK012YA15 of HeLa cells Cot 25-normalized of Homo sapiens (human) | --- | --- | 2.937275 | 0.659838 |
| 209924_at | endothelial PAS domain protein 1 | EPAS1 | 2034 | 2.935505 | 0.659838 |
| 207694_at | chemokine (C-C motif) ligand 18 (pulmonary and activation-regulated) | CCL18 | 6362 | 2.933877 | 0.659838 |
| 201246_s_at | POU class 3 homeobox 4 | POU3F4 | 5456 | 2.933324 | 0.659838 |
| 210638_s_at | OTU domain, ubiquitin aldehyde binding 1 | OTUB1 | 55611 | 2.932434 | 0.659838 |
| 201055_s_at | F-box protein 9 | FBXO9 | 26268 | 2.931394 | 0.659838 |
| 202435_s_at | heterogeneous nuclear ribonucleoprotein A0 | HNRNPA0 | 10949 | 2.930226 | 0.659838 |
| 216137_at | cytochrome P450, family 1, subfamily B, polypeptide 1 | CYP1B1 | 1545 | 2.927656 | 0.659838 |
| 1431_at | Mitogen-activated protein kinase 8 interacting protein 3 | MAPK8IP3 | 23162 | 2.92755 | 0.659838 |
| 221562_s_at | cytochrome P450, family 2, subfamily E, polypeptide 1 | CYP2E1 | 1571 | 2.925226 | 0.659838 |
| 219506_at | sirtuin (silent mating type information regulation 2 homolog) 3 (S. cerevisiae) | SIRT3 | 23410 | 2.915722 | 0.659838 |
| 205784_x_at | chromosome 1 open reading frame 54 | C1orf54 | 79630 | 2.9111 | 0.659838 |
| 221507_at | armadillo repeat gene deletes in velocardiofacial syndrome | ARVCF | 421 | 2.910897 | 0.659838 |
| 222200_s_at | transportin 2 (importin 3, karyopherin beta 2b) | TNPO2 | 30000 | 2.907218 | 0.659838 |
| 205796_s_at | BSD domain containing 1 | BSDC1 | 55108 | 2.907084 | 0.659838 |
| 45714_at | t-complex 11 (mouse)-like 1 | TCP11L1 | 55346 | 2.906775 | 0.659838 |
| 206100_at | host cell factor C1 regulator 1 (XPO1 dependent) | HCFC1R1 | 54985 | 2.904465 | 0.659838 |
| 206410_at | carboxypeptidase M | CPM | 1368 | 2.902093 | 0.659838 |
| 203304_at | nuclear receptor subfamily 0, group B, member 2 | NR0B2 | 8431 | 2.901963 | 0.659838 |
| 205116_at | BMP and activin membrane-bound inhibitor homolog (Xenopus laevis) | BAMBI | 25805 | 2.898868 | 0.659838 |
| 212007_at | laminin, alpha 2 (merosin, congenital muscular dystrophy) | LAMA2 | 3908 | 2.898746 | 0.659838 |
| 204759_at | UBX domain containing 2 | UBXD2 | 23190 | 2.897988 | 0.659838 |
|  | regulator of chromosome condensation (RCC1) and BTB (POZ) domain containing protein 2 | RCBTB2 | 1102 | 2.894497 | 0.659838 |

FIGURE 15 (CONTINUED)

| | | | | |
|---|---|---|---|---|
| 207084_at | POU class 3 homeobox 2 | POU3F2 | 5454 | 2.888394 | 0.659838 |
| 206804_at | CD3g molecule, gamma (CD3-TCR complex) | CD3G | 917 | 2.8863 | 0.659838 |
| 205852_at | cyclin-dependent kinase 5, regulatory subunit 2 (p39) | CDKSR2 | 8941 | 2.886288 | 0.659838 |
| 203005_at | lymphotoxin beta receptor (TNFR superfamily, member 3) | LTBR | 4055 | 2.885604 | 0.659838 |
| 204683_at | intercellular adhesion molecule 2 | ICAM2 | 3384 | 2.885463 | 0.659838 |
| 220909_at | tripartite motif-containing 46 | TRIM46 | 80128 | 2.882499 | 0.659838 |
| 213257_at | sterile alpha and TIR motif containing 1 | SARM1 | 23098 | 2.879932 | 0.659838 |
| 201012_at | annexin A1 | ANXA1 | 301 | 2.878469 | 0.659838 |
| 220740_s_at | solute carrier family 12 (potassium/chloride transporters), member 6 | SLC12A6 | 9990 | 2.876374 | 0.659838 |
| 215069_at | N-myristoyltransferase 2 | NMT2 | 9397 | 2.875929 | 0.659838 |
| 213757_at | Transcribed locus, weakly similar to XP_001478155.1 PREDICTED: hypothetical protein [Mus musculus] | | | 2.87568 | 0.659838 |
| 215259_s_at | cell adhesion molecule 4 | CADM4 | 199731 | 2.874941 | 0.659838 |
| 222041_at | DPH1 homolog (S. cerevisiae) /// candidate tumor suppressor in ovarian cancer 2 | DPH1 /// OVCA2 | 124641 /// 1801 | 2.872937 | 0.659838 |
| 215863_at | transferrin receptor 2 | TFR2 | 7036 | 2.871378 | 0.659838 |
| 221243_s_at | | | | 2.869943 | 0.659838 |
| 205556_at | clusterin-like 1 (retinal) | CLUL1 | 27098 | 2.867342 | 0.659838 |
| 210104_at | mediator complex subunit 6 | MED6 | 10001 | 2.865525 | 0.659838 |
| 202180_s_at | major vault protein | MVP | 9961 | 2.861996 | 0.659838 |
| 204350_s_at | mediator complex subunit 7 | MED7 | 9443 | 2.857736 | 0.659838 |
| 216127_at | protein disulfide isomerase family A, member 2 | PDIA2 | 64714 | 2.856509 | 0.659838 |
| 207090_x_at | zinc finger protein 30 homolog (mouse) | ZFP30 | 22835 | 2.85321 | 0.659838 |
| 205224_at | surfeit 2 | SURF2 | 6835 | 2.851708 | 0.659838 |
| 213931_at | inhibitor of DNA binding 2, dominant negative helix-loop-helix protein /// inhibitor of DNA binding 2B, dominant negative helix-loop-helix protein | ID2 /// ID2B | 3398 /// 84099 | 2.850662 | 0.659838 |
| 211753_s_at | relaxin 1 | RLN1 | 6013 | 2.850191 | 0.659838 |
| 201729_at | serum/glucocorticoid regulated kinase 1 | SGK1 | 6446 | 2.845651 | 0.659838 |
| 221210_s_at | N-acetylneuraminate pyruvate lyase (dihydrodipicolinate synthase) | NPL | 80896 | 2.845403 | 0.659838 |
| 204257_at | fatty acid desaturase 3 | FADS3 | 3995 | 2.843792 | 0.659838 |
| 203260_at | HD domain containing 2 | HDDC2 | 51020 | 2.84045 | 0.659838 |
| 218169_at | Vac14 homolog (S. cerevisiae) | VAC14 | 55697 | 2.834142 | 0.659838 |
| 221557_s_at | lymphoid enhancer-binding factor 1 | LEF1 | 51176 | 2.831736 | 0.660294 |
| 215797_at | T cell receptor alpha variable 8-3 | TRAV8-3 | 28683 | 2.817516 | 0.666139 |
| 206076_at | leucine rich repeat containing 23 | LRRC23 | 10233 | 2.815688 | 0.666139 |
| 202011_at | tight junction protein 1 (zona occludens 1) | TJP1 | 7082 | 2.813338 | 0.666139 |
| 201194_at | selenoprotein W, 1 | SEPW1 | 6415 | 2.812785 | 0.666139 |
| 219667_s_at | B-cell scaffold protein with ankyrin repeats 1 | BANK1 | 55024 | 2.811398 | 0.666139 |
| 209772_s_at | CD24 molecule | CD24 | 934 | 2.80833 | 0.666139 |
| 205343_at | sulfotransferase family, cytosolic, 1C, member 2 | SULT1C2 | 6819 | 2.8079 | 0.666139 |
| 211613_s_at | glycerol-3-phosphate dehydrogenase 2 (mitochondrial) | GPD2 | 2820 | 2.807271 | 0.666139 |
| 202298_at | NADH dehydrogenase (ubiquinone) 1 alpha subcomplex, 1, 7.5kDa | NDUFA1 | 4694 | 2.804105 | 0.667653 |
| 200605_s_at | protein kinase, cAMP-dependent, regulatory, type I, alpha (tissue specific extinguisher 1) | PRKAR1A | 5573 | 2.801286 | 0.669687 |
| 202929_s_at | D-dopachrome tautomerase | DDT | 1652 | 2.799737 | 0.670415 |
| 202446_s_at | phospholipid scramblase 1 | PLSCR1 | 5359 | 2.797744 | 0.670898 |
| 201628_s_at | Ras-related GTP binding A | RRAGA | 10670 | 2.796942 | 0.670898 |

FIGURE 15 (CONTINUED)

| Probe ID | Description | Gene Symbol | ID | ID2 | Value | p-value |
|---|---|---|---|---|---|---|
| 208104_s_at | TSC22 domain family, member 4 | TSC22D4 | 81628 | | 2.79553 | 0.670898 |
| 209168_at | glycoprotein M6B | GPM6B | 2824 | | 2.793972 | 0.670898 |
| 211902_x_at | T cell receptor alpha locus | TRA@ | 6955 | | 2.791069 | 0.670898 |
| 211986_at | AHNAK nucleoprotein | AHNAK | 79026 | | 2.789055 | 0.670898 |
| 212784_at | capicua homolog (Drosophila) | CIC | 23152 | | 2.788591 | 0.670898 |
| 218482_at | enhancer of yellow 2 homolog (Drosophila) | ENY2 | 56943 | | 2.787771 | 0.670898 |
| 207339_s_at | lymphotoxin beta (TNF superfamily, member 3) | LTB | 4050 | | 2.782622 | 0.670898 |
| 218815_s_at | transmembrane protein 51 | TMEM51 | 55092 | | 2.779073 | 0.672275 |
| 221185_s_at | IQ motif containing G | IQCG | 84223 | | 2.778605 | 0.672275 |
| 211861_x_at | CD28 molecule | CD28 | 940 | | 2.776363 | 0.672275 |
| 219113_x_at | hydroxysteroid (17-beta) dehydrogenase 14 | HSD17B14 | 51171 | | 2.771317 | 0.67416 |
| 211465_x_at | fucosyltransferase 6 (alpha (1,3) fucosyltransferase) | FUT6 | 2528 | | 2.761412 | 0.676651 |
| 209671_x_at | T cell receptor alpha locus /// T cell receptor alpha constant | TRA@ /// TRAC | 28755 /// 6955 | | 2.760719 | 0.677651 |
| 205579_at | histamine receptor H1 | HRH1 | 3269 | | 2.753222 | 0.677769 |
| 217332_at | similar to CTAGE family, member 5 | LOC647288 /// LOC730587 | 647288 /// 730587 | | 2.750663 | 0.677769 |
| 218376_s_at | microtubule associated monoxygenase, calponin and LIM domain containing 1 | MICAL1 | 64780 | | 2.750547 | 0.677769 |
| 219161_s_at | chemokine-like factor | CKLF | 51192 | | 2.749735 | 0.677769 |
| 211911_x_at | major histocompatibility complex, class I, B | HLA-B | 3106 | | 2.749108 | 0.677769 |
| 202637_s_at | intercellular adhesion molecule 1 (CD54), human rhinovirus receptor | ICAM1 | 3383 | | 2.7474 | 0.677769 |
| 221696_s_at | serine/threonine/tyrosine kinase 1 | STYK1 | 55359 | | 2.744325 | 0.677769 |
| 219214_s_at | 5',3'-nucleotidase, cytosolic | NT5C | 30833 | | 2.742564 | 0.677769 |
| 218118_s_at | translocase of inner mitochondrial membrane 23 homolog (yeast) | TIMM23 | 10431 | | 2.740762 | 0.677769 |
| 218369_s_at | exosome component 1 | EXOSC1 | 51013 | | 2.740281 | 0.677769 |
| 210218_s_at | SP100 nuclear antigen | SP100 | 6672 | | 2.739249 | 0.677769 |
| 219107_at | brevican | BCAN | 63827 | | 2.737701 | 0.677769 |
| 222356_at | Transcribed locus | --- | | | 2.73657 | 0.677769 |
| 203610_s_at | tripartite motif-containing 38 | TRIM38 | 10475 | | 2.73411 | 0.677769 |
| 209276_s_at | glutaredoxin (thioltransferase) | GLRX | 2745 | | 2.732356 | 0.677769 |
| 208659_at | chloride intracellular channel 1 | CLIC1 | 1192 | | 2.73142 | 0.677769 |
| 210693_at | signal peptide peptidase-like 2B | SPPL2B | 56928 | | 2.730862 | 0.677769 |
| 211098_x_at | transmembrane and coiled-coil domains 1 | TMCO1 | 54499 | | 2.727776 | 0.677769 |
| 215645_at | Folliculin | FLCN | 201163 | | 2.720219 | 0.677769 |
| 203037_s_at | metastasis suppressor 1 | MTSS1 | 9788 | | 2.719512 | 0.677769 |
| 214480_at | ets variant gene 3 | ETV3 | 2117 | | 2.71931 | 0.677769 |
| 202592_at | biogenesis of lysosome-related organelles complex-1, subunit 1 | BLOC1S1 | 2647 | | 2.717615 | 0.677769 |
| 213050_at | cordon-bleu homolog (mouse) | COBL | 23342 | | 2.717062 | 0.677769 |
| 215579_at | apolipoprotein B mRNA editing enzyme, catalytic polypeptide-like 3G | APOBEC3G | 60489 | | 2.716052 | 0.677769 |
| 202562_s_at | chromosome 14 open reading frame 1 | C14orf1 | 11161 | | 2.714535 | 0.677769 |
| 211120_x_at | estrogen receptor 2 (ER beta) | ESR2 | 2100 | | 2.713074 | 0.677769 |
| 207508_at | ATP synthase, H+ transporting, mitochondrial F0 complex, subunit C3 (subunit 9) | ATP5G3 | 518 | | 2.71119 | 0.677769 |
| 201514_s_at | GTPase activating protein (SH3 domain) binding protein 1 | G3BP1 | 10146 | | 2.710628 | 0.677769 |
| 220544_at | testis-specific kinase substrate | TSKS | 60385 | | 2.706436 | 0.677769 |
| 212087_s_at | Era G-protein-like 1 (E. coli) | ERAL1 | 26284 | | 2.705626 | 0.677769 |
| 204973_at | gap junction protein, beta 1, 32kDa | GJB1 | 2705 | | 2.704887 | 0.677769 |

FIGURE 15 (CONTINUED)

| | | | | |
|---|---|---|---|---|
| 217059_at | mucin 7, secreted | MUC7 | 4589 | 2.704338 | 0.677769 |
| 218491_s_at | thymocyte nuclear protein 1 | THYN1 | 29087 | 2.703529 | 0.677769 |
| 216598_s_at | interferon induced transmembrane protein 1 (9-27) | IFITM1 | 8519 | 2.702711 | 0.677769 |
| 201601_x_at | chemokine (C-C motif) ligand 2 | CCL2 | 6347 | 2.702394 | 0.677769 |
| 203485_at | reticulon 1 | RTN1 | 6252 | 2.697201 | 0.677769 |
| 201590_x_at | annexin A2 | ANXA2 | 302 | 2.696669 | 0.677769 |
| 203932_at | major histocompatibility complex, class II, DM beta | HLA-DMB | 3109 | 2.694472 | 0.677769 |
| 218282_at | ER degradation enhancer, mannosidase alpha-like 2 | EDEM2 | 55741 | 2.692505 | 0.677769 |
| 203008_x_at | thioredoxin domain containing 9 | TXNDC9 | 101190 | 2.690061 | 0.677769 |
| 201891_s_at | beta-2-microglobulin | B2M | 567 | 2.689404 | 0.677769 |
| 221816_s_at | PHD finger protein 11 | PHF11 | 51131 | 2.684377 | 0.677769 |
| 211031_s_at | CAP-GLY domain containing linker protein 2 | CLIP2 | 7461 | 2.683228 | 0.677769 |
| 210723_x_at | hypothetical protein MGC4771 | MGC4771 | 84754 | 2.681853 | 0.677769 |
| 217966_s_at | family with sequence similarity 129, member A | FAM129A | 116496 | 2.679718 | 0.677769 |
| 218117_at | ring-box 1 | RBX1 | 9978 | 2.679083 | 0.677769 |
| 212303_x_at | | | | 2.67643 | 0.677769 |
| 219147_s_at | chromosome 9 open reading frame 95 | C9orf95 | 54981 | 2.6756 | 0.677769 |
| 212079_s_at | myeloid/lymphoid or mixed-lineage leukemia (trithorax homolog, Drosophila) | MLL | 4297 | 2.675356 | 0.677769 |
| 218996_at | TCF3 (E2A) fusion partner (in childhood Leukemia) | TFPT | 29844 | 2.674804 | 0.677769 |
| 201641_at | bone marrow stromal cell antigen 2 | BST2 | 684 | 2.672552 | 0.677769 |
| 220941_s_at | chromosome 21 open reading frame 91 | C21orf91 | 54149 | 2.672014 | 0.677769 |
| 205179_s_at | ADAM metallopeptidase domain 8 | ADAM8 | 101 | 2.668417 | 0.677769 |
| 218048_at | COMM domain containing 3 | COMMD3 | 23412 | 2.666564 | 0.677769 |
| 206484_s_at | X-prolyl aminopeptidase (aminopeptidase P) 2, membrane-bound | XPNPEP2 | 7512 | 2.665828 | 0.677769 |
| 214150_x_at | ATPase, H+ transporting, lysosomal 9kDa, V0 subunit e1 | ATP6V0E1 | 8992 | 2.662168 | 0.677769 |
| 217497_at | endothelial cell growth factor 1 (platelet-derived) | ECGF1 | 1890 | 2.660791 | 0.677769 |
| 201631_s_at | immediate early response 3 | IER3 | 8870 | 2.659463 | 0.677769 |
| 202325_s_at | ATP synthase, H+ transporting, mitochondrial F0 complex, subunit F6 | ATP5J | 522 | 2.658999 | 0.677769 |
| 205345_at | BRCA1 associated RING domain 1 | BARD1 | 580 | 2.656693 | 0.677769 |
| 201927_s_at | plakophilin 4 | PKP4 | 8502 | 2.655599 | 0.677769 |
| 202040_s_at | jumonji, AT rich interactive domain 1A | JARID1A | 5927 | 2.654263 | 0.677769 |
| 219475_at | oxidative stress induced growth inhibitor 1 | OSGIN1 | 29948 | 2.652746 | 0.677769 |
| 207867_at | paired box 4 | PAX4 | 5078 | 2.652009 | 0.677769 |
| 205098_at | chemokine (C-C motif) receptor 1 | CCR1 | 1230 | 2.651702 | 0.677769 |
| 202497_x_at | solute carrier family 2 (facilitated glucose transporter), member 3 | SLC2A3 | 6515 | 2.650363 | 0.677769 |
| 204960_at | protein tyrosine phosphatase, receptor type, C-associated protein | PTPRCAP | 5790 | 2.648818 | 0.677769 |
| 211436_at | Clone FLB4228 PRO1095 | | | 2.647207 | 0.677769 |
| 208249_s_at | TDP-glucose 4,6-dehydratase | TGDS | 23463 | 2.645811 | 0.677769 |
| 202074_s_at | optineurin | OPTN | 10133 | 2.645191 | 0.677769 |
| 205681_at | BCL2-related protein A1 | BCL2A1 | 597 | 2.642668 | 0.677769 |
| 214200_s_at | Collagen, type VI, alpha 1 | COL6A1 | 1291 | 2.637952 | 0.677769 |
| 219950_s_at | T-cell lymphoma invasion and metastasis 2 | TIAM2 | 26230 | 2.637371 | 0.677769 |
| 213875_x_at | chromosome 6 open reading frame 62 | C6orf62 | 81688 | 2.636735 | 0.677769 |
| 215444_s_at | tripartite motif-containing 31 | TRIM31 | 11074 | 2.635291 | 0.677769 |
| 212979_s_at | family with sequence similarity 115, member A | FAM115A | 9747 | 2.633892 | 0.677769 |
| 210223_s_at | major histocompatibility complex, class I-related | MR1 | 3140 | 2.632832 | 0.677769 |

FIGURE 15 (CONTINUED)

| | | | | |
|---|---|---|---|---|
| 218232_at | complement component 1, q subcomponent, A chain | C1QA | 712 | 2.632177 | 0.677769 |
| 210865_at | Fas ligand (TNF superfamily, member 6) | FASLG | 356 | 2.631157 | 0.677769 |
| 218786_at | 5'-nucleotidase domain containing 3 | NT5DC3 | 51559 | 2.630898 | 0.677769 |
| 205721_at | GDNF family receptor alpha 2 | GFRA2 | 2675 | 2.628027 | 0.677769 |
| 214534_at | histone cluster 1, H1b | HIST1H1B | 3009 | 2.622854 | 0.677769 |
| 200785_s_at | low density lipoprotein-related protein 1 (alpha-2-macroglobulin receptor) | LRP1 | 4035 | 2.621803 | 0.677769 |
| 202022_at | aldolase C, fructose-bisphosphate | ALDOC | 230 | 2.61928 | 0.677769 |
| 216780_at | CDNA: FLJ21911 fis, clone HEP03855 | | | 2.618278 | 0.677769 |
| 209789_at | coronin, actin binding protein, 2B | CORO2B | 10391 | 2.616127 | 0.677769 |
| 213346_at | chromosome 13 open reading frame 27 | C13orf27 | 93081 | 2.615397 | 0.677769 |
| 201585_s_at | splicing factor proline/glutamine-rich (polypyrimidine tract binding protein associated) | SFPQ | 6421 | 2.613151 | 0.677769 |
| 205278_at | glutamate decarboxylase 1 (brain, 67kDa) | GAD1 | 2571 | 2.61178 | 0.677769 |
| 208963_x_at | fatty acid desaturase 1 | FADS1 | 3992 | 2.610965 | 0.677769 |
| 213260_at | forkhead box C1 | FOXC1 | 2296 | 2.609683 | 0.677769 |
| 201224_s_at | serine/arginine repetitive matrix 1 | SRRM1 | 10250 | 2.609477 | 0.677769 |
| 203851_at | insulin-like growth factor binding protein 6 | IGFBP6 | 3489 | 2.608294 | 0.677769 |
| 218251_at | MID1 interacting protein 1 (gastrulation specific G12 homolog (zebrafish)) | MID1IP1 | 58526 | 2.607466 | 0.677769 |
| 220291_at | glycerophosphodiester phosphodiesterase domain containing 2 | GDPD2 | 54857 | 2.605695 | 0.677769 |
| 214909_s_at | dimethylarginine dimethylaminohydrolase 2 | DDAH2 | 23564 | 2.602671 | 0.677769 |
| 209584_x_at | apolipoprotein B mRNA editing enzyme, catalytic polypeptide-like 3C | APOBEC3C | 27350 | 2.601623 | 0.677769 |
| 208890_s_at | signal sequence receptor, alpha (translocon-associated protein alpha) | SSR1 | 6745 | 2.598212 | 0.677769 |
| 214554_at | histone cluster 1, H2al | HIST1H2AL | 8332 | 2.596813 | 0.677769 |
| 207263_x_at | vezatin, adherens junctions transmembrane protein | VEZT | 55591 | 2.591569 | 0.677769 |
| 209483_s_at | | | | 2.591377 | 0.677769 |
| 216971_s_at | plectin 1, intermediate filament binding protein 500kDa | PLEC1 | 5339 | 2.589861 | 0.677769 |
| 211304_x_at | potassium inwardly-rectifying channel, subfamily J, member 5 | KCNJ5 | 3762 | 2.588996 | 0.677769 |
| 213806_at | Purine-rich element binding protein A | PURA | 5813 | 2.588207 | 0.677769 |
| 210042_s_at | cathepsin Z | CTSZ | 1522 | 2.588089 | 0.677769 |
| 203456_at | PRA1 domain family, member 2 | PRAF2 | 11230 | 2.587603 | 0.677769 |
| 221684_s_at | myctalopin | NYX | 60506 | 2.586138 | 0.677769 |
| 218742_at | nuclear prelamin A recognition factor-like | NARFL | 64428 | 2.584359 | 0.677769 |
| 204586_at | bassoon (presynaptic cytomatrix protein) | BSN | 8927 | 2.584095 | 0.677769 |
| 208020_s_at | calcium channel, voltage-dependent, L type, alpha 1C subunit | CACNA1C | 775 | 2.582774 | 0.677769 |
| 216628_at | | | | 2.581445 | 0.677769 |
| 221597_s_at | HSPC171 protein | HSPC171 | 29100 | 2.580699 | 0.677769 |
| 205139_s_at | uronyl-2-sulfotransferase | UST | 10090 | 2.580267 | 0.677769 |
| 212595_s_at | DAZ associated protein 2 | DAZAP2 | 9802 | 2.578054 | 0.677955 |
| 221617_at | TAF9B RNA polymerase II, TATA box binding protein (TBP)-associated factor, 31kDa | TAF9B | 51616 | 2.576151 | 0.678698 |
| 214177_s_at | pre-B-cell leukemia homeobox interacting protein 1 | PBXIP1 | 57326 | 2.575209 | 0.679061 |
| 219599_at | eukaryotic translation initiation factor 4B | EIF4B | 1975 | 2.573357 | 0.679125 |
| 220748_s_at | zinc finger protein 580 | ZNF580 | 51157 | 2.570412 | 0.680212 |
| 217867_x_at | beta-site APP-cleaving enzyme 2 | BACE2 | 25825 | 2.568516 | 0.680212 |
| 201480_s_at | suppressor of Ty 5 homolog (S. cerevisiae) | SUPT5H | 6829 | 2.567312 | 0.680212 |
| 216649_at | ras responsive element binding protein 1 | RREB1 | 6239 | 2.567245 | 0.680212 |
| 204565_at | thioesterase superfamily member 2 | THEM2 | 55856 | 2.566983 | 0.680212 |
| 218805_at | GTPase, IMAP family member 5 | GIMAP5 | 55340 | 2.565282 | 0.681388 |

FIGURE 15 (CONTINUED)

| Probe ID | Description | Symbol | Value 1 | Value 2 | Value 3 |
|---|---|---|---|---|---|
| 218685_s_at | single-strand-selective monofunctional uracil-DNA glycosylase 1 | SMUG1 | 23583 | 2.563839 | 0.682293 |
| 202518_at | B-cell CLL/lymphoma 7B | BCL7B | 9275 | 2.563223 | 0.682232 |
| 204994_at | myxovirus (influenza virus) resistance 2 (mouse) | MX2 | 4600 | 2.559994 | 0.682811 |
| 213826_s_at | --- | --- | | 2.559324 | 0.683802 |
| 221877_at | CDNA FLJ38849 fis, clone MESAN2008936 | --- | | 2.557714 | 0.684821 |
| 208945_s_at | beclin 1 (coiled-coil, myosin-like BCL2 interacting protein) | BECN1 | 8678 | 2.553835 | 0.685223 |
| 209890_at | tetraspanin 5 | TSPAN5 | 10098 | 2.551888 | 0.685223 |
| 210908_s_at | prefoldin subunit 5 | PFDN5 | 5204 | 2.551711 | 0.685344 |
| 206344_at | paraoxonase 1 | PON1 | 5444 | 2.550452 | 0.685344 |
| 221875_x_at | major histocompatibility complex, class I, F | HLA-F | 3134 | 2.549092 | 0.685344 |
| 217811_at | selenoprotein T | SELT | 51714 | 2.547193 | 0.685344 |
| 220989_s_at | amnionless homolog (mouse) | AMN | 81693 | 2.545981 | 0.685344 |
| 39549_at | neuronal PAS domain protein 2 | NPAS2 | 4862 | 2.540313 | 0.685344 |
| 203349_s_at | ets variant gene 5 (ets-related molecule) | ETV5 | 2119 | 2.539169 | 0.685344 |
| 208757_at | transmembrane emp24 protein transport domain containing 9 | TMED9 | 54732 | 2.536351 | 0.685344 |
| 216964_at | ubiquitin specific peptidase 22 | USP22 | 23326 | 2.535836 | 0.685344 |
| 200601_at | actinin, alpha 4 | ACTN4 | 81 | 2.5348 | 0.685344 |
| 214533_at | chymase 1, mast cell | CMA1 | 1215 | 2.533767 | 0.685344 |
| 216611_s_at | solute carrier family 6 (neurotransmitter transporter, noradrenalin), member 2 | SLC6A2 | 6530 | 2.532548 | 0.685344 |
| 211997_x_at | H3 histone, family 3B (H3.3B) | H3F3B | 3021 | 2.529995 | 0.685344 |
| 216843_x_at | postmeiotic segregation increased 2-like 1 /// similar to postmeiotic segregation increased 2-like 2 | LOC732139 /// PMS2L1 | 5379 /// 732139 | 2.52914 | 0.685344 |
| 201833_at | histone deacetylase 2 | HDAC2 | 3066 | 2.528667 | 0.685344 |
| 201983_s_at | epidermal growth factor receptor (erythroblastic leukemia viral (v-erb-b) oncogene homolog, avian) | EGFR | 1956 | 2.527836 | 0.685344 |
| 215359_x_at | zinc finger protein 44 | ZNF44 | 51710 | 2.52717 | 0.685344 |
| 203910_at | Rho GTPase activating protein 29 | ARHGAP29 | 9411 | 2.525466 | 0.685344 |
| 215088_s_at | succinate dehydrogenase complex, subunit C, integral membrane protein, 15kDa | SDHC | 6391 | 2.524155 | 0.685344 |
| 213350_at | homeobox C8 | HOXC8 | 3224 | 2.52376 | 0.685344 |
| 212223_at | iduronate 2-sulfatase (Hunter syndrome) | IDS | 3423 | 2.520859 | 0.685344 |
| 211030_s_at | solute carrier family 6 (neurotransmitter transporter, taurine), member 6 | SLC6A6 | 6533 | 2.518367 | 0.685344 |
| 209359_x_at | runt-related transcription factor 1 (acute myeloid leukemia 1; aml1 oncogene) | RUNX1 | 861 | 2.517362 | 0.685344 |
| 219533_at | cyclin-dependent kinase inhibitor 1C (p57, Kip2) | CDKN1C | 1028 | 2.514528 | 0.685344 |
| 221479_s_at | BCL2/adenovirus E1B 19kDa interacting protein 3-like | BNIP3L | 665 | 2.511276 | 0.685344 |
| 204607_at | 3-hydroxy-3-methylglutaryl-Coenzyme A synthase 2 (mitochondrial) | HMGCS2 | 3158 | 2.51098 | 0.685344 |
| 218357_s_at | translocase of inner mitochondrial membrane 8 homolog B (yeast) | TIMM8B | 26521 | 2.510156 | 0.685344 |
| 218861_at | ring finger protein 25 | RNF25 | 64320 | 2.508715 | 0.685344 |
| 201275_at | farnesyl diphosphate synthase (farnesyl pyrophosphate synthetase, dimethylallyltranstransferase, geranyltranstransferase) | FDPS | 2224 | 2.507374 | 0.685344 |
| 218634_at | pleckstrin homology-like domain, family A, member 3 | PHLDA3 | 23612 | 2.504763 | 0.685344 |
| 218031_s_at | forkhead box N3 | FOXN3 | 1112 | 2.50473 | 0.685344 |
| 209046_s_at | GABA(A) receptor-associated protein-like 2 | GABARAPL2 | 11345 | 2.504257 | 0.685344 |
| 206754_s_at | cytochrome P450, family 2, subfamily B, polypeptide 7 pseudogene 1 | CYP2B7P1 | 1556 | 2.502132 | 0.685344 |
| 218007_s_at | ribosomal protein S27-like | RPS27L | 51065 | 2.500566 | 0.685344 |
| 211529_x_at | major histocompatibility complex, class I, G | HLA-G | 3135 | 2.500225 | 0.685344 |
| 217950_at | nitric oxide synthase interacting protein | NOSIP | 51070 | 2.499986 | 0.685344 |
| 200885_at | ras homolog gene family, member C | RHOC | 389 | 2.499244 | 0.685344 |

FIGURE 15 (CONTINUED)

| | | | | | |
|---|---|---|---|---|---|
| 219386_s_at | SLAM family member 8 | SLAMF8 | 56833 | 2.499004 | 0.685344 |
| 219106_s_at | kelch repeat and BTB (POZ) domain containing 10 | KBTBD10 | 10324 | 2.496366 | 0.685344 |
| 214298_x_at | septin 6 | 6-Sep | 23157 | 2.494717 | 0.685344 |
| 219668_at | ganglioside-induced differentiation-associated protein 1-like 1 | GDAP1L1 | 78997 | 2.490818 | 0.685344 |
| 219871_at | hypothetical FLJ13197 | FLJ13197 | 79667 | 2.490472 | 0.685344 |
| 201531_at | zinc finger protein 36, C3H type, homolog (mouse) | ZFP36 | 7538 | 2.490183 | 0.685344 |
| 202961_s_at | ATP synthase, H+ transporting, mitochondrial F0 complex, subunit F2 | ATP5I2 | 9551 | 2.488572 | 0.685344 |
| 209156_s_at | collagen, type VI, alpha 2 | COL6A2 | 1292 | 2.486827 | 0.685344 |
| 216605_s_at | carcinoembryonic antigen-related cell adhesion molecule 21 | CEACAM21 | 90273 | 2.486406 | 0.685344 |
| 216122_at | cDNA: FLJ20890 fis, clone ADKA03323 | | | 2.481554 | 0.685344 |
| 219097_x_at | chromosome 19 open reading frame 42 | C19orf42 | 79086 | 2.48075 | 0.685344 |
| 215526_at | mRNA; cDNA DKFZp586C2020 (from clone DKFZp586C2020) | | | 2.478739 | 0.685344 |
| 214617_at | perforin 1 (pore forming protein) | PRF1 | 5551 | 2.478682 | 0.685344 |
| 221326_s_at | tubulin, delta 1 | TUBD1 | 51174 | 2.475581 | 0.685344 |
| 207401_at | prospero homeobox 1 | PROX1 | 5629 | 2.474158 | 0.685344 |
| 218439_s_at | COMM domain containing 10 | COMMD10 | 51397 | 2.472923 | 0.685344 |
| 210304_at | phosphodiesterase 6B, cGMP-specific, rod, beta (congenital stationary night blindness 3, autosomal dominant) | PDE6B | 5158 | 2.472216 | 0.685344 |
| 214157_at | GNAS complex locus | GNAS | 2778 | 2.471159 | 0.685344 |
| 204461_x_at | RAD1 homolog (S. pombe) | RAD1 | 5810 | 2.470726 | 0.685344 |
| 202747_s_at | integral membrane protein 2A | ITM2A | 9452 | 2.470191 | 0.685344 |
| 209216_at | WD repeat domain 45 | WDR45 | 11152 | 2.469745 | 0.685344 |
| 202641_at | ADP-ribosylation factor-like 3 | ARL3 | 403 | 2.469619 | 0.685344 |
| 213846_at | cytochrome c oxidase subunit VIIc | COX7C | 1350 | 2.469423 | 0.685344 |
| 201653_at | cornichon homolog (Drosophila) | CNIH | 10175 | 2.468773 | 0.685344 |
| 217717_s_at | tyrosine 3-monooxygenase/tryptophan 5-monooxygenase activation protein, beta polypeptide | YWHAB | 7529 | 2.46836 | 0.685344 |
| 33736_at | stomatin (EPB72)-like 1 | STOML1 | 9399 | 2.46806 | 0.685344 |
| 203508_at | tumor necrosis factor receptor superfamily, member 1B | TNFRSF1B | 7133 | 2.468014 | 0.685344 |
| 208792_s_at | clusterin | CLU | 1191 | 2.467382 | 0.685344 |
| 210241_at | TP53 activated protein 1 | TP53AP1 | 11257 | 2.465538 | 0.685344 |
| 212056_at | KIAA0182 | KIAA0182 | 23199 | 2.465133 | 0.685344 |
| 201331_s_at | signal transducer and activator of transcription 6, interleukin-4 induced | STAT6 | 6778 | 2.464769 | 0.685344 |
| 210188_at | GA binding protein transcription factor, alpha subunit 60kDa | GABPA | 2551 | 2.463944 | 0.685344 |
| 213560_at | Growth arrest and DNA-damage-inducible, beta | GADD45B | 4616 | 2.46292 | 0.685344 |
| 203591_s_at | colony stimulating factor 3 receptor (granulocyte) | CSF3R | 1441 | 2.462517 | 0.685344 |
| 217732_s_at | histamine N-methyltransferase | HNMT | 3176 | 2.461607 | 0.685344 |
| 207437_at | neuro-oncological ventral antigen 1 | NOVA1 | 4857 | 2.460697 | 0.685344 |
| 221599_at | chromosome 11 open reading frame 67 | C11orf67 | 28971 | 2.458657 | 0.685344 |
| 211799_x_at | major histocompatibility complex, class I, C | HLA-C | 3107 | 2.453284 | 0.685344 |
| 35436_at | golgi autoantigen, golgin subfamily a, 2 | GOLGA2 | 2801 | 2.452143 | 0.685344 |
| 222165_x_at | chromosome 9 open reading frame 16 | C9orf16 | 79095 | 2.451037 | 0.685344 |
| 221494_x_at | eukaryotic translation initiation factor 3, subunit K | EIF3K | 27335 | 2.450573 | 0.685344 |
| 211301_at | potassium voltage-gated channel, Shal-related subfamily, member 3 | KCND3 | 3752 | 2.449972 | 0.685344 |
| 204897_at | prostaglandin E receptor 4 (subtype EP4) | PTGER4 | 5734 | 2.446946 | 0.685344 |
| 205081_at | cysteine-rich protein 1 (intestinal) | CRIP1 | 1396 | 2.446518 | 0.685344 |
| 207531_at | crystallin, gamma C | CRYGC | 1420 | 2.446422 | 0.685344 |

FIGURE 15 (CONTINUED)

| Probe | Description | Gene Symbol | ID | Value | Value2 |
|---|---|---|---|---|---|
| 203960_s_at | chromosome 1 open reading frame 41 | C1orf41 | 51668 | 2.446014 | 0.685344 |
| 207115_x_at | mbt domain containing 1 | MBTD1 | 54799 | 2.44549 | 0.685344 |
| 220190_s_at | general transcription factor IIA, 1-like /// STON1-GTF2A1L | GTF2A1L /// STON1-GTF2A1L | 11036 /// 286749 | 2.44526 | 0.685344 |
| 212279_at | transmembrane protein 97 | TMEM97 | 27346 | 2.444399 | 0.685344 |
| 213676_at | transmembrane protein 151B | TMEM151B | 441151 | 2.444084 | 0.685344 |
| 214475_x_at | calpain 3, (p94) | CAPN3 | 825 | 2.443977 | 0.685344 |
| 220798_x_at | plasticity-related gene 2 | PRG2 | 79948 | 2.443451 | 0.685344 |
| 221563_at | dual specificity phosphatase 10 | DUSP10 | 11221 | 2.442232 | 0.685344 |
| 203928_x_at | microtubule-associated protein tau | MAPT | 4137 | 2.441271 | 0.685344 |
| 216882_s_at | nebulette | NEBL | 10529 | 2.438473 | 0.685344 |
| 211451_s_at | potassium inwardly-rectifying channel, subfamily J, member 4 | KCNJ4 | 3761 | 2.43702 | 0.685344 |
| 214526_x_at | postmeiotic segregation increased 2-like 1 | PMS2L1 | 5379 | 2.434364 | 0.685365 |
| 201541_s_at | zinc finger, HIT type 1 | ZNHIT1 | 10467 | 2.434071 | 0.685365 |
| 221212_x_at | polybromo 1 | PBRM1 | 55193 | 2.432558 | 0.685365 |
| 215640_at | TBC1 domain family, member 2B | TBC1D2B | 23102 | 2.432211 | 0.685365 |
| 210734_x_at | MYC associated factor X | MAX | 4149 | 2.431253 | 0.685365 |
| 203451_at | LIM domain binding 1 | LDB1 | 8861 | 2.431062 | 0.685365 |
| 221198_at | secretin | SCT | 6343 | 2.430977 | 0.685365 |
| 206993_at | ATP synthase, H+ transporting, mitochondrial F0 complex, subunit s (factor B) | ATP5S | 27109 | 2.429895 | 0.685365 |
| 213169_at | sema domain, seven thrombospondin repeats (type 1 and type 1-like), transmembrane domain (TM) and short cytoplasmic domain, (semaphorin) 5A | SEMA5A LOC645094 /// MRCL3 | 9037 | 2.428232 | 0.685365 |
| 201319_at | myosin regulatory light chain MRCL3 /// similar to myosin regulatory light chain-like | | 10627 /// 645094 | 2.428228 | 0.685365 |
| 215144_at | Transcribed locus | | | 2.4279 | 0.685365 |
| 214463_x_at | histone cluster 1, H4k /// histone cluster 1, H4j | HIST1H4J /// HIST1H4K | 8362 /// 8363 | 2.426872 | 0.685365 |
| 216210_x_at | TRIO and F-actin binding protein | TRIOBP | 11078 | 2.426764 | 0.685365 |
| 212003_at | chromosome 1 open reading frame 144 | C1orf144 | 26099 | 2.425967 | 0.685365 |
| 215392_at | CDNA FLJ14136 fis, clone MAMMA1002744 | | | 2.421503 | 0.685365 |
| 204530_s_at | thymocyte selection-associated high mobility group box | TOX | 9760 | 2.421259 | 0.685365 |
| 213383_at | SAPS domain family, member 2 | SAPS2 | 9701 | 2.42032 | 0.685365 |
| 205654_at | complement component 4 binding protein, alpha | C4BPA | 722 | 2.419779 | 0.685365 |
| 203056_s_at | PR domain containing 2, with ZNF domain | PRDM2 | 7799 | 2.41818 | 0.685365 |
| 216223_at | carboxypeptidase N, polypeptide 2 | CPN2 | 1370 | 2.417499 | 0.685365 |
| 220903_at | G elongation factor, mitochondrial 1 | GFM1 | 85476 | 2.41743 | 0.685365 |
| 219807_x_at | RAB4B, member RAS oncogene family | RAB4B | 53916 | 2.417185 | 0.685365 |
| 204479_at | osteoclast stimulating factor 1 | OSTF1 | 26578 | 2.415404 | 0.685365 |
| 216516_at | | | | 2.414743 | 0.685365 |
| 203709_at | phosphorylase kinase, gamma 2 (testis) | PHKG2 | 5261 | 2.413644 | 0.685365 |
| 200836_s_at | microtubule-associated protein 4 | MAP4 | 4134 | 2.412961 | 0.685365 |
| 209829_at | chromosome 6 open reading frame 32 | C6orf32 | 9750 | 2.411805 | 0.685365 |
| 221973_at | CDNA clone IMAGE:5217021, with apparent retained intron | | | 2.411769 | 0.685365 |
| 221720_s_at | lysosomal associated multispanning membrane protein 5 | LAPTM5 | 7805 | 2.410701 | 0.685365 |
| 206929_s_at | nuclear factor I/C (CCAAT-binding transcription factor) | NFIC | 4782 | 2.410506 | 0.685365 |

FIGURE 15 (CONTINUED)

| | | | | |
|---|---|---|---|---|
| 64488_at | cDNA FLJ38849 fis, clone MESAN2008936 | --- | --- | 2.410432 | 0.685365 |
| 207052_at | hepatitis A virus cellular receptor 1 | HAVCR1 | 26762 | 2.409681 | 0.685365 |
| 204769_s_at | transporter 2, ATP-binding cassette, sub-family B (MDR/TAP) | TAP2 | 6891 | 2.409004 | 0.685365 |
| 207127_s_at | heterogeneous nuclear ribonucleoprotein H3 (2H9) | HNRPH3 | 3189 | 2.40838 | 0.685365 |
| 208949_s_at | lectin, galactoside-binding, soluble, 3 | LGALS3 | 3958 | 2.407378 | 0.685365 |
| 219497_s_at | B-cell CLL/lymphoma 11A (zinc finger protein) | BCL11A | 53335 | 2.406401 | 0.685365 |
| 216222_s_at | myosin X | MYO10 | 4651 | 2.404643 | 0.685365 |
| 213018_at | GATA zinc finger domain containing 1 | GATAD1 | 57798 | 2.402838 | 0.685365 |
| 210807_s_at | solute carrier family 16, member 7 (monocarboxylic acid transporter 2) | SLC16A7 | 9194 | 2.401928 | 0.685365 |
| 202638_s_at | intercellular adhesion molecule 1 (CD54), human rhinovirus receptor | ICAM1 | 3383 | 2.401177 | 0.685365 |
| 201026_at | eukaryotic translation initiation factor 5B | EIF5B | 9669 | 2.399581 | 0.685365 |
| 214398_s_at | inhibitor of kappa light polypeptide gene enhancer in B-cells, kinase epsilon | IKBKE | 9641 | 2.398373 | 0.685365 |
| 220557_s_at | phosphofurin acidic cluster sorting protein 1 | PACS1 | 55690 | 2.397916 | 0.685365 |
| 201341_at | ectodermal-neural cortex (with BTB-like domain) | ENC1 | 8507 | 2.396271 | 0.685365 |
| 215625_at | hypothetical protein LOC644450 | LOC644450 | 644450 | 2.388714 | 0.685365 |
| 208204_s_at | caveolin 3 | CAV3 | 859 | 2.385785 | 0.685365 |
| 202331_at | branched chain keto acid dehydrogenase E1, alpha polypeptide | BCKDHA | 593 | 2.385376 | 0.685365 |
| 204658_at | transformer-2 alpha | TRA2A | 29896 | 2.383945 | 0.685365 |
| 205746_s_at | ADAM metallopeptidase domain 17 (tumor necrosis factor, alpha, converting enzyme) | ADAM17 | 6868 | 2.382838 | 0.685365 |
| 205005_s_at | N-myristoyltransferase 2 | NMT2 | 9397 | 2.381715 | 0.685365 |
| 222244_s_at | taurine upregulated gene 1 | TUG1 | 55000 | 2.380933 | 0.685365 |
| 201416_at | SRY (sex determining region Y)-box 4 | SOX4 | 6659 | 2.379837 | 0.685365 |
| 213717_at | LIM domain binding 3 | LDB3 | 11155 | 2.379835 | 0.685365 |
| 217419_x_at | agrin | AGRN | 375790 | 2.379116 | 0.685365 |
| 203987_at | frizzled homolog 6 (Drosophila) | FZD6 | 8323 | 2.376525 | 0.685365 |
| 208515_at | histone cluster 1, H2bm | HIST1H2BM | 8342 | 2.37339 | 0.685365 |
| 212642_s_at | human immunodeficiency virus type I enhancer binding protein 2 | HIVEP2 | 3097 | 2.370399 | 0.685365 |
| 205368_at | family with sequence similarity 131, member B | FAM131B | 9715 | 2.367576 | 0.685365 |
| 210990_s_at | laminin, alpha 4 | LAMA4 | 3910 | 2.366895 | 0.685365 |
| 204205_at | apolipoprotein B mRNA editing enzyme, catalytic polypeptide-like 3G | APOBEC3G | 60489 | 2.36614 | 0.685365 |
| 215572_at | Similar to Golgin subfamily A member 6 (Golgin linked to PML) (Golgin-like protein) | LOC646934 | 646934 | 2.365812 | 0.685365 |
| 216361_s_at | MYST histone acetyltransferase (monocytic leukemia) 3 | MYST3 | 7994 | 2.364447 | 0.685365 |
| 211833_s_at | BCL2-associated X protein | BAX | 581 | 2.363029 | 0.685365 |
| 206790_s_at | NADH dehydrogenase (ubiquinone) 1 beta subcomplex, 1, 7kDa | NDUFB1 | 4707 | 2.360036 | 0.685365 |
| 217249_x_at | | --- | --- | 2.359444 | 0.685365 |
| 221728_x_at | X (inactive)-specific transcript | XIST | 7503 | 2.359297 | 0.685365 |
| 216033_s_at | FYN oncogene related to SRC, FGR, YES | FYN | 2534 | 2.358959 | 0.685365 |
| 219927_at | FCF1 small subunit (SSU) processome component homolog (S. cerevisiae) | FCF1 | 51077 | 2.357155 | 0.685365 |
| 203792_x_at | polycomb group ring finger 2 | PCGF2 | 7703 | 2.357119 | 0.685365 |
| 214995_s_at | apolipoprotein B mRNA editing enzyme, catalytic polypeptide-like 3G /// apolipoprotein B mRNA editing enzyme, catalytic polypeptide-like 3F | APOBEC3F /// APOBEC3G | 200316 /// 60489 | 2.356971 | 0.685365 |
| 216449_x_at | heat shock protein 90kDa beta (Grp94), member 1 | HSP90B1 | 7184 | 2.354796 | 0.685365 |
| 208736_at | actin related protein 2/3 complex, subunit 3, 21kDa | ARPC3 | 10094 | 2.353836 | 0.685365 |
| 202595_s_at | leptin receptor overlapping transcript-like 1 | LEPROTL1 | 23484 | 2.353359 | 0.685365 |
| 206739_at | homeobox C5 | HOXC5 | 3222 | 2.349507 | 0.685365 |
| 206940_s_at | POU class 4 homeobox 1 | POU4F1 | 5457 | 2.348675 | 0.685365 |

FIGURE 15 (CONTINUED)

| | | | | |
|---|---|---|---|---|
| 200663_at | CD63 molecule | CD63 | 967 | 2.347926 | 0.685365 |
| 214788_x_at | dendrin | DDN | 23109 | 2.347333 | 0.685365 |
| 201859_at | serglycin | SRGN | 5552 | 2.346423 | 0.685365 |
| 217468_at | Cytochrome P450, family 2, subfamily D, polypeptide 6 | CYP2D6 | 1565 | 2.346057 | 0.685365 |
| 210715_s_at | serine peptidase inhibitor, Kunitz type, 2 | SPINT2 | 10653 | 2.34257 | 0.685365 |
| 205510_s_at | hypothetical protein FLJ10038 | FLJ10038 | 55056 | 2.342325 | 0.685365 |
| 218913_s_at | GEM interacting protein | GMIP | 51291 | 2.341721 | 0.685365 |
| 219236_at | progestin and adipoQ receptor family member VI | PAQR6 | 79957 | 2.34057 | 0.685365 |
| 217554_at | Transcribed locus | --- | --- | 2.340448 | 0.685365 |
| 218537_at | host cell factor C1 regulator 1 (XPO1 dependent) | HCFC1R1 | 54985 | 2.338598 | 0.685365 |
| 212952_at | Transcribed locus | --- | --- | 2.337874 | 0.685365 |
| 207986_x_at | cytochrome b-561 | CYB561 | 1534 | 2.336603 | 0.685365 |
| 203416_at | CD53 molecule | CD53 | 963 | 2.336025 | 0.685365 |
| 207099_s_at | choroideremia (Rab escort protein 1) | CHM | 1121 | 2.33508 | 0.685365 |
| 208042_s_at | angiogenic factor with G patch and FHA domains 1 | AGGF1 | 55109 | 2.333987 | 0.685365 |
| 220274_at | IQ motif containing with AAA domain | IQCA | 79781 | 2.333357 | 0.685365 |
| 208076_at | histone cluster 1, H4d | HIST1H4D | 8360 | 2.333251 | 0.685365 |
| 211868_x_at | Immunoglobulin heavy constant alpha 1 /// immunoglobulin heavy constant gamma 1 (G1m marker) /// immunoglobulin heavy constant gamma 3 (G3m marker) /// Immunoglobulin heavy constant mu /// immunoglobulin heavy variable 4-31 | IGHA1 /// IGHG1 /// IGHG3 /// IGHM /// IGHV4-31 | 28396 /// 3493 /// 3500 /// 3502 /// 3507 | 2.332643 | 0.685365 |
| 2166659_at | dihydrofolate reductase pseudogene | LOC1720 | 1720 | 2.332572 | 0.685365 |
| 214436_at | F-box and leucine-rich repeat protein 2 | FBXL2 | 25827 | 2.332083 | 0.685365 |
| 217677_at | pleckstrin homology domain containing, family A (phosphoinositide binding specific) member 2 | PLEKHA2 | 59339 | 2.331452 | 0.685365 |
| 214324_at | glycoprotein 2 (zymogen granule membrane) | GP2 | 2813 | 2.330371 | 0.685365 |
| 220609_at | hypothetical protein LOC202181 | LOC202181 | 202181 | 2.329875 | 0.685365 |
| 203534_at | LSM1 homolog, U6 small nuclear RNA associated (S. cerevisiae) | LSM1 | 27257 | 2.329813 | 0.685365 |
| 204170_s_at | CDC28 protein kinase regulatory subunit 2 | CKS2 | 1164 | 2.329535 | 0.685365 |
| 203247_s_at | zinc finger protein 24 | ZNF24 | 7572 | 2.329093 | 0.685365 |
| 216555_at | chromosome 22 open reading frame 30 | C22orf30 | 253143 | 2.32902 | 0.685365 |
| 211012_s_at | promyelocytic leukemia /// hypothetical protein LOC161527 | PML | 161527 /// 5371 | 2.328721 | 0.685365 |
| 215219_at | dopey family member 2 | DOPEY2 | 9980 | 2.327902 | 0.685365 |
| 205362_s_at | prefoldin subunit 4 | PFDN4 | 5203 | 2.326771 | 0.685365 |
| 213736_at | Cytochrome c oxidase subunit Vb | COX5B | 1329 | 2.326611 | 0.685365 |
| 212030_at | RNA binding motif protein 25 | RBM25 | 58517 | 2.326325 | 0.685365 |
| 210282_at | zinc finger, MYM-type 2 | ZMYM2 | 7750 | 2.325716 | 0.685365 |
| 221125_s_at | potassium large conductance calcium-activated channel, subfamily M beta member 3 | KCNMB3 | 27094 | 2.325421 | 0.685365 |
| 214419_s_at | Cytochrome P450, family 2, subfamily C, polypeptide 9 | CYP2C9 | 1559 | 2.325237 | 0.685365 |
| 202980_s_at | seven in absentia homolog 1 (Drosophila) | SIAH1 | 6477 | 2.324244 | 0.685365 |
| 202257_s_at | CD2 (cytoplasmic tail) binding protein 2 | CD2BP2 | 10421 | 2.323957 | 0.685365 |
| 208439_s_at | ficolin (collagen/fibrinogen domain containing lectin) 2 (hucolin) | FCN2 | 2220 | 2.32369 | 0.685365 |
| 212991_at | F-box protein 9 | FBXO9 | 26268 | 2.322894 | 0.685365 |
| 215924_at | CDNA FLJ12040 fis, clone HEMBB1001944 | --- | --- | 2.322551 | 0.685365 |
| 210102_at | loss of heterozygosity, 11, chromosomal region 2, gene A | LOH11CR2A | 4013 | 2.322301 | 0.685365 |

FIGURE 15 (CONTINUED)

| | | | | |
|---|---|---|---|---|
| 204175_at | zinc finger protein 593 | ZNF593 | 51042 | 2.321135 | 0.685365 |
| 206526_at | RIB43A domain with coiled-coils 2 | RIBC2 | 26150 | 2.317583 | 0.685365 |
| 214940_s_at | Smg-6 homolog, nonsense mediated mRNA decay factor (C. elegans) | SMG6 | 23293 | 2.316067 | 0.685365 |
| 221892_at | hexose-6-phosphate dehydrogenase (glucose 1-dehydrogenase) | H6PD | 9563 | 2.313815 | 0.685365 |
| 207398_at | homeobox D13 | HOXD13 | 3239 | 2.31349 | 0.685365 |
| 210605_s_at | milk fat globule-EGF factor 8 protein | MFGE8 | 4240 | 2.313454 | 0.685365 |
| 212239_at | phosphoinositide-3-kinase, regulatory subunit 1 (p85 alpha) | PIK3R1 | 5295 | 2.311151 | 0.685365 |
| 204671_s_at | ankyrin repeat domain 6 | ANKRD6 | 22881 | 2.310891 | 0.685365 |
| 220615_s_at | male sterility domain containing 1 | MLSTD1 | 55711 | 2.310606 | 0.685365 |
| 208664_s_at | tetratricopeptide repeat domain 3 | TTC3 | 7267 | 2.309084 | 0.685365 |
| 217188_s_at | chromosome 14 open reading frame 1 | C14orf1 | 11161 | 2.306911 | 0.685365 |
| 203167_at | TIMP metallopeptidase inhibitor 2 | TIMP2 | 7077 | 2.305578 | 0.685365 |
| 205376_at | inositol polyphosphate-4-phosphatase, type II, 105kDa | INPP4B | 8821 | 2.30436 | 0.685365 |
| 213001_at | angiopoietin-like 2 | ANGPTL2 | 23452 | 2.303988 | 0.685365 |
| 202785_at | NADH dehydrogenase (ubiquinone) 1 alpha subcomplex, 7, 14.5kDa | NDUFA7 | 4701 | 2.302922 | 0.685365 |
| 217755_at | hematological and neurological expressed 1 | HN1 | 51155 | 2.302605 | 0.685365 |
| 214695_at | ubiquitin associated protein 2-like | UBAP2L | 9898 | 2.302487 | 0.685365 |
| 220861_at | --- | --- | --- | 2.301407 | 0.685365 |
| 209563_x_at | calmodulin 1 (phosphorylase kinase, delta) | CALM1 | 801 | 2.301142 | 0.685365 |
| 215027_at | hypothetical protein HSU79275 | HSU79275 | 27105 | 2.298765 | 0.685365 |
| 205184_s_at | guanine nucleotide binding protein (G protein), gamma 4 | GNG4 | 2786 | 2.297879 | 0.685365 |
| 207731_at | --- | --- | --- | 2.297251 | 0.685365 |
| 203671_at | thiopurine S-methyltransferase | TPMT | 7172 | 2.296889 | 0.685365 |
| 210383_at | sodium channel, voltage-gated, type I, alpha subunit | SCN1A | 6323 | 2.296578 | 0.685365 |
| 213376_at | zinc finger and BTB domain containing 1 | ZBTB1 | 22890 | 2.296177 | 0.685365 |
| 201498_at | ubiquitin specific peptidase 7 (herpes virus-associated) | USP7 | 7874 | 2.295342 | 0.685365 |
| 214184_at | neuropeptide FF-amide peptide precursor | NPFF | 8620 | 2.295087 | 0.685365 |
| 212865_s_at | collagen, type XIV, alpha 1 (undulin) | COL14A1 | 7373 | 2.294995 | 0.685365 |
| 203484_at | Sec61 gamma subunit | SEC61G | 23480 | 2.294769 | 0.685365 |
| 202478_at | tribbles homolog 2 (Drosophila) | TRIB2 | 28951 | 2.294619 | 0.685365 |
| 216243_s_at | interleukin 1 receptor antagonist | IL1RN | 3557 | 2.294207 | 0.685365 |
| 220780_at | phospholipase A2, group III | PLA2G3 | 50487 | 2.292886 | 0.685365 |
| 219406_at | chromosome 1 open reading frame 50 | C1orf50 | 79078 | 2.292572 | 0.685365 |
| 209602_s_at | GATA binding protein 3 | GATA3 | 2625 | 2.292342 | 0.685365 |
| 205075_at | serpin peptidase inhibitor, clade F (alpha-2 antiplasmin, pigment epithelium derived factor), member 2 | SERPINF2 | 5345 | 2.291389 | 0.685365 |
| 220389_at | coiled-coil domain containing 81 | CCDC81 | 60494 | 2.291318 | 0.685365 |
| 213312_at | chromosome 6 open reading frame 162 | C6orf162 | 57150 | 2.290579 | 0.685365 |
| 217359_s_at | neural cell adhesion molecule 1 | NCAM1 | 4684 | 2.288542 | 0.685365 |
| 222088_s_at | solute carrier family 2 (facilitated glucose transporter), member 3 | SLC2A3 | 6515 | 2.287054 | 0.685365 |
| 202481_at | dehydrogenase/reductase (SDR family) member 3 | DHRS3 | 9249 | 2.286618 | 0.685365 |
| 214412_at | H2A histone family, member B3 /// H2A histone family, member B1 | H2AFB1 /// H2AFB3 | 474382 /// 83740 | 2.28626 | 0.685365 |
| 203904_x_at | CD82 molecule | CD82 | 3732 | 2.285981 | 0.685365 |
| 222216_s_at | mitochondrial ribosomal protein L17 | MRPL17 | 63875 | 2.285753 | 0.685365 |
| 219465_at | apolipoprotein A-II | APOA2 | 336 | 2.285733 | 0.685365 |

FIGURE 15 (CONTINUED)

| | | | | |
|---|---|---|---|---|
| 217069_at | myeloid/lymphoid or mixed-lineage leukemia 4 | MLL4 | 9757 | 2.284943 | 0.685365 |
| 215919_s_at | mitochondrial ribosomal protein S11 | MRPS11 | 64963 | 2.284846 | 0.685365 |
| 216686_at | Similar to protein immuno-reactive with anti-PTH polyclonal antibodies | FLJ40330 | 645784 | 2.284382 | 0.685365 |
| 219879_s_at | chromosome 17 open reading frame 53 | C17orf53 | 78995 | 2.281608 | 0.685365 |
| 209672_s_at | hypothetical protein FLJ20323 | FLJ20323 | 54468 | 2.279025 | 0.685365 |
| 221954_at | Chromosome 20 open reading frame 111 | C20orf111 | 51526 | 2.278848 | 0.685365 |
| 214997_at | Golgi autoantigen, golgin subfamily a, 1 | GOLGA1 | 2800 | 2.278316 | 0.685365 |
| 210352_at | bromodomain containing 8 | BRD8 | 10902 | 2.277381 | 0.685365 |
| 208673_s_at | splicing factor, arginine/serine-rich 3 | SFRS3 | 6428 | 2.27637 | 0.685365 |
| 217438_at | mRNA; clone:RES4-16 | | | 2.274527 | 0.685365 |
| 220864_s_at | NADH dehydrogenase (ubiquinone) 1 alpha subcomplex, 13 | NDUFA13 | 51079 | 2.274215 | 0.685365 |
| 206520_x_at | sialic acid binding Ig-like lectin 6 | SIGLEC6 | 946 | 2.273893 | 0.685365 |
| 218154_at | gasdermin domain containing 1 | GSDMDC1 | 79792 | 2.273098 | 0.685365 |
| 207663_x_at | G antigen 3 | GAGE3 | 2575 | 2.272838 | 0.685365 |
| 214740_at | polymerase (RNA) II (DNA directed) polypeptide J, 13.3kDa pseudogene /// DNA directed RNA polymerase II polypeptide J-related /// RPB11b2 protein | POLR2J2 /// POLR2J3 /// POLR2J4 | 246721 /// 548644 /// 84820 | 2.272776 | 0.685365 |
| 217499_x_at | olfactory receptor, family 7, subfamily E, member 37 pseudogene | OR7E37P | 26636 | 2.272436 | 0.685365 |
| 215279_at | Clone 23676 mRNA sequence | | | 2.272429 | 0.685365 |
| 218463_s_at | MUS81 endonuclease homolog (S. cerevisiae) | MUS81 | 80198 | 2.271188 | 0.685365 |
| 221555_x_at | CDC14 cell division cycle 14 homolog B (S. cerevisiae) | CDC14B | 8555 | 2.270668 | 0.685365 |
| 215554_at | glycosylphosphatidylinositol specific phospholipase D1 | GPLD1 | 2822 | 2.270387 | 0.685365 |
| 209762_x_at | SP110 nuclear body protein | SP110 | 3431 | 2.269991 | 0.685365 |
| 200622_x_at | calmodulin 3 (phosphorylase kinase, delta) | CALM3 | 808 | 2.269867 | 0.685365 |
| 208024_s_at | DiGeorge syndrome critical region gene 6 /// DiGeorge syndrome critical region gene 6-like | DGCR6 /// DGCR6L | 8214 /// 85359 | 2.269125 | 0.685365 |
| 217962_at | nucleolar protein family A, member 3 (H/ACA small nucleolar RNPs) | NOLA3 | 55505 | 2.267983 | 0.685365 |
| 202289_s_at | transforming, acidic coiled-coil containing protein 2 | TACC2 | 10579 | 2.267559 | 0.685365 |
| 217992_s_at | EF-hand domain family, member D2 | EFHD2 | 79180 | 2.26745 | 0.685365 |
| 221409_at | olfactory receptor, family 2, subfamily S, member 2 | OR2S2 | 56656 | 2.265153 | 0.685365 |
| 210446_at | GATA binding protein 1 (globin transcription factor 1) | GATA1 | 2623 | 2.265004 | 0.685365 |
| 221996_s_at | Clathrin, light chain (Lcb) | CLTB | 1212 | 2.264987 | 0.685365 |
| 210790_s_at | SAR1 gene homolog A (S. cerevisiae) | SAR1A | 56681 | 2.264337 | 0.685368 |
| 214715_x_at | zinc finger protein 160 | ZNF160 | 90338 | 2.264107 | 0.685368 |
| 209531_at | glutathione transferase zeta 1 (maleylacetoacetate isomerase) | GSTZ1 | 2954 | 2.263808 | 0.685368 |
| 214004_s_at | vestigial like 4 (Drosophila) | VGLL4 | 9686 | 2.262271 | 0.685408 |
| 220309_at | tetratricopeptide repeat domain 22 | TTC22 | 55001 | 2.261792 | 0.685408 |
| 218291_at | mitogen-activated protein-binding protein-interacting protein | MAPBPIP | 28956 | 2.260532 | 0.685408 |
| 211638_x_at | Similar to Ig heavy chain V-II region ARH-77 precursor | LOC652128 | 652128 | 2.2605 | 0.685408 |
| 202323_s_at | acyl-Coenzyme A binding domain containing 3 | ACBD3 | 64746 | 2.254929 | 0.686542 |
| 213955_at | myozenin 3 | MYOZ3 | 91977 | 2.254523 | 0.686542 |
| 201370_s_at | cullin 3 | CUL3 | 8452 | 2.253869 | 0.686542 |
| 207503_at | t-complex 10 (mouse) | TCP10 | 6953 | 2.253314 | 0.686542 |
| 217267_s_at | RAB7A, member RAS oncogene family | RAB7A | 7879 | 2.253126 | 0.686542 |
| 208133_at | replication factor C (activator 1) 1, 145kDa | RFC1 | 5981 | 2.251193 | 0.686542 |
| 221701_s_at | stimulated by retinoic acid gene 6 homolog (mouse) | STRA6 | 64220 | 2.249169 | 0.686542 |

FIGURE 15 (CONTINUED)

| | | | | |
|---|---|---|---|---|
| 202869_at | 2',5'-oligoadenylate synthetase 1, 40/46kDa | OAS1 | 4938 | 2.248862 | 0.686542 |
| 222381_at | Programmed cell death 6 /// CDNA FLJ37304 fis, clone BRAMY2016070 | PDCD6 | 10016 | 2.248641 | 0.686542 |
| 208604_s_at | homeobox A3 | HOXA3 | 3200 | 2.248318 | 0.686542 |
| 208032_s_at | glutamate receptor, ionotrophic, AMPA 3 | GRIA3 | 2892 | 2.247864 | 0.686542 |
| 209696_at | fructose-1,6-bisphosphatase 1 | FBP1 | 2203 | 2.247086 | 0.686542 |
| 206277_at | purinergic receptor P2Y, G-protein coupled, 2 | P2RY2 | 5029 | 2.246319 | 0.686542 |
| 213015_at | ARTC1 mRNA, complete sequence | | | 2.245347 | 0.686542 |
| 206915_at | NK2 homeobox 2 | NKX2-2 | 4821 | 2.245256 | 0.686542 |
| 204129_at | B-cell CLL/lymphoma 9 | BCL9 | 607 | 2.24416 | 0.686542 |
| 219352_at | centaurin, alpha 2 | CENTA2 | 55803 | 2.24281 | 0.686542 |
| 200923_at | lectin, galactoside-binding, soluble, 3 binding protein | LGALS3BP | 3959 | 2.241452 | 0.686542 |
| 208333_at | LIM homeobox 5 | LHX5 | 64211 | 2.240645 | 0.686542 |
| 215377_at | C-terminal binding protein 2 | CTBP2 | 1488 | 2.238911 | 0.686542 |
| 221566_s_at | nucleolar protein 3 (apoptosis repressor with CARD domain) | NOL3 | 8996 | 2.23834 | 0.686542 |
| 216494_at | similar to insulin-like growth factor 2 mRNA binding protein 3 /// similar to IGF-II mRNA-binding protein 3 | LOC645468 /// LOC651107 | 645468 /// 651107 | 2.23657 | 0.686542 |
| 204235_s_at | GULP, engulfment adaptor PTB domain containing 1 | GULP1 | 51454 | 2.23571 | 0.686542 |
| 216450_x_at | heat shock protein 90kDa beta (Grp94), member 1 | HSP90B1 | 7184 | 2.23556 | 0.686542 |
| 201028_s_at | CD99 molecule | CD99 | 4267 | 2.233166 | 0.686542 |
| 207847_s_at | mucin 1, cell surface associated | MUC1 | 4582 | 2.232621 | 0.686542 |
| 211008_s_at | ubiquitin-conjugating enzyme E2I (UBC9 homolog, yeast) | UBE2I | 7329 | 2.231888 | 0.686542 |
| 215961_at | coagulation factor XII (Hageman factor) | F12 | 2161 | 2.231611 | 0.686542 |
| 202952_s_at | ADAM metallopeptidase domain 12 (meltrin alpha) | ADAM12 | 8038 | 2.231472 | 0.686542 |
| 203486_s_at | armadillo repeat containing 8 | ARMC8 | 25852 | 2.22897 | 0.686542 |
| 213587_s_at | ATPase, H+ transporting V0 subunit e2 | ATP6V0E2 | 155066 | 2.228641 | 0.686542 |
| 206542_s_at | SWI/SNF related, matrix associated, actin dependent regulator of chromatin, subfamily a, member 2 | SMARCA2 | 6595 | 2.226959 | 0.686542 |
| 201871_s_at | SAPK substrate protein 1 | LOC51035 | 51035 | 2.221296 | 0.686542 |
| 218654_s_at | mitochondrial ribosomal protein S33 | MRPS33 | 51650 | 2.225808 | 0.686542 |
| 212634_at | KIAA0776 | KIAA0776 | 23376 | 2.225537 | 0.686542 |
| 207279_s_at | nebulette | NEBL | 10529 | 2.224584 | 0.686542 |
| 210756_s_at | Notch homolog 2 (Drosophila) | NOTCH2 | 4853 | 2.224404 | 0.686542 |
| 207027_at | HGF activator | HGFAC | 3083 | 2.224334 | 0.686542 |
| 206208_at | carbonic anhydrase IV | CA4 | 762 | 2.223236 | 0.686542 |
| 214040_s_at | gelsolin (amyloidosis, Finnish type) | GSN | 2934 | 2.223026 | 0.686542 |
| 201400_at | proteasome (prosome, macropain) subunit, beta type, 3 | PSMB3 | 5691 | 2.221302 | 0.686542 |
| 218540_at | thiamine triphosphatase | THTPA | 79178 | 2.221296 | 0.686542 |
| 210461_s_at | actin binding LIM protein 1 | ABLIM1 | 3983 | 2.221034 | 0.686542 |
| 213296_at | RER1 retention in endoplasmic reticulum 1 homolog (S. cerevisiae) | RER1 | 11079 | 2.220332 | 0.686542 |
| 213456_at | sclerostin domain containing 1 | SOSTDC1 | 25928 | 2.218429 | 0.686542 |
| 219834_at | amyotrophic lateral sclerosis 2 (juvenile) chromosome region, candidate 8 | ALS2CR8 | 79800 | 2.216558 | 0.686542 |
| 205965_at | basic leucine zipper transcription factor, ATF-like | BATF | 10538 | 2.216441 | 0.686542 |
| 203021_at | secretory leukocyte peptidase inhibitor | SLPI | 6590 | 2.21626 | 0.686542 |
| 208810_at | DnaJ (Hsp40) homolog, subfamily B, member 6 /// similar to DnaJ (Hsp40) homolog, subfamily B, member 6 isoform a | DNAJB6 /// LOC387820 | 10049 /// 387820 | 2.215277 | 0.686542 |
| 209716_at | colony stimulating factor 1 (macrophage) | CSF1 | 1435 | 2.21252 | 0.686542 |
| 215224_at | ribosomal protein L23 | RPL23 | 9349 | 2.21125 | 0.686542 |

FIGURE 15 (CONTINUED)

| Probe ID | Description | Gene Symbol | Gene ID | Value | Value 2 |
|---|---|---|---|---|---|
| 219910_at | F1C domain containing | F1CD | 11153 | 2.210662 | 0.686542 |
| 206281_at | adenylate cyclase activating polypeptide 1 (pituitary) | ADCYAP1 | 116 | 2.210606 | 0.686542 |
| 205007_s_at | calcium and integrin binding family member 2 | CIB2 | 10518 | 2.210098 | 0.686542 |
| 204786_s_at | interferon (alpha, beta and omega) receptor 2 | IFNAR2 | 3455 | 2.209646 | 0.686542 |
| 201908_at | dishevelled, dsh homolog 3 (Drosophila) | DVL3 | 1857 | 2.209346 | 0.686542 |
| 222371_at | mRNA; cDNA DKFZp686B1142 (from clone DKFZp686B1142) | | | 2.20858 | 0.686542 |
| 202452_at | zer-1 homolog (C. elegans) | ZER1 | 10444 | 2.208358 | 0.686542 |
| 222255_s_at | periaxin | PRX | 57716 | 2.207523 | 0.686542 |
| 206386_s_at | serpin peptidase inhibitor, clade A (alpha-1 antiproteinase, antitrypsin), member 7 | SERPINA7 | 6906 | 2.207396 | 0.686542 |
| 202004_x_at | succinate dehydrogenase complex, subunit C, integral membrane protein, 15kDa | SDHC | 6391 | 2.206949 | 0.686542 |
| 204428_s_at | lecithin-cholesterol acyltransferase | LCAT | 3931 | 2.206919 | 0.686542 |
| 202596_at | endosulfine alpha | ENSA | 2029 | 2.206692 | 0.686542 |
| 210138_at | regulator of G-protein signaling 20 | RGS20 | 8601 | 2.20624 | 0.686542 |
| 203700_s_at | deiodinase, iodothyronine, type II | DIO2 | 1734 | 2.20574 | 0.686542 |
| 216960_s_at | zinc finger protein 133 | ZNF133 | 7692 | 2.2054 | 0.686542 |
| 205006_s_at | N-myristoyltransferase 2 | NMT2 | 9397 | 2.204788 | 0.686542 |
| 218994_s_at | stromal antigen 3-like 4 | STAG3L4 | 64940 | 2.201562 | 0.686542 |
| 221484_at | UDP-Gal:betaGlcNAc beta 1,4- galactosyltransferase, polypeptide 5 | B4GALT5 | 9334 | 2.200931 | 0.686542 |
| 218311_at | mitogen-activated protein kinase kinase kinase 3 | MAP4K3 | 8491 | 2.199441 | 0.686542 |
| 217484_at | complement component (3b/4b) receptor 1 (Knops blood group) | CR1 | 1378 | 2.199143 | 0.686542 |
| 201296_s_at | WD repeat and SOCS box-containing 1 | WSB1 | 26118 | 2.197079 | 0.686542 |
| 219557_s_at | nuclear receptor interacting protein 3 | NRIP3 | 56675 | 2.195917 | 0.686542 |
| 200925_at | cytochrome c oxidase subunit VIa polypeptide 1 | COX6A1 | 1337 | 2.195285 | 0.686542 |
| 213327_s_at | ubiquitin specific peptidase 12 | USP12 | 219333 | 2.195071 | 0.686542 |
| 210972_x_at | T cell receptor alpha locus /// T cell receptor delta variable 2 /// T cell receptor alpha variable 20 /// T cell receptor alpha joining 17 /// T cell receptor alpha constant | TRA@ /// TRAC /// TRAJ17 /// TRAV20 /// TRDV2 | 28517 /// 28663 /// 28738 /// 28755 /// 6955 | 2.195039 | 0.686542 |
| 218773_s_at | methionine sulfoxide reductase B2 | MSRB2 | 22921 | 2.194751 | 0.686542 |
| 209441_at | Rho-related BTB domain containing 2 | RHOBTB2 | 23221 | 2.19239 | 0.686542 |
| 218429_s_at | hypothetical protein FLJ11286 | FLJ11286 | 55337 | 2.191984 | 0.686542 |
| 208475_at | FERM domain containing 4A | FRMD4A | 55591 | 2.190816 | 0.686542 |
| 221727_at | --- | | | 2.188555 | 0.686542 |
| 204179_at | myoglobin | MB | 4151 | 2.188163 | 0.686542 |
| 213644_at | coiled-coil domain containing 46 | CCDC46 | 201134 | 2.186955 | 0.686542 |
| 217536_x_at | Transcribed locus | | | 2.1846 | 0.686542 |
| 221994_at | PDZ and LIM domain 5 | PDLIM5 | 10611 | 2.184223 | 0.686542 |
| 207574_s_at | growth arrest and DNA-damage-inducible, beta | GADD45B | 4616 | 2.183148 | 0.686542 |
| 210213_s_at | eukaryotic translation initiation factor 6 | EIF6 | 3692 | 2.182961 | 0.686542 |
| 207643_s_at | tumor necrosis factor receptor superfamily, member 1A | TNFRSF1A | 7132 | 2.182931 | 0.686542 |
| 203254_s_at | talin 1 | TLN1 | 7094 | 2.182096 | 0.686542 |
| 211769_x_at | serine incorporator 3 | SERINC3 | 10955 | 2.181857 | 0.686542 |
| 209527_at | exosome component 2 | EXOSC2 | 23404 | 2.181689 | 0.686542 |
| 200700_s_at | KDEL (Lys-Asp-Glu-Leu) endoplasmic reticulum protein retention receptor 2 | KDELR2 | 11014 | 2.180996 | 0.686542 |
| 208317_at | xylulokinase homolog (H. influenzae) | XYLB | 9942 | 2.179615 | 0.686542 |

FIGURE 15 (CONTINUED)

| | | | | |
|---|---|---|---|---|
| 200921_s_at | B-cell translocation gene 1, anti-proliferative | BTG1 | 694 | 2.179412 | 0.686542 |
| 203692_s_at | E2F transcription factor 3 | E2F3 | 1871 | 2.179221 | 0.686542 |
| 213252_at | SH3 and PX domains 2A | SH3PXD2A | 9644 | 2.179136 | 0.686542 |
| 213547_at | cullin-associated and neddylation-dissociated 2 (putative) | CAND2 | 23066 | 2.178278 | 0.686542 |
| 219693_at | 1-acylglycerol-3-phosphate O-acyltransferase 4 (lysophosphatidic acid acyltransferase, delta) | AGPAT4 | 56895 | 2.177822 | 0.686542 |
| 213822_s_at | ubiquitin protein ligase E3B | UBE3B | 89910 | 2.17689 | 0.686542 |
| 219616_at | acyl-CoA synthetase short-chain family member 3 | ACSS3 | 79611 | 2.176475 | 0.686542 |
| 209066_x_at | ubiquinol-cytochrome c reductase binding protein | UQCRB | 7381 | 2.175597 | 0.686542 |
| 203300_x_at | adaptor-related protein complex 1, sigma 2 subunit | AP1S2 | 8905 | 2.175503 | 0.686542 |
| 208829_at | TAP binding protein (tapasin) | TAPBP | 6892 | 2.174176 | 0.686542 |
| 218628_at | coiled-coil domain containing 53 | CCDC53 | 51019 | 2.173592 | 0.686542 |
| 201846_s_at | RING1 and YY1 binding protein | RYBP | 23429 | 2.173463 | 0.686542 |
| 215796_at | T-cell receptor active alpha-chain V-region (V-J-C) mRNA, partial cds, clone AG212 | | | 2.173287 | 0.686542 |
| 206433_s_at | sparc/osteonectin, cwcv and kazal-like domains proteoglycan (testican) 3 | SPOCK3 | 50859 | 2.173097 | 0.686542 |
| 220982_s_at | sperm acrosome associated 1 | SPACA1 | 81833 | 2.170379 | 0.686542 |
| 210633_x_at | keratin 10 (epidermolytic hyperkeratosis; keratosis palmaris et plantaris) | KRT10 | 3858 | 2.169077 | 0.686542 |
| 210038_at | protein kinase C, theta | PRKCQ | 5588 | 2.168467 | 0.686542 |
| 220449_at | hypothetical protein MGC5566 | MGC5566 | 79015 | 2.168114 | 0.686542 |
| 203326_x_at | | | | 2.167762 | 0.686542 |
| 202864_s_at | SP100 nuclear antigen | SP100 | 6672 | 2.167579 | 0.686542 |
| 217721_at | Full-length cDNA clone CS0DB003YD12 of Neuroblastoma Cot 10-normalized of Homo sapiens (human) | | | 2.164745 | 0.686542 |
| 203176_s_at | transcription factor A, mitochondrial | TFAM | 7019 | 2.164343 | 0.686542 |
| 203983_at | translin-associated factor X | TSNAX | 7257 | 2.164018 | 0.686542 |
| 207588_at | myelin transcription factor 2 | MYT2 | 8827 | 2.16357 | 0.686542 |
| 220747_at | HSPC072 protein | HSPC072 | 29075 | 2.163561 | 0.686542 |
| 213669_at | FCH domain only 1 | FCHO1 | 23149 | 2.163116 | 0.686542 |
| 217396_at | mRNA; cDNA DKFZp434M0317 (from clone DKFZp434M0317) | | | 2.162694 | 0.686542 |
| 202909_at | EPM2A (laforin) interacting protein 1 | EPM2AIP1 | 9852 | 2.162674 | 0.686542 |
| 201095_at | death-associated protein | DAP | 1611 | 2.159332 | 0.686542 |
| 218288_s_at | coiled-coil domain containing 90B | CCDC90B | 60492 | 2.1586 | 0.686542 |
| 220698_at | hypothetical protein MGC4294 | MGC4294 | 79160 | 2.15846 | 0.686542 |
| 220565_at | chemokine (C-C motif) receptor 10 | CCR10 | 2826 | 2.158248 | 0.686542 |
| 214851_at | hepatocyte nuclear factor 4, alpha | HNF4A | 3172 | 2.157853 | 0.686542 |
| 207008_at | interleukin 8 receptor, beta | IL8RB | 3579 | 2.156955 | 0.686542 |
| 218029_at | family with sequence similarity 65, member A | FAM65A | 79567 | 2.156528 | 0.686542 |
| 202000_at | NADH dehydrogenase (ubiquinone) 1 alpha subcomplex, 6, 14kDa | NDUFA6 | 4700 | 2.156429 | 0.686542 |
| 202710_at | blocked early in transport 1 homolog (S. cerevisiae) | BET1 | 10282 | 2.155901 | 0.686542 |
| 207100_s_at | vesicle-associated membrane protein 1 (synaptobrevin 1) | VAMP1 | 6843 | 2.155753 | 0.686542 |
| 220091_at | solute carrier family 2 (facilitated glucose transporter), member 6 | SLC2A6 | 11182 | 2.155729 | 0.686542 |
| 221113_s_at | wingless-type MMTV integration site family, member 16 | WNT16 | 51384 | 2.154654 | 0.686542 |
| 218864_s_at | thioredoxin | TXN | 7295 | 2.154394 | 0.686542 |
| 214980_at | Ubiquitin protein ligase E3A (human papilloma virus E6-associated protein, Angelman syndrome) | UBE3A | 7337 | 2.153301 | 0.686542 |
| 203549_s_at | lipoprotein lipase | LPL | 4023 | 2.152699 | 0.686542 |
| 209788_s_at | endoplasmic reticulum aminopeptidase 1 | ERAP1 | 51752 | 2.151776 | 0.686542 |
| 210993_s_at | SMAD family member 1 | SMAD1 | 4086 | 2.151288 | 0.686542 |

FIGURE 15 (CONTINUED)

| Probe ID | Description | Gene Symbol | ID | Value | P-value |
|---|---|---|---|---|---|
| 210874_s_at | N-acetyltransferase 6 | NAT6 | 24142 | 2.150985 | 0.686542 |
| 208926_at | sialidase 1 (lysosomal sialidase) | NEU1 | 4758 | 2.150867 | 0.686542 |
| 220502_s_at | solute carrier family 13 (sodium/sulfate symporters), member 1 | SLC13A1 | 6561 | 2.150679 | 0.686542 |
| 204771_s_at | transcription termination factor, RNA polymerase I | TTF1 | 7270 | 2.150614 | 0.686542 |
| 212188_at | potassium channel tetramerisation domain containing 12 | KCTD12 | 115207 | 2.15002 | 0.686542 |
| 215784_at | CD1e molecule | CD1E | 913 | 2.149881 | 0.686542 |
| 217502_at | interferon-induced protein with tetratricopeptide repeats 2 | IFIT2 | 3433 | 2.149733 | 0.686542 |
| 201119_s_at | cytochrome c oxidase subunit 8A (ubiquitous) | COX8A | 1351 | 2.146657 | 0.686542 |
| 213940_s_at | formin binding protein 1 | FNBP1 | 23048 | 2.145019 | 0.686542 |
| 212082_s_at | myosin, light chain 6, alkali, smooth muscle and non-muscle | MYL6 | 4637 | 2.144227 | 0.686542 |
| 205939_at | cytochrome P450, family 3, subfamily A, polypeptide 7 | CYP3A7 | 1551 | 2.144084 | 0.686542 |
| 208278_s_at | --- | --- | --- | 2.144047 | 0.686542 |
| 213114_at | --- | --- | --- | 2.142667 | 0.686542 |
| 218010_x_at | chromosome 20 open reading frame 149 | C20orf149 | 79144 | 2.142565 | 0.686542 |
| 212081_x_at | HLA-B associated transcript 2 | BAT2 | 7916 | 2.141804 | 0.686542 |
| 220122_at | multiple C2 domains, transmembrane 1 | MCTP1 | 79772 | 2.140819 | 0.686542 |
| 213620_s_at | intercellular adhesion molecule 2 | ICAM2 | 3384 | 2.139908 | 0.686542 |
| 216815_at | --- | --- | --- | 2.139472 | 0.686542 |
| 217998_at | pleckstrin homology-like domain, family A, member 1 /// hypothetical LOC652993 | LOC652993 /// PHLDA1 | 22822 /// 652993 | 2.139247 | 0.686542 |
| 205209_at | activin A receptor, type IB | ACVR1B | 91 | 2.138683 | 0.686542 |
| 204090_at | serine/threonine kinase 19 | STK19 | 8859 | 2.138364 | 0.686542 |
| 214567_s_at | chemokine (C motif) ligand 1 /// chemokine (C motif) ligand 2 | XCL1 /// XCL2 | 6375 /// 6846 | 2.136803 | 0.686542 |
| 214984_at | PI-3-kinase-related kinase SMG-1 /// hypothetical gene LOC283846 /// hypothetical protein LOC440345 /// PI-3-kinase-related kinase SMG-1 pseudogene /// similar to PI-3-kinase-related kinase SMG-1 | DKFZp547E087 /// LOC440345 /// LOC440354 /// LOC595101 /// LOC728423 /// LOC730099 /// SMG1 | 23049 /// 283846 /// 440345 /// 440354 /// 595101 /// 728423 /// 730099 | 2.136729 | 0.686542 |
| 221905_at | cylindromatosis (turban tumor syndrome) | CYLD | 1540 | 2.136069 | 0.686542 |
| 220069_at | tubulin, alpha 8 | TUBA8 | 51807 | 2.135725 | 0.686542 |
| 201758_at | tumor susceptibility gene 101 | TSG101 | 7251 | 2.134177 | 0.686542 |
| 214637_at | oncostatin M | OSM | 5008 | 2.133991 | 0.686542 |
| 221438_s_at | testis expressed 12 | TEX12 | 56158 | 2.13269 | 0.686542 |
| 213995_at | ATP synthase, H+ transporting, mitochondrial F0 complex, subunit s (factor B) | ATP5S | 27109 | 2.131809 | 0.686542 |
| 211377_x_at | v-myc myelocytomatosis viral related oncogene, neuroblastoma derived (avian) | MYCN | 4613 | 2.13178 | 0.686542 |
| 212203_x_at | interferon induced transmembrane protein 3 (1-8U) | IFITM3 | 10410 | 2.131392 | 0.686542 |
| 203248_at | zinc finger protein 24 | ZNF24 | 7572 | 2.131298 | 0.686542 |
| 213241_at | plexin C1 | PLXNC1 | 10154 | 2.131291 | 0.686542 |
| 221613_s_at | zinc finger, AN1-type domain 6 | ZFAND6 | 54469 | 2.13113 | 0.686542 |
| 200751_s_at | heterogeneous nuclear ribonucleoprotein C (C1/C2) | HNRNPC | 3183 | 2.130673 | 0.686542 |
| 212994_at | THO complex 2 | THOC2 | 57187 | 2.1305 | 0.686542 |
| 206848_at | homeobox A7 | HOXA7 | 3204 | 2.130443 | 0.686542 |
| 222214_at | CDNA: FLJ21335 fis, clone COL02546 | --- | --- | 2.130439 | 0.686542 |

FIGURE 15 (CONTINUED)

| | | | | | |
|---|---|---|---|---|---|
| 206811_at | adenylate cyclase 8 (brain) | ADCY8 | | 114 | 2.129184 | 0.686542 |
| 204345_at | collagen, type XVI, alpha 1 | COL16A1 | | 1307 | 2.128767 | 0.686542 |
| 211595_s_at | mitochondrial ribosomal protein S11 | MRPS11 | | 64963 | 2.128085 | 0.686542 |
| 208184_s_at | transmembrane protein 1 | TMEM1 | | 7109 | 2.127982 | 0.686542 |
| 211398_at | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | FGFR2 | | 2263 | 2.127673 | 0.686542 |
| 219232_s_at | egl nine homolog 3 (C. elegans) | EGLN3 | | 112399 | 2.126346 | 0.686542 |
| 214723_x_at | KIAA1641 | KIAA1641 | | 57730 | 2.126087 | 0.686542 |
| 209795_at | CD69 molecule | CD69 | | 969 | 2.12557 | 0.686542 |
| 218921_at | single immunoglobulin and toll-interleukin 1 receptor (TIR) domain | SIGIRR | | 59307 | 2.125232 | 0.686542 |
| 212961_x_at | chromosome X open reading frame 40B | CXorf40B | | 541578 | 2.124805 | 0.686542 |
| 220475_at | solute carrier family 28 (sodium-coupled nucleoside transporter), member 3 | SLC28A3 | | 64078 | 2.124628 | 0.686542 |
| 202423_at | MYST histone acetyltransferase (monocytic leukemia) 3 | MYST3 | | 7994 | 2.124453 | 0.686542 |
| 220444_at | zinc finger protein 557 | ZNF557 | | 79230 | 2.123719 | 0.686542 |
| 210009_s_at | golgi SNAP receptor complex member 2 | GOSR2 | | 9570 | 2.123151 | 0.686542 |
| 219771_at | TBC1 domain family, member 8B (with GRAM domain) | TBC1D8B | | 54885 | 2.123065 | 0.686542 |
| 217617_at | Transcribed locus | --- | | | 2.122411 | 0.686542 |
| 211944_at | BAT2 domain containing 1 | BAT2D1 | | 23215 | 2.121578 | 0.686542 |
| 201825_s_at | saccharopine dehydrogenase (putative) | SCCPDH | | 51097 | 2.121248 | 0.686542 |
| 200736_s_at | glutathione peroxidase 1 | GPX1 | | 2876 | 2.121183 | 0.686542 |
| 204285_s_at | phorbol-12-myristate-13-acetate-induced protein 1 | PMAIP1 | | 5366 | 2.120986 | 0.686542 |
| 214238_at | Clone DT1P1B6 mRNA, CAG repeat region | --- | | | 2.119169 | 0.686728 |
| 210057_at | PI-3-kinase-related kinase SMG-1 | SMG1 | | 23049 | 2.118753 | 0.686728 |
| 215828_at | MRNA; cDNA DKFZp547C126 (from clone DKFZp547C126) | --- | | | 2.115299 | 0.686728 |
| 2008355_s_at | microtubule-associated protein 4 | MAP4 | | 4134 | 2.114987 | 0.686728 |
| 218609_s_at | nudix (nucleoside diphosphate linked moiety X)-type motif 2 | NUDT2 | | 318 | 2.114765 | 0.686728 |
| 201324_at | epithelial membrane protein 1 | EMP1 | | 2012 | 2.114244 | 0.686728 |
| 211074_at | folate receptor 1 (adult) | FOLR1 | | 2348 | 2.113322 | 0.686728 |
| 209020_at | chromosome 20 open reading frame 111 | C20orf111 | | 51526 | 2.111923 | 0.686728 |
| 218410_s_at | hypothetical protein LOC283871 | LOC283871 | | 283871 | 2.111561 | 0.686728 |
| 204499_at | ATP/GTP binding protein 1 | AGTPBP1 | | 23287 | 2.109359 | 0.686728 |
| 217044_s_at | pleckstrin homology domain containing, family G (with RhoGef domain) member 3 | PLEKHG3 | | 26030 | 2.108293 | 0.686728 |
| 221081_s_at | DENN/MADD domain containing 2D | DENND2D | | 79961 | 2.107415 | 0.686728 |
| 205418_at | feline sarcoma oncogene | FES | | 2242 | 2.106854 | 0.686728 |
| 213031_s_at | WD repeat domain 73 | WDR73 | | 84942 | 2.106808 | 0.686728 |
| 206602_s_at | homeobox D3 | HOXD3 | | 3232 | 2.10626 | 0.686728 |
| 219754_at | RNA binding motif protein 41 | RBM41 | | 55285 | 2.105277 | 0.686728 |
| 204334_at | Kruppel-like factor 7 (ubiquitous) | KLF7 | | 8609 | 2.10475 | 0.686728 |
| 221353_at | olfactory receptor, family 3, subfamily A, member 1 | OR3A1 | | 4994 | 2.104647 | 0.686728 |
| 202759_s_at | A kinase (PRKA) anchor protein 2 /// PALM2-AKAP2 | AKAP2 /// PALM2-AKAP2 | | 11217 /// 445815 | 2.104181 | 0.686916 |
| 204292_x_at | serine/threonine kinase 11 | STK11 | | 6794 | 2.103761 | 0.687055 |
| 52837_at | KIAA1644 protein | LL22NC03-75B3.6 | | 85352 | 2.101906 | 0.687862 |
| 220706_at | ADAM metallopeptidase with thrombospondin type 1 motif, 7 | ADAMTS7 | | 11173 | 2.101165 | 0.687862 |
| 206151_x_at | elastase 3B, pancreatic | ELA3B | | 23436 | 2.099434 | 0.689205 |

FIGURE 15 (CONTINUED)

| Probe ID | Description | Gene Symbol | Entrez ID | Value1 | Value2 |
|---|---|---|---|---|---|
| 208749_x_at | flotillin 1 | FLOT1 | 10211 | 2.09818 | 0.689932 |
| 216338_s_at | Yip1 domain family, member 3 | YIPF3 | 25844 | 2.097274 | 0.689975 |
| 219672_at | erythroid associated factor | ERAF | 51327 | 2.096058 | 0.690746 |
| 210370_s_at | lymphocyte antigen 9 | LY9 | 4063 | 2.095188 | 0.690746 |
| 206908_s_at | claudin 11 (oligodendrocyte transmembrane protein) | CLDN11 | 5010 | 2.094753 | 0.690746 |
| 214972_at | Meningioma expressed antigen 5 (hyaluronidase) | MGEA5 | 10724 | 2.094738 | 0.690746 |
| 217507_at | solute carrier family 11 (proton-coupled divalent metal ion transporters), member 1 | SLC11A1 | 6556 | 2.093673 | 0.690746 |
| 201456_s_at | BUB3 budding uninhibited by benzimidazoles 3 homolog (yeast) | BUB3 | 9184 | 2.093054 | 0.690746 |
| 204246_s_at | dynactin 3 (p22) | DCTN3 | 11258 | 2.091968 | 0.690746 |
| 214720_x_at | septin 10 | 10-Sep | 151011 | 2.091112 | 0.690746 |
| 208244_at | bone morphogenetic protein 3 (osteogenic) | BMP3 | 651 | 2.090262 | 0.690746 |
| 213067_at | myosin, heavy chain 10, non-muscle | MYH10 | 4628 | 2.08946 | 0.690746 |
| 206327_s_at | cadherin 15, M-cadherin (myotubule) | CDH15 | 1013 | 2.089449 | 0.690746 |
| 216161_at | Strawberry notch homolog 1 (Drosophila) | SBNO1 | 55206 | 2.089148 | 0.690746 |
| 214998_at | AP2 associated kinase 1 | AAK1 | 22848 | 2.087479 | 0.690746 |
| 221567_at | nucleolar protein 3 (apoptosis repressor with CARD domain) | NOL3 | 8996 | 2.087247 | 0.690746 |
| 203264_s_at | Cdc42 guanine nucleotide exchange factor (GEF) 9 | ARHGEF9 | 23229 | 2.086567 | 0.690746 |
| 212925_at | chromosome 19 open reading frame 21 | C19orf21 | 126353 | 2.08622 | 0.690746 |
| 211144_x_at | T cell receptor gamma constant 2 /// T cell receptor gamma variable 9 /// TCR gamma alternate reading frame protein | TARP /// TRGC2 /// TRGV9 | 445347 /// 6967 /// 6983 | 2.085175 | 0.690746 |
| 210610_at | carcinoembryonic antigen-related cell adhesion molecule 1 (biliary glycoprotein) | CEACAM1 | 634 | 2.08344 | 0.690746 |
| 211377_x_at | recombination signal binding protein for immunoglobulin kappa J region-like | RBPJL | 11317 | 2.083155 | 0.690746 |
| 211919_s_at | chemokine (C-X-C motif) receptor 4 | CXCR4 | 7852 | 2.082936 | 0.690746 |
| 214544_s_at | synaptosomal-associated protein, 23kDa | SNAP23 | 8773 | 2.082393 | 0.690746 |
| 221442_at | melanocortin 3 receptor | MC3R | 4159 | 2.081525 | 0.690746 |
| 210553_x_at | proprotein convertase subtilisin/kexin type 6 | PCSK6 | 5046 | 2.080664 | 0.690746 |
| 216315_x_at | ubiquitin-conjugating enzyme E2 variant 1 /// TMEM189-UBE2V1 /// similar to ubiquitin-conjugating enzyme E2 variant 1 isoform d | LOC730052 /// TMEM189-UBE2V1 /// UBE2V1 | 387522 /// 730052 /// 7335 | 2.080554 | 0.690746 |
| 202366_at | acyl-Coenzyme A dehydrogenase, C-2 to C-3 short chain | ACADS | 35 | 2.080237 | 0.690746 |
| 209993_at | ATP-binding cassette, sub-family B (MDR/TAP), member 1 | ABCB1 | 5243 | 2.079959 | 0.690746 |
| 219881_at | --- | --- | --- | 2.079153 | 0.690746 |
| 204130_at | hydroxysteroid (11-beta) dehydrogenase 2 | HSD11B2 | 3291 | 2.078996 | 0.690921 |
| 209405_s_at | family with sequence similarity 3, member A | FAM3A | 60343 | 2.077668 | 0.690921 |
| 217251_x_at | Isovaleryl Coenzyme A dehydrogenase | IVD | 3712 | 2.076359 | 0.691681 |
| 220670_at | --- | --- | --- | 2.075213 | 0.691792 |
| 216980_s_at | sialophorin (leukosialin, CD43) | SPN | 6693 | 2.074857 | 0.691792 |
| 219555_s_at | centromere protein N | CENPN | 55839 | 2.073749 | 0.692639 |
| 212486_s_at | FYN oncogene related to SRC, FGR, YES | FYN | 2534 | 2.071921 | 0.693749 |
| 217732_s_at | integral membrane protein 2B | ITM2B | 9445 | 2.07024 | 0.693852 |
| 208927_at | speckle-type POZ protein | SPOP | 8405 | 2.069217 | 0.693852 |
| 217316_at | olfactory receptor, family 7, subfamily A, member 10 | OR7A10 | 390892 | 2.069101 | 0.693852 |
| 217311_s_at | transcription factor 25 (basic helix-loop-helix) | TCF25 | 22980 | 2.068584 | 0.693852 |
| 210221_at | cholinergic receptor, nicotinic, alpha 3 | CHRNA3 | 1136 | 2.068357 | 0.693852 |

FIGURE 15 (CONTINUED)

| | | | | | |
|---|---|---|---|---|---|
| 205616_at | cDNA FLJ25134 fis, clone CBR06934 | | | 2.067962 | 0.693852 |
| 221998_s_at | vaccinia related kinase 3 | VRK3 | 51231 | 2.067095 | 0.694015 |
| 208406_s_at | GRB2-related adaptor protein 2 | GRAP2 | 9402 | 2.064681 | 0.694181 |
| 221014_s_at | RAB33B, member RAS oncogene family | RAB33B | 83452 | 2.064485 | 0.694181 |
| 201264_at | coatomer protein complex, subunit epsilon | COPE | 11316 | 2.062264 | 0.694215 |
| 214011_s_at | hypothetical protein HSPC111 | HSPC111 | 51491 | 2.06209 | 0.694215 |
| 218136_s_at | solute carrier family 25, member 37 | SLC25A37 | 51312 | 2.061799 | 0.694215 |
| 221515_s_at | leucine carboxyl methyltransferase 1 | LCMT1 | 51451 | 2.060269 | 0.694598 |
| 221797_at | chromosome 17 open reading frame 90 | C17orf90 | 339229 | 2.059472 | 0.694598 |
| 206535_s_at | solute carrier family 2 (facilitated glucose transporter), member 2 | SLC2A2 | 6514 | 2.058244 | 0.694598 |
| 212126_at | cDNA clone IMAGE:4842353 | | | 2.057114 | 0.694598 |
| 208799_at | proteasome (prosome, macropain) subunit, beta type, 5 | PSMB5 | 5693 | 2.05679 | 0.694598 |
| 214556_at | somatostatin receptor 4 | SSTR4 | 6754 | 2.055841 | 0.694598 |
| 202152_x_at | upstream transcription factor 2, c-fos interacting | USF2 | 7392 | 2.055689 | 0.694598 |
| 204713_s_at | coagulation factor V (proaccelerin, labile factor) | F5 | 2153 | 2.055032 | 0.694719 |
| 204440_at | CD83 molecule | CD83 | 9308 | 2.054483 | 0.695017 |
| 214296_x_at | chromosome 19 open reading frame 36 | C19orf36 | 113177 | 2.053631 | 0.695353 |
| 222267_at | hypothetical protein FLJ14803 | FLJ14803 | 84928 | 2.05133 | 0.696075 |
| 205882_x_at | adducin 3 (gamma) | ADD3 | 120 | 2.05089 | 0.696105 |
| 216068_at | mRNA; cDNA DKFZp434N021 (from clone DKFZp434N021) | | | 2.050488 | 0.696105 |
| 65630_at | transmembrane protein 80 | TMEM80 | 283232 | 2.049535 | 0.696209 |
| 208102_s_at | pleckstrin and Sec7 domain containing | PSD | 5662 | 2.049406 | 0.696209 |
| 208421_at | | | | 2.047489 | 0.696209 |
| 208966_x_at | interferon, gamma-inducible protein 16 | IFI16 | 3428 | 2.047386 | 0.696209 |
| 206420_at | immunoglobulin superfamily, member 6 | IGSF6 | 10261 | 2.047226 | 0.696209 |
| 221192_x_at | major facilitator superfamily domain containing 11 | MFSD11 | 79157 | 2.047147 | 0.696209 |
| 37462_i_at | splicing factor 3a, subunit 2, 66kDa | SF3A2 | 8175 | 2.046665 | 0.696438 |
| 203018_s_at | synovial sarcoma, X breakpoint 2 interacting protein | SSX2IP | 117178 | 2.046267 | 0.696577 |
| 205293_x_at | BAI1-associated protein 2 | BAIAP2 | 10458 | 2.04534 | 0.696807 |
| 207972_at | glycine receptor, alpha 1 (startle disease/hyperekplexia) | GLRA1 | 2741 | 2.044536 | 0.696807 |
| 209633_at | protein phosphatase 2 (formerly 2A), regulatory subunit B'', alpha | PPP2R3A | 5523 | 2.043908 | 0.696807 |
| 209205_s_at | LIM domain only 4 | LMO4 | 8543 | 2.043741 | 0.696807 |
| 207266_x_at | RNA binding motif, single stranded interacting protein 1 | RBMS1 | 5937 | 2.043634 | 0.697458 |
| 213979_s_at | C-terminal binding protein 1 | CTBP1 | 1487 | 2.042227 | 0.697492 |
| 214699_x_at | WD repeat domain, phosphoinositide interacting 2 | WIPI2 | 26100 | 2.041927 | 0.697859 |
| 210100_s_at | ATP-binding cassette, sub-family A (ABC1), member 2 | ABCA2 | 20 | 2.04132 | 0.697915 |
| 219033_at | poly (ADP-ribose) polymerase family, member 8 | PARP8 | 79668 | 2.040884 | 0.698889 |
| 214804_at | | | | 2.039566 | 0.700341 |
| 205503_at | protein tyrosine phosphatase, non-receptor type 14 | PTPN14 | 5784 | 2.037962 | |
| 215024_at | asparagine synthetase /// chromosome 7 open reading frame 28A /// chromosome 7 open reading frame 28B /// MGC72080 pseudogene /// similar to CG14980-PB | ASNS /// C7orf28A /// C7orf28B /// LOC652200 /// MGC72080 | 221960 /// 389538 /// 440 /// 51622 /// 652200 | 2.035138 | 0.701657 |
| 221957_at | pyruvate dehydrogenase kinase, isozyme 3 | PDK3 | 5165 | 2.035038 | 0.701657 |

FIGURE 15 (CONTINUED)

| Probe ID | Description | Gene Symbol | Gene ID | Value | P-value |
|---|---|---|---|---|---|
| 202760_s_at | A kinase (PRKA) anchor protein 2 /// PALM2-AKAP2 | AKAP2 /// PALM2-AKAP2 | 11217 /// 445815 | 2.033722 | 0.701657 |
| 213432_at | mucin 5B, oligomeric mucus/gel-forming | MUC5B | 727897 | 2.033377 | 0.701657 |
| 211744_s_at | CD58 molecule | CD58 | 965 | 2.032573 | 0.701657 |
| 206150_at | CD27 molecule | CD27 | 939 | 2.032149 | 0.701657 |
| 220606_s_at | chromosome 17 open reading frame 48 | C17orf48 | 56985 | 2.031601 | 0.701657 |
| 201435_s_at | eukaryotic translation initiation factor 4E | EIF4E | 1977 | 2.030359 | 0.701657 |
| 208478_s_at | BCL2-associated X protein | BAX | 581 | 2.030295 | 0.701657 |
| 218446_s_at | family with sequence similarity 18, member B | FAM18B | 51030 | 2.03009 | 0.701657 |
| 215492_x_at | pre T-cell antigen receptor alpha | PTCRA | 171558 | 2.030015 | 0.701657 |
| 210796_x_at | sialic acid binding Ig-like lectin 6 | SIGLEC6 | 946 | 2.029813 | 0.701657 |
| 218285_s_at | 3-hydroxybutyrate dehydrogenase, type 2 | BDH2 | 56898 | 2.029157 | 0.701657 |
| 218669_at | RAP2C, member of RAS oncogene family | RAP2C | 57826 | 2.02907 | 0.701657 |
| 201251_at | pyruvate kinase, muscle | PKM2 | 5315 | 2.028925 | 0.701657 |
| 221553_at | implantation-associated protein /// similar to implantation-associated protein | LOC728866 /// RP11-217H1.1 | 728866 /// 84061 | 2.027564 | 0.701657 |
| 214906_x_at | hypothetical gene CG018 | CG018 | 90634 | 2.027534 | 0.701657 |
| 205893_at | neuroligin 1 | NLGN1 | 22871 | 2.027108 | 0.701657 |
| 207130_at | zinc finger, MYND-type containing 8 | ZMYND8 | 23613 | 2.027097 | 0.701657 |
| 212241_at | glutamate receptor, ionotropic, N-methyl D-aspartate-like 1A /// GRINL1A combined protein /// similar to glutamate receptor, ionotropic, N-methyl D-aspartate-like 1A isoform 1 | Gcom1 /// GRINL1A /// LOC339970 | 145781 /// 339970 /// 81488 | 2.026624 | 0.701657 |
| 210037_s_at | nitric oxide synthase 2A (inducible, hepatocytes) | NOS2A | 4843 | 2.026548 | 0.701657 |
| 206982_at | crystallin, beta A1 | CRYBA1 | 1411 | 2.026499 | 0.701657 |
| 219026_s_at | RAS protein activator like 2 | RASAL2 | 9462 | 2.026072 | 0.701657 |
| 219385_at | SLAM family member 8 | SLAMF8 | 56833 | 2.02596 | 0.701657 |
| 205857_at | solute carrier family 18 (vesicular monoamine), member 2 | SLC18A2 | 6571 | 2.025399 | 0.701657 |
| 212631_at | Syntaxin 7 | STX7 | 8417 | 2.025176 | 0.701657 |
| 212103_at | karyopherin alpha 6 (importin alpha 7) | KPNA6 | 23633 | 2.025125 | 0.701657 |
| 219538_at | WD repeat domain 5B | WDR5B | 54554 | 2.024372 | 0.701657 |
| 218831_s_at | Fc fragment of IgG, receptor, transporter, alpha | FCGRT | 2217 | 2.023605 | 0.701657 |
| 216566_at | Ribosomal protein L14 | RPL14 | 9045 | 2.023178 | 0.701657 |
| 211422_at | transient receptor potential cation channel, subfamily M, member 3 | TRPM3 | 80036 | 2.022757 | 0.701657 |
| 219981_x_at | zinc finger protein 587 | ZNF587 | 84914 | 2.022097 | 0.701657 |
| 218240_at | NFKB inhibitor interacting Ras-like 2 | NKIRAS2 | 28511 | 2.021955 | 0.701657 |
| 216212_s_at | dyskeratosis congenita 1, dyskerin | DKC1 | 1736 | 2.021933 | 0.701657 |
| 221145_at | | | | 2.018788 | 0.701821 |
| 215199_at | caldesmon 1 | CALD1 | 800 | 2.018632 | 0.701821 |
| 201205_at | | | | 2.018631 | 0.701821 |
| 200001_at | calpain, small subunit 1 | CAPNS1 | 826 | 2.018556 | 0.701821 |
| 220326_s_at | hypothetical protein FLJ10357 | FLJ10357 | 55701 | 2.018222 | 0.701821 |
| 201876_at | paraoxonase 2 | PON2 | 5445 | 2.017604 | 0.701821 |
| 207034_s_at | GLI-Kruppel family member GLI2 | GLI2 | 2736 | 2.017196 | 0.701821 |
| 218708_at | NTF2-like export factor 1 | NXT1 | 29107 | 2.01716 | 0.701821 |
| 221234_s_at | BTB and CNC homology 1, basic leucine zipper transcription factor 2 | BACH2 | 60468 | 2.016732 | 0.701821 |
| 203024_s_at | chromosome 5 open reading frame 15 | C5orf15 | 56951 | 2.016486 | 0.701821 |

FIGURE 15 (CONTINUED)

| ID | Description | | Value1 | Value2 | Value3 |
|---|---|---|---|---|---|
| 203590_at | dynein, cytoplasmic 1, light intermediate chain 2 | DYNC1LI2 | | 1783 | 2.016396 | 0.701821 |
| 218027_at | mitochondrial ribosomal protein L15 | MRPL15 | | 29088 | 2.015465 | 0.701821 |
| 216607_s_at | cytochrome P450, family 51, subfamily A, polypeptide 1 | CYP51A1 | | 1595 | 2.014472 | 0.701821 |
| 217624_at | PDGFA associated protein 1 | PDAP1 | | 11333 | 2.01423 | 0.701821 |
| 217237_at | Cyritestin 2-like mRNA, partial sequence | | | | 2.012285 | 0.701821 |
| 219382_at | SERTA domain containing 3 | SERTAD3 | | 29946 | 2.012211 | 0.701821 |
| 202173_s_at | vascular endothelial zinc finger 1 | VEZF1 | | 7716 | 2.011852 | 0.701821 |
| 220713_at | cDNA FLJ12345 fis, clone MAMMA1002294 | | | | 2.011754 | 0.701821 |
| 216495_x_at | Isovaleryl Coenzyme A dehydrogenase | IVD | | 3712 | 2.011191 | 0.701821 |
| 201482_at | quiescin Q6 sulfhydryl oxidase 1 | QSOX1 | | 5768 | 2.011111 | 0.701821 |
| 211210_x_at | SH2 domain protein 1A, Duncan's disease (lymphoproliferative syndrome) | SH2D1A | | 4068 | 2.010776 | 0.701821 |
| 213639_s_at | zinc finger protein 500 | ZNF500 | | 26048 | 2.009621 | 0.701821 |
| 221896_s_at | HIG1 domain family, member 1A | HIGD1A | | 25994 | 2.00925 | 0.701821 |
| 206967_at | cyclin T1 | CCNT1 | | 904 | 2.008741 | 0.701821 |
| 206506_s_at | suppressor of Ty 3 homolog (S. cerevisiae) | SUPT3H | | 8464 | 2.008314 | 0.701821 |
| 209404_s_at | transmembrane emp24 protein transport domain containing 7 | TMED7 | | 51014 | 2.008168 | 0.701821 |
| 210427_at | annexin A2 | ANXA2 | | 302 | 2.008161 | 0.701821 |
| 213315_x_at | chromosome X open reading frame 40A | CXorf40A | | 91966 | 2.008044 | 0.701821 |
| 221790_s_at | low density lipoprotein receptor adaptor protein 1 | LDLRAP1 | | 26119 | 2.007726 | 0.701821 |
| 214034_at | endoplasmic reticulum aminopeptidase 1 | ERAP1 | | 51752 | 2.007357 | 0.701821 |
| 208746_x_at | ATP synthase, H+ transporting, mitochondrial F0 complex, subunit G | ATP5L | | 10632 | 2.006394 | 0.701821 |
| 202617_s_at | methyl CpG binding protein 2 (Rett syndrome) | MECP2 | | 4204 | 2.00608 | 0.701821 |
| 217042_at | retinol dehydrogenase 11 (all-trans/9-cis/11-cis) | RDH11 | | 51109 | 2.005352 | 0.701821 |
| 212868_x_at | chromosome 12 open reading frame 47 | C12orf47 | | 51275 | 2.005119 | 0.701821 |
| 210107_at | chloride channel, calcium activated, family member 1 | CLCA1 | | 1179 | 2.004572 | 0.701821 |
| 210131_x_at | succinate dehydrogenase complex, subunit C, integral membrane protein, 15kDa | SDHC | | 6391 | 2.003848 | 0.701821 |
| 207143_at | cyclin-dependent kinase 6 | CDK6 | | 1021 | 2.002531 | 0.702274 |
| 219806_s_at | chromosome 11 open reading frame 75 | C11orf75 | | 56935 | 2.001108 | 0.703269 |
| 219664_s_at | 2,4-dienoyl CoA reductase 2, peroxisomal | DECR2 | | 26063 | -2.00043 | 0.703454 |
| 209254_at | KIAA0265 protein | KIAA0265 | | 23008 | -2.000571 | 0.703454 |
| 219934_s_at | sulfotransferase family 1E, estrogen-preferring, member 1 | SULT1E1 | | 6783 | -2.001338 | 0.703269 |
| 200064_at | heat shock protein 90kDa alpha (cytosolic), class B member 1 | HSP90AB1 | | 3326 | -2.002673 | 0.702274 |
| 221101_at | chromosome 14 open reading frame 113 | C14orf113 | | 54792 | -2.003456 | 0.701821 |
| 204305_at | mitochondrial intermediate peptidase | MIPEP | | 4285 | -2.003511 | 0.701821 |
| 209339_at | seven in absentia homolog 2 (Drosophila) | SIAH2 | | 6478 | -2.003799 | 0.701821 |
| 201814_at | TBC1 domain family, member 5 | TBC1D5 | | 9779 | -2.004175 | 0.701821 |
| 220777_at | kinesin family member 13A | KIF13A | | 63971 | -2.004408 | 0.701821 |
| 209402_s_at | solute carrier family 12 (potassium/chloride transporters), member 4 | SLC12A4 | | 6560 | -2.004658 | 0.701821 |
| 209942_x_at | melanoma antigen family A, 3 | MAGEA3 | | 4102 | -2.004926 | 0.701821 |
| 213334_x_at | UCHL5 interacting protein | UCHL5IP | | 55559 | -2.005561 | 0.701821 |
| 205818_at | deleted in bladder cancer 1 | DBC1 | | 1620 | -2.005688 | 0.701821 |
| 221528_at | replication protein A1, 70kDa | RPA1 | | 6117 | -2.006227 | 0.701821 |
| 221923_s_at | nucleophosmin (nucleolar phosphoprotein B23, numatrin) | NPM1 | | 4869 | -2.006951 | 0.701821 |
| 211651_s_at | laminin, beta 1 | LAMB1 | | 3912 | -2.007124 | 0.701821 |
| 207756_at | | | | | -2.007216 | 0.701821 |
| 206563_s_at | opiate receptor-like 1 | OPRL1 | | 4987 | -2.008492 | 0.701821 |

FIGURE 15 (CONTINUED)

| Probe ID | Description | Gene | Value 1 | Value 2 | Value 3 |
|---|---|---|---|---|---|
| 202431_s_at | v-myc myelocytomatosis viral oncogene homolog (avian) | MYC | 4609 | -2.008501 | 0.701821 |
| 65493_at | HEAT repeat containing 6 | HEATR6 | 63897 | -2.008826 | 0.701821 |
| 213993_at | spondin 1, extracellular matrix protein | SPON1 | 10418 | -2.009684 | 0.701821 |
| 203493_s_at | centrosomal protein 57kDa | CEP57 | 9702 | -2.009696 | 0.701821 |
| 222077_s_at | Rac GTPase activating protein 1 | RACGAP1 | 29127 | -2.011196 | 0.701821 |
| 207357_s_at | UDP-N-acetyl-alpha-D-galactosamine:polypeptide N-acetylgalactosaminyltransferase 10 (GalNAc-T10) | GALNT10 | 55558 | -2.0116 | 0.701821 |
| 221849_s_at | hypothetical protein BC002926 | LOC90379 | 90379 | -2.011694 | 0.701821 |
| 204101_at | myotubularin 1 | MTM1 | 4534 | -2.012369 | 0.701821 |
| 213349_at | transmembrane and coiled-coil domain family 1 | TMCC1 | 23023 | -2.012496 | 0.701821 |
| 216511_s_at | transcription factor 7-like 2 (T-cell specific, HMG-box) | TCF7L2 | 6934 | -2.012646 | 0.701821 |
| 218052_s_at | ATPase type 13A1 | ATP13A1 | 57130 | -2.012863 | 0.701821 |
| 203196_at | ATP-binding cassette, sub-family C (CFTR/MRP), member 4 | ABCC4 | 10257 | -2.012868 | 0.701821 |
| 207264_at | KDEL (Lys-Asp-Glu-Leu) endoplasmic reticulum protein retention receptor 3 | KDELR3 | 11015 | -2.014337 | 0.701821 |
| 38707_r_at | E2F transcription factor 4, p107/p130-binding | E2F4 | 1874 | -2.0152 | 0.701821 |
| 213014_at | mitogen-activated protein kinase 8 interacting protein 1 | MAPK8IP1 | 9479 | -2.015757 | 0.701821 |
| 218536_at | MRS2-like, magnesium homeostasis factor (S. cerevisiae) | MRS2L | 57380 | -2.017258 | 0.701821 |
| 210687_at | carnitine palmitoyltransferase 1A (liver) | CPT1A | 1374 | -2.019357 | 0.701821 |
| 217457_s_at | RAP1, GTP-GDP dissociation stimulator 1 | RAP1GDS1 | 5910 | -2.019452 | 0.701821 |
| 65635_at | endo-beta-N-acetylglucosaminidase | FLJ21865 | 64772 | -2.019874 | 0.701821 |
| 206916_x_at | tyrosine aminotransferase | TAT | 6898 | -2.020475 | 0.701821 |
| 217725_x_at | SERPINE1 mRNA binding protein 1 | SERBP1 | 26135 | -2.021433 | 0.701821 |
| 201594_s_at | protein phosphatase 4, regulatory subunit 1 | PPP4R1 | 9989 | -2.022356 | 0.701657 |
| 212738_at | Rho GTPase activating protein 19 | ARHGAP19 | 84986 | -2.022382 | 0.701657 |
| 202239_at | poly (ADP-ribose) polymerase family, member 4 | PARP4 | 143 | -2.022719 | 0.701657 |
| 206780_at | glutamate decarboxylase 2 (pancreatic islets and brain, 65kDa) | GAD2 | 2572 | -2.022274 | 0.701657 |
| 218663_at | non-SMC condensin I complex, subunit G | NCAPG | 64151 | -2.022795 | 0.701657 |
| 205531_s_at | glutaminase 2 (liver, mitochondrial) | GLS2 | 27165 | -2.022807 | 0.701657 |
| 212379_at | phosphoribosylglycinamide formyltransferase, phosphoribosylglycinamide synthetase, phosphoribosylaminoimidazole synthetase | GART | 2618 | -2.023628 | 0.701657 |
| 208688_x_at | eukaryotic translation initiation factor 3, subunit B | EIF3B | 8662 | -2.024641 | 0.701657 |
| 217434_at | melanocortin 2 receptor (adrenocorticotropic hormone) | MC2R | 4158 | -2.02494 | 0.701657 |
| 210541_s_at | tripartite motif-containing 27 | TRIM27 | 5987 | -2.025389 | 0.701657 |
| 208454_s_at | plasma glutamate carboxypeptidase | PGCP | 10404 | -2.029082 | 0.701657 |
| 205489_at | crystallin, mu | CRYM | 1428 | -2.029929 | 0.701657 |
| 211525_x_at | glycoprotein V (platelet) | GP5 | 2814 | -2.030884 | 0.701657 |
| 203871_at | SUMO1/sentrin/SMT3 specific peptidase 3 | SENP3 | 26168 | -2.031191 | 0.701657 |
| 221096_s_at | transmembrane and coiled-coil domains 6 | TMCO6 | 55374 | -2.031825 | 0.701657 |
| 218818_at | four and a half LIM domains 3 | FHL3 | 2275 | -2.03252 | 0.701657 |
| 206990_at | tenascin R (restrictin, janusin) | TNR | 7143 | -2.033148 | 0.701657 |
| 211865_s_at | fizzy/cell division cycle 20 related 1 (Drosophila) | FZR1 | 51343 | -2.034789 | 0.701657 |
| 214331_at | Ts translation elongation factor, mitochondrial | TSFM | 10102 | -2.034896 | 0.701657 |
| 206695_x_at | zinc finger protein 43 | ZNF43 | 7594 | -2.035761 | 0.701657 |
| 206413_at | solute carrier family 39 (zinc transporter), member 2 | SLC39A2 | 29986 | -2.036782 | 0.701042 |
| 221328_at | claudin 17 | CLDN17 | 26285 | -2.037624 | 0.700417 |
| 202220_at | testis derived transcript (3 LIM domains) | TES | 26136 | -2.040733 | 0.697915 |
| 217370_x_at | fusion (involved in t(12;16) in malignant liposarcoma) | FUS | 2521 | -2.042745 | 0.697188 |

FIGURE 15 (CONTINUED)

| | | | | |
|---|---|---|---|---|
| 210658_s_at | golgi associated, gamma adaptin ear containing, ARF binding protein 2 | GGA2 | 23062 | -2.043191 | 0.696995 |
| 209645_s_at | aldehyde dehydrogenase 1 family, member B1 | ALDH1B1 | 219 | -2.044306 | 0.696807 |
| 202386_s_at | KIAA0430 | KIAA0430 | 9665 | -2.044456 | 0.696807 |
| 202320_at | general transcription factor IIIC, polypeptide 1, alpha 220kDa | GTF3C1 | 2975 | -2.044952 | 0.696807 |
| 209856_x_at | abl interactor 2 | ABI2 | 10152 | -2.045973 | 0.696604 |
| 220842_at | Abelson helper integration site 1 | AHI1 | 54806 | -2.047505 | 0.696209 |
| 202396_at | transcription elongation regulator 1 | TCERG1 | 10915 | -2.048332 | 0.696209 |
| 210228_at | colony stimulating factor 2 (granulocyte-macrophage) | CSF2 | 1437 | -2.048838 | 0.696209 |
| 219149_x_at | debranching enzyme homolog 1 (S. cerevisiae) | DBR1 | 51163 | -2.048508 | 0.696209 |
| 205990_s_at | wingless-type MMTV integration site family, member 5A | WNT5A | 7474 | -2.048627 | 0.696209 |
| 208627_s_at | Y box binding protein 1 | YBX1 | 4904 | -2.049175 | 0.696209 |
| 218057_x_at | COX4 neighbor | COX4NB | 10328 | -2.050527 | 0.696105 |
| 201736_s_at | membrane-associated ring finger (C3HC4) 6 | 6-Mar | 10299 | -2.051522 | 0.696075 |
| 215955_x_at | Rho GTPase activating protein 26 | ARHGAP26 | 23092 | -2.051159 | 0.696075 |
| 215106_at | tetratricopeptide repeat domain 22 | TTC22 | 55001 | -2.051656 | 0.696075 |
| 215980_s_at | immunoglobulin mu binding protein 2 | IGHMBP2 | 3508 | -2.053084 | 0.695353 |
| 203654_s_at | coilin | COIL | 8161 | -2.053128 | 0.695353 |
| 217127_at | cystathionase (cystathionine gamma-lyase) | CTH | 1491 | -2.053326 | 0.695353 |
| 205393_s_at | CHK1 checkpoint homolog (S. pombe) | CHEK1 | 1111 | -2.055081 | 0.694719 |
| 209871_s_at | amyloid beta (A4) precursor protein-binding, family A, member 2 (X11-like) | APBA2 | 321 | -2.056033 | 0.694598 |
| 209650_s_at | TBC1 domain family, member 22A | TBC1D22A | 25771 | -2.056161 | 0.694598 |
| 219940_s_at | PCI domain containing 2 | PCID2 | 55795 | -2.056326 | 0.694598 |
| 212085_at | solute carrier family 25 (mitochondrial carrier; adenine nucleotide translocator), member 6 | SLC25A6 | 293 | -2.056396 | 0.694598 |
| 212722_s_at | jumonji domain containing 6 | JMJD6 | 23210 | -2.057826 | 0.694598 |
| 216354_at | | | | -2.057904 | 0.694598 |
| 205129_at | nucleophosmin/nucleoplasmin, 3 | NPM3 | 10360 | -2.058662 | 0.694598 |
| 209138_x_at | Immunoglobulin lambda locus | IGL@ | 3535 | -2.058654 | 0.694598 |
| 209823_x_at | major histocompatibility complex, class II, DQ beta 1 | HLA-DQB1 | 3119 | -2.058661 | 0.694598 |
| 214096_s_at | serine hydroxymethyltransferase 2 (mitochondrial) | SHMT2 | 6472 | -2.059216 | 0.694598 |
| 37943_at | zinc finger, FYVE domain containing 26 | ZFYVE26 | 23503 | -2.059572 | 0.694598 |
| 213561_at | ASF1 anti-silencing function 1 homolog A (S. cerevisiae) | ASF1A | 25842 | -2.060117 | 0.694598 |
| 219084_at | nuclear receptor binding SET domain protein 1 | NSD1 | 64324 | -2.060804 | 0.694598 |
| 203145_at | sperm associated antigen 5 | SPAG5 | 10615 | -2.061519 | 0.694215 |
| 219847_at | histone deacetylase 11 | HDAC11 | 79885 | -2.061533 | 0.694215 |
| 202293_at | stromal antigen 1 | STAG1 | 10274 | -2.062926 | 0.694181 |
| 201255_x_at | HLA-B associated transcript 3 | BAT3 | 7917 | -2.062969 | 0.694181 |
| 208274_at | oculomedin | OCLM | 10896 | -2.063432 | 0.694181 |
| 201146_at | nuclear factor (erythroid-derived 2)-like 2 | NFE2L2 | 4780 | -2.063551 | 0.694181 |
| 218348_s_at | zinc finger CCCH-type containing 7A | ZC3H7A | 29066 | -2.063924 | 0.694181 |
| 211953_at | RAN binding protein 5 | RANBP5 | 3843 | -2.064133 | 0.694181 |
| 203377_s_at | cell division cycle 40 homolog (S. cerevisiae) | CDC40 | 51362 | -2.064164 | 0.694181 |
| 200779_at | activating transcription factor 4 (tax-responsive enhancer element B67) | ATF4 | 468 | -2.064636 | 0.694181 |
| 200749_at | RAN, member RAS oncogene family | RAN | 5901 | -2.065283 | 0.694181 |
| 200992_at | importin 7 | IPO7 | 10527 | -2.066117 | 0.694015 |
| 211019_s_at | lanosterol synthase (2,3-oxidosqualene-lanosterol cyclase) | LSS | 4047 | -2.066148 | 0.694015 |
| 40020_at | cadherin, EGF LAG seven-pass G-type receptor 3 (flamingo homolog, Drosophila) | CELSR3 | 1951 | -2.066292 | 0.694015 |

FIGURE 15 (CONTINUED)

| | | | | | |
|---|---|---|---|---|---|
| 214407_x_at | glycophorin B (MNS blood group) | GYPB | 2994 | -2.066496 | 0.694015 |
| 207926_at | glycoprotein V (platelet) | GP5 | 2814 | -2.067526 | 0.693989 |
| 217760_at | tripartite motif-containing 44 | TRIM44 | 54765 | -2.06793 | 0.693852 |
| 206037_at | cysteine conjugate-beta lyase; cytoplasmic (glutamine transaminase K. kyneurenine aminotransferase) | CCBL1 | 883 | -2.068385 | 0.693852 |
| 221666_s_at | PYD and CARD domain containing | PYCARD | 29108 | -2.068809 | 0.693852 |
| 218878_s_at | sirtuin (silent mating type information regulation 2 homolog) 1 (S. cerevisiae) | SIRT1 | 23411 | -2.069412 | 0.693852 |
| 212584_at | aquarius homolog (mouse) | AQR | 9716 | -2.069802 | 0.693852 |
| 216943_at | | | | -2.070088 | 0.693852 |
| 218948_at | glutaminyl-tRNA synthase (glutamine-hydrolyzing)-like 1 | QRSL1 | 55278 | -2.070823 | 0.693852 |
| 201790_s_at | 7-dehydrocholesterol reductase | DHCR7 | 1717 | -2.07159 | 0.693806 |
| 216784_at | CDNA: FLJ21769 fis, clone COLF7354 | | | -2.07281 | 0.693092 |
| 209622_at | serine/threonine kinase 16 | STK16 | 8576 | -2.07351 | 0.692639 |
| 204423_at | muskelin 1, intracellular mediator containing kelch motifs | MKLN1 | 4289 | -2.074993 | 0.691792 |
| 213234_at | KIAA1467 | KIAA1467 | 57613 | -2.075773 | 0.691708 |
| 209109_s_at | tetraspanin 6 | TSPAN6 | 7105 | -2.07582 | 0.691708 |
| 216633_s_at | phospholipase C, eta 1 | PLCH1 | 23007 | -2.076661 | 0.691657 |
| 206919_at | ELK4, ETS-domain protein (SRF accessory protein 1) | ELK4 | 2005 | -2.077626 | 0.690921 |
| 203863_at | actinin, alpha 2 | ACTN2 | 88 | -2.077948 | 0.690921 |
| 209442_x_at | ankyrin 3, node of Ranvier (ankyrin G) | ANK3 | 288 | -2.078631 | 0.690746 |
| 219041_s_at | replication initiator 1 | REPIN1 | 29803 | -2.078711 | 0.690746 |
| 203755_at | BUB1 budding uninhibited by benzimidazoles 1 homolog beta (yeast) | BUB1B | 701 | -2.078732 | 0.690746 |
| 208463_at | gamma-aminobutyric acid (GABA) A receptor, alpha 4 | GABRA4 | 2557 | -2.078739 | 0.690746 |
| 211643_x_at | Major histocompatibility complex, class I, C | HLA-C | 3107 | -2.078784 | 0.690746 |
| 215071_s_at | histone cluster 1, H2ac | HIST1H2AC | 8334 | -2.078902 | 0.690746 |
| 221297_at | G protein-coupled receptor, family C, group 5, member D | GPRC5D | 55507 | -2.07894 | 0.690746 |
| 219224_x_at | zinc finger protein 408 | ZNF408 | 79797 | -2.079864 | 0.690746 |
| 203363_s_at | KIAA0652 | KIAA0652 | 9776 | -2.079902 | 0.690746 |
| 212469_at | Nipped-B homolog (Drosophila) | NIPBL | 25836 | -2.081399 | 0.690746 |
| 214306_at | optic atrophy 1 (autosomal dominant) | OPA1 | 4976 | -2.081402 | 0.690746 |
| 214888_at | calpain 2, (m/II) large subunit | CAPN2 | 824 | -2.08157 | 0.690746 |
| 217761_at | acireductone dioxygenase 1 | ADI1 | 55256 | -2.081683 | 0.690746 |
| 208045_at | surfactant protein A binding protein | SPAR | 9981 | -2.082129 | 0.690746 |
| 216945_x_at | PAS domain containing serine/threonine kinase | PASK | 23178 | -2.082178 | 0.690746 |
| 200859_x_at | filamin A, alpha (actin binding protein 280) | FLNA | 2316 | -2.082903 | 0.690746 |
| 208340_at | Evolutionarily related interleukin-1beta converting enzyme | | | -2.083463 | 0.690746 |
| 211015_s_at | heat shock 70kDa protein 4 | HSPA4 | 3308 | -2.083981 | 0.690746 |
| 218080_x_at | Fas (TNFRSF6) associated factor 1 | FAF1 | 11124 | -2.084302 | 0.690746 |
| 219916_s_at | ring finger protein 39 | RNF39 | 80352 | -2.084744 | 0.690746 |
| 215942_s_at | G-2 and S-phase expressed 1 | GTSE1 | 51512 | -2.084968 | 0.690746 |
| 206070_s_at | EPH receptor A3 | EPHA3 | 2042 | -2.087681 | 0.690746 |
| 211952_at | RAN binding protein 5 | RANBP5 | 3843 | -2.087985 | 0.690746 |
| 218826_at | solute carrier family 35, member F2 | SLC35F2 | 54733 | -2.08825 | 0.690746 |
| 207081_s_at | phosphatidylinositol 4-kinase, catalytic, alpha | PI4KA | 5297 | -2.088335 | 0.690746 |
| 219253_at | transmembrane protein 185B | TMEM185B | 79134 | -2.088494 | 0.690746 |
| 206439_at | epiphycan | EPYC | 1833 | -2.088748 | 0.690746 |

FIGURE 15 (CONTINUED)

| Probe | Description | Gene | ID | Value1 | Value2 |
|---|---|---|---|---|---|
| 214908_s_at | transformation/transcription domain-associated protein | TRRAP | 8295 | -2.088777 | 0.690746 |
| 200917_s_at | signal recognition particle receptor ('docking protein') | SRPR | 6734 | -2.089363 | 0.690746 |
| 219034_at | poly (ADP-ribose) polymerase family, member 16 | PARP16 | 54956 | -2.090203 | 0.690746 |
| 204986_s_at | TAO kinase 2 | TAOK2 | 9344 | -2.090474 | 0.690746 |
| 217742_s_at | WW domain containing adaptor with coiled-coil | WAC | 51322 | -2.09089 | 0.690746 |
| 210988_s_at | prune homolog (Drosophila) | PRUNE | 58497 | -2.092776 | 0.690746 |
| 202983_at | helicase-like transcription factor | HLTF | 6596 | -2.095223 | 0.690746 |
| 215962_at | EST clone 22453 mariner transposon Hsmar1 sequence | | | -2.095559 | 0.690746 |
| 209894_at | leptin receptor | LEPR | 3953 | -2.097299 | 0.689975 |
| 206020_at | suppressor of cytokine signaling 6 | SOCS6 | 9306 | -2.097476 | 0.689975 |
| 206643_at | histidine ammonia-lyase | HAL | 3034 | -2.098356 | 0.689932 |
| 210776_x_at | transcription factor 3 (E2A immunoglobulin enhancer binding factors E12/E47) | TCF3 | 6929 | -2.100978 | 0.687862 |
| 200957_s_at | structure specific recognition protein 1 | SSRP1 | 6749 | -2.101388 | 0.687862 |
| 211971_s_at | leucine-rich PPR-motif containing | LRPPRC | 10128 | -2.101504 | 0.687862 |
| 202128_at | KIAA0317 | KIAA0317 | 9870 | -2.101795 | 0.687862 |
| 201073_s_at | SWI/SNF related, matrix associated, actin dependent regulator of chromatin, subfamily c, member 1 | SMARCC1 | 6599 | -2.101842 | 0.687862 |
| 206295_at | interleukin 18 (interferon-gamma-inducing factor) | IL18 | 3606 | -2.104929 | 0.686728 |
| 218103_at | Pts1 homolog 3 (E. coli) | FTSJ3 | 117246 | -2.105221 | 0.686728 |
| 218819_at | integrator complex subunit 6 | INTS6 | 26512 | -2.105946 | 0.686728 |
| 200723_s_at | cell cycle associated protein 1 | CAPRIN1 | 4076 | -2.106325 | 0.686728 |
| 221956_at | leucine-rich repeats and calponin homology (CH) domain containing 4 | LRCH4 | 4034 | -2.106531 | 0.686728 |
| 203331_s_at | inositol polyphosphate-5-phosphatase, 145kDa | INPP5D | 3635 | -2.106572 | 0.686728 |
| 209416_at | fizzy/cell division cycle 20 related 1 (Drosophila) | FZR1 | 51343 | -2.107804 | 0.686728 |
| 217723_x_at | | | | -2.108104 | 0.686728 |
| 205166_at | calpain 5 | CAPN5 | 726 | -2.108491 | 0.686728 |
| 205468_s_at | interferon regulatory factor 5 | IRF5 | 3663 | -2.108715 | 0.686728 |
| 201674_s_at | A kinase (PRKA) anchor protein 1 | AKAP1 | 8165 | -2.108877 | 0.686728 |
| 213023_at | utrophin | UTRN | 7402 | -2.10932 | 0.686728 |
| 209144_s_at | core-binding factor, runt domain, alpha subunit 2; translocated to, 2 | CBFA2T2 | 9139 | -2.10975 | 0.686728 |
| 218879_at | methenyltetrahydrofolate synthetase domain containing | MTHFSD | 64779 | -2.110068 | 0.686728 |
| 206796_at | WNT1 inducible signaling pathway protein 1 | WISP1 | 8840 | -2.110411 | 0.686728 |
| 212360_at | adenosine monophosphate deaminase 2 (isoform L) | AMPD2 | 271 | -2.111929 | 0.686728 |
| 215862_at | CDNA FLJ12301 fis, clone MAMMA1001858 | | | -2.112094 | 0.686728 |
| 204018_x_at | hemoglobin, alpha 1 /// hemoglobin, alpha 2 | HBA1 /// HBA2 | 3039 /// 3040 | -2.112173 | 0.686728 |
| 212878_s_at | kinesin light chain 1 | KLC1 | 3831 | -2.112648 | 0.686728 |
| 218832_x_at | arrestin, beta 1 | ARRB1 | 408 | -2.113476 | 0.686728 |
| 213155_at | WSC domain containing 1 | WSCD1 | 23302 | -2.113552 | 0.686728 |
| 202146_at | interferon-related developmental regulator 1 | IFRD1 | 3475 | -2.113685 | 0.686728 |
| 220632_s_at | protein-O-mannosyltransferase 2 | POMT2 | 29954 | -2.11401 | 0.686728 |
| 211123_at | solute carrier family 5 (sodium iodide symporter), member 5 | SLC5A5 | 6528 | -2.114491 | 0.686728 |
| 206438_x_at | tectonic family member 2 | TCTN2 | 79867 | -2.114874 | 0.686728 |
| 219508_at | glucosaminyl (N-acetyl) transferase 3, mucin type | GCNT3 | 9245 | -2.11492 | 0.686728 |
| 204812_at | ZW10, kinetochore associated, homolog (Drosophila) | ZW10 | 9183 | -2.116306 | 0.686728 |
| 209560_s_at | delta-like 1 homolog (Drosophila) | DLK1 | 8788 | -2.116453 | 0.686728 |
| 205603_s_at | diaphanous homolog 2 (Drosophila) | DIAPH2 | 1730 | -2.116627 | 0.686728 |

FIGURE 15 (CONTINUED)

| | | | | |
|---|---|---|---|---|
| 203239_s_at | CCR4-NOT transcription complex, subunit 3 | CNOT3 | 4849 | -2.117422 | 0.686728 |
| 206222_at | tumor necrosis factor receptor superfamily, member 10c, decoy without an intracellular domain | TNFRSF10C | 8794 | -2.117558 | 0.686728 |
| 204105_s_at | neuronal cell adhesion molecule | NRCAM | 4897 | -2.118006 | 0.686728 |
| 218272_at | hypothetical protein FLJ20699 | FLJ20699 | 55020 | -2.118028 | 0.686728 |
| 204729_s_at | syntaxin 1A (brain) | STX1A | 6804 | -2.119262 | 0.686728 |
| 219699_at | leucine-rich repeat LGI family, member 2 | LGI2 | 55203 | -2.119283 | 0.686728 |
| 206968_s_at | nuclear factor related to kappaB binding protein | NFRKB | 4798 | -2.119337 | 0.686728 |
| 209178_at | DEAH (Asp-Glu-Ala-His) box polypeptide 38 | DHX38 | 9785 | -2.119756 | 0.686728 |
| 1861_at | BCL2-antagonist of cell death | BAD | 572 | -2.12153 | 0.686542 |
| 214586_at | G protein-coupled receptor 37 (endothelin receptor type B-like) | GPR37 | 2861 | -2.121871 | 0.686542 |
| 218423_x_at | vacuolar protein sorting 54 homolog (S. cerevisiae) | VPS54 | 51542 | -2.121902 | 0.686542 |
| 203004_s_at | myocyte enhancer factor 2D | MEF2D | 4209 | -2.122219 | 0.686542 |
| 220531_at | hypothetical protein FLJ14126 | FLJ14126 | 79907 | -2.122334 | 0.686542 |
| 216999_at | erythropoietin receptor | EPOR | 2057 | -2.122534 | 0.686542 |
| 218187_s_at | chromosome 8 open reading frame 33 | C8orf33 | 65265 | -2.122742 | 0.686542 |
| 212695_at | cryptochrome 2 (photolyase-like) | CRY2 | 1408 | -2.123731 | 0.686542 |
| 219272_at | tripartite motif-containing 62 | TRIM62 | 55223 | -2.124852 | 0.686542 |
| 210419_at | BARX homeobox 2 | BARX2 | 8538 | -2.125676 | 0.686542 |
| 220872_at | hypothetical protein PRO2964 | PRO2964 | 55415 | -2.126031 | 0.686542 |
| 212145_at | mitochondrial ribosomal protein S27 | MRPS27 | 23107 | -2.126068 | 0.686542 |
| 204001_at | small nuclear RNA activating complex, polypeptide 3, 50kDa | SNAPC3 | 6619 | -2.126071 | 0.686542 |
| 204800_s_at | dehydrogenase/reductase (SDR family) member 12 | DHRS12 | 79758 | -2.130237 | 0.686542 |
| 215108_x_at | TOX high mobility group box family member 3 | TOX3 | 27324 | -2.130624 | 0.686542 |
| 202922_at | glutamate-cysteine ligase, catalytic subunit | GCLC | 2729 | -2.13114 | 0.686542 |
| 218898_at | family with sequence similarity 57, member A | FAM57A | 79850 | -2.131284 | 0.686542 |
| 213410_at | chromosome 10 open reading frame 137 | C10orf137 | 26098 | -2.131417 | 0.686542 |
| 221668_s_at | dynein, axonemal, intermediate chain 2 | DNAI2 | 64446 | -2.132977 | 0.686542 |
| 213330_s_at | stress-induced-phosphoprotein 1 (Hsp70/Hsp90-organizing protein) | STIP1 | 10963 | -2.133426 | 0.686542 |
| 215427_s_at | zinc finger, CCHC domain containing 14 | ZCCHC14 | 23174 | -2.133719 | 0.686542 |
| 202719_s_at | testis derived transcript (3 LIM domains) | TES | 26136 | -2.134118 | 0.686542 |
| 218156_s_at | TSR1, 20S rRNA accumulation, homolog (S. cerevisiae) | TSR1 | 55720 | -2.135615 | 0.686542 |
| 214300_s_at | topoisomerase (DNA) III alpha | TOP3A | 7156 | -2.135752 | 0.686542 |
| 202557_at | stress 70 protein chaperone, microsome-associated, 60kDa | STCH | 6782 | -2.135785 | 0.686542 |
| 215707_s_at | prion protein (p27-30) (Creutzfeldt-Jakob disease, Gerstmann-Strausler-Scheinker syndrome, fatal familial insomnia) | PRNP | 5621 | -2.136941 | 0.686542 |
| 202062_s_at | sel-1 suppressor of lin-12-like (C. elegans) | SEL1L | 6400 | -2.136946 | 0.686542 |
| 203334_at | DEAH (Asp-Glu-Ala-His) box polypeptide 8 | DHX8 | 1659 | -2.136985 | 0.686542 |
| 206053_at | zinc finger protein 510 | ZNF510 | 22869 | -2.137601 | 0.686542 |
| 213329_at | SLIT-ROBO Rho GTPase activating protein 2 | SRGAP2 | 23380 | -2.1388 | 0.686542 |
| 209206_at | SEC22 vesicle trafficking protein homolog B (S. cerevisiae) | SEC22B | 9554 | -2.138914 | 0.686542 |
| 203515_s_at | phosphomevalonate kinase | PMVK | 10654 | -2.139167 | 0.686542 |
| 206523_at | pleckstrin homology, Sec7 and coiled-coil domains 3 | PSCD3 | 9265 | -2.140126 | 0.686542 |
| 222094_at | sulfotransferase family, cytosolic, 1A, phenol-preferring, member 3 /// sulfotransferase family, cytosolic, 1A, phenol-preferring, member 4 | SULT1A3 /// SULT1A4 | 445329 /// 6818 | -2.140386 | 0.686542 |
| 204984_at | glypican 4 | GPC4 | 2239 | -2.140567 | 0.686542 |
| 201843_s_at | EGF-containing fibulin-like extracellular matrix protein 1 | EFEMP1 | 2202 | -2.140826 | 0.686542 |

FIGURE 15 (CONTINUED)

| | | | | | |
|---|---|---|---|---|---|
| 211121_s_at | docking protein 1, 62kDa (downstream of tyrosine kinase 1) | DOK1 | 1796 | -2.141491 | 0.686542 |
| 202978_s_at | CREB/ATF bZIP transcription factor | CREBZF | 58487 | -2.142049 | 0.686542 |
| 210040_at | solute carrier family 12, (potassium-chloride transporter) member 5 | SLC12A5 | 57468 | -2.142179 | 0.686542 |
| 210299_s_at | four and a half LIM domains 1 | FHL1 | 2273 | -2.142228 | 0.686542 |
| 201555_at | minichromosome maintenance complex component 3 | MCM3 | 4172 | -2.143043 | 0.686542 |
| 204366_s_at | general transcription factor IIIC, polypeptide 2, beta 110kDa | GTF3C2 | 2976 | -2.144035 | 0.686542 |
| 202294_at | stromal antigen 1 | STAG1 | 10274 | -2.144257 | 0.686542 |
| 215003_at | DiGeorge syndrome critical region gene 9 | DGCR9 | 25787 | -2.145093 | 0.686542 |
| 217674_at | Transcribed locus | | | -2.145515 | 0.686542 |
| 203734_at | forkhead box J2 | FOXJ2 | 55810 | -2.145855 | 0.686542 |
| 208914_at | golgi associated, gamma adaptin ear containing, ARF binding protein 2 | GGA2 | 23062 | -2.146197 | 0.686542 |
| 215938_s_at | phospholipase A2, group VI (cytosolic, calcium-independent) | PLA2G6 | 8398 | -2.146673 | 0.686542 |
| 213181_s_at | molybdenum cofactor synthesis 1 | MOCS1 | 4337 | -2.147583 | 0.686542 |
| 221806_s_at | SET domain containing 5 | SETD5 | 55209 | -2.147709 | 0.686542 |
| 207199_at | telomerase reverse transcriptase | TERT | 7015 | -2.148831 | 0.686542 |
| 213078_x_at | 1-acylglycerol-3-phosphate O-acyltransferase 7 (lysophosphatidic acid acyltransferase, eta) | AGPAT7 | 254531 | -2.149065 | 0.686542 |
| 203204_s_at | jumonji domain containing 2A | JMJD2A | 9682 | -2.150122 | 0.686542 |
| 200815_s_at | platelet-activating factor acetylhydrolase, isoform Ib, alpha subunit 45kDa | PAFAH1B1 | 5048 | -2.150662 | 0.686542 |
| 213137_s_at | protein tyrosine phosphatase, non-receptor type 2 | PTPN2 | 5771 | -2.150883 | 0.686542 |
| 216071_x_at | mediator complex subunit 12 | MED12 | 9968 | -2.151957 | 0.686542 |
| 219545_at | potassium channel tetramerisation domain containing 14 | KCTD14 | 65987 | -2.151986 | 0.686542 |
| 202012_s_at | exostoses (multiple) 2 | EXT2 | 2132 | -2.152582 | 0.686542 |
| 201803_at | polymerase (RNA) II (DNA directed) polypeptide B, 140kDa | POLR2B | 5431 | -2.153225 | 0.686542 |
| 218148_at | centromere protein T | CENPT | 80152 | -2.153251 | 0.686542 |
| 200027_at | asparaginyl-tRNA synthetase | NARS | 4677 | -2.154465 | 0.686542 |
| 209383_at | DNA-damage-inducible transcript 3 | DDIT3 | 1649 | -2.154921 | 0.686542 |
| 215087_at | chromosome 15 open reading frame 39 | C15orf39 | 56905 | -2.155535 | 0.686542 |
| 219436_s_at | endomucin | EMCN | 51705 | -2.155581 | 0.686542 |
| 210811_s_at | DEAD (Asp-Glu-Ala-Asp) box polypeptide 49 | DDX49 | 54555 | -2.155755 | 0.686542 |
| 201614_s_at | RuvB-like 1 (E. coli) | RUVBL1 | 8607 | -2.156781 | 0.686542 |
| 212001_at | splicing factor, arginine/serine-rich 14 | SFRS14 | 10147 | -2.157099 | 0.686542 |
| 205714_s_at | zinc finger, MYND-type containing 10 | ZMYND10 | 51364 | -2.157685 | 0.686542 |
| 218770_s_at | transmembrane protein 39B | TMEM39B | 55116 | -2.158253 | 0.686542 |
| 200895_s_at | FK506 binding protein 4, 59kDa | FKBP4 | 2288 | -2.159055 | 0.686542 |
| 207082_at | colony stimulating factor 1 (macrophage) | CSF1 | 1435 | -2.159385 | 0.686542 |
| 206219_s_at | vav 1 guanine nucleotide exchange factor | VAV1 | 7409 | -2.160304 | 0.686542 |
| 207262_at | apolipoprotein F | APOF | 319 | -2.162416 | 0.686542 |
| 215994_x_at | TBC1 domain family, member 9B (with GRAM domain) | TBC1D9B | 23061 | -2.162979 | 0.686542 |
| 213567_at | Clone 23728 mRNA sequence | | | -2.163094 | 0.686542 |
| 208250_s_at | deleted in malignant brain tumors 1 | DMBT1 | 1755 | -2.163388 | 0.686542 |
| 206816_s_at | sperm associated antigen 8 | SPAG8 | 26206 | -2.163838 | 0.686542 |
| 200976_s_at | Tax1 (human T-cell leukemia virus type I) binding protein 1 | TAX1BP1 | 8887 | -2.164035 | 0.686542 |
| 214759_at | Wilms tumor 1 associated protein | WTAP | 9589 | -2.164405 | 0.686542 |
| 202585_s_at | nuclear transcription factor, X-box binding 1 | NFX1 | 4799 | -2.164434 | 0.686542 |
| 220705_s_at | ADAM metallopeptidase with thrombospondin type 1 motif, 7 | ADAMTS7 | 11173 | -2.164575 | 0.686542 |
| 210220_at | frizzled homolog 2 (Drosophila) | FZD2 | 2535 | -2.164495 | 0.686542 |

FIGURE 15 (CONTINUED)

| | | | | |
|---|---|---|---|---|
| 218466_at | TBC1 domain family, member 17 | TBC1D17 | 79735 | -2.165674 | 0.686542 |
| 206223_at | lemur tyrosine kinase 2 | LMTK2 | 22853 | -2.166302 | 0.686542 |
| 211845_s_at | poliovirus receptor-related 1 (herpesvirus entry mediator C) | PVRL1 | 5818 | -2.166726 | 0.686542 |
| 213194_at | roundabout, axon guidance receptor, homolog 1 (Drosophila) | ROBO1 | 6091 | -2.167464 | 0.686542 |
| 203117_s_at | PAN2 polyA specific ribonuclease subunit homolog (S. cerevisiae) | PAN2 | 9924 | -2.167475 | 0.686542 |
| 212227_x_at | eukaryotic translation initiation factor 1 | EIF1 | 10209 | -2.168232 | 0.686542 |
| 217806_s_at | polymerase (DNA-directed), delta interacting protein 2 | POLDIP2 | 26073 | -2.168344 | 0.686542 |
| 208209_s_at | complement component 4 binding protein, beta | C4BPB | 725 | -2.168382 | 0.686542 |
| 202193_at | LIM domain kinase 2 | LIMK2 | 3985 | -2.169083 | 0.686542 |
| 36612_at | KIAA0280 | KIAA0280 | 23201 | -2.170443 | 0.686542 |
| 204633_s_at | ribosomal protein S6 kinase, 90kDa, polypeptide 5 | RPS6KA5 | 9252 | -2.170597 | 0.686542 |
| 208251_at | potassium voltage-gated channel, Shaw-related subfamily, member 4 | KCNC4 | 3749 | -2.171525 | 0.686542 |
| 209054_s_at | Wolf-Hirschhorn syndrome candidate 1 | WHSC1 | 7468 | -2.172839 | 0.686542 |
| 216133_at | T cell receptor V alpha gene segment V-alpha-w23, clone IGRa01 | --- | --- | -2.172954 | 0.686542 |
| 201925_s_at | CD55 molecule, decay accelerating factor for complement (Cromer blood group) | CD55 | 1604 | -2.17338 | 0.686542 |
| 212507_at | transmembrane protein 131 | TMEM131 | 23505 | -2.173763 | 0.686542 |
| 222315_at | Transcribed locus | --- | --- | -2.174098 | 0.686542 |
| 212945_s_at | MAX gene associated | MGA | 23269 | -2.17413 | 0.686542 |
| 214665_s_at | calcium binding protein P22 | CHP | 11261 | -2.174309 | 0.686542 |
| 201930_at | minichromosome maintenance complex component 6 | MCM6 | 4175 | -2.174455 | 0.686542 |
| 204760_s_at | thyroid hormone receptor, alpha (erythroblastic leukemia viral (v-erb-a) oncogene homolog, avian) /// nuclear receptor subfamily 1, group D, member 1 | NR1D1 /// THRA | 7067 /// 9572 | -2.174969 | 0.686542 |
| 217791_s_at | aldehyde dehydrogenase 18 family, member A1 | ALDH18A1 | 5832 | -2.175986 | 0.686542 |
| 214404_x_at | SAM pointed domain containing ets transcription factor | SPDEF | 25803 | -2.176221 | 0.686542 |
| 219627_at | zinc finger family member 767 | ZNF767 | 79970 | -2.176367 | 0.686542 |
| 219578_s_at | cytoplasmic polyadenylation element binding protein 1 | CPEB1 | 64506 | -2.177137 | 0.686542 |
| 207268_x_at | abl interactor 2 | ABI2 | 10152 | -2.178838 | 0.686542 |
| 37232_at | KIAA0586 | KIAA0586 | 9786 | -2.179151 | 0.686542 |
| 212826_s_at | solute carrier family 25 (mitochondrial carrier; adenine nucleotide translocator), member 6 | SLC25A6 | 293 | -2.179688 | 0.686542 |
| 207990_x_at | acrosomal vesicle protein 1 | ACRV1 | 56 | -2.180286 | 0.686542 |
| 214552_s_at | rabaptin, RAB GTPase binding effector protein 1 | RABEP1 | 9135 | -2.180834 | 0.686542 |
| 203841_x_at | microtubule-associated protein, RP/EB family, member 3 | MAPRE3 | 22924 | -2.181209 | 0.686542 |
| 218954_s_at | BRF2, subunit of RNA polymerase III transcription initiation factor, BRF1-like | BRF2 | 55290 | -2.181907 | 0.686542 |
| 202444_s_at | ER lipid raft associated 1 | ERLIN1 | 10613 | -2.182987 | 0.686542 |
| 210718_s_at | ADP-ribosylation factor-like 17 pseudogene 1 | ARL17P1 | 51326 | -2.184163 | 0.686542 |
| 218168_s_at | chaperone, ABC1 activity of bc1 complex homolog (S. pombe) | CABC1 | 56997 | -2.184196 | 0.686542 |
| 214323_s_at | UPF3 regulator of nonsense transcripts homolog A (yeast) | UPF3A | 65110 | -2.184649 | 0.686542 |
| 201195_s_at | solute carrier family 7 (cationic amino acid transporter, y+ system), member 5 | SLC7A5 | 8140 | -2.184749 | 0.686542 |
| 207915_at | --- | --- | --- | -2.184892 | 0.686542 |
| 201651_s_at | protein kinase C and casein kinase substrate in neurons 2 | PACSN2 | 11252 | -2.185535 | 0.686542 |
| 204373_s_at | centrosomal protein 350kDa | CEP350 | 9857 | -2.185897 | 0.686542 |
| 219615_s_at | potassium channel, subfamily K, member 5 | KCNK5 | 8645 | -2.188829 | 0.686542 |
| 213378_s_at | DEAD/H (Asp-Glu-Ala-Asp/His) box polypeptide 11 (CHL1-like helicase homolog, S. cerevisiae) /// DEAD/H (Asp-Glu-Ala-Asp/His) box polypeptide 12 (CHL1-like helicase homolog, S. cerevisiae) /// DEAD/H (Asp-Glu-Ala-Asp/His) box polypeptide 11-like | DDX11 /// DDX12 /// LOC642846 | 1663 /// 440081 /// 642846 | -2.189251 | 0.686542 |
| 203990_s_at | ubiquitously transcribed tetratricopeptide repeat, X chromosome | UTX | 7403 | -2.189485 | 0.686542 |

FIGURE 15 (CONTINUED)

| | | | | |
|---|---|---|---|---|
| 200806_s_at | heat shock 60kDa protein 1 (chaperonin) | HSPD1 | 3329 | -2.189498 | 0.686542 |
| 204849_at | transcription factor-like 5 (basic helix-loop-helix) | TCFL5 | 10732 | -2.18992 | 0.686542 |
| 208839_s_at | cullin-associated and neddylation-dissociated 1 | CAND1 | 55832 | -2.190477 | 0.686542 |
| 218889_at | nucleolar complex associated 3 homolog (S. cerevisiae) | NOC3L | 64318 | -2.191022 | 0.686542 |
| 204169_at | IMP (inosine monophosphate) dehydrogenase 1 | IMPDH1 | 3614 | -2.191228 | 0.686542 |
| 204502_at | SAM domain and HD domain 1 | SAMHD1 | 25939 | -2.191747 | 0.686542 |
| 213759_at | ADP-ribosylation factor-like 4C | ARL4C | 10123 | -2.192081 | 0.686542 |
| 54970_at | zinc finger, MIZ-type containing 2 | ZMIZ2 | 83637 | -2.19274 | 0.686542 |
| 213900_at | chromosome 9 open reading frame 61 | C9orf61 | 9413 | -2.193065 | 0.686542 |
| 211280_s_at | nuclear respiratory factor 1 | NRF1 | 4899 | -2.196489 | 0.686542 |
| 221868_at | poly(A) binding protein interacting protein 2B | PAIP2B | 400961 | -2.197351 | 0.686542 |
| 201561_s_at | calsyntenin 1 | CLSTN1 | 22883 | -2.19793 | 0.686542 |
| 219715_s_at | tyrosyl-DNA phosphodiesterase 1 | TDP1 | 55775 | -2.198645 | 0.686542 |
| 202100_at | v-ral simian leukemia viral oncogene homolog B (ras related; GTP binding protein) | RALB | 5899 | -2.199149 | 0.686542 |
| 205577_at | phosphorylase, glycogen; muscle (McArdle syndrome, glycogen storage disease type V) | PYGM | 5837 | -2.199636 | 0.686542 |
| 215696_s_at | SEC16 homolog A (S. cerevisiae) | SEC16A | 9919 | -2.2018 | 0.686542 |
| 208346_at | pro-platelet basic protein-like 2 | PPBPL2 | 10895 | -2.202144 | 0.686542 |
| 203623_at | plexin A3 | PLXNA3 | 55558 | -2.203018 | 0.686542 |
| 201385_at | DEAH (Asp-Glu-Ala-His) box polypeptide 15 | DHX15 | 1665 | -2.203038 | 0.686542 |
| 214934_at | ATPase, class II, type 9B | ATP9B | 374868 | -2.203082 | 0.686542 |
| 215481_s_at | peroxisomal biogenesis factor 5 | PEX5 | 5830 | -2.203987 | 0.686542 |
| 208117_s_at | LAS1-like (S. cerevisiae) | LAS1L | 81887 | -2.205221 | 0.686542 |
| 216277_at | BUB1 budding uninhibited by benzimidazoles 1 homolog (yeast) | BUB1 | 699 | -2.20638 | 0.686542 |
| 205080_at | retinoic acid receptor, beta | RARB | 5915 | -2.207232 | 0.686542 |
| 214640_at | opioid receptor, sigma 1 | OPRS1 | 10280 | -2.207807 | 0.686542 |
| 215180_at | mRNA full length insert cDNA clone EUROIMAGE 897021 | | | -2.208227 | 0.686542 |
| 214848_at | Clone 23548 mRNA sequence | | | -2.211651 | 0.686542 |
| 200866_s_at | prosaposin (variant Gaucher disease and variant metachromatic leukodystrophy) | PSAP | 5660 | -2.212461 | 0.686542 |
| 204355_at | DEAH (Asp-Glu-Ala-His) box polypeptide 30 | DHX30 | 22907 | -2.212603 | 0.686542 |
| 215258_at | cell adhesion molecule 4 | CADM4 | 199731 | -2.212824 | 0.686542 |
| 202547_s_at | Rho guanine nucleotide exchange factor (GEF) 7 | ARHGEF7 | 8874 | -2.213502 | 0.686542 |
| 203611_at | telomeric repeat binding factor 2 | TERF2 | 7014 | -2.214031 | 0.686542 |
| 210337_s_at | ATP citrate lyase | ACLY | 47 | -2.214344 | 0.686542 |
| 210812_at | X-ray repair complementing defective repair in Chinese hamster cells 4 | XRCC4 | 7518 | -2.214427 | 0.686542 |
| 207711_at | chromosome 20 open reading frame 117 | C20orf117 | 140710 | -2.214452 | 0.686542 |
| 203513_at | spastic paraplegia 11 (autosomal recessive) | SPG11 | 80208 | -2.2147 | 0.686542 |
| 221812_at | F-box protein 42 | FBXO42 | 54455 | -2.214808 | 0.686542 |
| 221121_at | chromosome X open reading frame 48 | CXorf48 | 54967 | -2.215704 | 0.686542 |
| 208368_s_at | breast cancer 2, early onset | BRCA2 | 675 | -2.216422 | 0.686542 |
| 202911_at | mutS homolog 6 (E. coli) | MSH6 | 2956 | -2.216674 | 0.686542 |
| 207529_at | defensin, alpha 5, Paneth cell-specific | DEFA5 | 1670 | -2.217038 | 0.686542 |
| 210958_s_at | microtubule associated serine/threonine kinase family member 4 | MAST4 | 375449 | -2.217666 | 0.686542 |
| 213530_at | RAB3 GTPase activating protein subunit 1 (catalytic) | RAB3GAP1 | 22930 | -2.21794 | 0.686542 |
| 218399_s_at | cell division cycle associated 4 | CDCA4 | 55038 | -2.218148 | 0.686542 |
| 220435_at | solute carrier family 30, member 10 | SLC30A10 | 55532 | -2.218493 | 0.686542 |
| 217678_at | solute carrier family 7, (cationic amino acid transporter, y+ system) member 11 | SLC7A11 | 23657 | -2.219935 | 0.686542 |

FIGURE 15 (CONTINUED)

| | | | | |
|---|---|---|---|---|
| 219027_s_at | myosin IXA | MYO9A | 4649 | -2.220165 | 0.686542 |
| 204584_at | L1 cell adhesion molecule | L1CAM | 3897 | -2.220599 | 0.686542 |
| 206414_s_at | development and differentiation enhancing factor 2 | DDEF2 | 8853 | -2.220922 | 0.686542 |
| 217954_s_at | PHD finger protein 3 | PHF3 | 23469 | -2.221766 | 0.686542 |
| 207620_s_at | calcium/calmodulin-dependent serine protein kinase (MAGUK family) | CASK | 8573 | -2.221926 | 0.686542 |
| 215832_x_at | phosphatidylinositol binding clathrin assembly protein | PICALM | 8301 | -2.22245 | 0.686542 |
| 214849_at | potassium channel tetramerisation domain containing 20 | KCTD20 | 222658 | -2.223403 | 0.686542 |
| 216491_x_at | immunoglobulin heavy constant mu | IGHM | 3507 | -2.225147 | 0.686542 |
| 206231_at | potassium intermediate/small conductance calcium-activated channel, subfamily N, member 1 | KCNN1 | 3780 | -2.225443 | 0.686542 |
| 203068_at | kelch-like 21 (Drosophila) | KLHL21 | 9903 | -2.225494 | 0.686542 |
| 201713_s_at | RAN binding protein 2 | RANBP2 | 5903 | -2.226792 | 0.686542 |
| 218009_s_at | protein regulator of cytokinesis 1 | PRC1 | 9055 | -2.227348 | 0.686542 |
| 217295_at | mucin 8 | MUC8 | 4590 | -2.227474 | 0.686542 |
| 211671_s_at | nuclear receptor subfamily 3, group C, member 1 (glucocorticoid receptor) | NR3C1 | 2908 | -2.228221 | 0.686542 |
| 220048_at | ectodysplasin A receptor | EDAR | 10913 | -2.229226 | 0.686542 |
| 212781_at | retinoblastoma binding protein 6 | RBBP6 | 5930 | -2.229234 | 0.686542 |
| 206817_x_at | trinucleotide repeat containing 4 | TNRC4 | 11189 | -2.234329 | 0.686542 |
| 211938_at | eukaryotic translation initiation factor 4B | EIF4B | 1975 | -2.234651 | 0.686542 |
| 217715_x_at | --- | --- | | -2.234661 | 0.686542 |
| 205437_at | zinc finger protein 211 | ZNF211 | 10520 | -2.235113 | 0.686542 |
| 220868_s_at | solute carrier family 7 (neutral amino acid transporter, y+ system) member 10 | SLC7A10 | 56301 | -2.236332 | 0.686542 |
| 202807_s_at | target of myb1 (chicken) | TOM1 | 10043 | -2.236589 | 0.686542 |
| 210420_at | solute carrier family 24 (sodium/potassium/calcium exchanger), member 1 | SLC24A1 | 9187 | -2.23922 | 0.686542 |
| 201905_s_at | CTD (carboxy-terminal domain, RNA polymerase II, polypeptide A) small phosphatase-like | CTDSPL | 10217 | -2.239226 | 0.686542 |
| 218636_s_at | mannosidase, alpha, class 1B, member 1 | MAN1B1 | 11253 | -2.239969 | 0.686542 |
| 210064_s_at | uroplakin 1B | UPK1B | 7348 | -2.240195 | 0.686542 |
| 203859_s_at | paralemmin | PALM | 5064 | -2.241415 | 0.686542 |
| 219832_s_at | homeobox C13 | HOXC13 | 3229 | -2.241665 | 0.686542 |
| 200687_s_at | splicing factor 3b, subunit 3, 130kDa | SF3B3 | 23450 | -2.242182 | 0.686542 |
| 209267_s_at | solute carrier family 39 (zinc transporter), member 8 | SLC39A8 | 64116 | -2.242247 | 0.686542 |
| 208623_s_at | ezrin | EZR | 7430 | -2.243041 | 0.686542 |
| 206052_s_at | stem-loop (histone) binding protein | SLBP | 7884 | -2.243111 | 0.686542 |
| 215039_at | Hypothetical protein LOC339524 | LOC339524 | 339524 | -2.243978 | 0.686542 |
| 221939_at | Yip1 domain family, member 2 | YIPF2 | 78992 | -2.245067 | 0.686542 |
| 213304_at | KIAA0423 | KIAA0423 | 23116 | -2.245211 | 0.686542 |
| 204370_at | CLP1, cleavage and polyadenylation factor I subunit, homolog (S. cerevisiae) | CLP1 | 10978 | -2.245755 | 0.686542 |
| 201583_s_at | Sec23 homolog B (S. cerevisiae) | SEC23B | 10483 | -2.246997 | 0.686542 |
| 213436_at | cannabinoid receptor 1 (brain) | CNR1 | 1268 | -2.247831 | 0.686542 |
| 219611_s_at | coiled-coil domain containing 21 | CCDC21 | 64793 | -2.248277 | 0.686542 |
| 212352_s_at | transmembrane emp24-like trafficking protein 10 (yeast) | TMED10 | 10972 | -2.249222 | 0.686542 |
| 222078_at | Transcribed locus | --- | | -2.250674 | 0.686542 |
| 206260_at | transglutaminase 4 (prostate) | TGM4 | 7047 | -2.251007 | 0.686542 |
| 203338_at | protein phosphatase 2, regulatory subunit B', epsilon isoform | PPP2R5E | 5529 | -2.25102 | 0.686542 |
| 209318_x_at | pleiomorphic adenoma gene-like 1 | PLAGL1 | 5325 | -2.251729 | 0.686542 |
| 209777_s_at | ribosomal protein S6 kinase, 70kDa, polypeptide 2 | RPS6KB2 | 6199 | -2.252934 | 0.686542 |
| 216399_s_at | S phase cyclin A-associated protein in the ER | SCAPER | 49855 | -2.256001 | 0.686542 |

FIGURE 15 (CONTINUED)

| | | | | | |
|---|---|---|---|---|---|
| 208227_x_at | ADAM metallopeptidase domain 22 | ADAM22 | 53616 | -2.256773 | 0.686542 |
| 208160_at | hypothetical protein FLJ10232 | FLJ10232 | 55099 | -2.25808 | 0.685974 |
| 207722_s_at | BTB (POZ) domain containing 2 | BTBD2 | 55643 | -2.258385 | 0.685974 |
| 203083_at | thrombospondin 2 | THBS2 | 7058 | -2.259101 | 0.685567 |
| 207752_x_at | proline-rich protein BstNI subfamily 1 | PRB1 | 5542 | -2.259564 | 0.685566 |
| 213323_s_at | zinc finger CCCH-type containing 7B | ZC3H7B | 23264 | -2.260079 | 0.685408 |
| 219048_at | phosphatidylinositol glycan anchor biosynthesis, class N | PIGN | 23556 | -2.260154 | 0.685408 |
| 206882_at | solute carrier family 1 (high affinity aspartate/glutamate transporter), member 6 | SLC1A6 | 6511 | -2.260321 | 0.685408 |
| 206960_at | G protein-coupled receptor 23 | GPR23 | 2846 | -2.260431 | 0.685408 |
| 220939_s_at | dipeptidyl-peptidase 8 | DPP8 | 54878 | -2.261081 | 0.685408 |
| 206798_x_at | deleted in lung and esophageal cancer 1 | DLEC1 | 9940 | -2.261741 | 0.685408 |
| 206942_s_at | pro-melanin-concentrating hormone | PMCH | 5367 | -2.264922 | 0.685365 |
| 211815_s_at | golgi associated, gamma adaptin ear containing, ARF binding protein 3 | GGA3 | 23163 | -2.26522 | 0.685365 |
| 212674_s_at | DEAH (Asp-Glu-Ala-His) box polypeptide 30 | DHX30 | 22907 | -2.265978 | 0.685365 |
| 211207_s_at | acyl-CoA synthetase long-chain family member 6 | ACSL6 | 23305 | -2.266437 | 0.685365 |
| 202309_at | methylenetetrahydrofolate dehydrogenase (NADP+ dependent) 1, methenyltetrahydrofolate cyclohydrolase, formyltetrahydrofolate synthetase | MTHFD1 | 4522 | -2.266963 | 0.685365 |
| 203636_at | midline 1 (Opitz/BBB syndrome) | MID1 | 4281 | -2.267064 | 0.685365 |
| 222353_at | LIM domains containing 1 | LIMD1 | 8994 | -2.268024 | 0.685365 |
| 208225_at | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | FGFR2 | 2263 | -2.268229 | 0.685365 |
| 203077_s_at | SMAD family member 2 | SMAD2 | 4087 | -2.268909 | 0.685365 |
| 206419_at | RAR-related orphan receptor C | RORC | 6097 | -2.270099 | 0.685365 |
| 209291_at | inhibitor of DNA binding 4, dominant negative helix-loop-helix protein | ID4 | 3400 | -2.270506 | 0.685365 |
| 216676_x_at | killer cell immunoglobulin-like receptor, three domains, long cytoplasmic tail, 3 | KIR3DL3 | 115653 | -2.271168 | 0.685365 |
| 211185_s_at | splicing factor 3b, subunit 1, 155kDa | SF3B1 | 23451 | -2.271568 | 0.685365 |
| 211599_x_at | met proto-oncogene (hepatocyte growth factor receptor) | MET | 4233 | -2.271828 | 0.685365 |
| 206412_at | fer (fps/fes related) tyrosine kinase (phosphoprotein NCP94) | FER | 2241 | -2.272748 | 0.685365 |
| 214387_x_at | surfactant, pulmonary-associated protein C | SFTPC | 6440 | -2.272893 | 0.685365 |
| 213318_s_at | HLA-B associated transcript 3 | BAT3 | 7917 | -2.273493 | 0.685365 |
| 221870_at | EH-domain containing 2 | EHD2 | 30846 | -2.273936 | 0.685365 |
| 210157_at | chromosome 19 open reading frame 2 | C19orf2 | 8725 | -2.274789 | 0.685365 |
| 214198_s_at | DiGeorge syndrome critical region gene 2 | DGCR2 | 9993 | -2.275103 | 0.685365 |
| 216825_s_at | myeloproliferative leukemia virus oncogene | MPL | 4352 | -2.275909 | 0.685365 |
| 215624_at | tuberous sclerosis 2 | TSC2 | 7249 | -2.277161 | 0.685365 |
| 202159_at | phenylalanyl-tRNA synthetase, alpha subunit | FARSA | 2193 | -2.277216 | 0.685365 |
| 201079_at | synaptogyrin 2 | SYNGR2 | 9144 | -2.277694 | 0.685365 |
| 222038_s_at | Non-metastatic cells 1, protein (NM23A) expressed in | NME1 | 4830 | -2.27775 | 0.685365 |
| 206730_at | glutamate receptor, ionotropic, AMPA 3 | GRIA3 | 2892 | -2.27797 | 0.685365 |
| 203902_at | hephaestin | HEPH | 9843 | -2.27797 | 0.685365 |
| 220206_at | zinc finger, MYM-type 1 | ZMYM1 | 79830 | -2.278194 | 0.685365 |
| 201490_s_at | peptidylprolyl isomerase F (cyclophilin F) | PPIF | 10105 | -2.279127 | 0.685365 |
| 218794_s_at | thioredoxin-like 4B | TXNL4B | 54957 | -2.279673 | 0.685365 |
| 206748_s_at | sperm associated antigen 9 | SPAG9 | 9043 | -2.280403 | 0.685365 |
| 213191_at | toll-like receptor adaptor molecule 1 | TICAM1 | 148022 | -2.280527 | 0.685365 |
| 220332_at | claudin 16 | CLDN16 | 10686 | -2.280852 | 0.685365 |

FIGURE 15 (CONTINUED)

| | | | | |
|---|---|---|---|---|
| 205282_at | low density lipoprotein receptor-related protein 8, apolipoprotein e receptor | LRP8 | 7804 | -2.280869 | 0.685365 |
| 216155_at | CDNA: FLJ20890 fis, clone ADKA03323 | | | -2.281237 | 0.685365 |
| 220124_at | giant axonal neuropathy (gigaxonin) | GAN | 8139 | -2.281394 | 0.685365 |
| 213511_s_at | myotubularin related protein 1 | MTMR1 | 8776 | -2.28229 | 0.685365 |
| 209424_s_at | alpha-methylacyl-CoA racemase | AMACR | 23600 | -2.282733 | 0.685365 |
| 209776_s_at | solute carrier family 19 (folate transporter), member 1 | SLC19A1 | 6573 | -2.283009 | 0.685365 |
| 207275_s_at | acyl-CoA synthetase long-chain family member 1 | ACSL1 | 2180 | -2.283874 | 0.685365 |
| 217532_x_at | Transcribed locus | | | -2.284628 | 0.685365 |
| 200000_s_at | PRP8 pre-mRNA processing factor 8 homolog (S. cerevisiae) | PRPF8 | 10594 | -2.285924 | 0.685365 |
| 201386_s_at | DEAH (Asp-Glu-Ala-His) box polypeptide 15 | DHX15 | 1665 | -2.287825 | 0.685365 |
| 211199_s_at | inducible T-cell co-stimulator ligand | ICOSLG | 23308 | -2.288636 | 0.685365 |
| 205074_at | solute carrier family 22 (organic cation transporter), member 5 | SLC22A5 | 6584 | -2.289157 | 0.685365 |
| 200699_at | KDEL (Lys-Asp-Glu-Leu) endoplasmic reticulum protein retention receptor 2 | KDELR2 | 11014 | -2.290323 | 0.685365 |
| 204077_x_at | ectonucleoside triphosphate diphosphohydrolase 4 | ENTPD4 | 9583 | -2.290761 | 0.685365 |
| 209256_s_at | KIAA0265 protein | KIAA0265 | 23008 | -2.29189 | 0.685365 |
| 207865_s_at | bone morphogenetic protein 8b (osteogenic protein 2) | BMP8B | 656 | -2.292354 | 0.685365 |
| 210194_at | phospholipase A2 receptor 1, 180kDa | PLA2R1 | 22925 | -2.292799 | 0.685365 |
| 218093_s_at | ankyrin repeat domain 10 | ANKRD10 | 55608 | -2.294319 | 0.685365 |
| 200860_s_at | CCR4-NOT transcription complex, subunit 1 | CNOT1 | 23019 | -2.294494 | 0.685365 |
| 202140_s_at | CDC-like kinase 3 | CLK3 | 1198 | -2.295039 | 0.685365 |
| 204374_s_at | galactokinase 1 | GALK1 | 2584 | -2.296676 | 0.685365 |
| 212331_at | retinoblastoma-like 2 (p130) | RBL2 | 5934 | -2.296832 | 0.685365 |
| 212098_at | hypothetical protein LOC151162 | LOC151162 | 151162 | -2.297328 | 0.685365 |
| 211527_x_at | vascular endothelial growth factor A | VEGFA | 7422 | -2.297748 | 0.685365 |
| 215913_s_at | GULP, engulfment adaptor PTB domain containing 1 | GULP1 | 51454 | -2.298642 | 0.685365 |
| 203721_s_at | UTP18, small subunit (SSU) processome component, homolog (yeast) | UTP18 | 51096 | -2.299919 | 0.685365 |
| 214840_at | target of myb1-like 2 (chicken) | TOM1L2 | 146691 | -2.300746 | 0.685365 |
| 208030_s_at | adducin 1 (alpha) | ADD1 | 118 | -2.301123 | 0.685365 |
| 211160_x_at | actinin, alpha 1 | ACTN1 | 87 | -2.303101 | 0.685365 |
| 215954_s_at | chromosome 19 open reading frame 29 | C19orf29 | 58509 | -2.303515 | 0.685365 |
| 210475_at | POU class 3 homeobox 1 | POU3F1 | 5453 | -2.304302 | 0.685365 |
| 219650_at | excision repair cross-complementing rodent repair deficiency, complementation group 6-like | ERCC6L | 54821 | -2.30513 | 0.685365 |
| 205935_at | forkhead box F1 | FOXF1 | 2294 | -2.306617 | 0.685365 |
| 201380_at | cartilage associated protein | CRTAP | 10491 | -2.306769 | 0.685365 |
| 209345_s_at | phosphatidylinositol 4-kinase type 2 alpha | PI4K2A | 55361 | -2.306846 | 0.685365 |
| 202186_x_at | protein phosphatase 2, regulatory subunit B', alpha isoform | PPP2R5A | 5525 | -2.306997 | 0.685365 |
| 202407_s_at | PRP31 pre-mRNA processing factor 31 homolog (S. cerevisiae) | PRPF31 | 26121 | -2.308361 | 0.685365 |
| 212214_at | optic atrophy 1 (autosomal dominant) | OPA1 | 4976 | -2.309132 | 0.685365 |
| 208918_s_at | NAD kinase | NADK | 65220 | -2.309924 | 0.685365 |
| 203315_at | NCK adaptor protein 2 /// similar to NCK adaptor protein 2 | LOC729030 /// NCK2 | 729030 /// 8440 | -2.309435 | 0.685365 |
| 220911_s_at | KIAA1305 | KIAA1305 | 57523 | -2.310209 | 0.685365 |
| 204824_at | endonuclease G | ENDOG | 2021 | -2.310731 | 0.685365 |
| 221987_s_at | TSR1, 20S rRNA accumulation, homolog (S. cerevisiae) | TSR1 | 55720 | -2.31182 | 0.685365 |
| 211934_x_at | glucosidase, alpha; neutral AB | GANAB | 23193 | -2.311841 | 0.685365 |
| 205911_at | parathyroid hormone receptor 1 | PTHR1 | 5745 | -2.311931 | 0.685365 |

FIGURE 15 (CONTINUED)

| Probe ID | Description | Gene | ID | Value1 | Value2 |
|---|---|---|---|---|---|
| 203743_s_at | thymine-DNA glycosylase | TDG | 6996 | -2.312533 | 0.685365 |
| 201516_at | spermidine synthase | SRM | 6723 | -2.314169 | 0.685365 |
| 200659_s_at | prohibitin | PHB | 5245 | -2.314251 | 0.685365 |
| 211391_s_at | POZ (BTB) and AT hook containing zinc finger 1 | PATZ1 | 23598 | -2.314692 | 0.685365 |
| 211852_s_at | attractin | ATRN | 8455 | -2.316475 | 0.685365 |
| 215072_x_at | chromosome 10 open reading frame 137 | C10orf137 | 26098 | -2.316519 | 0.685365 |
| 205236_x_at | superoxide dismutase 3, extracellular | SOD3 | 6649 | -2.316625 | 0.685365 |
| 222161_at | N-acetylated alpha-linked acidic dipeptidase 2 | NAALAD2 | 10003 | -2.318389 | 0.685365 |
| 204119_s_at | adenosine kinase | ADK | 132 | -2.319495 | 0.685365 |
| 208694_at | protein kinase, DNA-activated, catalytic polypeptide | PRKDC | 5591 | -2.321562 | 0.685365 |
| 211519_s_at | kinesin family member 2C | KIF2C | 11004 | -2.32162 | 0.685365 |
| 210789_x_at | carcinoembryonic antigen-related cell adhesion molecule 3 | CEACAM3 | 1084 | -2.321977 | 0.685365 |
| 55065_at | MAP/microtubule affinity-regulating kinase 4 | MARK4 | 57787 | -2.323205 | 0.685365 |
| 216696_s_at | proline dehydrogenase (oxidase) 2 | PRODH2 | 58510 | -2.323785 | 0.685365 |
| 215644_at | zinc finger protein 518A | ZNF518A | 9849 | -2.324186 | 0.685365 |
| 215261_at | Clone 23578 mRNA sequence | --- | | -2.325709 | 0.685365 |
| 214511_x_at | Fc fragment of IgG, high affinity Ib, receptor (CD64) | FCGR1B | 2210 | -2.327473 | 0.685365 |
| 202679_at | Niemann-Pick disease, type C1 | NPC1 | 4864 | -2.328666 | 0.685365 |
| 210620_s_at | general transcription factor IIIC, polypeptide 2, beta 110kDa | GTF3C2 | 2976 | -2.329217 | 0.685365 |
| 216389_x_at | WD repeat domain 23 | WDR23 | 80344 | -2.329373 | 0.685365 |
| 57516_at | zinc finger protein 764 | ZNF764 | 92595 | -2.3302 | 0.685365 |
| 211673_s_at | molybdenum cofactor synthesis 1 | MOCS1 | 4337 | -2.330765 | 0.685365 |
| 202009_at | twinfilin, actin-binding protein, homolog 2 (Drosophila) | TWF2 | 11344 | -2.330858 | 0.685365 |
| 212739_s_at | non-metastatic cells 4, protein expressed in | NME4 | 4833 | -2.331026 | 0.685365 |
| 215379_x_at | immunoglobulin lambda locus /// Immunoglobulin lambda variable 3-25 /// Immunoglobulin lambda variable 2-14 /// immunoglobulin lambda joining 3 | IGL@ /// IGL3 /// IGLV2-14 /// IGLV3-25 | 28793 /// 28815 /// 28831 /// 3535 | -2.333067 | 0.685365 |
| 218137_s_at | stromal membrane-associated protein 1 | SMAP1 | 60682 | -2.333254 | 0.685365 |
| 209582_s_at | CD200 molecule | CD200 | 4345 | -2.333521 | 0.685365 |
| 203637_s_at | midline 1 (Opitz/BBB syndrome) | MID1 | 4281 | -2.333611 | 0.685365 |
| 201802_at | solute carrier family 29 (nucleoside transporters), member 1 | SLC29A1 | 2030 | -2.334749 | 0.685365 |
| 218813_s_at | SH3-domain GRB2-like endophilin B2 | SH3GLB2 | 56904 | -2.334893 | 0.685365 |
| 202571_s_at | discs, large (Drosophila) homolog-associated protein 4 | DLGAP4 | 22839 | -2.3351 | 0.685365 |
| 209006_s_at | chromosome 1 open reading frame 63 | C1orf63 | 57035 | -2.335214 | 0.685365 |
| 220743_at | --- | --- | | -2.33566 | 0.685365 |
| 215113_s_at | SUMO1/sentrin/SMT3 specific peptidase 3 | SENP3 | 26168 | -2.336467 | 0.685365 |
| 214550_s_at | transportin 3 | TNPO3 | 23534 | -2.338635 | 0.685365 |
| 214614_at | motor neuron and pancreas homeobox 1 | MNX1 | 3110 | -2.338754 | 0.685365 |
| 210500_at | --- | --- | | -2.338995 | 0.685365 |
| 218639_s_at | ZXD family zinc finger C | ZXDC | 79364 | -2.339756 | 0.685365 |
| 214738_s_at | NIMA (never in mitosis gene a)- related kinase 9 | NEK9 | 91754 | -2.33984 | 0.685365 |
| 207635_s_at | potassium voltage-gated channel, subfamily H (eag-related), member 1 | KCNH1 | 3756 | -2.340166 | 0.685365 |
| 221056_x_at | epidermal growth factor receptor pathway substrate 15-like 1 | EPS15L1 | 58513 | -2.340366 | 0.685365 |
| 217855_x_at | stromal cell derived factor 4 | SDF4 | 51150 | -2.342152 | 0.685365 |
| 201941_at | carboxypeptidase D | CPD | 1362 | -2.343245 | 0.685365 |

FIGURE 15 (CONTINUED)

| | | | | | |
|---|---|---|---|---|---|
| 203073_at | component of oligomeric golgi complex 2 | COG2 | 22796 | -2.344046 | 0.685365 |
| 210962_s_at | A kinase (PRKA) anchor protein (yotiao) 9 | AKAP9 | 10142 | -2.34415 | 0.685365 |
| 216052_x_at | artemin | ARTN | 9048 | -2.345033 | 0.685365 |
| 204043_at | transcobalamin II; macrocytic anemia | TCN2 | 6948 | -2.346284 | 0.685365 |
| 210930_s_at | v-erb-b2 erythroblastic leukemia viral oncogene homolog 2, neuro/glioblastoma derived oncogene homolog (avian) | ERBB2 | 2064 | -2.348138 | 0.685365 |
| 218221_at | aryl hydrocarbon receptor nuclear translocator | ARNT | 405 | -2.348315 | 0.685365 |
| 201421_s_at | WD repeat domain 77 | WDR77 | 79084 | -2.349401 | 0.685365 |
| 219202_at | rhomboid 5 homolog 2 (Drosophila) | RHBDF2 | 79651 | -2.349621 | 0.685365 |
| 220232_at | stearoyl-CoA desaturase 5 | SCD5 | 79966 | -2.350153 | 0.685365 |
| 221404_at | interleukin 1 family, member 6 (epsilon) | IL1F6 | 27179 | -2.350505 | 0.685365 |
| 206333_at | musashi homolog 1 (Drosophila) | MSI1 | 4440 | -2.350669 | 0.685365 |
| 218645_at | zinc finger protein 277 | ZNF277 | 11179 | -2.352026 | 0.685365 |
| 201289_at | cysteine-rich, angiogenic inducer, 61 | CYR61 | 3491 | -2.352145 | 0.685365 |
| 221755_at | EH domain binding protein 1-like 1 | EHBP1L1 | 254102 | -2.352364 | 0.685365 |
| 219720_s_at | chromosome 14 open reading frame 118 | C14orf118 | 55668 | -2.354206 | 0.685365 |
| 202054_s_at | aldehyde dehydrogenase 3 family, member A2 | ALDH3A2 | 224 | -2.354724 | 0.685365 |
| 210741_at | Rho guanine nucleotide exchange factor (GEF) 12 | ARHGEF12 | 23365 | -2.355883 | 0.685365 |
| 208625_s_at | eukaryotic translation initiation factor 4 gamma, 1 | EIF4G1 | 1981 | -2.357007 | 0.685365 |
| 203620_s_at | FCH and double SH3 domains 2 | FCHSD2 | 9873 | -2.357986 | 0.685365 |
| 220060_s_at | chromosome 12 open reading frame 48 | C12orf48 | 55010 | -2.359063 | 0.685365 |
| 202310_at | melanoma inhibitory activity family, member 3 | MIA3 | 375056 | -2.360437 | 0.685365 |
| 201689_s_at | tumor protein D52 | TPD52 | 7163 | -2.360594 | 0.685365 |
| 221314_at | growth differentiation factor 9 | GDF9 | 2661 | -2.361871 | 0.685365 |
| 210463_x_at | TRM1 tRNA methyltransferase 1 homolog (S. cerevisiae) | TRMT1 | 55621 | -2.362536 | 0.685365 |
| 219829_at | integrin beta 1 binding protein (melusin) 2 | ITGB1BP2 | 26548 | -2.36288 | 0.685365 |
| 211205_x_at | phosphatidylinositol-4-phosphate 5-kinase, type I, alpha | PIP5K1A | 8394 | -2.363046 | 0.685365 |
| 215217_at | | | | -2.364227 | 0.685365 |
| 202642_s_at | transformation/transcription domain-associated protein | TRRAP | 8295 | -2.364658 | 0.685365 |
| 215847_at | hypothetical protein LOC283755 | LOC283755 | 283755 | -2.365307 | 0.685365 |
| 216860_s_at | growth differentiation factor 11 | GDF11 | 10220 | -2.365759 | 0.685365 |
| 207074_s_at | solute carrier family 18 (vesicular monoamine), member 1 | SLC18A1 | 6570 | -2.36641 | 0.685365 |
| 212387_at | transcription factor 4 | TCF4 | 6925 | -2.366796 | 0.685365 |
| 206209_s_at | carbonic anhydrase IV | CA4 | 762 | -2.368052 | 0.685365 |
| 209729_at | growth arrest-specific 2 like 1 | GAS2L1 | 10634 | -2.369159 | 0.685365 |
| 215928_at | CDNA FLJ12130 fis, clone MAMMA1000251 | | | -2.36917 | 0.685365 |
| 200939_s_at | arginine-glutamic acid dipeptide (RE) repeats | RERE | 473 | -2.369223 | 0.685365 |
| 203660_s_at | pericentrin (kendrin) | PCNT | 5116 | -2.370059 | 0.685365 |
| 218412_s_at | GTF2I repeat domain containing 1 | GTF2IRD1 | 9569 | -2.371453 | 0.685365 |
| 221490_at | ubiquitin associated protein 1 | UBAP1 | 51271 | -2.37163 | 0.685365 |
| 220095_at | chromosome 9 open reading frame 39 | C9orf39 | 54875 | -2.373883 | 0.685365 |
| 207205_at | carcinoembryonic antigen-related cell adhesion molecule 4 | CEACAM4 | 1089 | -2.374159 | 0.685365 |
| 219481_at | tetratricopeptide repeat domain 13 | TTC13 | 79573 | -2.375585 | 0.685365 |
| 213845_at | glutamate receptor, ionotropic, kainate 2 | GRIK2 | 2898 | -2.375823 | 0.685365 |
| 212574_x_at | chromosome 19 open reading frame 6 | C19orf6 | 91304 | -2.37745 | 0.685365 |
| 201542_at | SAR1 gene homolog A (S. cerevisiae) | SAR1A | 56681 | -2.378148 | 0.685365 |

FIGURE 15 (CONTINUED)

| Probe | Description | Symbol | Gene ID | Value | Score |
|---|---|---|---|---|---|
| 206470_at | plexin C1 | PLXNC1 | 10154 | -2.378448 | 0.685365 |
| 203764_at | discs, large homolog 7 (Drosophila) | DLG7 | 9787 | -2.378796 | 0.685365 |
| 217935_s_at | ubiquinol-cytochrome c reductase complex chaperone, CBP3 homolog (yeast) | UQCC | 55245 | -2.378985 | 0.685365 |
| 208275_x_at | undifferentiated embryonic cell transcription factor 1 | UTF1 | 8433 | -2.379448 | 0.685365 |
| 212065_s_at | ubiquitin specific peptidase 34 | USP34 | 9736 | -2.3801 | 0.685365 |
| 221916_at | neurofilament, light polypeptide 68kDa | NEFL | 4747 | -2.380808 | 0.685365 |
| 211807_x_at | protocadherin gamma subfamily B, 5 | PCDHGB5 | 56101 | -2.381777 | 0.685365 |
| 206845_s_at | ring finger protein 40 | RNF40 | 9810 | -2.38221 | 0.685365 |
| 212219_at | proteasome (prosome, macropain) activator subunit 4 | PSME4 | 23198 | -2.382821 | 0.685365 |
| 209684_at | Ras and Rab interactor 2 | RIN2 | 54453 | -2.385389 | 0.685365 |
| 213707_s_at | distal-less homeobox 5 | DLX5 | 1749 | -2.386812 | 0.685365 |
| 208619_at | damage-specific DNA binding protein 1, 127kDa | DDB1 | 1642 | -2.3882 | 0.685365 |
| 218252_at | cytoskeleton associated protein 2 | CKAP2 | 26586 | -2.388424 | 0.685365 |
| 212846_at | ribosomal RNA processing 1 homolog B (S. cerevisiae) | RRP1B | 23076 | -2.389091 | 0.685365 |
| 212072_s_at | casein kinase 2, alpha 1 polypeptide | CSNK2A1 | 1457 | -2.389376 | 0.685365 |
| 218596_at | TBC1 domain family, member 13 | TBC1D13 | 54662 | -2.390208 | 0.685365 |
| 218918_at | mannosidase, alpha, class 1C, member 1 | MAN1C1 | 57134 | -2.39499 | 0.685365 |
| 44146_at | glucocorticoid modulatory element binding protein 2 | GMEB2 | 26205 | -2.396197 | 0.685365 |
| 215119_at | myosin XVI | MYO16 | 23026 | -2.397469 | 0.685365 |
| 214771_x_at | CDC42 effector protein (Rho GTPase binding) 4 | CDC42EP4 | 23580 | -2.398135 | 0.685365 |
| 202798_at | SEC24 related gene family, member B (S. cerevisiae) | SEC24B | 10427 | -2.398942 | 0.685365 |
| 218656_s_at | lipoma HMGIC fusion partner | LHFP | 10186 | -2.399281 | 0.685365 |
| 207575_at | golgin-like protein /// golgi autoantigen, golgin subfamily a, 6 /// similar to Golgin subfamily A member 6 (Golgin linked to PML) (Golgin-like protein) | GOLGA /// GOLGA6 /// LOC653641 | 342096 /// 55889 /// 653641 | -2.400009 | 0.685365 |
| 210017_at | mucosa associated lymphoid tissue lymphoma translocation gene 1 | MALT1 | 10892 | -2.402101 | 0.685365 |
| 201929_s_at | plakophilin 4 | PKP4 | 8502 | -2.402221 | 0.685365 |
| 218803_at | checkpoint with forkhead and ring finger domains | CHFR | 55743 | -2.403077 | 0.685365 |
| 219378_at | NMDA receptor regulated 1-like | NARG1L | 79612 | -2.403949 | 0.685365 |
| 209929_s_at | inhibitor of kappa light polypeptide gene enhancer in B-cells, kinase gamma | IKBKG | 8517 | -2.405699 | 0.685365 |
| 214513_s_at | cAMP responsive element binding protein 1 | CREB1 | 1385 | -2.406554 | 0.685365 |
| 202787_s_at | mitogen-activated protein kinase-activated protein kinase 3 | MAPKAPK3 | 7867 | -2.407131 | 0.685365 |
| 215104_at | nuclear receptor interacting protein 2 | NRIP2 | 83714 | -2.407308 | 0.685365 |
| 211555_s_at | guanylate cyclase 1, soluble, beta 3 | GUCY1B3 | 2983 | -2.408504 | 0.685365 |
| 207983_s_at | stromal antigen 2 | STAG2 | 10735 | -2.409478 | 0.685365 |
| 211711_s_at | phosphatase and tensin homolog (mutated in multiple advanced cancers 1) | PTEN | 5728 | -2.410335 | 0.685365 |
| 221038_at | PRO1942 | | | -2.41101 | 0.685365 |
| 212556_at | scribbled homolog (Drosophila) | SCRIB | 23513 | -2.411883 | 0.685365 |
| 209784_s_at | jagged 2 | JAG2 | 3714 | -2.412885 | 0.685365 |
| 213682_at | nucleoporin 50kDa | NUP50 | 10762 | -2.413768 | 0.685365 |
| 213909_at | angel homolog 1 (Drosophila) | ANGEL1 | 23357 | -2.414372 | 0.685365 |
| 207020_at | heat shock transcription factor 2 binding protein | HSF2BP | 11077 | -2.415318 | 0.685365 |
| 200614_at | clathrin, heavy chain (Hc) | CLTC | 1213 | -2.415906 | 0.685365 |
| 209000_s_at | septin 8 | 8-Sep | 23176 | -2.416741 | 0.685365 |
| 210318_at | retinol binding protein 3, interstitial | RBP3 | 5949 | -2.421761 | 0.685365 |
| 211089_s_at | NIMA (never in mitosis gene a)-related kinase 3 | NEK3 | 4752 | -2.422279 | 0.685365 |

FIGURE 15 (CONTINUED)

| | | | | |
|---|---|---|---|---|
| 59999_at | hypoxia-inducible factor 1, alpha subunit inhibitor | HIF1AN | 55662 | -2.423303 | 0.685365 |
| 212563_at | block of proliferation 1 /// similar to block of proliferation 1 | BOP1 /// LOC727967 | 23246 /// 727967 | -2.424067 | 0.685365 |
| 209055_s_at | CDC5 cell division cycle 5-like (S. pombe) | CDC5L | 988 | -2.425212 | 0.685365 |
| 221733_s_at | G patch domain containing 4 | GPATCH4 | 54865 | -2.429712 | 0.685365 |
| 204894_s_at | amine oxidase, copper containing 3 (vascular adhesion protein 1) | AOC3 | 8639 | -2.430867 | 0.685365 |
| 220819_at | FERM domain containing 1 | FRMD1 | 79981 | -2.432723 | 0.685365 |
| 206110_at | histone cluster 1, H3h | HIST1H3H | 8357 | -2.432928 | 0.685365 |
| 207317_s_at | calsequestrin 2 (cardiac muscle) | CASQ2 | 845 | -2.43558 | 0.685365 |
| 214429_at | myotubularin related protein 6 | MTMR6 | 9107 | -2.437402 | 0.685344 |
| 211913_s_at | c-mer proto-oncogene tyrosine kinase | MERTK | 10461 | -2.437435 | 0.685344 |
| 218595_s_at | HEAT repeat containing 1 | HEATR1 | 55127 | -2.437683 | 0.685344 |
| 201997_s_at | spen homolog, transcriptional regulator (Drosophila) | SPEN | 23013 | -2.438393 | 0.685344 |
| 203471_s_at | pleckstrin | PLEK | 5341 | -2.438571 | 0.685344 |
| 219318_x_at | mediator complex subunit 31 | MED31 | 51003 | -2.439188 | 0.685344 |
| 207391_s_at | phosphatidylinositol-4-phosphate 5-kinase, type I, alpha | PIP5K1A | 8394 | -2.439928 | 0.685344 |
| 221195_at | PTD016 protein | LOC51136 | 51136 | -2.440993 | 0.685344 |
| 202314_at | cytochrome P450, family 51, subfamily A, polypeptide 1 | CYP51A1 | 1595 | -2.44138 | 0.685344 |
| 211447_s_at | phosphodiesterase 4A, cAMP-specific (phosphodiesterase E2 dunce homolog, Drosophila) | PDE4A | 5141 | -2.441963 | 0.685344 |
| 202182_at | solute carrier family 25 (mitochondrial carrier; phosphate carrier), member 23 | SLC25A23 | 79085 | -2.442225 | 0.685344 |
| 202021_x_at | eukaryotic translation initiation factor 1 | EIF1 | 10209 | -2.442766 | 0.685344 |
| 202819_s_at | transcription elongation factor B (SIII), polypeptide 3 (110kDa, elongin A) | TCEB3 | 6924 | -2.44313 | 0.685344 |
| 220325_at | TAF7-like RNA polymerase II, TATA box binding protein (TBP)-associated factor, 50kDa | TAF7L | 54457 | -2.445122 | 0.685344 |
| 221853_s_at | NODAL modulator 1 /// NODAL modulator 2 /// NODAL modulator 3 | NOMO1 /// NOMO2 /// NOMO3 | 23420 /// 283820 /// 408050 | -2.445609 | 0.685344 |
| 1494_f_at | cytochrome P450, family 2, subfamily A, polypeptide 6 | CYP2A6 | 1548 | -2.446052 | 0.685344 |
| 211101_x_at | leukocyte immunoglobulin-like receptor, subfamily A (with TM domain), member 2 | LILRA2 | 11027 | -2.446908 | 0.685344 |
| 201571_s_at | dCMP deaminase | DCTD | 1635 | -2.449242 | 0.685344 |
| 204040_at | ring finger protein 144A | RNF144A | 9781 | -2.449365 | 0.685344 |
| 214994_at | apolipoprotein B mRNA editing enzyme, catalytic polypeptide-like 3F | APOBEC3F | 200316 | -2.449632 | 0.685344 |
| 206085_s_at | cystathionase (cystathionine gamma-lyase) | CTH | 1491 | -2.452718 | 0.685344 |
| 211501_s_at | eukaryotic translation initiation factor 3, subunit B | EIF3B | 8662 | -2.452858 | 0.685344 |
| 218771_at | pantothenate kinase 4 | PANK4 | 55229 | -2.454032 | 0.685344 |
| 215857_at | nicalin homolog (zebrafish) | NCLN | 56926 | -2.454363 | 0.685344 |
| 210995_s_at | tripartite motif-containing 23 | TRIM23 | 373 | -2.455597 | 0.685344 |
| 217424_at | MRNA; cDNA DKFZp434L098 (from clone DKFZp434L098) | | | -2.456005 | 0.685344 |
| 201282_at | oxoglutarate (alpha-ketoglutarate) dehydrogenase (lipoamide) | OGDH | 4967 | -2.45629 | 0.685344 |
| 207254_at | solute carrier family 15 (oligopeptide transporter), member 1 | SLC15A1 | 6564 | -2.457005 | 0.685344 |
| 200793_s_at | aconitase 2, mitochondrial | ACO2 | 50 | -2.45721 | 0.685344 |
| 214310_s_at | zinc finger protein-like 1 | ZFPL1 | 7542 | -2.457213 | 0.685344 |
| 219904_at | zinc finger and SCAN domain containing 5 | ZSCAN5 | 79149 | -2.457399 | 0.685344 |
| 210754_s_at | v-yes-1 Yamaguchi sarcoma viral related oncogene homolog | LYN | 4067 | -2.457399 | 0.685344 |
| 208787_at | mitochondrial ribosomal protein L3 | MRPL3 | 11222 | -2.458274 | 0.685344 |
| 221418_s_at | mediator complex subunit 16 | MED16 | 10025 | -2.45877 | 0.685344 |
| 219610_at | Rho-guanine nucleotide exchange factor | RGNEF | 64283 | -2.45887 | 0.685344 |

FIGURE 15 (CONTINUED)

| | | | | |
|---|---|---|---|---|
| 218782_s_at | ATPase family, AAA domain containing 2 | ATAD2 | 29028 | -2.459308 | 0.685344 |
| 210473_s_at | G protein-coupled receptor 125 | GPR125 | 166647 | -2.459875 | 0.685344 |
| 201946_s_at | chaperonin containing TCP1, subunit 2 (beta) | CCT2 | 10576 | -2.45999 | 0.685344 |
| 209247_s_at | ATP-binding cassette, sub-family F (GCN20), member 2 | ABCF2 | 10061 | -2.460919 | 0.685344 |
| 218236_s_at | protein kinase D3 | PRKD3 | 23683 | -2.461095 | 0.685344 |
| 212306_at | cytoplasmic linker associated protein 2 | CLASP2 | 23122 | -2.461105 | 0.685344 |
| 214030_at | hypothetical protein DKFZp667G2110 | DKFZp667G2110 | 0 | -2.461612 | 0.685344 |
| 215272_at | transcriptional adaptor 3 (NGG1 homolog, yeast)-like | TADA3L | 131544 | -2.462776 | 0.685344 |
| 215551_at | estrogen receptor 1 | ESR1 | 10474 | -2.462889 | 0.685344 |
| 222006_at | Leucine zipper-EF-hand containing transmembrane protein 1 | LETM1 | 2099 | -2.463389 | 0.685344 |
| 212997_s_at | tousled-like kinase 2 | TLK2 | 3994 | -2.46341 | 0.685344 |
| 213049_at | GTPase activating Rap/RanGAP domain-like 1 | GARNL1 | 11011 | -2.464024 | 0.685344 |
| 208595_s_at | methyl-CpG binding domain protein 1 | MBD1 | 253959 | -2.464419 | 0.685344 |
| 201401_s_at | adrenergic, beta, receptor kinase 1 | ADRBK1 | 4152 | -2.469221 | 0.685344 |
| 209390_at | tuberous sclerosis 1 | TSC1 | 156 | -2.469378 | 0.685344 |
| 214604_at | homeobox D11 | HOXD11 | 7248 | -2.469687 | 0.685344 |
| 218189_s_at | N-acetylneuraminic acid synthase (sialic acid synthase) | NANS | 3237 | -2.47103 | 0.685344 |
| 211256_x_at | butyrophilin, subfamily 2, member A1 | BTN2A1 | 54187 | -2.471393 | 0.685344 |
| 213739_at | CDNA clone IMAGE:4801297 | | 11120 | -2.472666 | 0.685344 |
| 203445_s_at | CTD (carboxy-terminal domain, RNA polymerase II, polypeptide A) small phosphatase 2 | CTDSP2 | 10106 | -2.473639 | 0.685344 |
| 216251_s_at | tubulin tyrosine ligase-like family, member 12 | TTLL12 | 23170 | -2.474117 | 0.685344 |
| 202633_at | topoisomerase (DNA) II binding protein 1 | TOPBP1 | 11073 | -2.475946 | 0.685344 |
| 205273_s_at | pitrilysin metallopeptidase 1 | PITRM1 | 10531 | -2.47626 | 0.685344 |
| 214657_s_at | Trophoblast-derived noncoding RNA | TncRNA | 283131 | -2.477821 | 0.685344 |
| 210060_at | phosphodiesterase 6G, cGMP-specific, rod, gamma | PDE6G | 5148 | -2.478084 | 0.685344 |
| 218781_at | structural maintenance of chromosomes 6 | SMC6 | 79677 | -2.479473 | 0.685344 |
| 203789_s_at | sema domain, immunoglobulin domain (Ig), short basic domain, secreted, (semaphorin) 3C | SEMA3C | 10512 | -2.47991 | 0.685344 |
| 217448_s_at | TOX high mobility group box family member 4 /// similar to Epidermal Langerhans cell protein LCP1 | LOC285412 /// TOX4 | 285412 /// 9878 | -2.483929 | 0.685344 |
| 218131_s_at | GATA zinc finger domain containing 2A | GATAD2A | 54815 | -2.484529 | 0.685344 |
| 218590_at | chromosome 10 open reading frame 2 | C10orf2 | 56652 | -2.484853 | 0.685344 |
| 216300_x_at | retinoic acid receptor, alpha | RARA | 5914 | -2.48576 | 0.685344 |
| 202521_at | CCCTC-binding factor (zinc finger protein) | CTCF | 10664 | -2.486121 | 0.685344 |
| 212015_x_at | polypyrimidine tract binding protein 1 | PTBP1 | 5725 | -2.486965 | 0.685344 |
| 220824_at | CDNA FLJ20123 fis, clone COL06041 | | | -2.488086 | 0.685344 |
| 210347_s_at | B-cell CLL/lymphoma 11A (zinc finger protein) | BCL11A | 53335 | -2.488812 | 0.685344 |
| 204395_s_at | G protein-coupled receptor kinase 5 | GRK5 | 2869 | -2.4902 | 0.685344 |
| 203566_s_at | amylo-1, 6-glucosidase, 4-alpha-glucanotransferase (glycogen debranching enzyme, glycogen storage disease type III) | AGL | 178 | -2.490899 | 0.685344 |
| 206510_at | SIX homeobox 2 | SIX2 | 10736 | -2.49148 | 0.685344 |
| 208773_s_at | ankyrin repeat and KH domain containing 1 /// ANKHD1-EIF4EBP3 | ANKHD1 /// ANKHD1-EIF4EBP3 | 404734 /// 54882 | -2.493806 | 0.685344 |
| 208309_s_at | mucosa associated lymphoid tissue lymphoma translocation gene 1 | MALT1 | 10892 | -2.495158 | 0.685344 |
| 204797_s_at | echinoderm microtubule associated protein like 1 | EML1 | 2009 | -2.495162 | 0.685344 |

FIGURE 15 (CONTINUED)

| | | | | | |
|---|---|---|---|---|---|
| 210144_at | TBC1 domain family, member 22A | TBC1D22A | | 25771 | -2.495712 | 0.685344 |
| 207071_s_at | aconitase 1, soluble | ACO1 | | 48 | -2.496354 | 0.685344 |
| 202779_s_at | ubiquitin-conjugating enzyme E2S /// similar to Ubiquitin-conjugating enzyme E2-24 kDa) (Ubiquitin-protein ligase) (Ubiquitin carrier protein) (E2-EPF5) | LOC731049 /// UBE2S | 27338 /// 731049 | -2.497197 | 0.685344 |
| 211502_s_at | PFTAIRE protein kinase 1 | PFTK1 | | 5218 | -2.499433 | 0.685344 |
| 208029_s_at | lysosomal associated protein transmembrane 4 beta | LAPTM4B | | 55353 | -2.499919 | 0.685344 |
| 203838_s_at | tyrosine kinase, non-receptor, 2 | TNK2 | | 10188 | -2.500086 | 0.685344 |
| 217007_s_at | ADAM metallopeptidase domain 15 | ADAM15 | | 8751 | -2.501117 | 0.685344 |
| 206590_x_at | dopamine receptor D2 | DRD2 | | 1813 | -2.502495 | 0.685344 |
| 206625_at | peripherin 2 (retinal degeneration, slow) | PRPH2 | | 5961 | -2.50253 | 0.685344 |
| 209981_at | cold shock domain containing C2, RNA binding | CSDC2 | | 27254 | -2.503751 | 0.685344 |
| 204822_at | TTK protein kinase | TTK | | 7272 | -2.504792 | 0.685344 |
| 205921_s_at | solute carrier family 6 (neurotransmitter transporter, taurine), member 6 | SLC6A6 | | 6533 | -2.506431 | 0.685344 |
| 202861_at | period homolog 1 (Drosophila) | PER1 | | 5187 | -2.50714 | 0.685344 |
| 201104_x_at | neuroblastoma breakpoint family, member 14 /// neuroblastoma breakpoint family, member 11 /// neuroblastoma breakpoint family, member 15 /// neuroblastoma breakpoint family, member 20 /// neuroblastoma breakpoint family, member 10 /// neuroblastoma breakpoint family, member 8 /// CLIP-190-like /// neuroblastoma breakpoint family, member 16 /// hypothetical protein LOC728980 /// hypothetical protein LOC730476 | LOC728980 /// LOC730476 /// NBPF10 /// NBPF11 /// NBPF14 /// NBPF15 /// NBPF16 /// NBPF20 /// NBPF8 /// XXyac-YX155B6.1 | 200030 /// 25832 /// 284565 /// 400818 /// 440673 /// 641559 /// 728912 /// 728936 /// 728980 /// 730476 | -2.507143 | 0.685344 |
| 221581_at | linker for activation of T cells family, member 2 | LAT2 | | 7462 | -2.507961 | 0.685344 |
| 219016_at | FAST kinase domains 5 | FASTKD5 | | 60493 | -2.5085 | 0.685344 |
| 209839_at | dynamin 3 | DNM3 | | 26052 | -2.510319 | 0.685344 |
| 214220_s_at | Alstrom syndrome 1 | ALMS1 | | 7840 | -2.510432 | 0.685344 |
| 215178_x_at | N-acylsphingosine amidohydrolase (acid ceramidase)-like | ASAHL | | 27163 | -2.512118 | 0.685344 |
| 209186_at | ATPase, Ca++ transporting, cardiac muscle, slow twitch 2 | ATP2A2 | | 488 | -2.512233 | 0.685344 |
| 204930_s_at | BCL2/adenovirus E1B 19kDa interacting protein 1 | BNIP1 | | 662 | -2.513369 | 0.685344 |
| 221749_at | SH2 domain containing 4A | SH2D4A | | 63898 | -2.51425 | 0.685344 |
| 215976_at | CDNA FLJ12040 fis, clone HEMBB1001944 | | | | -2.514425 | 0.685344 |
| 205344_at | chondroitin sulfate proteoglycan 5 (neuroglycan C) | CSPG5 | | 10675 | -2.514819 | 0.685344 |
| 210014_x_at | isocitrate dehydrogenase 3 (NAD+) beta | IDH3B | | 3420 | -2.515182 | 0.685344 |
| 209295_at | tumor necrosis factor receptor superfamily, member 10b | TNFRSF10B | | 8795 | -2.515933 | 0.685344 |
| 201883_s_at | UDP-Gal:betaGlcNAc beta 1,4- galactosyltransferase, polypeptide 1 | B4GALT1 | | 2683 | -2.516366 | 0.685344 |
| 202019_s_at | LanC lantibiotic synthetase component C-like 1 (bacterial) | LANCL1 | | 10314 | -2.517284 | 0.685344 |
| 210570_x_at | mitogen-activated protein kinase 9 | MAPK9 | | 5601 | -2.517319 | 0.685344 |
| 221571_at | TNF receptor-associated factor 3 | TRAF3 | | 7187 | -2.518109 | 0.685344 |
| 210243_s_at | UDP-Gal:betaGlcNAc beta 1,4- galactosyltransferase, polypeptide 3 | B4GALT3 | | 8703 | -2.519776 | 0.685344 |
| 212712_at | calmodulin regulated spectrin-associated protein 1 | CAMSAP1 | | 157922 | -2.528222 | 0.685344 |
| 213552_at | glucuronic acid epimerase | GLCE | | 26035 | -2.528502 | 0.685344 |
| 203048_s_at | KIAA0372 | KIAA0372 | | 9652 | -2.528676 | 0.685344 |
| 204647_at | homer homolog 3 (Drosophila) | HOMER3 | | 9454 | -2.528967 | 0.685344 |

FIGURE 15 (CONTINUED)

| | | | | |
|---|---|---|---|---|
| 210905_x_at | POU class 5 homeobox 1 pseudogene 4 | POU5F1P4 | 645682 | -2.530453 | 0.685344 |
| 211133_x_at | leukocyte immunoglobulin-like receptor, subfamily B (with TM and ITIM domains), member 3 | LILRB3 | 11025 | -2.531278 | 0.685344 |
| 202111_at | solute carrier family 4, anion exchanger, member 2 (erythrocyte membrane protein band 3-like 1) | SLC4A2 | 6522 | -2.531979 | 0.685344 |
| 209380_s_at | ATP-binding cassette, sub-family C (CFTR/MRP), member 5 | ABCC5 | 10057 | -2.533885 | 0.685344 |
| 212713_at | microfibrillar-associated protein 4 | MFAP4 | 4239 | -2.534089 | 0.685344 |
| 214748_at | phosphonoformate immuno-associated protein 5 | RP11-298P3.3 | 10443 | -2.539163 | 0.685344 |
| 221226_s_at | amiloride-sensitive cation channel 4, pituitary | ACCN4 | 55515 | -2.543363 | 0.685344 |
| 219390_at | FK506 binding protein 14, 22 kDa | FKBP14 | 55033 | -2.544849 | 0.685344 |
| 212542_s_at | pleckstrin homology domain interacting protein | PHIP | 55023 | -2.546445 | 0.685344 |
| 212568_s_at | dihydrolipoamide S-acetyltransferase (E2 component of pyruvate dehydrogenase complex) | DLAT | 1737 | -2.547529 | 0.685344 |
| 202661_at | inositol 1,4,5-triphosphate receptor, type 2 | ITPR2 | 3709 | -2.548146 | 0.685344 |
| 201013_s_at | phosphoribosylaminoimidazole carboxylase, phosphoribosylaminoimidazole succinocarboxamide synthetase | PAICS | 10606 | -2.549691 | 0.685344 |
| 221317_x_at | protocadherin beta 6 | PCDHB6 | 56130 | -2.550375 | 0.685344 |
| 218277_s_at | DEAH (Asp-Glu-Ala-His) box polypeptide 40 | DHX40 | 79665 | -2.552392 | 0.685223 |
| 210270_at | regulator of G-protein signaling 6 | RGS6 | 9628 | -2.554586 | 0.684643 |
| 54632_at | thyroid adenoma associated | THADA | 63892 | -2.554923 | 0.684643 |
| 217293_at | | | | -2.555509 | 0.684643 |
| 217564_s_at | carbamoyl-phosphate synthetase 1, mitochondrial | CPS1 | 1373 | -2.556778 | 0.684175 |
| 49111_at | mRNA; cDNA DKFZp762M127 (from clone DKFZp762M127) | | | -2.559232 | 0.682811 |
| 218081_at | chromosome 20 open reading frame 27 | C20orf27 | 54976 | -2.559438 | 0.682811 |
| 221893_s_at | aarF domain containing kinase 2 | ADCK2 | 90956 | -2.559819 | 0.682811 |
| 210542_s_at | solute carrier organic anion transporter family, member 3A1 | SLCO3A1 | 28232 | -2.561301 | 0.682811 |
| 214161_at | Oxidative stress induced growth inhibitor family member 2 | OSGIN2 | 734 | -2.567061 | 0.680212 |
| 221253_s_at | thioredoxin domain containing 5 | TXNDC5 | 81567 | -2.569194 | 0.680212 |
| 203889_at | secretogranin V (7B2 protein) | SCG5 | 6447 | -2.569349 | 0.680212 |
| 205003_at | dedicator of cytokinesis 4 | DOCK4 | 9732 | -2.570368 | 0.680212 |
| 217716_s_at | Sec61 alpha 1 subunit (S. cerevisiae) | SEC61A1 | 29927 | -2.573388 | 0.679125 |
| 218768_at | nucleoporin 107kDa | NUP107 | 57122 | -2.573555 | 0.679125 |
| 207174_at | glypican 5 | GPC5 | 2262 | -2.576361 | 0.678698 |
| 214626_s_at | glucosidase, alpha; neutral AB | GANAB | 23193 | -2.578552 | 0.677955 |
| 202715_at | carbamoyl-phosphate synthetase 2, aspartate transcarbamylase, and dihydroorotase | CAD | 790 | -2.579188 | 0.677955 |
| 219432_at | | | | -2.580033 | 0.677769 |
| 208065_at | ST8 alpha-N-acetyl-neuraminide alpha-2,8-sialyltransferase 3 | ST8SIA3 | 51046 | -2.581146 | 0.677769 |
| 213270_at | membrane protein, palmitoylated 2 (MAGUK p55 subfamily member 2) | MPP2 | 4355 | -2.582229 | 0.677769 |
| 212457_at | transcription factor binding to IGHM enhancer 3 | TFE3 | 7030 | -2.582827 | 0.677769 |
| 218044_at | parathymosin | PTMS | 5763 | -2.582927 | 0.677769 |
| 204545_at | peroxisomal biogenesis factor 6 | PEX6 | 5190 | -2.585253 | 0.677769 |
| 218355_at | kinesin family member 4A /// kinesin family member 4B | KIF4A /// KIF4B | 24137 /// 285643 | -2.586005 | 0.677769 |
| 211062_s_at | carboxypeptidase Z | CPZ | 8532 | -2.586752 | 0.677769 |
| 206099_at | protein kinase C, eta | PRKCH | 5583 | -2.587293 | 0.677769 |
| 203286_at | ring finger protein 44 | RNF44 | 22838 | -2.587358 | 0.677769 |
| 210005_at | phosphoribosylglycinamide formyltransferase, phosphoribosylglycinamide synthetase, phosphoribosylaminoimidazole synthetase | GART | 2618 | -2.58878 | 0.677769 |

FIGURE 15 (CONTINUED)

| | | HIST2H2AA3 /// HIST2H2AA4 | 723790 /// 8337 | -2.589673 | 0.677769 |
|---|---|---|---|---|---|
| 214290_s_at | histone cluster 2, H2aa3 /// histone cluster 2, H2aa4 | | | | |
| 216913_s_at | ribosomal RNA processing 12 homolog (S. cerevisiae) | RRP12 | 23223 | -2.590475 | 0.677769 |
| 214056_at | Myeloid cell leukemia sequence 1 (BCL2-related) | MCL1 | 4170 | -2.59162 | 0.677769 |
| 222192_s_at | chromosome 2 open reading frame 43 | C2orf43 | 60526 | -2.592113 | 0.677769 |
| 202672_s_at | activating transcription factor 3 | ATF3 | 467 | -2.59414 | 0.677769 |
| 222114_x_at | WD repeat domain 55 | WDR55 | 54853 | -2.594462 | 0.677769 |
| 219271_at | UDP-N-acetyl-alpha-D-galactosamine:polypeptide N-acetylgalactosaminyltransferase 14 (GalNAc-T14) | GALNT14 | 79623 | -2.596929 | 0.677769 |
| 217635_s_at | polymerase (DNA directed), gamma | POLG | 5428 | -2.596945 | 0.677769 |
| 211271_x_at | polypyrimidine tract binding protein 1 | PTBP1 | 5725 | -2.597433 | 0.677769 |
| 218308_at | transforming, acidic coiled-coil containing protein 3 | TACC3 | 10460 | -2.597859 | 0.677769 |
| 219410_at | transmembrane protein 45A | TMEM45A | 55076 | -2.599313 | 0.677769 |
| 202189_x_at | polypyrimidine tract binding protein 1 | PTBP1 | 5725 | -2.599966 | 0.677769 |
| 211851_x_at | breast cancer 1, early onset | BRCA1 | 672 | -2.600013 | 0.677769 |
| 210052_s_at | TPX2, microtubule-associated, homolog (Xenopus laevis) | TPX2 | 22974 | -2.600916 | 0.677769 |
| 220357_s_at | serum/glucocorticoid regulated kinase 2 | SGK2 | 10110 | -2.601453 | 0.677769 |
| 213073_at | zinc finger, FYVE domain containing 26 | ZFYVE26 | 23503 | -2.602283 | 0.677769 |
| 209822_s_at | very low density lipoprotein receptor | VLDLR | 7436 | -2.602789 | 0.677769 |
| 203154_s_at | p21(CDKN1A)-activated kinase 4 | PAK4 | 10298 | -2.604554 | 0.677769 |
| 217771_at | golgi membrane protein 1 | GOLM1 | 51280 | -2.607065 | 0.677769 |
| 203879_at | phosphoinositide-3-kinase, catalytic, delta polypeptide | PIK3CD | 5293 | -2.60731 | 0.677769 |
| 207000_s_at | protein phosphatase 3 (formerly 2B), catalytic subunit, gamma isoform | PPP3CC | 5533 | -2.608889 | 0.677769 |
| 202195_s_at | transmembrane emp24 protein transport domain containing 5 | TMED5 | 50999 | -2.609134 | 0.677769 |
| 220599_s_at | caspase recruitment domain family, member 14 | CARD14 | 79092 | -2.609842 | 0.677769 |
| 204153_s_at | MFNG O-fucosylpeptide 3-beta-N-acetylglucosaminyltransferase | MFNG | 4242 | -2.612307 | 0.677769 |
| 208591_s_at | phosphodiesterase 3B, cGMP-inhibited | PDE3B | 5140 | -2.612962 | 0.677769 |
| 210269_s_at | splicing factor, arginine/serine-rich 17A | SFRS17A | 8227 | -2.614108 | 0.677769 |
| 211443_x_at | prolactin releasing hormone | PRLH | 51052 | -2.614455 | 0.677769 |
| 219126_at | PHD finger protein 10 | PHF10 | 55274 | -2.615397 | 0.677769 |
| 206550_s_at | nucleoporin 155kDa | NUP155 | 9631 | -2.615577 | 0.677769 |
| 218783_at | integrator complex subunit 7 | INTS7 | 25896 | -2.6159 | 0.677769 |
| 211136_s_at | cleft lip and palate associated transmembrane protein 1 | CLPTM1 | 1209 | -2.615969 | 0.677769 |
| 211258_s_at | transforming growth factor, alpha | TGFA | 7039 | -2.616477 | 0.677769 |
| 213656_s_at | kinesin light chain 1 | KLC1 | 3831 | -2.61871 | 0.677769 |
| 218765_at | SID1 transmembrane family, member 2 | SIDT2 | 51092 | -2.621293 | 0.677769 |
| 209260_at | stratifin | SFN | 2810 | -2.623495 | 0.677769 |
| 206471_s_at | plexin C1 | PLXNC1 | 10154 | -2.624523 | 0.677769 |
| 215827_x_at | ciliary rootlet coiled-coil, rootletin-like 2 | CROCCL2 | 114819 | -2.625228 | 0.677769 |
| 212248_at | CDNA FLJ41088 fis, clone ASTRO2002459 /// Metadherin | MTDH | 92140 | -2.627065 | 0.677769 |
| 220826_at | chromosome 21 open reading frame 77 | C21orf77 | 55264 | -2.62745 | 0.677769 |
| 201344_at | ubiquitin-conjugating enzyme E2D 2 (UBC4/5 homolog, yeast) | UBE2D2 | 7322 | -2.629755 | 0.677769 |
| 216294_s_at | KIAA1109 | KIAA1109 | 84162 | -2.630419 | 0.677769 |
| 214364_at | MTERF domain containing 2 | MTERFD2 | 130916 | -2.633407 | 0.677769 |
| 219745_at | transmembrane protein 180 | TMEM180 | 79847 | -2.633861 | 0.677769 |
| 202184_s_at | nucleoporin 133kDa | NUP133 | 55746 | -2.634026 | 0.677769 |

FIGURE 15 (CONTINUED)

| | | | | |
|---|---|---|---|---|
| 220607_x_at | TH1-like (Drosophila) | TH1L | 51497 | -2.634134 | 0.677769 |
| 206074_s_at | high mobility group AT-hook 1 | HMGA1 | 3159 | -2.634337 | 0.677769 |
| 217305_s_at | testicular soluble adenylyl cyclase | SAC | 55811 | -2.638782 | 0.677769 |
| 203961_at | nebulette | NEBL | 10529 | -2.64196 | 0.677769 |
| 218331_s_at | chromosome 10 open reading frame 18 | C10orf18 | 54906 | -2.643984 | 0.677769 |
| 201662_s_at | acyl-CoA synthetase long-chain family member 3 | ACSL3 | 2181 | -2.644598 | 0.677769 |
| 203701_s_at | TRM1 tRNA methyltransferase 1 homolog (S. cerevisiae) | TRMT1 | 55621 | -2.646432 | 0.677769 |
| 200662_s_at | translocase of outer mitochondrial membrane 20 homolog (yeast) | TOMM20 | 9804 | -2.647788 | 0.677769 |
| 203991_s_at | ubiquitously transcribed tetratricopeptide repeat, X chromosome | UTX | 7403 | -2.64886 | 0.677769 |
| 209859_at | tripartite motif-containing 9 | TRIM9 | 114088 | -2.64996 | 0.677769 |
| 205794_s_at | neuro-oncological ventral antigen 1 | NOVA1 | 4857 | -2.650414 | 0.677769 |
| 212074_at | unc-84 homolog A (C. elegans) | UNC84A | 23353 | -2.653991 | 0.677769 |
| 36545_s_at | Sf1 homolog, spindle assembly associated (yeast) | SFI1 | 9814 | -2.654315 | 0.677769 |
| 221632_s_at | WD repeat domain 4 | WDR4 | 10785 | -2.654646 | 0.677769 |
| 215317_at | CDNA FLJ37610 fis, clone BRCOC2011398 | --- | --- | -2.655751 | 0.677769 |
| 205520_at | striatin, calmodulin binding protein | STRN | 6801 | -2.656257 | 0.677769 |
| 216332_at | POU class 6 homeobox 1 | POU6F1 | 5463 | -2.656899 | 0.677769 |
| 215642_at | Clone HQ0085 | --- | --- | -2.657265 | 0.677769 |
| 205996_s_at | adenylate kinase 2 | AK2 | 204 | -2.659454 | 0.677769 |
| 218139_s_at | chromosome 14 open reading frame 108 | C14orf108 | 55745 | -2.65994 | 0.677769 |
| 211068_x_at | family with sequence similarity 21, member C /// family with sequence similarity 21, member D | FAM21C /// FAM21D | 253725 /// 653450 | -2.662309 | 0.677769 |
| 209824_s_at | aryl hydrocarbon receptor nuclear translocator-like | ARNTL | 406 | -2.662397 | 0.677769 |
| 212963_at | TM2 domain containing 1 | TM2D1 | 83941 | -2.663311 | 0.677769 |
| 202188_at | nucleoporin 93kDa | NUP93 | 9688 | -2.663453 | 0.677769 |
| 219822_at | mitochondrial translational release factor 1 | MTRF1 | 9617 | -2.665183 | 0.677769 |
| 200690_at | heat shock 70kDa protein 9 (mortalin) | HSPA9 | 3313 | -2.665411 | 0.677769 |
| 205963_s_at | DnaJ (Hsp40) homolog, subfamily A, member 3 | DNAJA3 | 9093 | -2.666504 | 0.677769 |
| 205867_at | protein tyrosine phosphatase, non-receptor type 11 (Noonan syndrome 1) | PTPN11 | 5781 | -2.666885 | 0.677769 |
| 203929_s_at | microtubule-associated protein tau | MAPT | 4137 | -2.667747 | 0.677769 |
| 204702_s_at | nuclear factor (erythroid-derived 2)-like 3 | NFE2L3 | 9603 | -2.667883 | 0.677769 |
| 204473_s_at | zinc finger protein 592 | ZNF592 | 9640 | -2.675603 | 0.677769 |
| 204079_at | tyrosylprotein sulfotransferase 2 | TPST2 | 8459 | -2.675921 | 0.677769 |
| 218124_at | retinol saturase (all-trans-retinol 13,14-reductase) | RETSAT | 54884 | -2.677667 | 0.677769 |
| 206720_at | mannosyl (alpha-1,6-)-glycoprotein beta-1,6-N-acetyl-glucosaminyltransferase | MGAT5 | 4249 | -2.680582 | 0.677769 |
| 207046_at | histone cluster 2, H4a /// histone cluster 2, H4b | HIST2H4A /// HIST2H4B | 554313 /// 8370 | -2.681133 | 0.677769 |
| 204677_at | cadherin 5, type 2, VE-cadherin (vascular epithelium) | CDH5 | 1003 | -2.681451 | 0.677769 |
| 215099_s_at | retinoid X receptor, beta | RXRB | 6257 | -2.682345 | 0.677769 |
| 215870_s_at | phospholipase A2, group V | PLA2G5 | 5322 | -2.683809 | 0.677769 |
| 215849_x_at | CDNA FLJ12173 fis, clone MAMMA1000696 | --- | --- | -2.683929 | 0.677769 |
| 202220_at | KIAA0907 | KIAA0907 | 22889 | -2.686147 | 0.677769 |
| 217900_at | isoleucyl-tRNA synthetase 2, mitochondrial | IARS2 | 55699 | -2.686714 | 0.677769 |
| 201000_at | alanyl-tRNA synthetase | AARS | 16 | -2.689408 | 0.677769 |
| 37079_at | YDD19 protein | YDD19 | 11049 | -2.689782 | 0.677769 |
| 221118_at | tripartite motif-containing 27 | TRIM27 | 5987 | -2.690117 | 0.677769 |

FIGURE 15 (CONTINUED)

| | | | | |
|---|---|---|---|---|
| 209336_at | PWP2 periodic tryptophan protein homolog (yeast) | PWP2 | 5822 | -2.690979 | 0.677769 |
| 222245_s_at | fer-1-like 4 (C. elegans) | FER1L4 | 80307 | -2.692154 | 0.677769 |
| 204089_x_at | mitogen-activated protein kinase kinase kinase 4 | MAP3K4 | 4216 | -2.692314 | 0.677769 |
| 206473_at | membrane-bound transcription factor peptidase, site 2 | MBTPS2 | 51360 | -2.692255 | 0.677769 |
| 209615_s_at | p21/Cdc42/Rac1-activated kinase 1 (STE20 homolog, yeast) | PAK1 | 5058 | -2.692753 | 0.677769 |
| 217168_s_at | homocysteine-inducible, endoplasmic reticulum stress-inducible, ubiquitin-like domain member 1 | HERPUD1 | 9709 | -2.694847 | 0.677769 |
| 217399_s_at | forkhead box O3 | FOXO3 | 2309 | -2.695697 | 0.677769 |
| 202491_s_at | inhibitor of kappa light polypeptide gene enhancer in B-cells, kinase complex-associated protein | IKBKAP | 8518 | -2.695956 | 0.677769 |
| 215513_at | hydatidiform mole associated and imprinted | HYMAI | 57061 | -2.697634 | 0.677769 |
| 208700_s_at | transketolase (Wernicke-Korsakoff syndrome) | TKT | 7086 | -2.698039 | 0.677769 |
| 206499_s_at | regulator of chromosome condensation 1 /// SNHG3-RCC1 | RCC1 /// SNHG3-RCC1 | 1104 /// 751867 | -2.698862 | 0.677769 |
| 201697_s_at | DNA (cytosine-5-)-methyltransferase 1 | DNMT1 | 1786 | -2.699453 | 0.677769 |
| 212949_at | non-SMC condensin I complex, subunit H | NCAPH | 23397 | -2.70129 | 0.677769 |
| 212338_at | myosin ID | MYO1D | 4642 | -2.703924 | 0.677769 |
| 215167_at | mediator complex subunit 14 | MED14 | 9282 | -2.704087 | 0.677769 |
| 213092_x_at | DnaJ (Hsp40) homolog, subfamily C, member 9 | DNAJC9 | 23234 | -2.704277 | 0.677769 |
| 201973_s_at | chromosome 7 open reading frame 28A | C7orf28A | 51622 | -2.706342 | 0.677769 |
| 201746_at | tumor protein p53 (Li-Fraumeni syndrome) | TP53 | 7157 | -2.707826 | 0.677769 |
| 218125_s_at | coiled-coil domain containing 25 | CCDC25 | 55246 | -2.709459 | 0.677769 |
| 207891_s_at | UCHL5 interacting protein | UCHL5IP | 55559 | -2.710299 | 0.677769 |
| 222132_s_at | acylglycerol kinase | AGK | 55750 | -2.71142 | 0.677769 |
| 203223_at | rabaptin, RAB GTPase binding effector protein 1 | RABEP1 | 9135 | -2.712777 | 0.677769 |
| 203050_at | tumor protein p53 binding protein 1 | TP53BP1 | 7158 | -2.714858 | 0.677769 |
| 210512_s_at | vascular endothelial growth factor A | VEGFA | 7422 | -2.718555 | 0.677769 |
| 214448_x_at | nuclear factor of kappa light polypeptide gene enhancer in B-cells inhibitor, beta | NFKBIB | 4793 | -2.720854 | 0.677769 |
| 202176_at | excision repair cross-complementing rodent repair deficiency, complementation group 3 (xeroderma pigmentosum group B complementing) | ERCC3 | 2071 | -2.724266 | 0.677769 |
| 217786_at | protein arginine methyltransferase 5 | PRMT5 | 10419 | -2.724482 | 0.677769 |
| 212389_at | SET binding factor 1 | SBF1 | 6305 | -2.725384 | 0.677769 |
| 207061_at | endoplasmic reticulum to nucleus signaling 1 | ERN1 | 2081 | -2.727189 | 0.677769 |
| 217944_at | protein O-linked mannose beta1,2-N-acetylglucosaminyltransferase | POMGNT1 | 55624 | -2.727284 | 0.677769 |
| 202855_s_at | solute carrier family 16, member 3 (monocarboxylic acid transporter 4) | SLC16A3 | 9123 | -2.730027 | 0.677769 |
| 222235_s_at | chondroitin sulfate GalNAcT-2 | GALNACT-2 | 55454 | -2.732504 | 0.677769 |
| 210398_x_at | fucosyltransferase 6 (alpha (1,3) fucosyltransferase) | FUT6 | 2528 | -2.732506 | 0.677769 |
| 204817_at | extra spindle pole bodies homolog 1 (S. cerevisiae) | ESPL1 | 9700 | -2.732787 | 0.677769 |
| 212316_at | nucleoporin 210kDa | NUP210 | 23225 | -2.733436 | 0.677769 |
| 215230_x_at | eukaryotic translation initiation factor 3, subunit C /// eukaryotic translation initiation factor 3, subunit C-like | EIF3C /// EIF3CL | 728689 /// 8663 | -2.735905 | 0.677769 |
| 219278_at | mitogen-activated protein kinase kinase 6 | MAP3K6 | 9064 | -2.737079 | 0.677769 |
| 212025_s_at | flightless I homolog (Drosophila) | FLII | 2314 | -2.742227 | 0.677769 |
| 203226_s_at | tetraspanin 31 | TSPAN31 | 6302 | -2.743346 | 0.677769 |
| 202013_s_at | exostoses (multiple) 2 | EXT2 | 2132 | -2.745667 | 0.677769 |
| 208923_at | cytoplasmic FMR1 interacting protein 1 | CYFIP1 | 23191 | -2.746498 | 0.677769 |
| 211279_at | nuclear respiratory factor 1 | NRF1 | 4899 | -2.74745 | 0.677769 |
| 213199_at | C2 calcium-dependent domain containing 3 | C2CD3 | 26005 | -2.748129 | 0.677769 |

FIGURE 15 (CONTINUED)

| | | | | |
|---|---|---|---|---|
| 215332_s_at | CD8b molecule | CD8B | 926 | -2.748315 | 0.677769 |
| 218973_at | elongation factor Tu GTP binding domain containing 1 | EFTUD1 | 79631 | -2.748594 | 0.677769 |
| 207648_at | dystrophin related protein 2 | DRP2 | 1821 | -2.748618 | 0.677769 |
| 210076_x_at | SERPINE1 mRNA binding protein 1 | SERBP1 | 26135 | -2.754077 | 0.677769 |
| 207387_s_at | glycerol kinase | GK | 2710 | -2.755004 | 0.677769 |
| 220634_at | T-box 4 | TBX4 | 9496 | -2.759779 | 0.677769 |
| 222231_s_at | leucine rich repeat containing 59 | LRRC59 | 55379 | -2.761272 | 0.677651 |
| 212667_at | secreted protein, acidic, cysteine-rich (osteonectin) | SPARC | 6678 | -2.761438 | 0.677651 |
| 215781_s_at | topoisomerase (DNA) III beta | TOP3B | 8940 | -2.761458 | 0.677651 |
| 219705_at | glutamine and serine rich 1 | QSER1 | 79832 | -2.761468 | 0.677651 |
| 206129_s_at | arylsulfatase B | ARSB | 411 | -2.766572 | 0.676577 |
| 216692_at | MRNA; cDNA DKFZp761N1323 (from clone DKFZp761N1323) | --- | --- | -2.76672 | 0.676577 |
| 211543_s_at | G protein-coupled receptor kinase 6 | GRK6 | 2870 | -2.769131 | 0.675594 |
| 212749_at | ring finger and CHY zinc finger domain containing 1 | RCHY1 | 25898 | -2.771994 | 0.67416 |
| 215760_s_at | strawberry notch homolog 2 (Drosophila) | SBNO2 | 22904 | -2.772749 | 0.67416 |
| 214130_s_at | phosphodiesterase 4D interacting protein (myomegalin) /// similar to phosphodiesterase 4D interacting protein isoform 2 | LOC727942 /// PDE4DIP | 727942 /// 9659 | -2.774869 | 0.673001 |
| 207359_at | calcium/calmodulin-dependent protein kinase kinase 2, beta | CAMKK2 | 10645 | -2.775901 | 0.672775 |
| 201819_at | scavenger receptor class B, member 1 | SCARB1 | 949 | -2.77658 | 0.672775 |
| 208438_s_at | Gardner-Rasheed feline sarcoma viral (v-fgr) oncogene homolog | FGR | 2268 | -2.777808 | 0.672775 |
| 213097_s_at | zuotin related factor 1 | ZRF1 | 27000 | -2.782801 | 0.670898 |
| 202395_at | N-ethylmaleimide-sensitive factor | NSF | 4905 | -2.782939 | 0.670898 |
| 204272_at | lectin, galactoside-binding, soluble, 4 (galectin 4) | LGALS4 | 3960 | -2.782974 | 0.670898 |
| 218594_at | HEAT repeat containing 1 | HEATR1 | 55127 | -2.783348 | 0.670898 |
| 219270_at | ChaC, cation transport regulator homolog 1 (E. coli) | CHAC1 | 79094 | -2.783922 | 0.670898 |
| 221156_x_at | cell cycle progression 1 | CCPG1 | 9236 | -2.785387 | 0.670898 |
| 217955_at | BCL2-like 13 (apoptosis facilitator) | BCL2L13 | 23786 | -2.788516 | 0.670898 |
| 205222_at | enoyl-Coenzyme A, hydratase/3-hydroxyacyl Coenzyme A dehydrogenase | EHHADH | 1962 | -2.788582 | 0.670898 |
| 204512_at | human immunodeficiency virus type I enhancer binding protein 1 | HIVEP1 | 3096 | -2.789053 | 0.670898 |
| 220806_x_at | guanine nucleotide binding protein (G protein), gamma 13 | GNG13 | 51764 | -2.792734 | 0.670898 |
| 208851_s_at | Thy-1 cell surface antigen | THY1 | 7070 | -2.79336 | 0.670898 |
| 207050_at | calcium channel, voltage-dependent, alpha 2/delta subunit 1 | CACNA2D1 | 781 | -2.805538 | 0.66705 |
| 216641_s_at | ladinin 1 | LAD1 | 3898 | -2.807319 | 0.666139 |
| 206291_at | neurotensin | NTS | 4922 | -2.808148 | 0.666139 |
| 218228_s_at | tankyrase, TRF1-interacting ankyrin-related ADP-ribose polymerase 2 | TNKS2 | 80351 | -2.8123 | 0.666139 |
| 212946_at | KIAA0564 | KIAA0564 | 23078 | -2.812606 | 0.666139 |
| 222308_x_at | Transcribed locus | --- | --- | -2.812773 | 0.666139 |
| 219154_at | Ras homolog gene family, member F (in filopodia) | RHOF | 54509 | -2.81728 | 0.666139 |
| 211269_s_at | interleukin 2 receptor, alpha | IL2RA | 3559 | -2.818701 | 0.666139 |
| 211016_x_at | heat shock 70kDa protein 4 | HSPA4 | 3308 | -2.819278 | 0.666139 |
| 215756_at | hypothetical protein LOC730227 | LOC730227 | 730227 | -2.821346 | 0.665777 |
| 217805_at | interleukin enhancer binding factor 3, 90kDa | ILF3 | 3609 | -2.821995 | 0.665777 |
| 208952_s_at | La ribonucleoprotein domain family, member 5 | LARP5 | 23185 | -2.822781 | 0.655777 |
| 217099_s_at | gem (nuclear organelle) associated protein 4 | GEMIN4 | 50628 | -2.825648 | 0.664041 |
| 201064_s_at | poly(A) binding protein, cytoplasmic 4 (inducible form) | PABPC4 | 8761 | -2.826461 | 0.664041 |
| 212720_at | poly(A) polymerase alpha | PAPOLA | 10914 | -2.831068 | 0.660294 |

FIGURE 15 (CONTINUED)

| | | | | | |
|---|---|---|---|---|---|
| 212247_at | nucleoporin 205kDa | NUP205 | | 23165 | -2.83174 | 0.660294 |
| 203944_x_at | butyrophilin, subfamily 2, member A1 | BTN2A1 | | 11120 | -2.834712 | 0.659838 |
| 213363_at | Homo sapiens, clone IMAGE:5244869, mRNA | --- | | --- | -2.834993 | 0.659838 |
| 221329_at | olfactory receptor, family 52, subfamily A, member 1 | OR52A1 | | 23538 | -2.835532 | 0.659838 |
| 207300_s_at | coagulation factor VII (serum prothrombin conversion accelerator) | F7 | | 2155 | -2.837244 | 0.659838 |
| 214359_s_at | heat shock protein 90kDa alpha (cytosolic), class B member 1 | HSP90AB1 | | 3326 | -2.838452 | 0.659838 |
| 211982_x_at | exportin 6 | XPO6 | | 23214 | -2.838847 | 0.659838 |
| 202083_s_at | SEC14-like 1 (S. cerevisiae) | SEC14L1 | | 6397 | -2.839853 | 0.659838 |
| 201928_at | plakophilin 4 | PKP4 | | 8502 | -2.841018 | 0.659838 |
| 211365_s_at | protocadherin alpha 2 | PCDHA2 | | 56146 | -2.842468 | 0.659838 |
| 206766_at | integrin, alpha 10 | ITGA10 | | 8515 | -2.84248 | 0.659838 |
| 218395_at | ARP6 actin-related protein 6 homolog (yeast) | ACTR6 | | 64431 | -2.84267 | 0.659838 |
| 214672_at | tubulin tyrosine ligase-like family, member 5 | TTLL5 | | 23093 | -2.843454 | 0.659838 |
| 217401_at | --- | --- | | --- | -2.843475 | 0.659838 |
| 219369_s_at | OTU domain, ubiquitin aldehyde binding 2 | OTUB2 | | 78990 | -2.844774 | 0.659838 |
| 206050_s_at | ribonuclease/angiogenin inhibitor 1 | RNH1 | | 6050 | -2.845847 | 0.659838 |
| 216969_s_at | kinesin family member 22 /// kinesin-like DNA-binding protein pseudogene | KIF22 /// LOC728037 | 3835 /// 728037 | | -2.84965 | 0.659838 |
| 221379_at | --- | --- | | --- | -2.85234 | 0.659838 |
| 220547_s_at | family with sequence similarity 35, member A | FAM35A | | 54537 | -2.85405 | 0.659838 |
| 212197_x_at | myosin phosphatase-Rho interacting protein | M-RIP | | 23164 | -2.855566 | 0.659838 |
| 216360_x_at | ribosomal RNA processing 12 homolog (S. cerevisiae) | RRP12 | | 23223 | -2.855982 | 0.659838 |
| 201112_s_at | CSE1 chromosome segregation 1-like (yeast) | CSE1L | | 1434 | -2.857241 | 0.659838 |
| 211042_x_at | melanoma cell adhesion molecule | MCAM | | 4162 | -2.860596 | 0.659838 |
| 212105_s_at | DEAH (Asp-Glu-Ala-His) box polypeptide 9 | DHX9 | | 1660 | -2.860912 | 0.659838 |
| 220809_at | hypothetical protein FLJ14327 | FLJ14327 | | 79972 | -2.862177 | 0.659838 |
| 211270_x_at | polypyrimidine tract binding protein 1 | PTBP1 | | 5725 | -2.863465 | 0.659838 |
| 202414_at | excision repair cross-complementing rodent repair deficiency, complementation group 5 (xeroderma pigmentosum, complementation group G (Cockayne syndrome)) | ERCC5 | | 2073 | -2.863683 | 0.659838 |
| 209921_at | solute carrier family 7 (cationic amino acid transporter, y+ system) member 11 | SLC7A11 | | 23657 | -2.864739 | 0.659838 |
| 222249_at | KIAA1651 protein | --- | | --- | -2.866844 | 0.659838 |
| 218153_at | cysteinyl-tRNA synthetase 2, mitochondrial (putative) | CARS2 | | 79587 | -2.867047 | 0.659838 |
| 217632_at | guanine nucleotide binding protein-like 3 (nucleolar)-like | GNL3L | | 54552 | -2.867895 | 0.659838 |
| 219321_at | membrane protein, palmitoylated 5 (MAGUK p55 subfamily member 5) | MPP5 | | 64398 | -2.868159 | 0.659838 |
| 203506_s_at | mediator complex subunit 12 | MED12 | | 9968 | -2.868665 | 0.659838 |
| 215910_s_at | fibronectin type III domain containing 3A | FNDC3A | | 22862 | -2.869086 | 0.659838 |
| 222047_s_at | arsenate resistance protein 2 | ARS2 | | 51593 | -2.87061 | 0.659838 |
| 218511_s_at | pyridoxamine 5'-phosphate oxidase | PNPO | | 55163 | -2.871684 | 0.659838 |
| 215413_at | exocyst complex component 7 | EXOC7 | | 23265 | -2.87229 | 0.659838 |
| 202290_at | PDGFA associated protein 1 | PDAP1 | | 11333 | -2.872778 | 0.659838 |
| 216373_at | transmembrane anterior posterior transformation 1 | TAPT1 | | 202018 | -2.875988 | 0.659838 |
| 211027_s_at | inhibitor of kappa light polypeptide gene enhancer in B-cells, kinase beta | IKBKB | | 3551 | -2.881524 | 0.659838 |
| 200647_x_at | eukaryotic translation initiation factor 3, subunit C /// eukaryotic translation initiation factor 3, subunit C-like | EIF3C /// EIF3CL | 728689 /// 8663 | | -2.882124 | 0.659838 |
| 221276_s_at | syncoilin, intermediate filament 1 | SYNC1 | | 81493 | -2.884527 | 0.659838 |

FIGURE 15 (CONTINUED)

| Probe ID | Description | Gene | ID | Value | Value2 |
|---|---|---|---|---|---|
| 209699_x_at | aldo-keto reductase family 1, member C2 (dihydrodiol dehydrogenase 2; bile acid binding protein; 3-alpha hydroxysteroid dehydrogenase, type III) | AKR1C2 | 1645 | -2.884794 | 0.659838 |
| 201774_s_at | non-SMC condensin I complex, subunit D2 | NCAPD2 | 9918 | -2.885752 | 0.659838 |
| 207622_s_at | ATP-binding cassette, sub-family F (GCN20), member 2 | ABCF2 | 10061 | -2.88778 | 0.659838 |
| 203935_at | activin A receptor, type I | ACVR1 | 90 | -2.890088 | 0.659838 |
| 201086_x_at | SON DNA binding protein | SON | 6651 | -2.89182 | 0.659838 |
| 218838_s_at | tetratricopeptide repeat domain 31 | TTC31 | 64427 | -2.89251 | 0.659838 |
| 207579_at | melanoma antigen family B, 3 | MAGEB3 | 4114 | -2.894599 | 0.659838 |
| 217156_at | --- | --- | --- | -2.895667 | 0.659838 |
| 204157_s_at | KIAA0999 protein | KIAA0999 | 23387 | -2.895754 | 0.659838 |
| 201680_at | arsenate resistance protein 2 | ARS2 | 51593 | -2.895824 | 0.659838 |
| 202893_at | unc-13 homolog B (C. elegans) | UNC13B | 10497 | -2.89693 | 0.659838 |
| 202070_s_at | isocitrate dehydrogenase 3 (NAD+) alpha | IDH3A | 3419 | -2.897518 | 0.659838 |
| 221817_at | dolichyl pyrophosphate phosphatase 1 | DOLPP1 | 57171 | -2.899453 | 0.659838 |
| 205748_s_at | ring finger protein 126 | RNF126 | 55658 | -2.899626 | 0.659838 |
| 209777_s_at | solute carrier family 19 (folate transporter), member 1 | SLC19A1 | 6573 | -2.901126 | 0.659838 |
| 201563_at | sorbitol dehydrogenase | SORD | 6652 | -2.901571 | 0.659838 |
| 214050_at | --- | --- | --- | -2.90191 | 0.659838 |
| 203550_s_at | chromosome 1 open reading frame 2 | C1orf2 | 10712 | -2.903663 | 0.659838 |
| 204536_s_at | --- | --- | --- | -2.904602 | 0.659838 |
| 209320_at | adenylate cyclase 3 | ADCY3 | 109 | -2.904722 | 0.659838 |
| 206997_s_at | heparan sulfate 6-O-sulfotransferase 1 /// similar to Heparan-sulfate 6-O-sulfotransferase 1 (HS6ST-1) | HS6ST1 /// LOC728969 | 728969 /// 9394 | -2.905705 | 0.659838 |
| 221626_at | zinc finger protein 506 | ZNF506 | 440515 | -2.906564 | 0.659838 |
| 201529_s_at | replication protein A1, 70kDa | RPA1 | 6117 | -2.91405 | 0.659838 |
| 203289_at | chromosome 16 open reading frame 35 | C16orf35 | 8131 | -2.909359 | 0.659838 |
| 217136_at | peptidylprolyl isomerase A (cyclophilin A)-like 4 /// similar to peptidylprolyl isomerase A (cyclophilin A)-like 4 | LOC653505 /// LOC653598 /// PPIA14 | 164022 /// 653505 /// 653598 | -2.909391 | 0.659838 |
| 202558_s_at | stress 70 protein chaperone, microsome-associated, 60kDa | STCH | 6782 | -2.913598 | 0.659838 |
| 203443_at | echinoderm microtubule associated protein like 3 | EML3 | 256364 | -2.91405 | 0.659838 |
| 216205_s_at | mitofusin 2 | MFN2 | 9927 | -2.914629 | 0.659838 |
| 204072_s_at | furry homolog (Drosophila) | FRY | 10129 | -2.914833 | 0.659838 |
| 202565_s_at | supervillin | SVIL | 6840 | -2.917728 | 0.659838 |
| 217492_s_at | phosphatase and tensin homolog (mutated in multiple advanced cancers 1) /// phosphatase and tensin homolog (mutated in multiple advanced cancers 1), pseudogene 1 /// similar to Phosphatidylinositol-3,4,5-trisphosphate 3-phosphatase and dual-specificity protein phosphatase PTEN (Phosphatase and tensin homolog) (Mutated in multiple advanced cancers 1) | LOC731292 /// PTEN /// PTENP1 | 11191 /// 5728 /// 731292 | -2.9189 | 0.659838 |
| 201476_s_at | ribonucleotide reductase M1 polypeptide | RRM1 | 6240 | -2.9221 | 0.659838 |
| 200643_at | high density lipoprotein binding protein (vigilin) | HDLBP | 3069 | -2.922339 | 0.659838 |
| 207134_x_at | tryptase alpha/beta 1 | TPSAB1 | 7177 | -2.922383 | 0.659838 |
| 214336_s_at | coatomer protein complex, subunit alpha | COPA | 1314 | -2.923415 | 0.659838 |
| 220761_s_at | TAO kinase 3 | TAOK3 | 51347 | -2.924593 | 0.659838 |
| 208034_s_at | protein Z, vitamin K-dependent plasma glycoprotein | PROZ | 8858 | -2.926092 | 0.659838 |
| 217525_at | olfactomedin-like 1 | OLFML1 | 283298 | -2.926247 | 0.659838 |
| 208202_s_at | PHD finger protein 15 | PHF15 | 23338 | -2.926422 | 0.659838 |

FIGURE 15 (CONTINUED)

| | | | | | |
|---|---|---|---|---|---|
| 201578_at | podocalyxin-like | PODXL | 5420 | -2.928591 | 0.659838 |
| 217333_at | keratin 18 pseudogene 44 | KRT18P44 | 139748 | -2.928839 | 0.659838 |
| 217825_s_at | ubiquitin-conjugating enzyme E2, J1 (UBC6 homolog, yeast) | UBE2J1 | 51465 | -2.931948 | 0.659838 |
| 219884_at | LIM homeobox 6 | LHX6 | 26468 | -2.934571 | 0.659838 |
| 214771_x_at | myosin phosphatase-Rho interacting protein | M-RIP | 23164 | -2.941299 | 0.659838 |
| 218306_s_at | hect (homologous to the E6-AP (UBE3A) carboxyl terminus) domain and RCC1 (CHC1)-like domain (RLD) 1 | HERC1 | 8925 | -2.941586 | 0.659838 |
| 205252_at | zinc finger protein 174 | ZNF174 | 7727 | -2.941655 | 0.659838 |
| 212618_at | zinc finger protein 609 | ZNF609 | 23060 | -2.942197 | 0.659838 |
| 202636_at | ring finger protein 103 | RNF103 | 7844 | -2.942925 | 0.659838 |
| 210256_s_at | phosphatidylinositol-4-phosphate 5-kinase, type I, alpha | PIP5K1A | 8394 | -2.943648 | 0.659838 |
| 216203_s_at | GCN1 general control of amino-acid synthesis 1-like 1 (yeast) | GCN1L1 | 10985 | -2.947385 | 0.659838 |
| 202107_s_at | minichromosome maintenance complex component 2 | MCM2 | 4171 | -2.950055 | 0.659838 |
| 219426_at | eukaryotic translation initiation factor 2C, 3 | EIF2C3 | 192669 | -2.951402 | 0.659838 |
| 204243_at | rearranged L-myc fusion | RLF | 6018 | -2.952424 | 0.659838 |
| 203690_at | tubulin, gamma complex associated protein 3 | TUBGCP3 | 10426 | -2.953104 | 0.659838 |
| 203580_s_at | solute carrier family 7 (cationic amino acid transporter, y+ system), member 6 | SLC7A6 | 9057 | -2.953437 | 0.659838 |
| 203372_s_at | suppressor of cytokine signaling 2 | SOCS2 | 8835 | -2.955747 | 0.659838 |
| 222087_at | Pvt1 oncogene homolog, MYC activator (mouse) | PVT1 | 5820 | -2.955868 | 0.659838 |
| 212575_at | chromosome 19 open reading frame 6 | C19orf6 | 91304 | -2.955954 | 0.659838 |
| 203120_at | tumor protein p53 binding protein, 2 | TP53BP2 | 7159 | -2.957876 | 0.659838 |
| 207524_at | suppression of tumorigenicity 7 | ST7 | 7982 | -2.958305 | 0.659838 |
| 201384_s_at | neighbor of BRCA1 gene 1 /// similar to neighbor of BRCA1 gene 1 | LOC727732 /// NBR1 | 4077 /// 727732 | -2.958683 | 0.659838 |
| 204206_at | MAX binding protein | MNT | 4335 | -2.95914 | 0.659838 |
| 212110_at | solute carrier family 39 (zinc transporter), member 14 | SLC39A14 | 23516 | -2.960955 | 0.659838 |
| 216008_s_at | ariadne homolog 2 (Drosophila) | ARIH2 | 10425 | -2.962294 | 0.659838 |
| 220288_at | myosin XVA | MYO15A | 51168 | -2.966403 | 0.659838 |
| 203875_at | SWI/SNF related, matrix associated, actin dependent regulator of chromatin, subfamily a, member 1 | SMARCA1 | 6594 | -2.966509 | 0.659838 |
| 209203_s_at | bicaudal D homolog 2 (Drosophila) | BICD2 | 23299 | -2.967285 | 0.659838 |
| 222021_x_at | succinate dehydrogenase complex, subunit A, flavoprotein pseudogene 1 | SDHALP1 | 255812 | -2.968924 | 0.659838 |
| 205839_s_at | benzodiazapine receptor (peripheral) associated protein 1 | BZRAP1 | 9256 | -2.971092 | 0.659838 |
| 220840_s_at | chromosome 1 open reading frame 112 | C1orf112 | 55732 | -2.971318 | 0.659838 |
| 204444_at | kinesin family member 11 | KIF11 | 3832 | -2.973032 | 0.659838 |
| 221879_at | calmodulin-like 4 | CALML4 | 91860 | -2.975206 | 0.659838 |
| 216090_x_at | --- | --- | --- | -2.978601 | 0.659838 |
| 203648_at | TatD DNase domain containing 2 | TATDN2 | 9797 | -2.982513 | 0.659838 |
| 201266_at | thioredoxin reductase 1 | TXNRD1 | 7296 | -2.982972 | 0.659838 |
| 217687_at | adenylate cyclase 2 (brain) | ADCY2 | 108 | -2.985605 | 0.659838 |
| 215170_s_at | centrosomal protein 152kDa | CEP152 | 22995 | -2.986306 | 0.659838 |
| 204240_s_at | structural maintenance of chromosomes 2 | SMC2 | 10592 | -2.994212 | 0.659838 |
| 209386_at | transmembrane 4 L six family member 1 | TM4SF1 | 4071 | -2.994983 | 0.659838 |
| 204947_at | E2F transcription factor 1 | E2F1 | 1869 | -2.99637 | 0.659838 |
| 206854_s_at | mitogen-activated protein kinase kinase kinase 7 | MAP3K7 | 6885 | -3.000481 | 0.659838 |
| 209352_s_at | SIN3 homolog B, transcription regulator (yeast) | SIN3B | 23309 | -3.006793 | 0.659838 |
| 215195_at | protein kinase C, alpha | PRKCA | 5578 | -3.008978 | 0.659838 |

FIGURE 15 (CONTINUED)

| | | | | |
|---|---|---|---|---|
| 213059_at | cAMP responsive element binding protein 3-like 1 | CREB3L1 | 90993 | -3.010615 | 0.659838 |
| 203040_s_at | hydroxymethylbilane synthase | HMBS | 3145 | -3.01265 | 0.659838 |
| 200028_s_at | StAR-related lipid transfer (START) domain containing 7 | STARD7 | 56910 | -3.014835 | 0.659838 |
| 209724_s_at | zinc finger protein 161 homolog (mouse) | ZFP161 | 7541 | -3.019622 | 0.659838 |
| 220276_at | RERG/RAS-like | RERGL | 79685 | -3.02006 | 0.659838 |
| 211375_s_at | interleukin enhancer binding factor 3, 90kDa | ILF3 | 3609 | -3.022281 | 0.659838 |
| 201598_s_at | inositol polyphosphate phosphatase-like 1 | INPPL1 | 3636 | -3.022463 | 0.659838 |
| 210061_at | zinc finger protein 589 | ZNF589 | 51385 | -3.027497 | 0.659838 |
| 212159_x_at | adaptor-related protein complex 2, alpha 2 subunit | AP2A2 | 161 | -3.031842 | 0.659838 |
| 203438_at | stanniocalcin 2 | STC2 | 8614 | -3.032651 | 0.659838 |
| 220852_at | PRO1768 protein | PRO1768 | 29018 | -3.037981 | 0.659838 |
| 208231_at | neuregulin 1 | NRG1 | 3084 | -3.040949 | 0.659838 |
| 212381_at | ubiquitin specific peptidase 24 | USP24 | 23358 | -3.043775 | 0.659838 |
| 218269_at | ribonuclease III, nuclear | RNASEN | 29102 | -3.044677 | 0.659838 |
| 207614_s_at | cullin 1 | CUL1 | 8454 | -3.049613 | 0.659838 |
| 201800_s_at | oxysterol binding protein | OSBP | 5007 | -3.049985 | 0.659838 |
| 212992_at | AHNAK nucleoprotein 2 | AHNAK2 | 113146 | -3.05414 | 0.659838 |
| 208258_s_at | growth arrest-specific 2 like 1 | GAS2L1 | 10634 | -3.057215 | 0.659838 |
| 211561_x_at | mitogen-activated protein kinase 14 | MAPK14 | 1432 | -3.058794 | 0.659838 |
| 201622_at | staphylococcal nuclease and tudor domain containing 1 | SND1 | 27044 | -3.064297 | 0.659838 |
| 220363_s_at | engulfment and cell motility 2 | ELMO2 | 63916 | -3.065556 | 0.659838 |
| 221972_s_at | stromal cell derived factor 4 | SDF4 | 51110 | -3.069527 | 0.659838 |
| 209599_s_at | prune homolog (Drosophila) | PRUNE | 58497 | -3.069964 | 0.659838 |
| 201729_s_at | KIAA0100 | KIAA0100 | 9703 | -3.073301 | 0.659838 |
| 203601_s_at | zinc finger and BTB domain containing 17 | ZBTB17 | 7709 | -3.075183 | 0.659838 |
| 204152_s_at | MFNG O-fucosylpeptide 3-beta-N-acetylglucosaminyltransferase | MFNG | 4242 | -3.08229 | 0.659838 |
| 204360_s_at | N-acetylglucosaminidase, alpha- (Sanfilippo disease IIIB) | NAGLU | 4669 | -3.093124 | 0.659838 |
| 201622_at | WW domain containing transcription regulator 1 | WWTR1 | 25937 | -3.09341 | 0.659838 |
| 202132_at | tripartite motif-containing 28 | TRIM28 | 10155 | -3.100609 | 0.659838 |
| 200990_at | ubiquitin specific peptidase 1 | USP1 | 7398 | -3.103641 | 0.659838 |
| 202413_s_at | activating signal cointegrator 1 complex subunit 3 | ASCC3 | 10973 | -3.104893 | 0.659838 |
| 212815_at | zinc finger protein 227 | ZNF227 | 7770 | -3.107458 | 0.659838 |
| 217403_s_at | zinc finger protein 207 | ZNF207 | 7756 | -3.111647 | 0.659838 |
| 200828_s_at | leucyl-tRNA synthetase 2, mitochondrial | LARS2 | 23395 | -3.11324 | 0.659838 |
| 34764_at | tubby homolog (mouse) | TUB | 7275 | -3.115667 | 0.659838 |
| 208431_s_at | protocadherin alpha 3 | PCDHA3 | 56145 | -3.116323 | 0.659838 |
| 211870_at | methionyl-tRNA synthetase | MARS | 4141 | -3.117677 | 0.659838 |
| 213672_at | cytochrome P450, family 2, subfamily E, polypeptide 1 | CYP2E1 | 1571 | -3.119674 | 0.659838 |
| 209975_at | receptor-interacting serine-threonine kinase 4 | RIPK4 | 54101 | -3.122246 | 0.659838 |
| 221215_s_at | chromosome 10 open reading frame 84 | C10orf84 | 63877 | -3.124169 | 0.659838 |
| 218390_s_at | zinc finger, AN1-type domain 3 | ZFAND3 | 60685 | -3.12464 | 0.659838 |
| 218020_s_at | mitochondrial translation optimization 1 homolog (S. cerevisiae) | MTO1 | 25821 | -3.125901 | 0.659838 |
| 222014_x_at | CDNA FLJ12226 fis, clone MAMMA1001143 | --- | --- | -3.126418 | 0.659838 |
| 215995_at | mucosa associated lymphoid tissue lymphoma translocation gene 1 | MALT1 | 10892 | -3.128328 | 0.659838 |
| 210018_x_at | RAB3 GTPase activating protein subunit 1 (catalytic) | RAB3GAP1 | 22930 | -3.128875 | 0.659838 |
| 212932_at | quaking homolog, KH domain RNA binding (mouse) | QKI | 9444 | -3.128914 | 0.659838 |

FIGURE 15 (CONTINUED)

| | | | | |
|---|---|---|---|---|
| 211615_s_at | leucine-rich PPR-motif containing | LRPPRC | 10128 | -3.130975 | 0.659838 |
| 219484_at | host cell factor C2 | HCFC2 | 29915 | -3.132682 | 0.659838 |
| 206352_at | peroxisome biogenesis factor 10 | PEX10 | 5192 | -3.135224 | 0.659838 |
| 208955_at | deoxyuridine triphosphatase | DUT | 1854 | -3.14338 | 0.659838 |
| 207788_s_at | sorbin and SH3 domain containing 3 | SORBS3 | 10174 | -3.147085 | 0.659838 |
| 212370_x_at | family with sequence similarity 21, member B /// family with sequence similarity 21, member A | FAM21A /// FAM21B | 387680 /// 55747 | -3.147427 | 0.659838 |
| 216767_at | CDNA: FLJ21710 fis, clone COL10087 | --- | --- | -3.147823 | 0.659838 |
| 203422_at | polymerase (DNA directed), delta 1, catalytic subunit 125kDa | POLD1 | 5424 | -3.151891 | 0.659838 |
| 203745_at | interleukin 19 | IL19 | 29949 | -3.152826 | 0.659838 |
| 203099_s_at | chromodomain protein, Y-like | CDYL | 9425 | -3.152886 | 0.659838 |
| 202968_s_at | dual-specificity tyrosine-(Y)-phosphorylation regulated kinase 2 | DYRK2 | 8445 | -3.153709 | 0.659838 |
| 202364_at | MAX interactor 1 | MXI1 | 4601 | -3.157846 | 0.659838 |
| 202049_s_at | zinc finger, MYM-type 4 | ZMYM4 | 9202 | -3.177339 | 0.659838 |
| 218604_at | LEM domain containing 3 | LEMD3 | 23592 | -3.181182 | 0.659838 |
| 207559_s_at | zinc finger, MYM-type 3 | ZMYM3 | 9203 | -3.18285 | 0.659838 |
| 201461_s_at | mitogen-activated protein kinase-activated protein kinase 2 | MAPKAPK2 | 9261 | -3.190135 | 0.659838 |
| 220130_x_at | leukotriene B4 receptor 2 | LTB4R2 | 56413 | -3.191735 | 0.659838 |
| 219515_at | PR domain containing 10 | PRDM10 | 56980 | -3.192417 | 0.659838 |
| 220349_s_at | endo-beta-N-acetylglucosaminidase | FLJ21865 | 64772 | -3.192798 | 0.659838 |
| 217601_at | N-myristoyltransferase 1 | NUP188 | 23511 | -3.197626 | 0.659838 |
| 219490_s_at | DNA cross-link repair 1B (PSO2 homolog, S. cerevisiae) | DCLRE1B | 64858 | -3.19834 | 0.659838 |
| 212439_at | inositol hexaphosphate kinase 1 | IHPK1 | 9807 | -3.198576 | 0.659838 |
| 210983_s_at | minichromosome maintenance complex component 7 | MCM7 | 4176 | -3.200229 | 0.659838 |
| 212388_at | ubiquitin specific peptidase 24 | USP24 | 23358 | -3.209458 | 0.659838 |
| 203809_s_at | v-akt murine thymoma viral oncogene homolog 2 | AKT2 | 208 | -3.209949 | 0.659838 |
| 201159_s_at | N-myristoyltransferase 1 | NMT1 | 4836 | -3.210127 | 0.659838 |
| 212084_at | testis expressed 261 | TEX261 | 113419 | -3.211376 | 0.659838 |
| 206498_at | oculocutaneous albinism II (pink-eye dilution homolog, mouse) | OCA2 | 4948 | -3.211379 | 0.659838 |
| 210455_at | chromosome 10 open reading frame 28 | C10orf28 | 27291 | -3.212398 | 0.659838 |
| 38158_at | extra spindle pole bodies homolog 1 (S. cerevisiae) | ESPL1 | 9700 | -3.214741 | 0.659838 |
| 213112_s_at | sequestosome 1 | SQSTM1 | 8878 | -3.215405 | 0.659838 |
| 203157_s_at | glutaminase | GLS | 2744 | -3.218287 | 0.659838 |
| 200722_s_at | cell cycle associated protein 1 | CAPRIN1 | 4076 | -3.221415 | 0.659838 |
| 212196_at | Interleukin 6 signal transducer (gp130, oncostatin M receptor) | IL6ST | 3572 | -3.222908 | 0.659838 |
| 215194_at | protein kinase C, alpha | PRKCA | 5578 | -3.233247 | 0.659838 |
| 209997_x_at | pericentriolar material 1 | PCM1 | 5108 | -3.236244 | 0.659838 |
| 222039_at | hypothetical protein LOC146909 | LOC146909 | 146909 | -3.240897 | 0.659838 |
| 218016_s_at | polymerase (RNA) III (DNA directed) polypeptide E (80kD) | POLR3E | 55718 | -3.249579 | 0.659838 |
| 220768_s_at | casein kinase 1, gamma 3 | CSNK1G3 | 1456 | -3.250021 | 0.659838 |
| 214582_at | phosphodiesterase 3B, cGMP-inhibited | PDE3B | 5140 | -3.251366 | 0.659838 |
| 217735_s_at | eukaryotic translation initiation factor 2-alpha kinase 1 | EIF2AK1 | 27102 | -3.253415 | 0.659838 |
| 210787_s_at | calcium/calmodulin-dependent protein kinase kinase 2, beta | CAMKK2 | 10645 | -3.254698 | 0.659838 |
| 215960_at | solute carrier family 5 (low affinity glucose cotransporter), member 4 | SLC5A4 | 6527 | -3.255202 | 0.659838 |
| 216599_x_at | solute carrier family 22 (organic anion transporter), member 6 | SLC22A6 | 9356 | -3.257306 | 0.659838 |
| 206445_s_at | protein arginine methyltransferase 1 | PRMT1 | 3276 | -3.259405 | 0.659838 |

FIGURE 15 (CONTINUED)

| | | | | |
|---|---|---|---|---|
| 204744_s_at | Isoleucyl-tRNA synthetase | IARS | 3376 | -3.260419 | 0.659838 |
| 217895_at | Pentatricopeptide repeat domain 3 | PTCD3 | 55037 | -3.271357 | 0.659838 |
| 218343_s_at | general transcription factor IIIC, polypeptide 3, 102kDa | GTF3C3 | 9330 | -3.2729 | 0.659838 |
| 211724_x_at | hypothetical protein FLJ20323 | FLJ20323 | 54468 | -3.278673 | 0.659838 |
| 44120_at | aarF domain containing kinase 2 | ADCK2 | 90956 | -3.286476 | 0.659838 |
| 210544_s_at | aldehyde dehydrogenase 3 family, member A2 | ALDH3A2 | 224 | -3.288576 | 0.659838 |
| 205700_at | hydroxysteroid (17-beta) dehydrogenase 6 homolog (mouse) | HSD17B6 | 8630 | -3.289485 | 0.659838 |
| 202477_s_at | tubulin, gamma complex associated protein 2 | TUBGCP2 | 10844 | -3.290951 | 0.659838 |
| 210692_s_at | solute carrier family 43, member 3 | SLC43A3 | 29015 | -3.293499 | 0.659838 |
| 208979_at | nuclear receptor coactivator 6 | NCOA6 | 23054 | -3.298875 | 0.659838 |
| 213807_x_at | met proto-oncogene (hepatocyte growth factor receptor) | MET | 4233 | -3.299836 | 0.659838 |
| 202653_s_at | membrane-associated ring finger (C3HC4) 7 | 7-Mar | 64844 | -3.303499 | 0.659838 |
| 213929_at | cDNA clone IMAGE:4733238 | | | -3.30791 | 0.659838 |
| 218479_s_at | exportin 4 | XPO4 | 64328 | -3.308857 | 0.659838 |
| 202095_s_at | baculoviral IAP repeat-containing 5 (survivin) | BIRC5 | 332 | -3.310453 | 0.659838 |
| 203890_s_at | death-associated protein kinase 3 | DAPK3 | 1613 | -3.322887 | 0.659838 |
| 217449_at | mRNA; cDNA DKFZp434D1516 (from clone DKFZp434D1516) | | | -3.327842 | 0.659838 |
| 205544_s_at | complement component (3d/Epstein Barr virus) receptor 2 | CR2 | 1380 | -3.33664 | 0.659838 |
| 219918_s_at | asp (abnormal spindle) homolog, microcephaly associated (Drosophila) | ASPM | 259266 | -3.339053 | 0.659838 |
| 202094_at | baculoviral IAP repeat-containing 5 (survivin) | BIRC5 | 332 | -3.33953 | 0.659838 |
| 207890_s_at | matrix metallopeptidase 25 | MMP25 | 64386 | -3.341023 | 0.659838 |
| 204651_at | nuclear respiratory factor 1 | NRF1 | 4899 | -3.34182 | 0.659838 |
| 201977_s_at | KIAA0141 | KIAA0141 | 9812 | -3.341932 | 0.659838 |
| 210206_s_at | DEAD/H (Asp-Glu-Ala-Asp/His) box polypeptide 11 (CHL1-like helicase homolog, S. cerevisiae) | DDX11 | 1663 | -3.345102 | 0.659838 |
| 215509_s_at | BUB1 budding uninhibited by benzimidazoles 1 homolog (yeast) | BUB1 | 699 | -3.346864 | 0.659838 |
| 220236_at | pyruvate dehydrogenase phosphatase regulatory subunit | PDPR | 55066 | -3.348782 | 0.659838 |
| 212689_s_at | jumonji domain containing 1A | JMJD1A | 55818 | -3.349623 | 0.659838 |
| 215897_at | mediator complex subunit 25 | MED25 | 81857 | -3.350978 | 0.659838 |
| 203118_at | proprotein convertase subtilisin/kexin type 7 | PCSK7 | 9159 | -3.351132 | 0.659838 |
| 217445_s_at | phosphoribosylglycinamide formyltransferase, phosphoribosylglycinamide synthetase, phosphoribosylaminoimidazole synthetase | GART | 2618 | -3.353902 | 0.659838 |
| 203092_at | translocase of inner mitochondrial membrane 44 homolog (yeast) | TIMM44 | 10469 | -3.355713 | 0.659838 |
| 213209_at | TAF6-like RNA polymerase II, p300/CBP-associated factor (PCAF)-associated factor, 65kDa | TAF6L | 10629 | -3.356676 | 0.659838 |
| 218575_at | anaphase promoting complex subunit 1 | ANAPC1 | 64682 | -3.358109 | 0.659838 |
| 213223_at | ribosomal protein L28 | RPL28 | 6158 | -3.360826 | 0.659838 |
| 202226_s_at | v-crk sarcoma virus CT10 oncogene homolog (avian) | CRK | 1398 | -3.365529 | 0.659838 |
| 207629_s_at | rho/rac guanine nucleotide exchange factor (GEF) 2 | ARHGEF2 | 9181 | -3.366402 | 0.659838 |
| 212669_at | calcium/calmodulin-dependent protein kinase (CaM kinase) II gamma | CAMK2G | 818 | -3.371637 | 0.659838 |
| 203194_s_at | nucleoporin 98kDa | NUP98 | 4928 | -3.382784 | 0.659838 |
| 219566_at | pleckstrin homology domain containing, family F (with FYVE domain) member 1 | PLEKHF1 | 79156 | -3.383601 | 0.659838 |
| 211109_at | Janus kinase 3 (a protein tyrosine kinase, leukocyte) | JAK3 | 3718 | -3.387591 | 0.659838 |
| 220212_at | thyroid adenoma associated | THADA | 63892 | -3.387613 | 0.659838 |
| 206425_s_at | transient receptor potential cation channel, subfamily C, member 3 | TRPC3 | 7222 | -3.393535 | 0.659838 |
| 209453_at | solute carrier family 9 (sodium/hydrogen exchanger), member 1 (antiporter, Na+/H+, amiloride sensitive) | SLC9A1 | 6548 | -3.398832 | 0.659838 |
| 210053_at | TAF5 RNA polymerase II, TATA box binding protein (TBP)-associated factor, 100kDa | TAF5 | 6877 | -3.414184 | 0.659838 |

FIGURE 15 (CONTINUED)

| Probe ID | Description | Symbol | ID | Value | Score |
|---|---|---|---|---|---|
| 219098_at | MYB binding protein (P160) 1a | MYBBP1A | 10514 | -3.416388 | 0.659838 |
| 210457_x_at | high mobility group AT-hook 1 | HMGA1 | 3159 | -3.42584 | 0.659838 |
| 214820_at | bromodomain and WD repeat domain containing 1 | BRWD1 | 54014 | -3.426963 | 0.659838 |
| 204736_s_at | chondroitin sulfate proteoglycan 4 | CSPG4 | 1464 | -3.438347 | 0.659838 |
| 205667_at | Werner syndrome | WRN | 7486 | -3.439393 | 0.659838 |
| 217750_s_at | ubiquitin-conjugating enzyme E2Z | UBE2Z | 65264 | -3.445538 | 0.659838 |
| 208021_s_at | replication factor C (activator 1) 1, 145kDa | RFC1 | 5981 | -3.452363 | 0.659838 |
| 211955_at | RAN binding protein 5 | RANBP5 | 3843 | -3.457148 | 0.659838 |
| 210949_s_at | eukaryotic translation initiation factor 3, subunit C /// eukaryotic translation initiation factor 3, subunit C-like | EIF3C /// EIF3CL | 728689 /// 8663 | -3.457437 | 0.659838 |
| 213118_at | UHRF1 (ICBP90) binding protein 1-like | UHRF1BP1L | 23074 | -3.457614 | 0.659838 |
| 203947_at | cleavage stimulation factor, 3' pre-RNA, subunit 3, 77kDa | CSTF3 | 1479 | -3.459899 | 0.659838 |
| 205726_at | splicing factor, arginine/serine-rich 11 | SFRS11 | 9295 | -3.46931 | 0.659838 |
| 200685_at | procollagen-proline, 2-oxoglutarate 4-dioxygenase (proline 4-hydroxylase), beta polypeptide | P4HB | 5034 | -3.469481 | 0.659838 |
| 212315_s_at | nucleoporin 210kDa | NUP210 | 23225 | -3.473049 | 0.659838 |
| 37860_at | zinc finger protein 337 | ZNF337 | 26152 | -3.473772 | 0.659838 |
| 47083_at | chromosome 7 open reading frame 26 | C7orf26 | 79034 | -3.481351 | 0.659838 |
| 220275_at | CUB and zona pellucida-like domains 1 | CUZD1 | 50624 | -3.486819 | 0.659838 |
| 204190_at | ubiquitin specific peptidase like 1 | USPL1 | 10208 | -3.493441 | 0.659838 |
| 203395_s_at | hairy and enhancer of split 1, (Drosophila) | HES1 | 3280 | -3.503021 | 0.659838 |
| 202458_at | protease, serine, 23 | PRSS23 | 11098 | -3.513778 | 0.659838 |
| 203630_s_at | component of oligomeric golgi complex 5 | COG5 | 10466 | -3.515034 | 0.659838 |
| 207895_at | N-acetylated alpha-linked acidic dipeptidase-like 1 | NAALADL1 | 10004 | -3.51824 | 0.659838 |
| 213302_at | phosphoribosylformylglycinamidine synthase (FGAR amidotransferase) | PFAS | 5198 | -3.520731 | 0.659838 |
| 205726_at | diaphanous homolog 2 (Drosophila) | DIAPH2 | 1730 | -3.533306 | 0.659838 |
| 201391_at | TNF receptor-associated protein 1 | TRAP1 | 10131 | -3.535212 | 0.659838 |
| 204016_at | leucyl-tRNA synthetase 2, mitochondrial | LARS2 | 23395 | -3.538666 | 0.659838 |
| 218755_at | kinesin family member 20A | KIF20A | 10112 | -3.540792 | 0.659838 |
| 208127_s_at | suppressor of cytokine signaling 5 | SOCS5 | 9655 | -3.543413 | 0.659838 |
| 216397_s_at | block of proliferation 1 /// similar to block of proliferation 1 | BOP1 /// LOC727967 | 23246 /// 727967 | -3.556269 | 0.659838 |
| 215357_s_at | polymerase (DNA-directed), delta interacting protein 3 | POLDIP3 | 84271 | -3.558791 | 0.659838 |
| 212756_s_at | ubiquitin protein ligase E3 component n-recognin 2 | UBR2 | 23304 | -3.575786 | 0.659838 |
| 210505_at | alcohol dehydrogenase 7 (class IV), mu or sigma polypeptide | ADH7 | 131 | -3.58159 | 0.659838 |
| 219702_at | placenta-specific 1 | PLAC1 | 10761 | -3.581873 | 0.659838 |
| 204835_at | polymerase (DNA directed), alpha 1 | POLA1 | 5422 | -3.581904 | 0.659838 |
| 200903_s_at | S-adenosylhomocysteine hydrolase | AHCY | 191 | -3.585197 | 0.659838 |
| 212471_at | KIAA0241 | KIAA0241 | 23080 | -3.588245 | 0.659838 |
| 203106_s_at | vacuolar protein sorting 41 homolog (S. cerevisiae) | VPS41 | 27072 | -3.596842 | 0.659838 |
| 216682_s_at | family with sequence similarity 48, member A | FAM48A | 55578 | -3.610767 | 0.659838 |
| 221965_at | M-phase phosphoprotein 9 | MPHOSPH9 | 10198 | -3.619428 | 0.659838 |
| 213756_s_at | heat shock transcription factor 1 | HSF1 | 3297 | -3.619831 | 0.659838 |
| 212016_s_at | polypyrimidine tract binding protein 1 | PTBP1 | 5725 | -3.622621 | 0.659838 |
| 201918_at | solute carrier family 25, member 36 | SLC25A36 | 55186 | -3.625142 | 0.659838 |
| 212125_at | Ran GTPase activating protein 1 | RANGAP1 | 5905 | -3.63484 | 0.659838 |
| 203115_at | ferrochelatase (protoporphyria) | FECH | 2235 | -3.636278 | 0.659838 |

FIGURE 15 (CONTINUED)

| | | | | | |
|---|---|---|---|---|---|
| 220773_s_at | gephyrin | GPHN | 10243 | -3.641602 | 0.659838 |
| 212789_at | non-SMC condensin II complex, subunit D3 | NCAPD3 | 23310 | -3.652501 | 0.659838 |
| 221147_x_at | WW domain containing oxidoreductase | WWOX | 51741 | -3.661956 | 0.659838 |
| 205450_at | phosphorylase kinase, alpha 1 (muscle) | PHKA1 | 5255 | -3.678124 | 0.659838 |
| 216021_s_at | glycine receptor, alpha 3 | GLRA3 | 8001 | -3.687395 | 0.659838 |
| 203567_at | cut-like homeobox 1 | CUX1 | 1523 | -3.692489 | 0.659838 |
| 212896_at | superkiller viralicidic activity 2-like 2 (S. cerevisiae) | SKIV2L2 | 23517 | -3.694827 | 0.659838 |
| 206923_at | protein kinase C, alpha | PRKCA | 5578 | -3.695092 | 0.659838 |
| 202476_s_at | tubulin, gamma complex associated protein 2 | TUBGCP2 | 10844 | -3.696805 | 0.659838 |
| 205584_at | integrin, alpha 4 (antigen CD49D, alpha 4 subunit of VLA-4 receptor) | ITGA4 | 3676 | -3.704958 | 0.659838 |
| 212048_s_at | tyrosyl-tRNA synthetase | YARS | 8565 | -3.708899 | 0.659838 |
| 216736_at | transmembrane 6 superfamily member 2 | TM6SF2 | 53345 | -3.714685 | 0.659838 |
| 212238_at | additional sex combs like 1 (Drosophila) | ASXL1 | 171023 | -3.730621 | 0.659838 |
| 216757_at | CDNA: FLJ21342 fis, clone COL02673 | | | -3.734329 | 0.659838 |
| 213222_at | phospholipase C, beta 1 (phosphoinositide-specific) | PLCB1 | 23236 | -3.736999 | 0.659838 |
| 203783_x_at | polymerase (RNA) mitochondrial (DNA directed) | POLRMT | 5442 | -3.737653 | 0.659838 |
| 214158_s_at | PR domain containing 10 | PRDM10 | 56980 | -3.741032 | 0.659838 |
| 203195_s_at | nucleoporin 98kDa | NUP98 | 4928 | -3.768153 | 0.659838 |
| 209408_at | kinesin family member 2C | KIF2C | 11004 | -3.770192 | 0.659838 |
| 205581_s_at | nitric oxide synthase 3 (endothelial cell) | NOS3 | 4846 | -3.789026 | 0.659838 |
| 216199_s_at | mitogen-activated protein kinase kinase kinase 4 | MAP3K4 | 4216 | -3.789942 | 0.659838 |
| 211550_at | epidermal growth factor receptor (erythroblastic leukemia viral (v-erb-b) oncogene homolog, avian) | EGFR | 1956 | -3.792789 | 0.659838 |
| 216305_at | chromosome 2 open reading frame 3 | C2orf3 | 6936 | -3.796848 | 0.659838 |
| 219320_at | myosin XIX | MYO19 | 80179 | -3.810062 | 0.659838 |
| 210114_at | inversin | INVS | 27130 | -3.826297 | 0.659838 |
| 203100_s_at | chromodomain protein, Y-like | CDYL | 9425 | -3.82816 | 0.659838 |
| 209229_s_at | SAPS domain family, member 1 | SAPS1 | 22870 | -3.829086 | 0.659838 |
| 208597_at | ciliary neurotrophic factor | CNTF | 1270 | -3.837091 | 0.659838 |
| 203235_at | thimet oligopeptidase 1 | THOP1 | 7064 | -3.845062 | 0.659838 |
| 209642_at | BUB1 budding uninhibited by benzimidazoles 1 homolog (yeast) | BUB1 | 699 | -3.847238 | 0.659838 |
| 219017_at | ethanolamine kinase 1 | ETNK1 | 55500 | -3.859679 | 0.659838 |
| 36830_at | mitochondrial intermediate peptidase | MIPEP | 4285 | -3.861645 | 0.659838 |
| 208699_x_at | transketolase (Wernicke-Korsakoff syndrome) | TKT | 7086 | -3.862596 | 0.659838 |
| 212272_at | lipin 1 | LPIN1 | 23175 | -3.872718 | 0.659838 |
| 219307_at | prenyl (decaprenyl) diphosphate synthase, subunit 2 | PDSS2 | 57107 | -3.872858 | 0.659838 |
| 203462_x_at | eukaryotic translation initiation factor 3, subunit B | EIF3B | 8662 | -3.886074 | 0.659838 |
| 210412_at | glutamate receptor, ionotropic, N-methyl D-aspartate 2B | GRIN2B | 2904 | -3.920012 | 0.659838 |
| 210625_s_at | A kinase (PRKA) anchor protein 1 | AKAP1 | 8165 | -3.936975 | 0.659838 |
| 220988_s_at | C1q and tumor necrosis factor related protein 3 | C1QTNF3 | 114899 | -3.954415 | 0.659838 |
| 210555_s_at | nuclear factor of activated T-cells, cytoplasmic, calcineurin-dependent 3 | NFATC3 | 4775 | -3.965315 | 0.659838 |
| 212164_at | transmembrane protein 183A | TMEM183A | 92703 | -3.989355 | 0.659838 |
| 203835_at | leucine rich repeat containing 32 | LRRC32 | 2615 | -4.021946 | 0.659838 |
| 203373_at | suppressor of cytokine signalling 2 | SOCS2 | 8835 | -4.02917 | 0.659838 |
| 47571_at | zinc finger protein 236 | ZNF236 | 7776 | -4.035174 | 0.659838 |
| 203202_s_at | arginine/serine-rich coiled-coil 2 | RSRC2 | 65117 | -4.054584 | 0.659838 |
| 211791_s_at | potassium voltage-gated channel, shaker-related subfamily, beta member 2 | KCNAB2 | 8514 | -4.086634 | 0.659838 |

FIGURE 15 (CONTINUED)

| | | | | |
|---|---|---|---|---|
| 203578_s_at | solute carrier family 7 (cationic amino acid transporter, y+ system), member 6 | SLC7A6 | 9057 | -4.092662 | 0.659838 |
| 215747_s_at | regulator of chromosome condensation 1 /// SNHG3-RCC1 | RCC1 /// SNHG3-RCC1 | 1104 /// 751867 | -4.093268 | 0.659838 |
| 219608_at | F-box protein 38 | FBXO38 | 81545 | -4.1201 | 0.659838 |
| 215581_s_at | minichromosome maintenance complex component 3 associated protein | MCM3AP | 8888 | -4.169899 | 0.659838 |
| 202099_s_at | DiGeorge syndrome critical region gene 2 | DGCR2 | 9993 | -4.170982 | 0.659838 |
| 212653_s_at | EH domain binding protein 1 | EHBP1 | 23301 | -4.187376 | 0.659838 |
| 202496_at | enhancer of mRNA decapping 4 | EDC4 | 23644 | -4.193291 | 0.659838 |
| 201167_x_at | Rho GDP dissociation inhibitor (GDI) alpha | ARHGDIA | 396 | -4.196988 | 0.659838 |
| 201479_at | dyskeratosis congenita 1, dyskerin | DKC1 | 1736 | -4.224747 | 0.659838 |
| 204275_at | small optic lobes homolog (Drosophila) | SOLH | 6650 | -4.232288 | 0.659838 |
| 211337_s_at | tubulin, gamma complex associated protein 4 | TUBGCP4 | 27229 | -4.244358 | 0.659838 |
| 212431_at | KIAA0194 protein | KIAA0194 | 22993 | -4.319757 | 0.659838 |
| 216217_at | phospholipase C-like 2 | PLCL2 | 23228 | -4.353492 | 0.659838 |
| 218927_s_at | carbohydrate (chondroitin 4) sulfotransferase 12 | CHST12 | 55501 | -4.409404 | 0.659838 |
| 201842_s_at | EGF-containing fibulin-like extracellular matrix protein 1 | EFEMP1 | 2202 | -4.47356 | 0.658014 |
| 205895_s_at | nucleolar and coiled-body phosphoprotein 1 | NOLC1 | 9221 | -4.523706 | 0.643373 |
| 222113_s_at | epidermal growth factor receptor pathway substrate 15-like 1 | EPS15L1 | 58513 | -4.550499 | 0.640184 |
| 202179_at | bleomycin hydrolase | BLMH | 642 | -4.569564 | 0.634111 |
| 213077_at | YTH domain containing 2 | YTHDC2 | 64848 | -4.594537 | 0.623444 |
| 212893_at | zinc finger, ZZ-type containing 3 | ZZZ3 | 26009 | -4.634696 | 0.623444 |
| 201796_s_at | valyl-tRNA synthetase | VARS | 7407 | -4.650356 | 0.623444 |
| 203159_at | glutaminase | GLS | 2744 | -4.748201 | 0.585101 |
| 218382_s_at | U2 small nuclear RNA auxiliary factor 2 | U2AF2 | 11338 | -4.774282 | 0.576315 |
| 205095_s_at | ATPase, H+ transporting, lysosomal V0 subunit a1 | ATP6V0A1 | 535 | -4.921941 | 0.487407 |
| 205461_at | RAB35, member RAS oncogene family | RAB35 | 11021 | -4.973428 | 0.482434 |
| 201478_s_at | dyskeratosis congenita 1, dyskerin | DKC1 | 1736 | -5.246881 | 0.392181 |
| 220950_s_at | KIAA1310 | KIAA1310 | 55683 | -5.424994 | 0.368172 |
| 203644_s_at | MON1 homolog B (yeast) | MON1B | 22879 | -5.673282 | 0.368172 |
| 213578_at | bone morphogenetic protein receptor, type IA | BMPR1A | 657 | -6.010642 | 0.295814 |
| 201638_s_at | cleavage and polyadenylation specific factor 1, 160kDa | CPSF1 | 29894 | -7.908362 | 0.105387 |

FIGURE 16

| probeset_id | GeneTitle | GeneSymbol | t |
|---|---|---|---|
| 210164_at | granzyme B (granzyme 2, cytotoxic T-lymphocyte-associated serine esterase 1) | GZMB | 21.620876 |
| 209969_s_at | signal transducer and activator of transcription 1, 91kDa | STAT1 | 19.349693 |
| 202269_x_at | guanylate binding protein 1, interferon-inducible, 67kDa | GBP1 | 13.790309 |
| 202417_s_at | interferon-induced protein 35 | IFI35 | 13.758327 |
| 202659_at | proteasome (prosome, macropain) subunit, beta type, 10 | PSMB10 | 9.567776 |
| 204415_at | interferon, alpha-inducible protein 6 | IFI6 | 9.376857 |
| 202307_s_at | transporter 1, ATP-binding cassette, sub-family B (MDR/TAP) | TAP1 | 9.037264 |
| 204279_at | proteasome (prosome, macropain) subunit, beta type, 9 (large multifunctional peptidase 2) | PSMB9 | 8.909184 |
| 203882_at | interferon regulatory factor 9 | IRF9 | 8.694727 |
| 34210_at | CD52 molecule | CD52 | 8.48951 |
| 209670_at | T cell receptor alpha constant | TRAC | 8.145286 |
| 203729_at | epithelial membrane protein 3 | EMP3 | 8.119499 |
| 210140_at | cystatin F (leukocystatin) | CST7 | 7.86001 |
| 209732_at | C-type lectin domain family 2, member B | CLEC2B | 7.856387 |
| 209813_x_at | T cell receptor gamma constant 2 /// T cell receptor gamma variable 9 /// TCR gamma alternate reading frame protein | TARP /// TRGC2 /// TRGV9 | 7.525085 |
| 214669_x_at | immunoglobulin kappa locus | IGK@ | 7.403741 |
| 202270_at | guanylate binding protein 1, interferon-inducible, 67kDa | GBP1 | 7.219952 |
| 204747_at | interferon-induced protein with tetratricopeptide repeats 3 | IFIT3 | 7.204917 |
| 204661_at | CD52 molecule | CD52 | 6.915314 |
| 218400_at | 2'-5'-oligoadenylate synthetase 3, 100kDa | OAS3 | 6.903254 |
| 201762_s_at | proteasome (prosome, macropain) activator subunit 2 (PA28 beta) | PSME2 | 6.886636 |
| 200750_s_at | ADP-ribosylation-like factor 6 interacting protein 5 | ARL6IP5 | 6.759636 |
| 200965_s_at | interferon, gamma-inducible protein 16 | IFI16 | 6.528202 |
| 214617_at | perforin 1 (pore forming protein) | PRF1 | 6.359152 |
| 216920_s_at | T cell receptor gamma constant 2 /// T cell receptor gamma variable 9 /// TCR gamma alternate reading frame protein | TARP /// TRGC2 /// TRGV9 | 6.319274 |
| 201641_at | bone marrow stromal cell antigen 2 | BST2 | 6.252856 |
| 205965_at | basic leucine zipper transcription factor, ATF-like | BATF | 6.235932 |
| 215806_x_at | T cell receptor gamma constant 2 /// T cell receptor gamma variable 9 /// TCR gamma alternate reading frame protein | TARP /// TRGC2 /// TRGV9 | 6.235368 |
| 210951_x_at | RAB27A, member RAS oncogene family | RAB27A | 6.18875 |
| 213060_s_at | chitinase 3-like 2 | CHI3L2 | 6.050052 |

FIGURE 16 (CONTINUED)

| | | | |
|---|---|---|---|
| 213915_at | natural killer cell group 7 sequence | NKG7 | 6.044779 |
| 209514_s_at | RAB27A, member RAS oncogene family | RAB27A | 5.824808 |
| 211796_s_at | T cell receptor beta variable 19 /// T cell receptor beta variable 7-2 /// T cell receptor beta variable 5-4 /// T cell receptor beta variable 3-1 /// T cell receptor beta constant 1 | TRBC1 /// TRBV19 /// TRBV3-1 /// TRBV5-4 /// TRBV7-2 | 5.664187 |
| 202592_at | biogenesis of lysosome-related organelles complex-1, subunit 1 | BLOC1S1 | 5.566296 |
| 202101_s_at | v-ral simian leukemia viral oncogene homolog B (ras related; GTP binding protein) | RALB | 5.519963 |
| 212203_x_at | interferon induced transmembrane protein 3 (1-8U) | IFITM3 | 5.44233 |
| 201541_s_at | zinc finger, HIT type 1 | ZNHIT1 | 5.432486 |
| 208659_at | chloride intracellular channel 1 | CLIC1 | 5.430092 |
| 214004_s_at | vestigial like 4 (Drosophila) | VGLL4 | 5.380125 |
| 201601_x_at | interferon induced transmembrane protein 1 (9-27) | IFITM1 | 5.374556 |
| 200814_at | proteasome (prosome, macropain) activator subunit 1 (PA28 alpha) | PSME1 | 5.367468 |
| 204994_at | myxovirus (influenza virus) resistance 2 (mouse) | MX2 | 5.316415 |
| 205081_at | cysteine-rich protein 1 (intestinal) | CRIP1 | 5.314466 |
| 209890_at | tetraspanin 5 | TSPAN5 | 5.276698 |
| 212784_at | capicua homolog (Drosophila) | CIC | 5.269762 |
| 209671_x_at | T cell receptor alpha locus /// T cell receptor alpha constant | TRA@ /// TRAC | 5.267778 |
| 201194_at | selenoprotein W, 1 | SEPW1 | 5.245011 |
| 211144_x_at | T cell receptor gamma constant 2 /// T cell receptor gamma variable 9 /// TCR gamma alternate reading frame protein | TARP /// TRGC2 /// TRGV9 | 5.228222 |
| 220449_at | hypothetical protein MGC5566 | MGC5566 | 5.22753 |
| 217497_at | endothelial cell growth factor 1 (platelet-derived) | ECGF1 | 5.20215 |
| 215797_at | T cell receptor alpha variable 8-3 | TRAV8-3 | 5.201479 |
| 205345_at | BRCA1 associated RING domain 1 | BARD1 | 5.189021 |
| 217755_at | hematological and neurological expressed 1 | HN1 | 5.102404 |
| 214343_s_at | ataxin 7-like 1 | ATXN7L1 | 5.058278 |
| 208492_at | regulatory factor X-associated protein | RFXAP | 5.01901 |
| 201275_at | farnesyl diphosphate synthase (farnesyl pyrophosphate synthetase, dimethylallyltranstransferase, geranyltranstransferase) | FDPS | 4.992341 |
| 202760_s_at | A kinase (PRKA) anchor protein 2 /// PALM2-AKAP2 | AKAP2 /// PALM2-AKAP2 | 4.98906 |
| 216298_at | hypothetical protein LOC648852 | LOC648852 | 4.861568 |
| 206484_s_at | X-prolyl aminopeptidase (aminopeptidase P) 2, membrane-bound | XPNPEP2 | 4.838981 |

FIGURE 16 (CONTINUED)

| | | | |
|---|---|---|---|
| 202747_s_at | integral membrane protein 2A | ITM2A | 4.823814 |
| 206687_s_at | protein tyrosine phosphatase, non-receptor type 6 | PTPN6 | 4.78005 |
| 203595_s_at | interferon-induced protein with tetratricopeptide repeats 5 | IFIT5 | 4.732435 |
| 202446_s_at | phospholipid scramblase 1 | PLSCR1 | 4.699799 |
| 217962_at | nucleolar protein family A, member 3 (H/ACA small nucleolar RNPs) | NOLA3 | 4.657467 |
| 210972_x_at | T cell receptor alpha locus /// T cell receptor delta variable 2 /// T cell receptor alpha variable 20 /// T cell receptor alpha joining 17 /// T cell receptor alpha constant | TRA@ /// TRAC /// TRAJ17 /// TRAV20 /// TRDV2 | 4.647777 |
| 214995_s_at | apolipoprotein B mRNA editing enzyme, catalytic polypeptide-like 3G /// apolipoprotein B mRNA editing enzyme, catalytic polypeptide-like 3F | APOBEC3F /// APOBEC3G | 4.629687 |
| 218913_s_at | GEM interacting protein | GMIP | 4.617402 |
| 219807_x_at | RAB4B, member RAS oncogene family | RAB4B | 4.609035 |
| 210807_s_at | solute carrier family 16, member 7 (monocarboxylic acid transporter 2) | SLC16A7 | 4.535773 |
| 202323_s_at | acyl-Coenzyme A binding domain containing 3 | ACBD3 | 4.462806 |
| 206150_at | CD27 molecule | CD27 | 4.462507 |
| 209389_x_at | diazepam binding inhibitor (GABA receptor modulator, acyl-Coenzyme A binding protein) | DBI | 4.45446 |
| 222369_at | N-acetyltransferase 11 | NAT11 | 4.394234 |
| 206332_s_at | interferon, gamma-inducible protein 16 | IFI16 | 4.375824 |
| 212082_s_at | myosin, light chain 6, alkali, smooth muscle and non-muscle | MYL6 | 4.21968 | a

```
SEQUENCE LISTING

<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 953
<212> TYPE: DNA
<213> ORGANISM: Homo sapiens

<400> SEQUENCE: 2
caagagagag agagagcgtg caagccccaa agcgagcgac atgtcccttt ggggagcagt      60
ccctctgcac cccagagtga ggaggacgca ggggtcagag gtggctacag ggcaggcaga     120
ggaggcacct gtaggggtg gtgggctggt ggcccaggag aagtcaggaa gggagcccag     180
ctggtgacaa gagagcccag aggtgcctgg ggctgagtgt gagagcccgg aagatttcag     240
ccatgcctca cagctccgac agcagtgact ccagcttcag ccgctctcct cccctggca     300 aacaggactc atctgatgat gtgagaagag ttcagaggag ggagaaaaat cgtattgccg     360
cccagaagag ccgacagagg cagacacaga aggccgacac cctgcacctg gagagcgaag     420
acctggagaa acagaacgcg gctctacgca aggagatcaa gcagctcaca gaggaactga     480
agtacttcac gtcggtgctg aacagccacg agccctgtg ctcggtgctg gccgccagca     540
cgccctcgcc ccccgaggtg gtgtacagcg cccacgcatt ccaccaacct catgtcagct     600
ccccgcgctt ccagccctga gcttccgatg cggggagagc agagcctcgg gaggggcaca     660
cagactgtgg cagagctgcg cccatcccgc agaggcccct gtccacctgg agacccggag     720
acagaggcct ggacaaggag tgaacacggg aactgtcacg actggaaggg cgtgaggcct     780
cccagcagtg ccgcagcgtt tcgagggggcg tgtgctggac cccaccactg tgggttgcag     840
```

```
gcccaatgca gaagagtatt aagaaagatg ctcaagtccc atggcacaga gcaaggcggg    900
cagggaacgg ttattttct aaataaatgc tttaaaagaa aaaaaaaaaa aaa           953
```

<210> SEQ ID NO 3
<211> LENGTH: 125
<212> TYPE: PRT
<213> ORGANISM: Homo sapiens

<400> SEQUENCE: 3

```
Met Pro His Ser Ser Asp Ser Asp Ser Phe Ser Arg Ser Pro
1               5                   10                  15

Pro Pro Gly Lys Gln Asp Ser Ser Asp Val Arg Arg Val Gln Arg
            20                  25                  30

Arg Glu Lys Asn Arg Ile Ala Ala Gln Lys Ser Arg Gln Arg Gln Thr
                35                  40                  45

Gln Lys Ala Asp Thr Leu His Leu Glu Ser Glu Asp Leu Glu Lys Gln
50                  55                  60

Asn Ala Ala Leu Arg Lys Glu Ile Lys Gln Leu Thr Glu Glu Leu Lys
65                  70                  75                  80

Tyr Phe Thr Ser Val Leu Asn Ser His Glu Pro Leu Cys Ser Val Leu
                85                  90                  95

Ala Ala Ser Thr Pro Ser Pro Pro Glu Val Val Tyr Ser Ala His Ala
                100                 105                 110

Phe His Gln Pro His Val Ser Ser Pro Arg Phe Gln Pro
            115                 120                 125
```

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Glu Ala His
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Thr Glu Leu
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Glu Ala Asp
1

```
<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Asp Glu Leu
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp or His

<400> SEQUENCE: 8

Asp Glu Ala Xaa
1
```

US 9,164,094 B2

BIOMARKERS TO IDENTIFY HIV-SPECIFIC T-CELL SUBSETS

RELATED APPLICATION

This application is a continuation application of international application no. PCT/US2010/002662, filed on Oct. 1, 2010, which claims the benefit of and priority to U.S. Provisional Application 61/279,587, filed on Oct. 22, 2009. The contents of the entirety of these applications are incorporated herein by reference.

SEQUENCE LISTING

The instant application contains a Sequence Listing which has been submitted in ASCII format via EFS-Web and in paper format and is hereby incorporated by reference in its entirety. Said ASCII copy, created on Sep. 7, 2012, is named 83219_CON_207032_Sequence_Listing_ST25.txt and is 3,930 bytes in size.

FIELD OF THE INVENTION

The invention relates to expression profiles of HIV-specific T-cells and their methods of use. The invention also relates to agents for treatment of HIV.

BACKGROUND OF THE INVENTION

Functional impairment of antigen-specific T cells is a defining characteristic of chronic infections in humans but the molecular mechanisms underlying this T-cell dysfunction are not well understood[1]. In contrast to the T cell response in acute infections, CD8[+] T cells in chronic infection develop a range of functional defects that include the loss of IL2 secretion and proliferative potential[2,3]. Because cytokine secretion and proliferation are essential for effective control of viral replication, these defects—collectively referred to as T cell exhaustion—play a central role in the immunological failure to clear chronic viral pathogens such as HIV, HCV and HBV[1].

HIV infection provides a paradigm of T cell dysfunction in humans. The majority of individuals infected with HIV show elevation of viral load in the absence of anti-viral therapy (hereafter, "chronic progressors") associated with defects in HIV-specific T cell cytokine secretion, proliferation and survival[12,13]. In contrast, spontaneous control of viral replication has been documented for a small minority of individuals ('controllers')[11].

BATF is a highly conserved member of the AP-1/ATF family, a group of transcription factors that regulate many aspects of cellular function in the immune system, including cytokine secretion and proliferation[30]. BATF antagonizes AP-1 function by dimerizing to Jun, disrupting the active Jun:Fos complex of AP-1, and reducing expression of AP-1 target genes[20,24,31]. Consistent with this, enforced expression of BATF in T cells inhibited the secretion of IL2, an AP-1 dependent gene, but not IFNγ which is not primarily regulated by AP-1.

Schraml et al. have found BATF to be required for Th17 differentiation in CD4[+] T cells[33].

BRIEF SUMMARY OF THE INVENTION

The present invention is directed to expression profiles of HIV-specific T-cells and their methods of use. The present invention is also directed to agents useful for treatment of HIV.

The invention provides a method of classifying an immune response in an individual infected with HIV comprising: determining an expression profile of HIV specific T-cells from the HIV infected individual and comparing the expression profile to at least one of: the expression profile of T-cells from a subject that is not infected with HIV; the expression profile of HIV-specific T-cells that are controllers; and the expression profile of HIV-specific T-cells that are chronic progressors; thereby determining an immune response.

The invention also provides a method of classifying an immune response in an individual who has been vaccinated with an HIV vaccine comprising: determining an expression profile of HIV specific T-cells from the HIV infected individual and comparing the expression profile to at least one of: the expression profile of T-cells from a subject that is not infected with HIV; the expression profile of HIV-specific T-cells that are controllers; and the expression profile of HIV-specific T-cells that are chronic progressors; thereby determining an immune response.

The invention also provides a method of increasing HIV specific T-cell function in an HIV-infected subject comprising: determining the expression profile of HIV specific T-cells of the subject; and administering to the subject an agent that alters the expression profile such that the expression profile is substantially similar to the expression profile of T-cells of a subject that are not infected with HIV or HIV specific T-cells that are controllers, thereby increasing T-cell function in the subject.

The invention also provides a method for increasing the survival of HIV-specific T-cells in an HIV-infected subject, the method comprising: determining the expression profile of HIV specific T-cells of the subject; and; administering to the subject an agent that alters the expression profile of the subject in need such that the expression profile of the subject in need is substantially similar to the expression profile of T-cells of a subject that is not infected with HIV or HIV specific T-cells that are controllers, thereby increasing the survival of HIV specific T-cells in the subject.

The invention also provides a method of treating an HIV infection in a subject in need of treatment comprising administering to the subject a therapeutically effective amount of an agent that inhibits BATF expression in T-cells, wherein BATF expression is inhibited, thereby treating the subject for HIV.

The invention also provides a method of treating HIV infection in a subject in need thereof, comprising: determining the expression profile of the HIV specific T-cells of the subject; and administering to the subject a therapeutically effective amount of an agent that inhibits BATF expression in T-cells wherein BATF expression is inhibited, thereby increasing HIV specific T-cell function in the subject.

The invention also provides a method of treating an HIV infection in a subject in need thereof, comprising: determining the expression profile of HIV specific T-cells of the subject in need, administering a therapeutically effective amount of an agent or a pharmaceutically acceptable salt or prodrug thereof, or a pharmaceutical composition comprising a therapeutically effective amount of an agent or a pharmaceutically acceptable salt or prodrug thereof, wherein the agent alters the expression profile of the HIV specific T-cells of the subject in need such that the expression profile of the HIV specific T-cells is substantially similar to the expression profile of T-cells from a subject that is not infected with HIV or reference HIV specific T-cells that are controllers, thereby treating the subject for HIV infection.

The invention also provides a method of treating HIV infection in a subject in need thereof comprising: identifying a subject that is in need of treatment for HIV infection; selecting the identified subject for treatment for HIV infection; determining the expression profile of HIV specific T-cells of the subject in need, and administering a therapeutically effective amount of an agent or a pharmaceutically acceptable salt or prodrug thereof, or a pharmaceutical composition comprising a therapeutically effective amount of an agent or a pharmaceutically acceptable salt or prodrug thereof, wherein the agent alters the expression profile of the HIV specific T-cells of the subject in need such that the expression profile of the HIV specific T-cells is substantially similar to the expression profile of T-cells from a subject that is not infected with HIV or reference HIV specific T-cells that are controllers, thereby treating HIV infection in a subject.

In one embodiment the agent is administered in an amount that is therapeutically effective to decrease the activity or expression of BATF In another embodiment the agent is an inhibitory nucleic acid molecule at least a portion of which is complementary to the BATF mRNA or an antibody that specifically binds the BATF polypeptide.

In another embodiment the inhibitory nucleic acid molecule is an antisense molecule, shRNA, or siRNA.

In another embodiment the method comprises obtaining the inhibitor or the pharmaceutically acceptable salt or prodrug thereof.

In another embodiment the agent decreases BATF expression in HIV specific T-cells that are positive for at least one of CD4 or CD8, decreases BATF expression in HIV specific T-cells that are positive for at least one of CD4 or CD8 to thereby increase the function of CD4 positive and/or CD8 positive T-cells in the subject, and/or decreases the viral load of the subject, thereby treating the subject for HIV infection.

In another embodiment the T-cell is positive for at least one of CD4 or CD8.

The invention also provides a method of monitoring the efficacy of an anti HIV therapy in an HIV infected subject, comprising determining the expression profile of HIV-specific T-cells of the HIV infected subject, wherein the HIV specific T-cells of the HIV infected subject are obtained before and after initiating treatment, and wherein an expression profile of the HIV specific T-cells of the HIV infected subject that is obtained after treatment that is substantially similar to the expression profile of T-cells from a subject that is not infected with HIV or HIV specific T-cells that are controllers indicates that the treatment is effective.

The invention also provides a method of selecting an anti-HIV therapy for an HIV infected subject, comprising: determining the expression profile of HIV specific T-cells of the HIV infected subject; comparing the expression profile of the HIV-infected subject to the expression profile of T-cells from a subject that is not infected with HIV or HIV specific T-cells that are controllers or HIV specific T-cells that are chronic progressors; and selecting the therapy.

In one embodiment the therapy is selected from the group consisting of: highly active antiretroviral therapy (HAART), protease inhibitors, fusion inhibitors, integrase inhibitors, co-receptor specific agents, 3TC, AZT, nevirapine, non-nucleoside analogue reverse transcriptase inhibitors, nucleoside analogue reverse transcriptase inhibitors and vaccine therapy.

The invention also provides a method of monitoring HIV disease progression in an HIV infected subject undergoing HIV treatment, comprising: determining the expression profile of HIV specific T-cells of the HIV infected subject; administering to the HIV infected subject a pharmaceutically effective amount of an agent that alters the expression profile of step (a); wherein an expression profile of the HIV infected subject that is substantially similar to the expression profile of T-cells from a subject that is not infected with HIV or HIV specific T-cells that are controllers after the administration of the agent indicates a decrease in HIV disease progression in the HIV infected subject.

The invention also provides a method of determining the prognosis of an HIV infected subject, comprising determining the expression profile of HIV positive T-cells of the subject; and determining the expression profile of reference T-cells, wherein the reference T-cells comprise any one of T-cells of a subject that is not infected with HIV, HIV specific T-cells that are controllers and HIV specific T-cells that are chronic progressors, wherein a comparison of the expression profile of the HIV infected subject and the expression profiles of the reference T-cells determines the prognosis.

The invention also provides a method of identifying an HIV infected subject as a chronic progressor comprising determining the expression profile of HIV positive T-cells from the subject, wherein an expression profile that is substantially similar to the expression profile of an HIV specific T-cell that is a chronic progressor identifies an HIV infected subject as a chronic progressor.

The invention also provides a method of identifying an HIV infected subject as a controller comprising determining the expression profile of HIV positive T-cells from the subject, wherein an expression profile that is substantially similar to the expression profile of an HIV specific T-cell that is a controller identifies an HIV infected subject as a controller.

In one embodiment the subject is human.

The invention also provides an expression profile of an HIV-specific T-cell from an HIV infected subject comprising at least two genes selected from the genes presented in FIG. 11.

In one embodiment the at least two genes are selected from the group consisting of genes 1-10 presented in FIG. 11 or the group consisting of genes 1-5 presented in FIG. 1.

In another embodiment the expression profile is that of an HIV-specific T-cell that is a chronic progressor or a controller.

In another embodiment the expression profile is that of an HIV specific T-cell that is CD8 positive and/or CD4 positive.

In another embodiment the expression profile is used for at least one of: identifying HIV infected individuals as a chronic progressor or a controller, monitoring the efficacy of an anti HIV therapy in an HIV infected subject, selecting an anti-HIV therapy for an HIV infected subject, determining the prognosis of an HIV infected subject, treating HIV infection, or identifying an HIV infected subject as a chronic progressor or a controller.

The invention also provides a method for determining the expression profile of an HIV infected subject, comprising quantifying the level of two or more genes from the genes presented in FIG. 11 in an HIV-specific T-cell derived from the HIV infected subject, wherein the level of the two or more genes in the sample relative to the level in a reference determines the marker profile of the subject.

The invention also provides a packaged pharmaceutical comprising an agent that alters the expression profile of an HIV specific T-cell of a subject such that the expression profile of the HIV specific T-cell of the subject is substantially similar to an expression profile of T-cells of a subject that are not infected with HIV or HIV specific T-cells that are controllers.

In one embodiment the agent inhibits BATF expression.

In another embodiment the instructions are for use of any of the claimed methods.

The invention also provides a kit for classifying the immune response of an HIV-infected subject or a subject that has been vaccinated with an HIV vaccine, the kit comprising at least one primer or antibody capable of specifically binding or hybridizing to a polypeptide or nucleic acid molecule corresponding to any one of the genes of the expression profile of the invention, and directions for using the primer or antibody for the analysis of the polypeptide or nucleic acid molecule.

The invention also provides a kit to treat HIV infection in an HIV infected subject comprising: an agent that alters the expression profile of an HIV specific T-cell of a subject such that the expression profile of the HIV specific T-cell of the subject is substantially similar to an expression profile of T-cells of a subject that is not infected with HIV or HIV specific T-cells that are controllers; and associated instructions for using the agent to treat HIV infection.

In one embodiment the kit also comprises packaging means thereof.

In another embodiment, antibody binding is detected by fluorescence, by autoradiography, by an immunoassay, by an enzymatic assay, or by a colorimetric assay.

The invention also provides a packaged pharmaceutical to treat HIV infection in an HIV infected subject comprising: an agent that alters the expression profile of an HIV specific T-cell of a subject such that the expression profile of the HIV specific T-cell of the subject is substantially similar to an expression profile of T-cells of a subject that is not infected with HIV or HIV specific T-cells that are controllers; and associated instructions for using the agent to treat HIV infection.

The invention also provides a packaged pharmaceutical to inhibit HIV disease progression in an HIV infected subject comprising: an agent that alters the expression profile of an HIV specific T-cell of a subject such that the expression profile of the HIV specific T-cell of the subject is substantially similar to an expression profile of T-cells of a subject that is not infected with HIV or HIV specific T-cells that are controllers; and associated instructions for using the agent to inhibit HIV disease progression.

In one embodiment of the invention the agent of the packaged pharmaceuticals or kits described here comprises an antisense molecule, shRNA or siRNA.

(a) Efficacy of siRNA uptake in CD3$^+$ T cells cultured with a mixture of an siRNA pool and fluorescent oligonucleotides (to monitor transduction) either with (black histogram) or without (grey histogram) electroporation. (b) Silencing of BATF by siRNA sequences targeting BATF in CD3$^+$ T cells from a representative chronic progressor. Expression (mean, SEM) normalized to a housekeeping gene is presented as fold change relative to control siRNA (c-e). BATF silencing enhances HIV-specific cytokine secretion in CD8$^+$ (c) and CD4$^+$ (d,e) T cells from chronic progressors. PBMC depleted CD4$^+$ (a) or CD8$^+$ (b,c) T cells were electroporated with siRNA pools targeting the genes indicated and cultured with or without HIV Gag peptides for four days, and IFN-γ (c,e) or IL-2 (d) was measured using a highly-sensitive cytokine bead assay. In each figure the left panel shows a representative patient, and the right panel summary data (CD8$^+$ responses, 26 HIV epitope responses in four subjects; CD4$^+$ responses, HIV Gag peptide pool in seven subjects). Cytokine levels shown are adjusted for background secretion, and statistical significance evaluated with the paired t test. (f) Proliferation of CFSE CD8$^+$ T cells was measured by the fraction of CFSE$^{dim}$, CD25$^+$ cells six days after transfection and peptide stimulation of PBMCs. Data represent nine HIV epitope-specific responses in four subjects.

Figure 7:
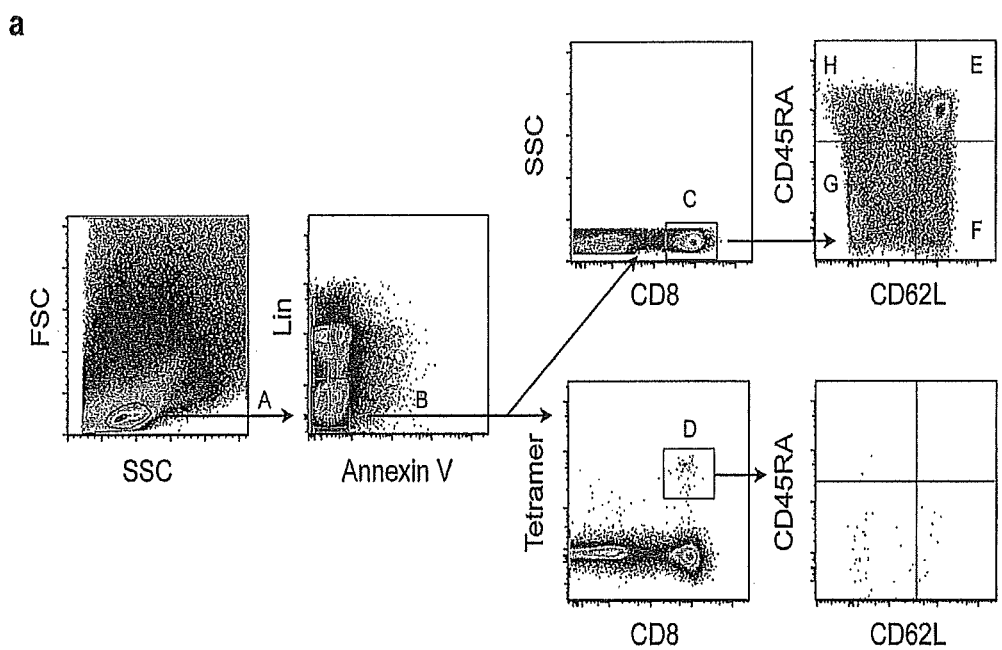
Figure 7:
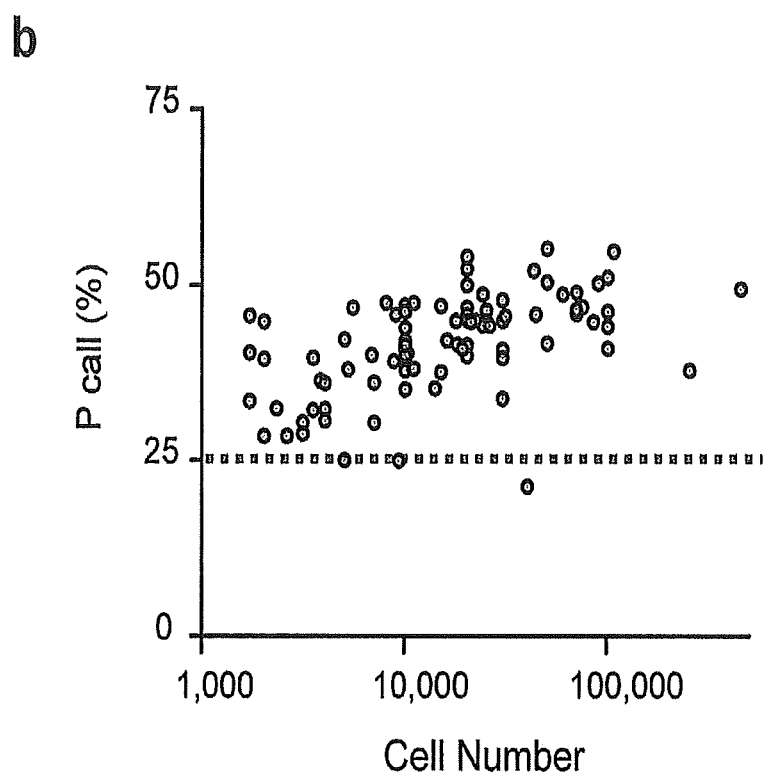
Figure 7:
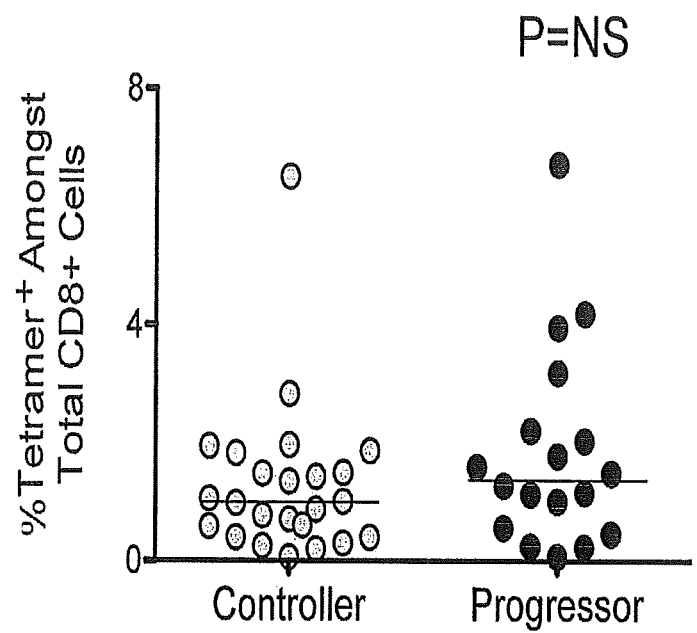
Figure 7:
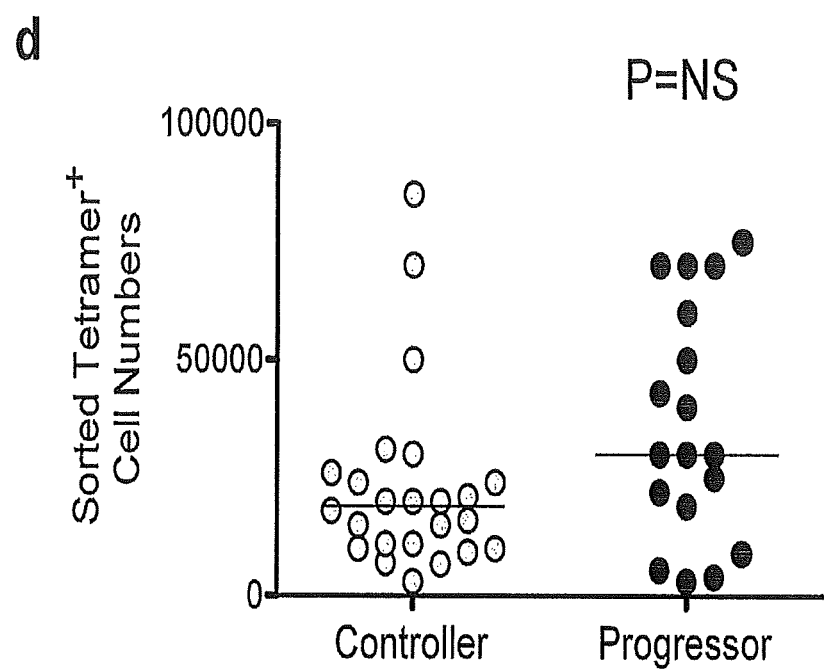
Figure 7:
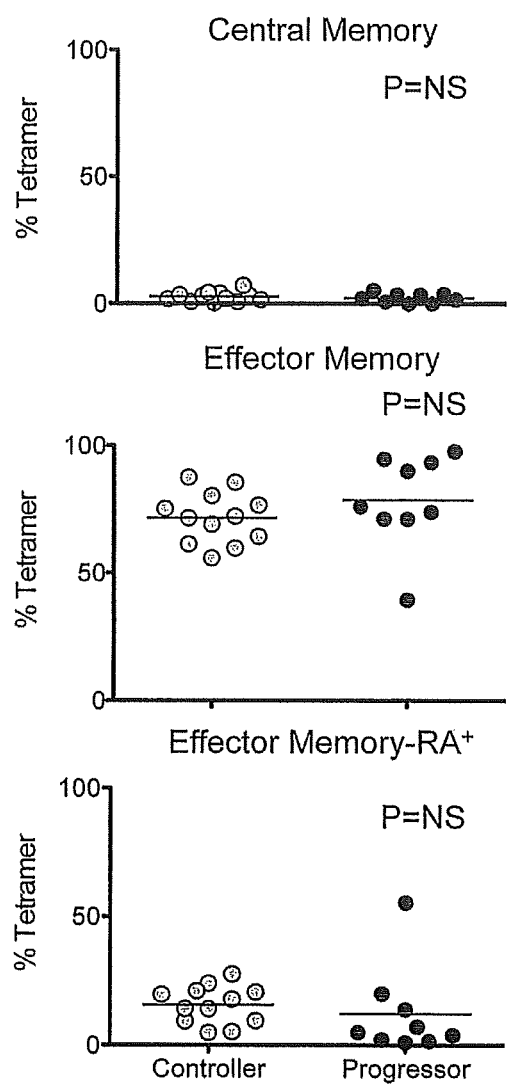

FIG. 7 demonstrates the results of microarray analysis of patients (a) Flow cytometry gating strategy for sorting of HIV Gag-tetramer$^+$ CD8 T cells and memory phenotype analysis. (b) Quality of microarray data generated from small numbers of HIV Gag-specific CD8$^+$ T cells as determined by percent P call. (c and d) Percent of tetramer$^+$ cells in total CD8$^+$ T cells (d) and numbers of cells recovered post-sort in controllers (grey circles) and progressors (black circles) cohorts. (e) Fraction of HIV Gag-specific CD8 T cells with a central memory (upper plot), effector memory (middle plot) or effector memory-RA$^+$ (lower plot) phenotype in controllers (grey circles) and progressors (black circles).

Figure 8:
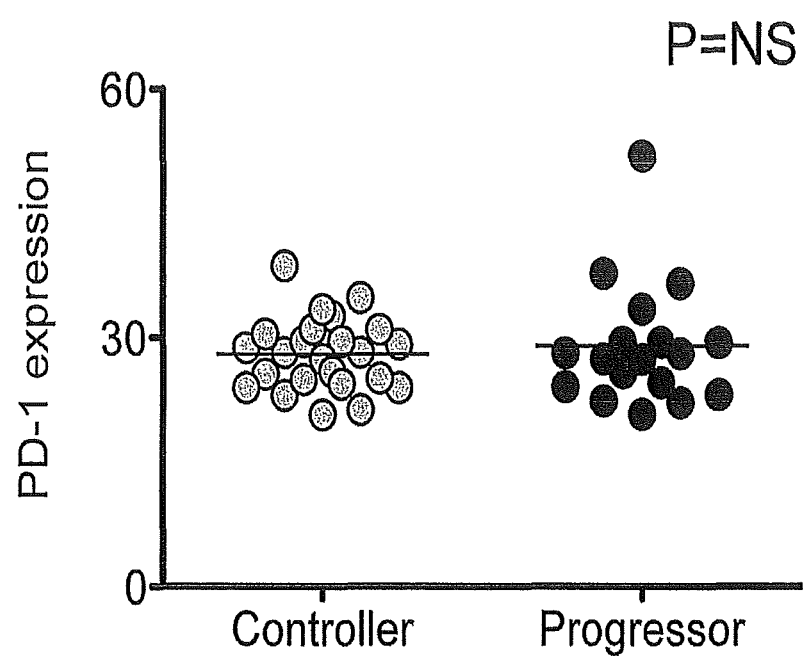

FIG. 8 demonstrates PD-1 expression in controllers and progressors 8 Relative PD-1 expression in arbitrary expression units from Affymetrix analysis of sorted HIV Gag-specific CD8 T cell populations from controllers (grey circles) and progressors (black circles).

Figure 9:
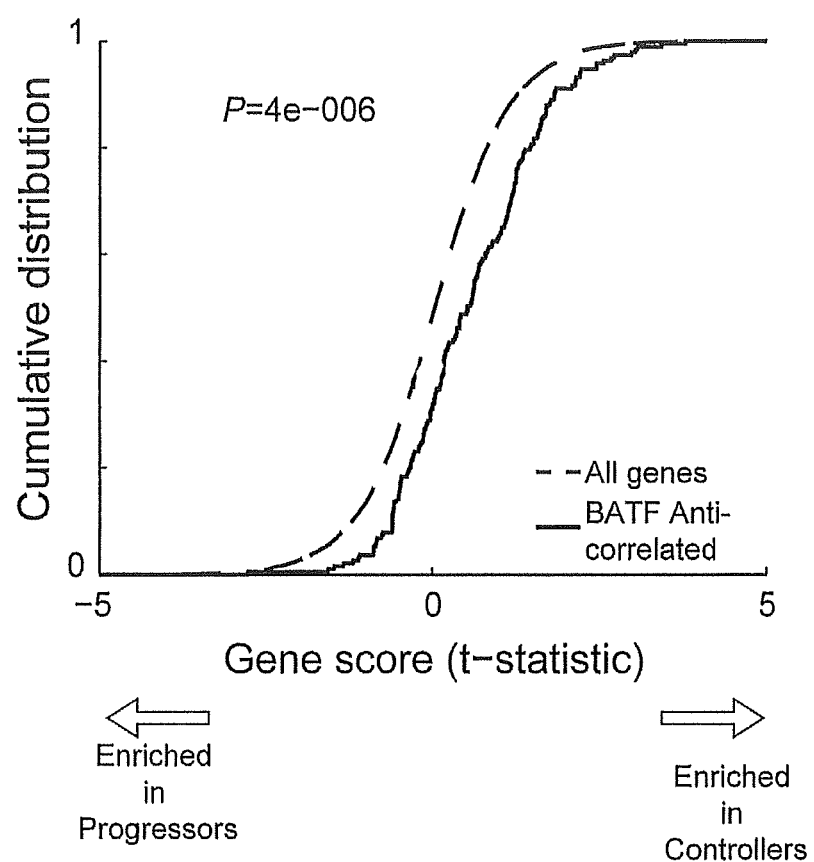

FIG. 9 presents the results of an enrichment analysis demonstrating enrichment of BATF anti-correlated genes in Gag-specific profiles from controllers compared with progressors.

Figure 10:
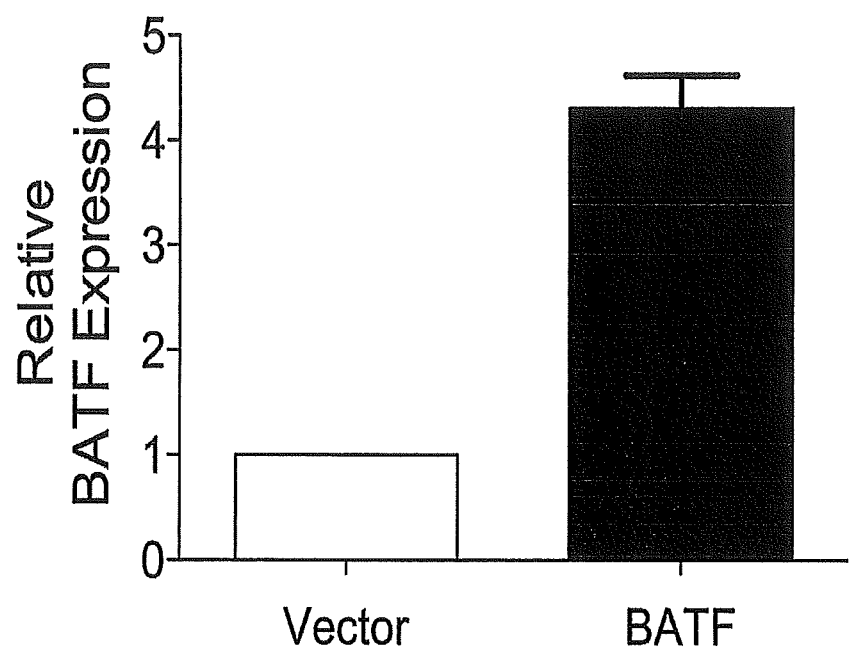

FIG. 10 demonstrates relative BATF expression by quantitative PCR analysis in primary human T cells transduced with empty vector (white bar) or overexpressing BATF (black bar).

FIG. 11 demonstrated a list of informative genes useful for the methods of the invention.

Figure 12:
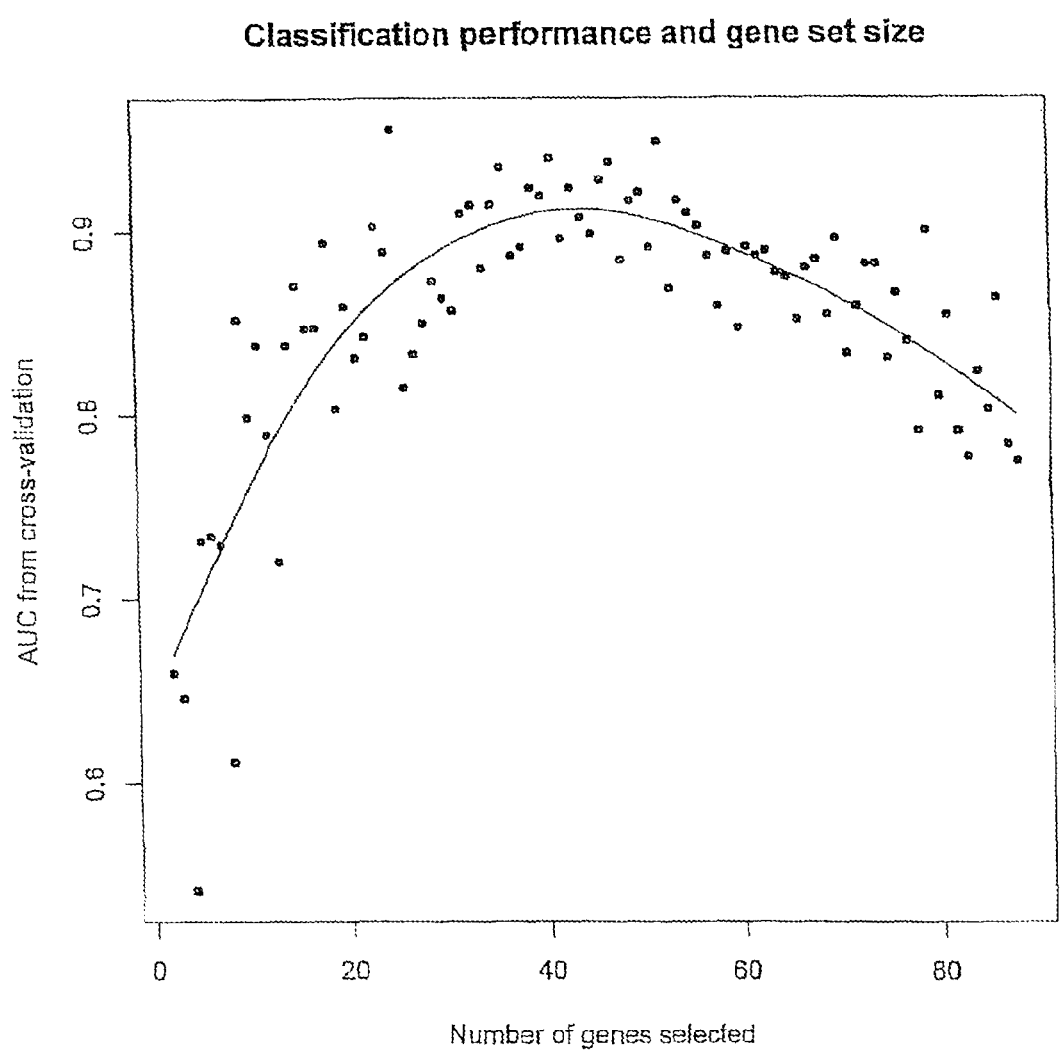

FIG. 12 demonstrates prediction accuracy (AUC) for the controller:progressor class distinction using gene lists of varying lengths in a support vector machine algorithm.

FIG. 13 presents the nucleic acid (A) and amino acid (B) sequence of BATF.

FIG. 14 presents differentially expressed genes (t>2.0 or t<−2.0) in either direction between HIV-gag specific CD8 positive T cells from HIV Controllers compared with Progressors.

FIG. 15 presents differentially expressed genes (t>2.0 or t<−2.0) in either direction between PD-1 Jurkat cells stimulated with PD1/CD3/CD28 beads and those stimulated with CD3/CD28 beads.

FIG. 16 presents a list of genes at the Venn intersect between genes upregulated by PD-1 stimulation in Jurkat cells (t>2.0) and in HIV Progressors as compared with controllers (t>2.0 or t<−2.0).

Figure 17:
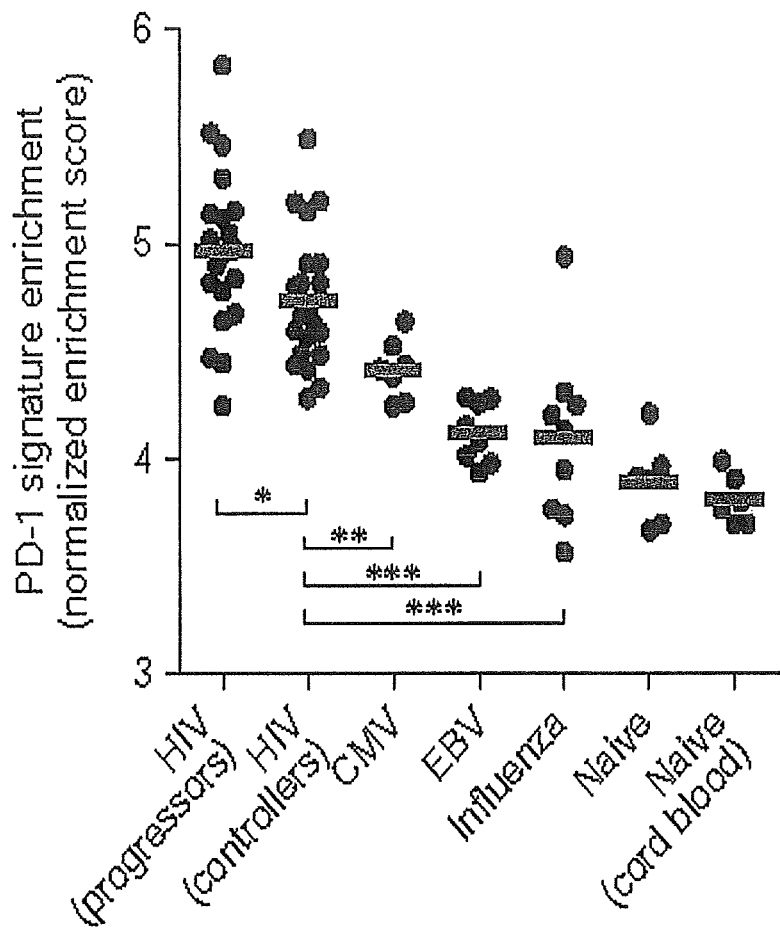

FIG. 17 presents the enrichment of PD-1 signature genes in tetramer-sorted CD8$^+$ T cells specific for various human viral pathogens.

Figure 18:
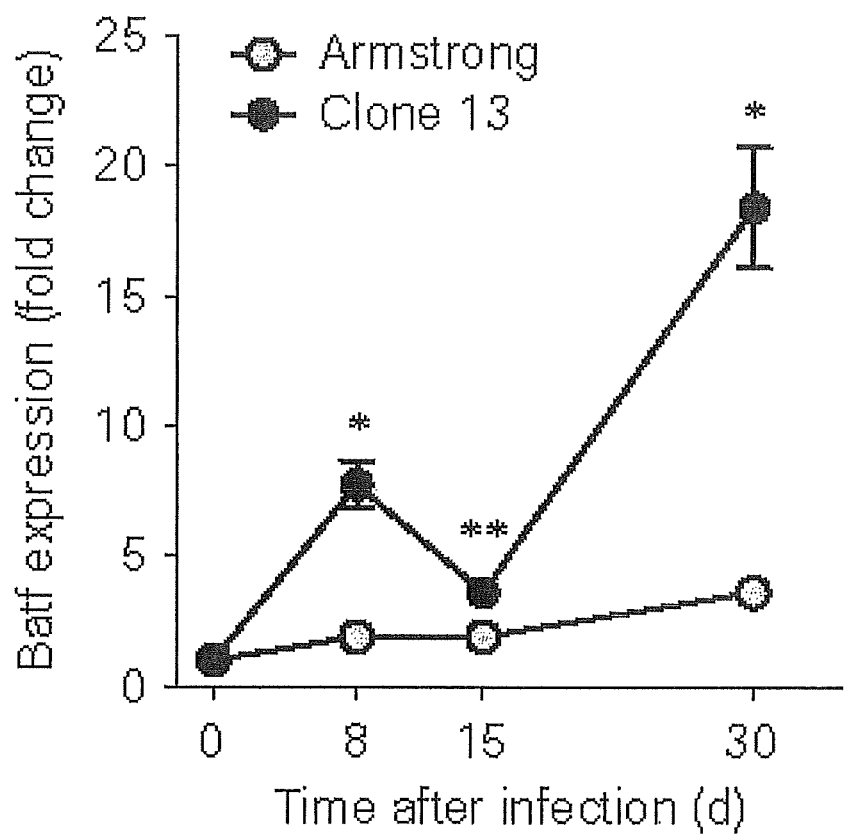
Figure 18:
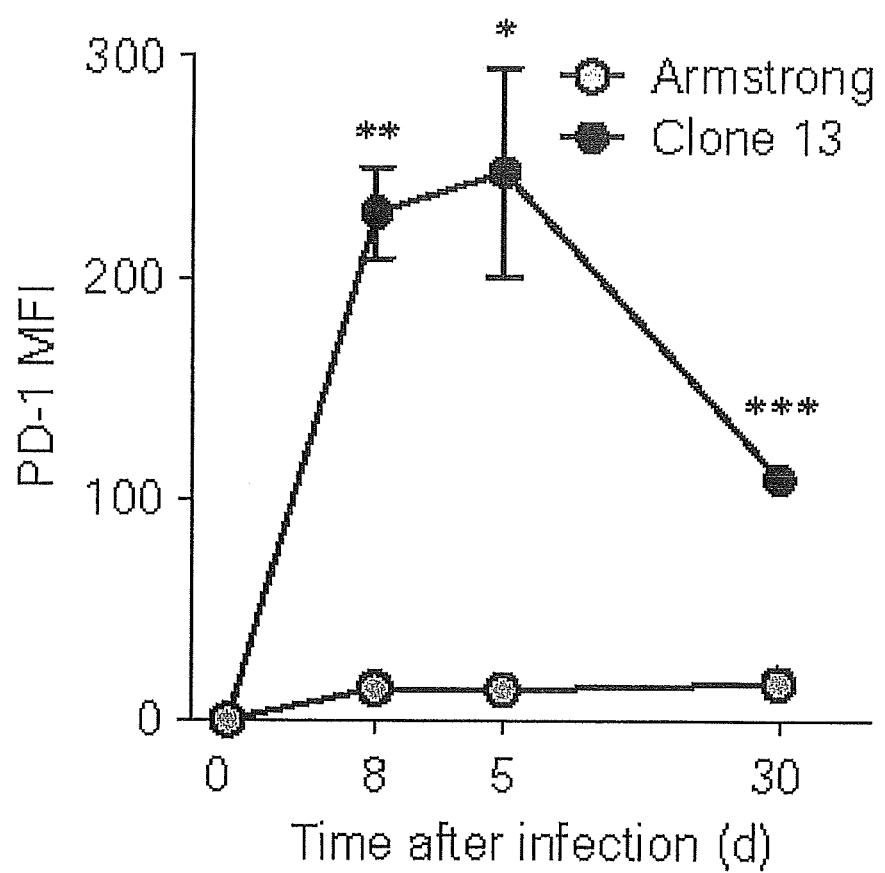

FIGS. 18A and 18B present the expression of Batf (FIG. 18A) and PD-1 (FIG. 18B) in LCMV-specific CD8$^+$ T cells from mice infected with LCMV Armstrong or LCMV clone 13 relative to naïve mice (*P<0.05; **P<0.01).

Figure 19:
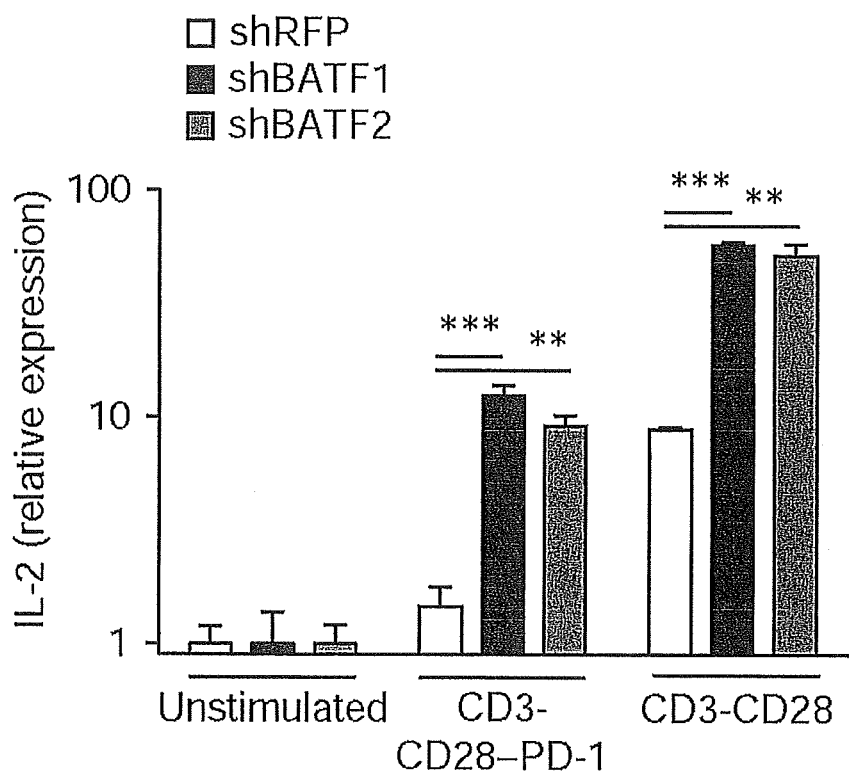
Figure 19:
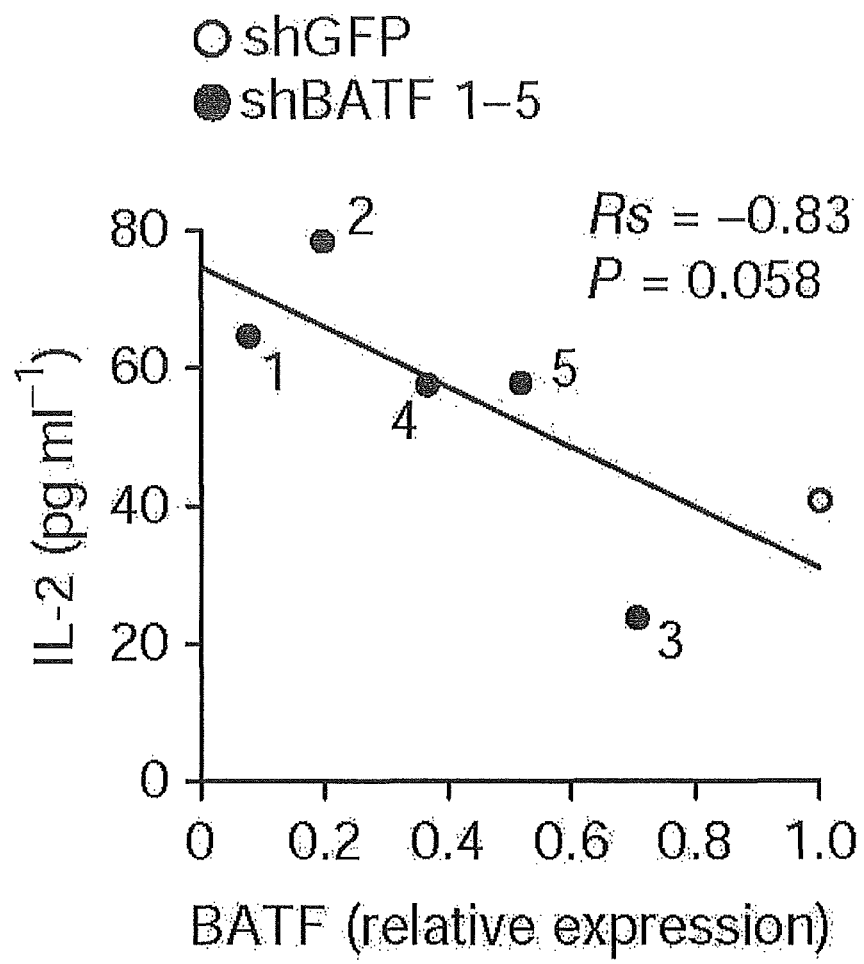

FIGS. 19A and 19B present the effects of BATF silencing on IL-2 expression by PD-1 Jurkat cells.

DETAILED DESCRIPTION OF THE INVENTION

The present invention is directed to expression profiles of HIV-specific T-cells and their methods of use, including but not limited to treatment of HIV, increasing HIV specific T-cell function in HIV infected subjects, increasing the survival of HIV specific T-cells in HIV infected subjects, monitoring the efficacy of an anti HIV therapy in an HIV infected subject, monitoring HIV disease progression, and identifying HIV infected subjects that are controllers or chronic progressors. The present invention is also directed to agents useful for treatment of HIV.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

I. Definitions

As used herein, "classifying an immune response", for example in an individual infected with HIV, means determining if the individual is a chronic progressor or a controller, as defined herein. "Classifying" or "characterizing" means obtaining T-cells from the HIV infected individual and determining if the T-cells are those of a chronic progressor or a controller. Classifying or characterizing an immune response from an HIV infected subject comprises determining an expression profile, as defined hereinbelow, of an individual infected with HIV, by methods defined hereinbelow, and comparing the expression profile to 1) the expression profile of HIV-specific T-cells that are controllers and 2) the expression profile of HIV specific T-cells that are chronic progressors. An expression profile of an individual infected with HIV that is substantially similar, as defined herein, to the expression profile of HIV-specific T-cells that are controllers, classifies or characterizes the immune response of the individual infected with HIV as that of a controller. An expression profile of an individual infected with HIV that is substantially similar, as defined herein, to the expression profile of HIV-specific T-cells that are chronic progressors classifies or characterizes the immune response of the individual infected with HIV as that of a chronic progressor.

As used herein, "expression profile" or "marker profile" is meant a characterization of the expression or expression level of two or more polypeptides or polynucleotides.

As used herein, "expression profile" refers to the level or amount of gene expression of particular genes as assessed by methods described herein. The gene expression profile can comprise data for one or more genes and can be measured at a single time point or over a period of time. The expression profile of an HIV-infected T-cell of a chronic progressor is presented in FIG. 1b. The expression profile of an HIV-infected T-cell of a controller is presented in FIG. 1b.

"Determining an expression profile" means performing a phenotype classification (e.g., chronic progressor or controller) by comparing the gene expression profile of the test sample with respect to one or more informative genes with one or more gene expression profiles (e.g., in a database). Informative genes include, but are not limited to, those shown in FIG. 11. Using the methods described herein, expression of numerous genes can be measured simultaneously. The assessment of numerous genes provides for a more accurate evaluation of the sample because there are more genes that can assist in classifying the sample. The "test sample" or "test cell" from which a gene expression profile is determined is an HIV specific T-cell from an HIV-infected individual that contains a gene expression product. A "reference sample" or "reference cell" or "control sample" or "control cell" can be any one of a T-cell from an HIV-infected subject that is a chronic progressor, a T-cell from an HIV-infected subject that is a controller, a T-cell from a subject that is not HIV-infected or a cell that is not a T-cell from an HIV-infected or non-HIV-infected subject.

As used herein, expression refers to a protein or the RNA/transcript derived from the gene of interest of the expression profile. In such instances the expression of a gene of interest can be determined by measuring the amount of transcript directly or by measuring the amount of the protein product of the RNA of interest. Protein can be measured in protein assays such as by staining or immunoblotting or, if the protein catalyzes a reaction that can be measured, by measuring reaction rates. All such methods are known in the art and can be used. Any art-recognized methods for detecting RNA levels can be used (e.g., RT-PCR, Northern Blotting, etc.).

As used herein, "chronic progressor, refers to an individual that is infected with HIV and that exhibits and increase in viral load over time, following the initial infection. A chronic progressor refers to an individual that has an expression profile that is substantially similar to that presented in FIG. 1b.

As used herein a "controller" refers to a subject infected with HIV that exhibits a decrease in HIV viral load after the individual is infected with HIV and maintains the decreased HIV viral load over time. A "controller" also refers to an HIV-infected subject who remains asymptomatic with normal CD4 positive T-cell counts and low or undetectable plasma viral loads despite having never been treated with antiretroviral medications. A controller refers to an individual that has an expression profile that is substantially similar to that presented in FIG. 1b.

As used herein, "increased" as it refers to the viral load of a subject means at least about 1-fold greater (for example 1, 2, 3, 4, 5, 10, 20, 30, 40, 50, 60, 70, 80, 90, 100, 1000, 10,000-fold or more) than the viral load of a control subject. "Increased" as it refers to the viral load of a subject also means at least about 5% greater (for example 5, 6, 7, 8, 9, 10, 15, 20, 25, 30, 35, 40, 45, 50, 55, 60, 65, 70, 75, 80, 85, 90, 95, 99 or 100%) than the viral load of a control subject.

As used herein, "decreased" as it refers to viral load of a subject means at least about 1-fold (for example 1, 2, 3, 4, 5, 10, 20, 30, 40, 50, 60, 70, 80, 90, 100, 1000, 10,000-fold or more) less than the viral load of a control subject. "Decreased" as it refers to the viral load of a subject also means at least about 5% less than (for example 5, 6, 7, 8, 9, 10, 15, 20, 25, 30, 35, 40, 45, 50, 55, 60, 65, 70, 75, 80, 85, 90, 95, 99 or 100%) the viral load of a control subject.

As used herein, the phrase "substantially similar" refers to a similarity of at least 1 gene with respect to the genes of the expression profile.

As used herein, "substantially similar" as it refers to an expression profile, means an expression profile wherein at least one of the genes of an expression profile of a test subject is expressed in the expression profile of a controller or a chronic progressor. At least one means one or more, for example, 1, 2, 3, 4, 5, 6, 7, 8, 9, 10, 15, 16, 17, 18, 19, 20, 21, 22, 23, 24, 25, 30, 35, 40, 45, 50, 55, 60, 65, 70, 75, 80, 85, 90, 95, 100 or more genes.

As used herein, the phrase "substantially similar" refers to a similarity of at least 1% of the genes with respect to the genes of the expression profile.

"Substantially similar" as it refers to an expression profile, also means an expression profile wherein at least 1% of the genes of an expression profile of a test sample are expressed in the expression profile of a controller or a chronic progressor. At least 1% means, for example, 1, 2, 3, 4, 5, 6, 7, 8, 9, 10, 15, 16, 17, 18, 19, 20, 21, 22, 23, 24, 25, 30, 35, 40, 45, 50, 55, 60, 65, 70, 75, 80, 85, 90, 95 or 100%.

As used herein, the phrase "substantially similar" refers to a similarity of the level of expression of at least 1 gene with respect to the genes of the expression profile.

As used herein, "substantially similar" as it refers to an expression profile, also means an expression profile wherein at least one of the genes of an expression profile of a test subject is expressed at a level that is equal to the level of expression of the same gene in the expression profile of a controller or a chronic progressor.

Equal means at least 50% or more, for example, 50, 55, 60, 65, 70, 75, 80, 85, 86, 87, 88, 89, 90, 91, 92, 93, 94, 95, 96, 97, 98, 99 or 100%.

The correlation between gene expression and class distinction can be determined using a variety of methods. Methods for defining classes and classifying samples are described, for example, in U.S. patent application Ser. No. 09/544,627, filed Apr. 6, 2000 by Golub et al. the teaching of which are incorporated herein by reference in their entirety. The information provided by the present invention alone or in conjunction with other test results, aids in sample classification (U.S.S.N. 2002/0155480, incorporated by reference in its entirety).

As used herein, "immune response" refers to a response made by the immune system of an organism to a substance, which includes but is not limited to foreign or self proteins. Particularly, "immune response" refers to a CD8-positive T-cell mediated immune response to HIV infection. There are three general types of "immune response" including, but not limited to mucosal, humoral, and cellular "immune responses."

An "immune response" may be measured using a technique known to those of skill in the art. For example, enzyme-linked immuno-absorbent assay (ELISA; U.S. Pat. No. 5,951,988; Ausubel et al., Short Protocols in Molecular Biology 3rd Ed. John Wiley & Sons, Inc. 1995). According to the present invention, an antigen can be said to stimulate an "immune response" if the quantitative measure of immunoglobulins in an animal treated with an antigen detected by ELISA is statistically different from the measure of immunoglobulins detected in an animal not treated with the antigen, wherein the immunoglobulins are specific for the antigen. A statistical test known in the art may be used to determine the difference in measured immunoglobulin levels including, but not limited to ANOVA, Student's T-test, and the like, wherein the P value is at least <0.1, <0.05, <0.01, <0.005, <0.001, and even <0.0001.

An immune response to HIV may be measured by measuring anyone of viral load, T-cell proliferation, T-cell survival and cytokine secretion by T-cells. An immune response to HIV is also measure or determined or characterized by detecting and/or measuring the amount of HIV specific T-cells that controllers and by detecting an/or measuring the amount of HIV specific T-cells that are chronic progressors.

As used herein, "HIV disease" means the continuum from an initial HIV infection to AIDS.

As used herein, "disease" refers to any condition or disorder that damages or interferes with the normal function of a cell, tissue, or organ.

As used herein, "HIV infection" refers to introduction of HIV into the blood of a subject following exposure of the subject to the virus.

As used herein, "subject" or "individual" refers to a mammal A human subject can be known as a patient. In one embodiment, "subject" or "subject in need" refers to a mammal that is infected with HIV or is suspected of being infected with HIV or has been diagnosed with HIV infection. As used herein, an "HIV infected subject" refers to a mammal that is infected with HIV or has been diagnosed with HIV infection.

A "control subject" refers to a mammal that is not infected with HIV, and is not suspected of being diagnosed with HIV.

The infectious AIDS virus can be, but is not limited to, HIV-1 and HIV-2.

As used herein, "mammal" refers to any mammal including but not limited to human, mouse, rat, sheep, monkey, goat, rabbit, hamster, horse, cow or pig.

As used herein, a "non-human mammal" refers to any mammal that is not a human.

As used herein, "reference" is meant a standard of comparison or control condition. For example, the expression profile of an HIV-specific T-cell that is a chronic progressor is a reference for a test sample. The expression profile of an HIV-specific T-cell that is a controller is also a reference for a test sample.

A "control subject" refers to a subject that is not infected with HIV, is seronegative for the HIV virus or a subject that is infected with HIV virus, wherein the HIV viral load is determined at a first time point, or a subject that is infected with HIV and has been receiving treatment or has not yet begun treatment.

A "control subject" can also be a subject that is infected with HIV virus and is identified as a controller. A "control subject" can also be a subject that is infected with HIV virus and is identified as a chronic progressor.

As used herein, "T-cell" refers to a group of white blood cells known as T-lymphocytes that play a central role in cell-mediated immunity.

As used herein, "CD4 positive T cells" refer to helper T cells.

As used herein, "CD8 positive T cells" refer to T cells that express CD8 and may include but are not limited to cytotoxic T-lymphocytes.

As used herein, "CD4 positive T cell function" refers to the ability of CD4 positive T cells to recognize antigens on the surface of a virus-infected cell and secrete lymphokines that stimulate B cells and killer T cells.

As used herein, "vaccinated" means administered a "vaccine."

A used herein, a "vaccine" is a preparation which is used to increase immunity of a subject to a particular condition or antigen.

As used herein, an "HIV vaccine" means a preparation which is used to increase immunity of a subject to HIV. A vaccine according to the invention includes but is not limited to recombinant or viral based vaccines.

As used herein, "T-cell function" means any activities which are inherent to a T-cell. T-cell function means any one of cytokine secretion, (for example, IL-2), proliferation or survival.

As used herein, "T-cell survival" means, the ability of a T-cell to persist in a host organism.

As used herein, "proliferation" refers to a process by which a cell undergoes mitosis, or increases in number, size or content.

As used herein, "increased" as it refers to the number of T-cells means at least about 1-fold greater (for example 1, 2, 3, 4, 5, 10, 20, 30, 40, 50, 60, 70, 80, 90, 100, 1000, 10,000-fold or more) than the number of T-cells, for example, prior to or following treatment, at a different time point or obtained from an HIV infected individual of a seronegative individual. "Increased" as it refers to the number of T cells also means at least about 5% greater (for example 5, 6, 7, 8, 9, 10, 15, 20, 25, 30, 35, 40, 45, 50, 55, 60, 65, 70, 75, 80, 85, 90, 95, 99 or 100%) than the number of T cells, for example, prior to or following treatment, at a different time point or obtained from an HIV infected individual of a seronegative individual.

As used herein, "decreased" as it refers to the number of T-cells means at least about 1-fold (for example 1, 2, 3, 4, 5, 10, 20, 30, 40, 50, 60, 70, 80, 90, 100, 1000, 10,000-fold or more) less than the number of CD4 positive T cells, for example, prior to or following treatment, at a different time point or obtained from an HIV infected individual or a seronegative individual. "Decreased" as it refers to the number of T cells also means at least about 5% (for example 5, 6, 7, 8, 9, 10, 15, 20, 25, 30, 35, 40, 45, 50, 55, 60, 65, 70, 75, 80, 85, 90, 95, 99 or 100%) less than the number of T cells, for example, prior to or following treatment, at a different time point or obtained from an HIV infected individual or a seronegative individual.

As used herein, "increasing" or "increased" as it refers to HIV specific T-cell function or T-cell survival or proliferation means at least about 1-fold greater (for example 1, 2, 3, 4, 5, 10, 20, 30, 40, 50, 60, 70, 80, 90, 100, 1000, 10,000-fold or more) than the HIV specific T-cell function or HIV-specific T-cell survival or proliferation prior to or following treatment, at a different time point or obtained from an HIV infected individual of a seronegative individual. "Increasing" or "Increased" as it refers to HIV specific T-cell function or T-cell survival or proliferation also means at least about 5% greater (for example 5, 6, 7, 8, 9, 10, 15, 20, 25, 30, 35, 40, 45, 50, 55, 60, 65, 70, 75, 80, 85, 90, 95, 99 or 100%) than the HIV specific T-cell function or HIV-specific T-cell survival or proliferation prior to or following treatment, at a different time point or obtained from an HIV infected individual of a seronegative individual.

As used herein, "decreasing" or "decreased" as it refers to HIV specific T-cell function or T-cell survival or proliferation means at least about 1-fold less than (for example 1, 2, 3, 4, 5, 10, 20, 30, 40, 50, 60, 70, 80, 90, 100, 1000, 10,000-fold or more) than the HIV specific T-cell function or HIV-specific T-cell survival or proliferation prior to or following treatment, at a different time point or obtained from an HIV infected individual of a seronegative individual. "Decreasing" or "decreased" as it refers to HIV specific T-cell function or T-cell survival or proliferation also means at least about 5% less than (for example 5, 6, 7, 8, 9, 10, 15, 20, 25, 30, 35, 40, 45, 50, 55, 60, 65, 70, 75, 80, 85, 90, 95, 99 or 100%) than the HIV specific T-cell function or HIV-specific T-cell survival or proliferation prior to or following treatment, at a different time point or obtained from an HIV infected individual of a seronegative individual.

As used herein, "administering" refers to any method according to the invention including but not limited to injection, subcutaneous, transcutaneous, intramuscular, intraperitoneal, intracranial and spinal injection, administration directly to a blood vessel, including artery, vein or capillary, intravenous drip, ingestion via the oral route, inhalation, trans-epithelial diffusion (such as via a drug-impregnated, adhesive patch) or by the use of an implantable, time-release drug delivery device, which may comprise a reservoir of exogenously-produced agent or may, instead, comprise cells that produce and secrete the therapeutic agent or topical application. Additional methods of administration are provided herein below in the section entitled "Dosage and Administration."

As used herein, "contacting" means exposing a subject to, for example by any of the methods of administration described herein. "Contacting" refers to exposing a subject to, for example, an agent for a duration of about 1, 5, 10, 20, 30, 40, 50 minutes, about 1, 2, 5, 10, 20, 24 hours, about 2, 3, 4, 5, 6, 7, 8, 9, 10 days or more. In one embodiment, "contacting" refers to exposing a subject more than once, for example about 2, 3, 4, 5, 6, 7, 8, 9, 10 times or more.

As used herein, "agent" refers to any protein, recombinant protein, small molecule, DNA, RNA, antigen, parasite, virus, bacteria, or other prokaryotic or eukaryotic cells, either whole cells or fragments thereof, a nucleic acid therapeutic or nucleic acid antagonist or combination thereof.

An "agent" also includes a vaccine.

An "antigen" is understood as any compound that can be used to stimulate a specific immune response. An antigen can be an isolated or purified protein, nucleic acid, carbohydrate, small molecule, and the like. Alternatively, an antigen can be a complex mixture, naturally or artificially generated including a mixture of one or more of protein, nucleic acid, carbohydrate, small molecule optionally in the form of a pathogen, particularly a killed or attenuated pathogen. Antigens include self- and non-self antigens. For example, an antigen can be a protein that is not normally present in a subject, e.g., a cancer cell.

A "nucleic acid therapeutic" or "nucleic acid antagonist" can be any nucleic acid (DNA, RNA, or a combination thereof) or an analog thereof (e.g., PNA) optionally including one or more modifications (see, e.g., U.S. Pat. Nos. 7,015,315 and 6,670,461, incorporated herein by reference) to modulate pharmacokinetic or pharmacodynamic properties of the nucleic acid. Nucleic acid antagonists can be antisense oligonucleotides (see, e.g., U.S. Pat. No. 5,366,878; or 6,921,812, both incorporated herein by reference), small interfering (si) RNA (see, e.g., U.S. Pat. No. 7,056,704, incorporated herein by reference), short hairpin RNA (see, e.g., US Patent publication 20080119427, incorporated herein by reference), or other double stranded RNA molecules (see, e.g., US Patent publication 20070265220, incorporated herein by reference). Nucleic acid antagonists are well known in the art.

As used herein, "inhibitory nucleic acid" refers to a double-stranded RNA, siRNA, shRNA, or antisense RNA, or a portion thereof, or a mimetic thereof, that when administered to mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule.

As used herein, "inhibits" means decreases expression or activity by at least 1-fold (for example, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000, 10,000 or more) as compared to the expression or activity in the absence of an inhibitor.

As used herein, "inhibits" also means decreases expression or activity by at least 10% (for example, 10, 20, 25, 30, 35, 40, 45, 50, 55, 60, 65, 70, 75, 80, 81, 82, 83, 84, 85, 86, 87, 88, 90, 91, 92, 93, 94, 95, 96, 97, 98, 99 or 100%) as compared to the expression or activity in the absence of an inhibitor.

A "small molecule" refers to a compound having a molecular weight of no more than about 1500 daltons, 1000 daltons, 750 daltons, 500 daltons. A small molecule is not a nucleic acid or polypeptide.

By "analog" is meant a molecule that is not identical, but has analogous functional or structural features.

As used herein, "antibody" refers to immunoglobulin molecules and immunologically active portions of immunoglobulin molecules, and more specifically, molecules that contain an antigen binding site that specifically binds an antigen. The immunoglobulin molecules of the invention can be of any type (for example, IgG, IgE, IgM, IgD, IgA and IgY), and of any class (for example, IgG1, IgG2, IgG3, IgG4, IgA1 and IgA2) or subclass of an immunoglobulin molecule. Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, for example, anti-Id antibodies to antibodies of the invention), and epitope-binding fragments of any of the above.

As used herein, "specifically binds" means via covalent or hydrogen bonding or electrostatic attraction.

As used herein, "BATF polypeptide" is meant a polypeptide or fragment thereof having at least 85% amino acid identity to NCBI Accession No. NM_006390 (presented in FIG. 13) and having DNA binding activity.

As used herein, "fragment" refers to a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

As used herein, "BATF nucleic acid molecule" is meant a polynucleotide encoding a BATF polypeptide. An exemplary BATF nucleic acid molecule is provided at NCBI Accession No. NM_006399) (presented in FIG. 13).

In one embodiment, "reference" or standard of comparison is BATF polypeptide or polynucleotide level present in a patient sample as compared to the level of said polypeptide or polynucleotide present in a healthy subject.

As used herein, "therapeutically effective amount" refers to an amount of an agent compound useful in the present invention to treat HIV disease or to treat the symptoms of HIV disease.

In one embodiment, the "effective amount" refers to the amount of an agent that inhibits or reduces expression or activity of BATF. An effective amount reduces the expression or activity by at least 10%, for example, 10%, 20%, 30%, 40%, 50%, 60%, 70%, 80%, 90%, 95%, 96%, 97%, 98%, 99%, or 100%.

In another embodiment, the "effective amount" refers to the amount of an agent that reduces the expression or activity by at least 2-fold, for example, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 1000, 10,000 or more.

As used herein, "increased" as it refers to the amount of BATF expression of an HIV-specific T-cell means at least about 1-fold more than (for example 1, 2, 3, 4, 5, 10, 20, 30, 40, 50, 60, 70, 80, 90, 100, 1000, 10,000-fold or more) the amount of BATF expression of a control T cell.

"Increased" as it refers to the amount of BATF expression on an HIV-specific T cell also means at least about 5% more than (for example 5, 6, 7, 8, 9, 10, 15, 20, 25, 30, 35, 40, 45, 50, 55, 60, 65, 70, 75, 80, 85, 90, 95, 99 or 100%) the amount of BATF expression of a control T cell.

As used herein, "decreased" as it refers to the amount of BATF expression of a HIV-specific T-cell means at least about 1-fold (for example 1, 2, 3, 4, 5, 10, 20, 30, 40, 50, 60, 70, 80, 90, 100, 1000, 10,000-fold or more) less than the amount of BATF expression of a control CD4 positive T cell. "Decreased" as it refers to the amount of BATF expression on an HIV-specific T cell also means at least about 5% (for example 5, 6, 7, 8, 9, 10, 15, 20, 25, 30, 35, 40, 45, 50, 55, 60, 65, 70, 75, 80, 85, 90, 95, 99 or 100%) less than the amount of BATF expression of a control HIV specific T cell.

As used herein, "pharmaceutical composition", as used herein, means an agent or composition containing a compound that may be administered to treat HIV-disease in an individual.

As used herein, the term "pharmaceutically acceptable salts" refers to salts that retain the biological effectiveness and properties of the agents or compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. The term "pharmaceutically acceptable salt" also refers to a salt prepared from an agent or compound disclosed herein, having a basic functional group, such as an amino functional group, and a pharmaceutically acceptable inorganic or organic acid. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these agents or compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in Remington's Pharmaceutical Sciences, 20th ed., Mack Publishing Company, Easton, Pa., (1985), which is herein incorporated by reference.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

As used herein, the terms "treat," treating," "treatment," and the like refer to reducing or ameliorating the symptoms of a disorder (e.g., HIV infection) and/or symptoms associated therewith. It will be appreciated that, although not precluded, treating a disorder or condition does not require that the disorder, condition or symptoms associated therewith be completely eliminated.

As used herein "treating" a disease in a subject or "treating" a subject having a disease refers to subjecting the subject to a pharmaceutical treatment, e.g., the administration of a drug, such that the extent of the disease is decreased or prevented. For example, treating results in the reduction of at least one sign or symptom of the disease or condition. Treatment includes (but is not limited to) administration of a composition, such as a pharmaceutical composition, and may be performed either prophylactically, or subsequent to the initiation of a pathologic event. Treatment can require administration of an agent and/or treatment more than once.

As used herein, "in need of treatment" means an individual that has been diagnosed with HIV.

As used herein, "initiating treatment" refers to beginning administration of an agent of the invention.

As used herein, "effective treatment" refers to treatment that reduces, delays, or eliminates symptoms of HIV disease.

As used herein, "efficacy" refers to the capacity for beneficial change of a given intervention.

As used herein, "diagnosis" or "identifying a subject having" refers to a process of determining if an individual is afflicted with a disease or ailment (e.g., HIV). HIV is diagnosed for example by detecting either the presence of an HIV polypeptide, HIV nucleic acid, or a marker associated with HIV.

As used herein, "identifying" as it refers to a subject that has a condition refers to the process of assessing a subject and determining that the subject has a condition, for example, is infected with HIV.

As used herein, "selecting" refers to the process of determining that an identified subject will receive an agent to treat the occurrence of a condition. Selecting can be based on an individuals susceptibility to a particular disease or condition due to, for example, family history, lifestyle, age, ethnicity, or other factors.

As used herein, "selecting" refers to the process of determining that an identified subject will receive treatment for a disease (e.g., HIV).

As used herein, "diagnosis" refers to a process of determining if an individual is afflicted with a disease or ailment, for example human immunodeficiency virus (HIV). Methods of diagnosing HIV include screening for HIV antibodies or HIV nucleic acid molecules in the blood of an individual.

As used herein, "prognosis" refers to a process of predicting the probable course and outcome of a disease in an individual afflicted with a disease or ailment (e.g., HIV), or the likelihood of recovery of an individual from a disease (e.g., HIV).

As used herein, "monitoring disease progression" refers to a process of determining the severity or stage of a disease in an individual afflicted with the disease or ailment (e.g., HIV), for example, as described in the section entitled "HIV Disease" herein below.

As used herein, "altering" as it refers to an expression profile, means increasing or decreasing the level of expression of a gene of the expression profile.

As used herein, "marker" refers to a nucleic acid or polypeptide whose presence indicates or is associated with a phenotype, state, or characteristic in an individual, e.g., elite suppressor or chronic progressor. A marker may be a nucleic acid, i.e., a "nucleic acid marker" or a polypeptide, i.e., a "polypeptide marker." A nucleic acid marker may encode a polypeptide marker. In diseases and disorders, markers may directly or indirectly contribute to the disease or disorder.

As used herein, the term "biological sample" or "sample" refers to a whole organism or a subset of its tissues, cells or component parts (e.g. blood vessel, including artery, vein and capillary, body fluids, including but not limited to blood, serum, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

As used herein, "seronegative" refers to an individual with no detectable antibodies to a virus (e.g., HIV) in the blood.

II. HIV Disease

HIV disease, as used herein, refers to the continuum from an initial HIV infection to AIDS.

Since HIV may begin causing subtle changes in the immune system long before an infected subject feels sick, the term "HIV disease" is commonly used to encompass the entire HIV spectrum, from initial infection to full-blown AIDS (which is also called "advanced HIV disease").

The HIV continuum described herein is representative of the experience of many subjects infected with HIV. The time that it takes for each individual to go through these stages varies. For most individuals, however, the progression of HIV disease is fairly slow, taking several years from infection to the development of severe immune suppression.

Infection

Following exposure to the virus, HIV enters the bloodstream and begins to take up residence in the cells; this is when HIV infection occurs. Individuals with HIV are considered to be infectious (able to transmit HIV to others) immediately after infection with the virus.

An individual with HIV is infectious at all times. Also, an individual does not need to have symptoms or look sick to have HIV. In fact, individuals may look perfectly healthy for many years despite the fact that they have HIV in their bodies. The only way to confirm HIV infection is by taking an HIV test (that is detecting the presence of HIV antibodies in the bloodstream).

Primary Infection (or Acute Infection)

Primary HIV infection is the first stage of HIV disease, typically lasting only a week or two, when the virus first establishes itself in the body. Acute HIV infection describes the period of time between when an individual is first infected with HIV and when antibodies against the virus are produced by the body (usually 6 to 12 weeks) and can be detected by an HIV test.

Up to approximately 70% of individuals newly infected with HIV will experience some "flu-like" symptoms during this stage. These symptoms, which usually last no more than several days, might include fevers, chills, night sweats, and rashes. Afterward, the infected individual returns to feeling and looking completely well. The remaining percentage of individuals either do not experience symptoms of acute infection or have symptoms so mild that they may not notice them.

During acute HIV infection, the virus makes its way to the lymph nodes, a process which is believed to take three to five days. Then HIV actively replicates (makes copies of itself) and releases new viral particles into the bloodstream. This burst of rapid HIV replication usually lasts about two months. Individuals at this stage often have a very high HIV "viral load". However, people with acute HIV infection usually will not test positive for HIV antibodies, since it takes the body approximately one to three months to produce antibodies against HIV.

Seroconversion

"Seroconversion" refers to production of antibodies to the virus by an HIV positive individual's immune system, in response to the infection. Most infected individuals develop antibodies within three months after infection, and some can take up to six months.

The Asymptomatic Stage

After the acute stage of HIV infection, individuals infected with HIV continue to look and feel completely well for long periods, usually for many years. During this time, the only indication that an individual is infected with HIV is a positive HIV antibody test.

Early- and Medium-Stage HIV Symptomatic Disease

When the immune system is compromised by HIV infection, many individuals begin to experience some mild HIV disease symptoms, such as skin rashes, fatigue, night sweats, slight weight loss, mouth ulcers, and fungal skin and nail infections. Most, though not all, will experience mild symptoms such as these before developing more serious illnesses. Although prognosis varies greatly depending on a number of factors, it is generally believed that it takes five to seven years for the first mild symptoms to appear. These symptoms mark the early and medium stages of HIV symptomatic disease.

As the disease progresses, some individuals may become quite ill even if they have not yet been diagnosed with AIDS, the late stage of HIV disease. Typical problems include chronic oral or vaginal thrush (a fungal rash or spots), recurrent herpes blisters on the mouth (cold sores) or genitals, ongoing fevers, persistent diarrhea, and significant weight loss.

These symptoms are not necessarily specific to HIV or the development of AIDS. However, they should be of concern to those who have tested positive for HIV. Usually, symptoms occur when the virus has already caused considerable damage to the immune system.

Late-Stage HIV Disease (AIDS)

When immune system damage is more severe, HIV positive individuals may experience opportunistic infections (called "opportunistic" because they are caused by organisms which do not ordinarily induce illness in people with normal immune systems, but take the opportunity to flourish in people with compromised immune systems). Some of the most common opportunistic infections include *Pneumocystis carinii* pneumonia (PCP), *Mycobacterium avium* complex (MAC) disease, cytomegalovirus (CMV), toxoplasmosis, and candidiasis.

III. Chronic Progressors or Controllers

Chronic progressors or controllers can be identified within the first few months following HIV infection.

HIV infected subjects can be classified as chronic progressors or controllers.

Chronic Progressor

Chronic progressor HIV infected individuals exhibit a high viral load, for example plasma HIV RNA levels >10,000 copies/mL, as compared to an individual that is not infected with HIV.

The viral load of a chronic progressor increases over time, for example months (for example 1, 2, 3, 4, 5, 6, 7, 8, 9, 10, 11 or 12 months) or years (for example 2, 3, 4, 5, 6, 7, 8, 9, 10 years.

Figure 1:
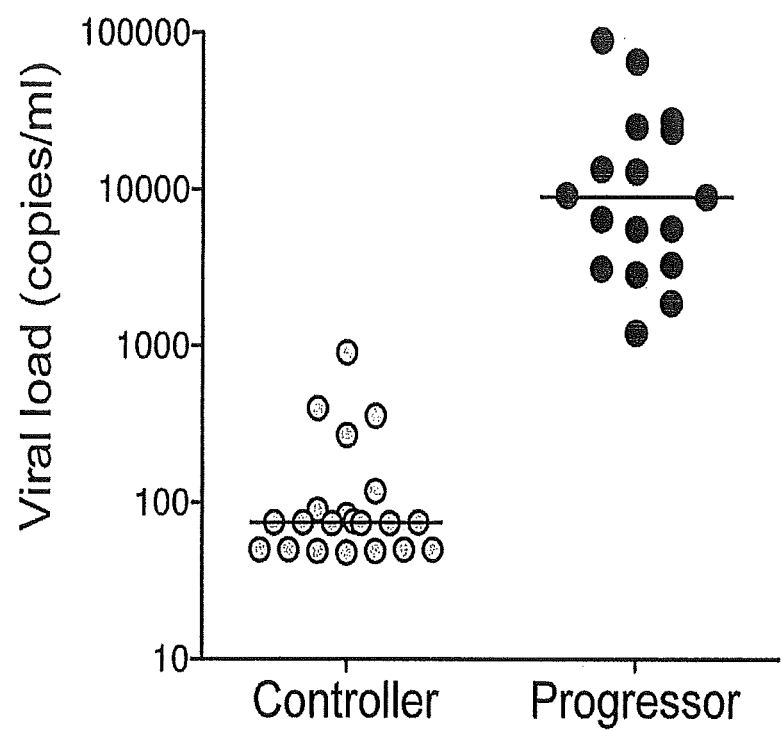
FIG. 1 presents identification of a conserved transcriptional signature of exhaustion in HIV and chronic LCMV infection. (a) HIV viral load in controllers (grey circles) and progressors (black circles). Horizontal lines indicate median viral from each cohort. (b) Genes differentially expressed in Gag-specific CD8 T cells from controllers (grey bars) or progressors (black bars) ranked by moderated t-statistic. Top 200 genes in either direction shown. (c) Enrichment analysis of progressor signature in exhausted LCMV-specific profiles. The top 200 genes in the HIV progressor Gag-specific signature were tested for enrichment in the rank-ordered list of genes differentially expressed in exhausted LCMV-specific vs. functional memory LCMV-specific T cells. X-axis indicates the t-statistic measured for each of the ~11,000 genes featured on the array, ranked in order of their differential expression in the two classes. Y-axis indicates the cumulative distribution of all genes (dotted lines) or of a set of 200 HIV-progressor genes (black line). Gene sets that are related to the class distinction on the X-axis would be expected to deviate from the dotted line (i.e. shifted towards the left if enriched in progressors or shifted towards the right if enriched in controllers). (d) differences in gene expression profiles between HIV chronic progressors and controllers.
Figure 1:
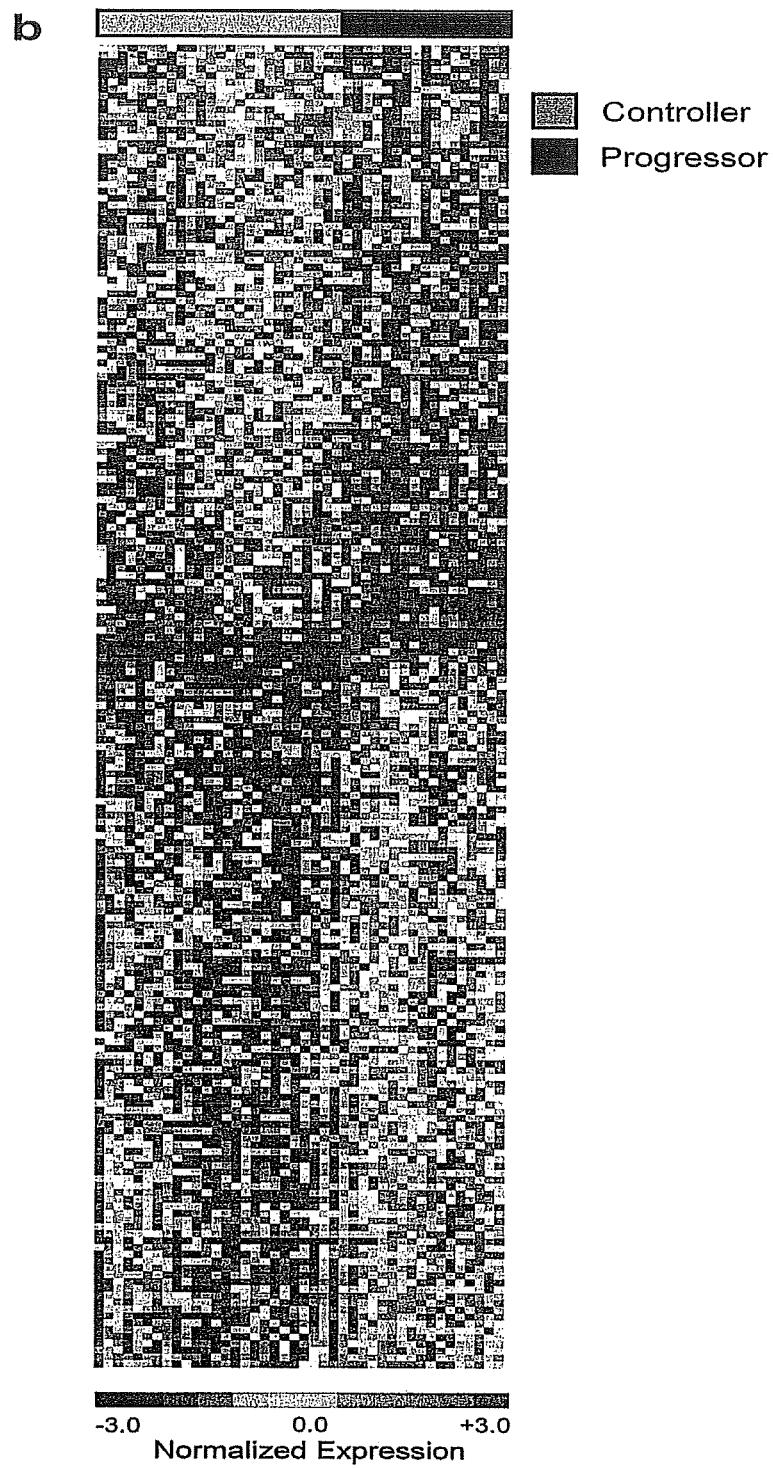
Figure 1:
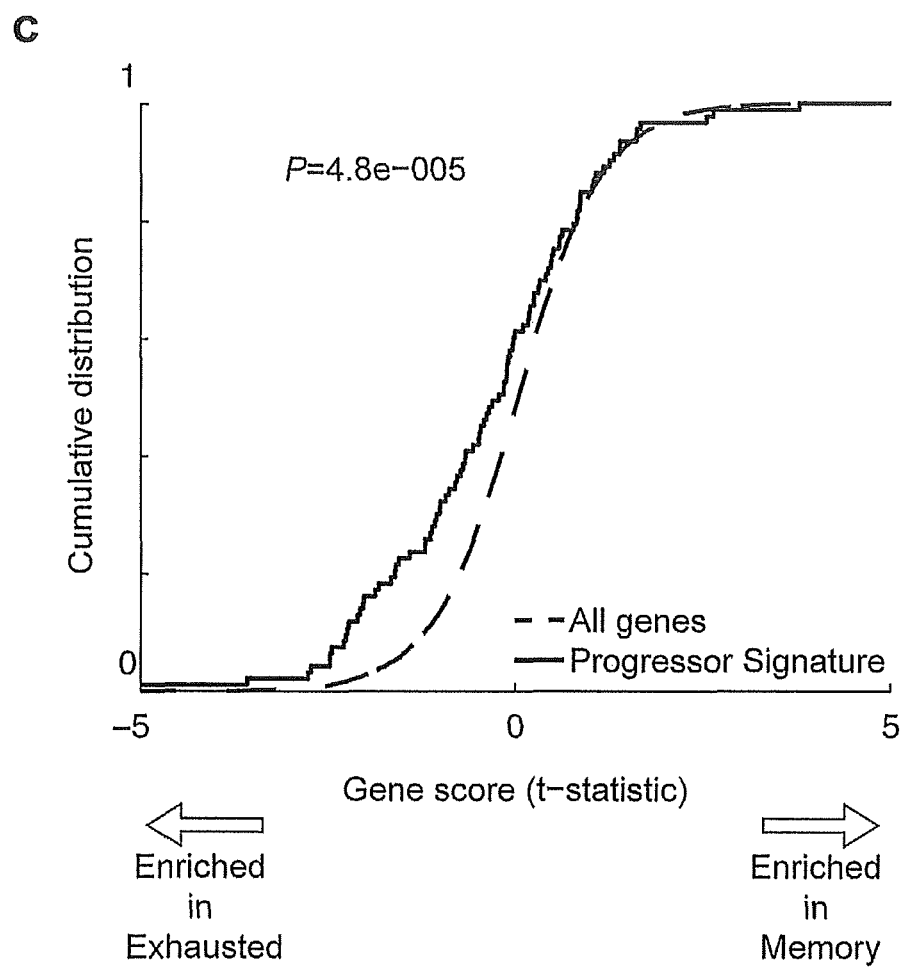

An HIV-specific T-cell isolated from a chronic progressor has an expression profile as presented in FIG. 1b.

Controllers

HIV infected individuals that are controllers are capable of maintaining their viral load at a very low levels, for example plasma HIV RNA levels <2000 copies/mL in the absence of antiretroviral therapy, measured three times over a period spanning at least 12 months.

An HIV-specific T-cell isolated from a chronic progressor has an expression profile as presented in FIG. 1b.

IV. Expression Profile

The present invention relates to methods for classifying a sample according to the gene expression profile of the sample. In one embodiment, the present invention is directed to classifying a biological sample with respect to a phenotypic effect, e.g., viral load of an HIV-infected subject or predicted treatment outcome, comprising the steps of isolating a gene expression product from a sample, for example from a (one or more) cell in the sample, and determining a gene expression profile of at least one informative gene, wherein the gene expression profile is correlated with a phenotypic effect, thereby classifying the sample with respect to phenotypic effect. According to the methods of the invention, samples can be classified as belonging to (i.e., derived from) an individual who is not infected with HIV, an individual that is infected with HIV and is a controller or an individual who is infected with HIV and is a chronic progressor.

As used herein, by a "gene having increased expression" is meant a gene from an HIV-specific T-cell that has increased expression as compared to either a T-cell from an individual who is not infected with HIV or as compared to an HIV-specific T-cell from a controller or as compared to an HIV-specific T-cell from a chronic progressor. These genes are therefore helpful in classifying and/or identifying an HIV infected individual as a controller or a chronic progressor. Examples of such genes are provided herein at FIG. 11.

As used herein, by a "gene having decreased expression" is meant a gene from an HIV-specific T-cell that has decreased expression as compared to either a T-cell from an individual who is not infected with HIV or as compared to an HIV-specific T-cell from a controller or as compared to an HIV-specific T-cell from a chronic progressor. These genes are therefore helpful in classifying and/or identifying an HIV infected individual as a controller or a chronic progressor. Examples of such genes are provided herein at FIG. 11.

As used herein, gene expression products are proteins, peptides, or nucleic acid molecules (e.g., mRNA, tRNA, rRNA, or cRNA) that are involved in transcription or translation. The present invention can be effectively used to analyze proteins, peptides, or nucleic acid molecules that are involved in transcription or translation. The nucleic acid molecule levels measured can be derived directly from the gene or, alternatively, from a corresponding regulatory gene. All forms of gene expression products can be measured, including, for example, spliced variants. Similarly, gene expression can be measured by assessing the level of protein or derivative thereof translated from mRNA. The sample to be assessed can be any sample that contains a gene expression product. Suitable sources of gene expression products, i.e., samples, can include cells, lysed cells, cellular material for determining gene expression, or material containing gene expression products. Examples of such samples are blood, plasma, lymph, urine, tissue, mucus, sputum, saliva or other cell samples. Methods of obtaining such samples are known in the art. In a preferred embodiment, the sample is derived from an individual who has been clinically diagnosed as being infected with HIV. As used herein "obtaining" means acquiring a sample, either by directly procuring a sample from a patient or a sample (tissue biopsy, primary cell, cultured cells), or by receiving the sample from one or more people who procured the sample from the patient or sample.

Genes that are particularly relevant for classification have been identified as a result of work described herein and are shown in FIG. 11. The genes that are relevant for classification are referred to herein as "informative genes." Informative genes can be, for example, all or a subset of the genes shown in FIG. 11. Not all informative genes for a particular class distinction must be assessed in order to classify a sample. Similarly, the set of informative genes for one phenotypic effect may or may not be the same as the set of informative genes for a different phenotypic effect. For example, a subset of the informative genes which demonstrate a high correlation with a class distinction can be used. This subset can be, for example, 1 or more genes, 2 or more genes, 3 or more genes, 4 or more genes, 5 or more genes, 10 or more genes, 25 or more genes, or 50 or more genes. For example, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 or more genes. It will be understood that the methods of the present invention can classify a sample by evaluating a sample for a combination of genes whose expression is increased in HIV-specific T-cells from a controller as compared to a chronic progressor and/or genes that are decreased in HIV-specific T-cells from a controller as compared to a chronic progressor. It will also be understood that the methods of the present invention can classify a sample by evaluating a sample for a combination of genes whose expression is increased in HIV-specific T-cells from a chronic progressor as compared to a controller and/or genes that are decreased in HIV-specific T-cells from a chronic progressor as compared to a controller. It will also be understood that the methods of the present invention can classify a sample by evaluating a sample for a combination of genes whose expression is increased in HIV-specific T-cells from a chronic progressor as compared to a T-cells from a healthy individual and/or genes that are decreased in HIV-specific T-cells from a chronic progressor as compared to T-cells from a healthy individual. It will also be understood that the methods of the present invention can classify a sample by evaluating a sample for a combination of genes whose expression is increased in HIV-specific T-cells from a controller as compared to a T-cells from a healthy individual and/or genes that are decreased in HIV-specific T-cells from a controller as compared to T-cells from a healthy individual.

In one embodiment, the gene expression product is a protein or polypeptide. In this embodiment, determination of the gene expression profile can be made using techniques for protein detection and quantitation known in the art. For example, antibodies specific for the protein or polypeptide can be obtained using methods that are routine in the art, and the specific binding of such antibodies to protein or polypeptide gene expression products can be detected and measured.

"Gene expression profile" or "expression profile" as used herein is defined as the level or amount of gene expression of particular genes as assessed by methods described herein. The gene expression profile can comprise data for one or more genes and can be measured at a single time point or over a period of time. Phenotype classification (e.g., chronic progressor or controller or treatment outcome) can be made by comparing the gene expression profile of the sample with respect to one or more informative genes with one or more gene expression profiles (e.g., in a database). Informative genes include, but are not limited to, those shown in FIG. 11. Using the methods described herein, expression of numerous genes can be measured simultaneously. The assessment of numerous genes provides for a more accurate evaluation of the sample because there are more genes that can assist in classifying the sample. As discussed above, the sample from which a gene expression profile is determined can be any sample that contains a gene expression product, including cells, lysed cells, cellular material for determining gene expression, or material containing gene expression products. Examples of such samples are blood, plasma, lymph, urine, tissue, mucus, sputum, saliva or other cell samples. In a preferred embodiment, the sample is derived from an individual who has been clinically diagnosed as infected with HIV.

In a preferred embodiment, the gene expression product is mRNA and the gene expression levels are obtained, e.g., by contacting the sample with a suitable microarray on which probes specific for all or a subset of the informative genes have been immobilized, and determining the extent of hybridization of the nucleic acid in the sample to the probes on the microarray. Such microarrays are also within the scope of the invention. Examples of methods of making oligonucleotide microarrays are described, for example, in WO 95/11995. Other methods will be readily known to the skilled artisan.

Once the gene expression levels of the sample are obtained, the levels are compared or evaluated against the appropriate control, and then the sample is classified. The evaluation of the sample determines whether or not the sample should be assigned to the particular phenotypic class being studied.

The gene expression value measured or assessed is the numeric value obtained from an apparatus that can measure gene expression levels. Gene expression levels refer to the amount of expression of the gene expression product, as described herein. The values are raw values from the apparatus, or values that are optionally rescaled, filtered and/or normalized. Such data is obtained, for example, from a Gene-Chip® probe array or Microarray (Affymetrix, Inc.) (U.S. Pat. Nos. 5,631,734, 5,874,219, 5,861,242, 5,858,659, 5,856,174, 5,843,655, 5,837,832, 5,834,758, 5,770,722, 5,770,456, 5,733,729, 5,556,752, all of which are incorporated herein by reference in their entirety), and the expression levels are calculated with software (e.g., Affymetrix GENECHIP software). Nucleic acids (e.g., mRNA) from a sample which has been subjected to particular stringency conditions hybridize to the probes on the chip. The nucleic acid to be analyzed (e.g., the target) is isolated, amplified and labeled with a detectable label (e.g., $^{32}P$ or fluorescent label) prior to hybridization to the arrays. Once hybridization occurs, the arrays are inserted into a scanner which can detect patterns of hybridization. The hybridization data are collected as light emitted from the labeled groups which are now bound to the probe array. The probes that perfectly match the target produce a stronger signal than those that have mismatches. Since the sequence and position of each probe on the array are known, by complementarity, the identity of the target nucleic acid applied to the probe is determined.

Quantitation of gene profiles from the hybridization of labeled mRNA/DNA microarrays can be performed by scanning the microarrays to measure the amount of hybridization at each position on the microarray with an Affymetrix scanner (Affymetrix, Santa Clara, Calif.). For each stimulus, a time series of mRNA levels ($C=\{C1, C2, C3, \ldots Cn\}$) and a corresponding time series of mRNA levels ($M=\{M1, M2, M3, \ldots Mn\}$) in control medium in the same experiment as the stimulus is obtained. Quantitative data is then analyzed. "Ci" and "Mi" are defined as relative steady-state mRNA levels, where "i" refers to the ith timepoint and "n" to the total number of time points of the entire time course. "µM" and "σM" are defined as the mean and standard deviation of the control time course, respectively. Microarrays are only one method of obtaining gene expression values. Other methods for obtaining gene expression values known in the art or developed in the future can be used with the present invention. Once the gene expression values are prepared, the sample can be classified.

The correlation between gene expression and class distinction can be determined using a variety of methods. Methods of defining classes and classifying samples are described, for example, in U.S. patent application Ser. No. 09/544,627, filed Apr. 6, 2000 by Golub et al., the teachings of which are incorporated herein by reference in their entirety. In one embodiment, gene expression levels are detected and evaluated for expression levels, where genes without variation (e.g., having 5-fold or less variation between any two samples) are filtered out of the analysis. The information provided by the present invention, alone or in conjunction with other test results, aids in sample classification.

In one embodiment, the sample is classified using a weighted voting scheme. The weighted voting scheme advantageously allows for the classification of a sample on the basis of multiple gene expression values. In one embodiment the sample is a sample derived from an HIV-infected subject patient sample. In one aspect, the sample is HIV-specific T-cells derived from an HIV-infected subject. In a preferred embodiment the sample is classified as belonging to a particular treatment outcome class, for example, controllers or chronic progressors. In another embodiment the gene is selected from a group of informative genes, including, but not limited to, the genes listed in FIG. 11.

For example, one aspect of the present invention is a method of assigning a sample to a known or putative class, e.g., controller or chronic progressor HIV-infected individuals, comprising determining a weighted vote of one or more informative genes (e.g., greater than 1, 2, 3, 4, 5, 10, 20, 30, 40 or 50 genes) for one of the classes in accordance with a model built with a weighted voting scheme, wherein the magnitude of each vote depends on the expression level of the gene in the sample and on the degree of correlation of the gene's expression with class distinction; and summing the votes to determine the winning class. The weighted voting scheme is:

$$V_g = a_g(x_g - b_g),$$

wherein $V_g$ is the weighted vote of the gene, g; $a_g$ is the correlation between gene expression values and class distinction, P(g,c), as defined herein; $b_g = (m_1(g) + m_2(g))/2$ which is the average of the mean $\log_{10}$ expression value in a first class and a second class; $x_g$ is the $\log_{10}$ gene expression value in the sample to be tested; and wherein a positive V value indicates a vote for the first class, and a negative V value indicates a negative vote for the class. A prediction strength can also be determined, wherein the sample is assigned to the winning class if the prediction strength is greater than a particular threshold, e.g., 0.3. The prediction strength is determined by:

$$(V_{win} - V_{lose})/(V_{win} + V_{lose}),$$

wherein $V_{win}$ and $V_{lose}$ are the vote totals for the winning and losing classes, respectively. Moreover, as a consequence of the identification of informative genes for the classification of an HIV-infected subject or prediction of treatment outcome, the present invention provides methods for determining a treatment plan for an individual. That is, a determination of whether an HIV-infected subject is a controller or a chronic progressor or treatment outcome class to which the sample belongs may dictate that a treatment regimen be implemented. For example, once a health care provider knows to which treatment outcome class the sample, and therefore, the individual from which it was obtained, belongs, the health care provider can determine an adequate treatment plan for the individual. For example, in the treatment of a patient whose gene expression profile, as determined by the present invention, correlates with a poor prognosis, a health care provider could utilize a more aggressive treatment for the patient, or at minimum provide the patient with a realistic assessment of his or her prognosis.

The present invention also provides methods for monitoring the effect of a treatment regimen in an individual by monitoring the gene expression profile for one or more informative genes. For example, a baseline gene expression profile for the individual can be determined, and repeated gene expression profiles can be determined at time points during treatment. A shift in gene expression profile from a profile correlated with poor treatment outcome to a profile correlated with improved treatment outcome is evidence of an effective therapeutic regimen, while a repeated profile correlated with poor treatment outcome is evidence of an ineffective therapeutic regimen.

The invention also provides reference HIV disease expression profiles for a phenotype that is one of: (a) chronic progressor or chronic progressor; or (b) controller. The reference HIV disease reference expression profile is recorded on a computer readable medium.

The present invention also provides information regarding the genes that are important in HIV treatment response, thereby providing additional targets for diagnosis and therapy. It is also clear that the present invention can be used to generate databases comprising informative genes which will have many applications in medicine, research and industry, and in particular, in treatment of HIV infection.

Also provided are databases of expression profiles of genes useful for characterizing or classifying an immune response of an HIV-infected subjects, and for identifying HIV-specific T-cells that are controllers or chronic progressors. Such databases will typically comprise expression profiles derived HIV-specific T-cell. The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression profile.

V. BATF

BATF is a highly conserved member of the AP-1/ATF family, a group of transcription factors that regulate many aspects of cellular function in the immune system, including cytokine secretion and proliferation[30]. BATF antagonizes AP-1 function by dimerizing to Jun, disrupting the active Jun:Fos complex of AP-1, and reducing expression of AP-1 target genes[20,24,31]. Consistent with this, enforced expression of BATF in T cells inhibited the secretion of IL2, an AP-1 dependent gene, but not IFNγ which is not primarily regulated by AP-1.

As used herein, "BATF polypeptide" is meant a polypeptide or fragment thereof having at least 85% amino acid identity to NCBI Accession No. NP_006390.1 and having DNA binding activity.

As used herein, "BATF nucleic acid molecule" is meant a polynucleotide encoding a BATF polypeptide. An exemplary BATF nucleic acid molecule is provided at NCBI Accession No. NM_006399.

V. PD-1

PD-1 is a type I transmembrane protein that is transcriptionally induced in activated T cells, B cells and myeloid cells. The extracellular region of PD-1 consists of a single Ig-like variable (IgV) domain, and the cytoplasmic region contains an immunoreceptor tyrosine-based inhibitory motif. The PD-1 receptor acts to downregulate immune responses and its loss leads to a breakdown of peripheral tolerance (reviewed in Freeman et al., 2000 J. Exp. Med. 192:1027-1034 and US 2006/0034826, both of which are incorporated by reference herein in their entirety).

PD-1 is a member of the immunoglobulin family of molecules (Ishida et al. (1992) EMBO J. 11:3887; Shinohara et al. (1994) Genomics 23:704). PD-1 was previously identified using a subtraction cloning based approach designed to identify modulators of programmed cell death (Ishida et al. (1992) EMBO. J. 11:3887-95; Woronicz et al. (1995) Curr. Top. Microbiol. Immunol. 200:137). PD-1 is believed to play a role in lymphocyte survival, e.g., during clonal selection (Honjo (1992) Science 258:591; Agata et al. (1996) Int. Immunology. 8:765; Nishimura et al. (1996) Int. Immunology 8:773). PD-1 was also implicated as a regulator of B cell responses (Nishimura (1998) Int. Immunology 10:1563). Unlike CTLA4, which is found only on T cells, PD-1 is also found on B cells and myeloid cells (reviewed in US 2006/0034826, incorporated by reference herein in its entirety).

PD-1 molecules are members of the immunoglobulin gene superfamily. PD-1 (Ishida et al. (1992) EMBO J. 11:3887; Shinohara et al. (1994) Genomics 23:704; U.S. Pat. No. 5,698,520) has an extracellular region containing immunoglobulin superfamily domain, a transmembrane region, and an intracellular region including an immunoreceptor tyrosine-based inhibitory motif (ITIM). These features also define a larger family of molecules, called the immunoinhibitory receptors, which also includes gp49B, PIR-B, and the killer inhibitory receptors (KIRs) (Vivier and Daeron (1997) Immunol. Today 18:286). It is often assumed that the tyrosyl phosphorylated ITIM motif of these receptors interacts with S112-domain containing phosphatase, which leads to inhibitory signals. A subset of these immunoinhibitory receptors bind to MHC molecules, for example the KIRs, and CTLA4 bind to B7-1 and B7-2. It has been proposed that there is a phylogenetic relationship between the MHC and B7 genes (Henry et al. (1999) Immunol. Today 20(6):285-8) (reviewed in US 2006/0034826, incorporated by reference herein in its entirety).

PD-L1 and PD-L2 have been identified as ligands for PD-1 (reviewed in US 2006/0034826).

As used herein, the term "activity" with respect to a PD-1 ligand or PD-1 protein includes activities which are inherent in the structure of a PD-1 ligand or PD-1 protein. With regard to PD-1 ligand, the term "activity" includes the ability to modulate immune cell costimulation, e.g., by modulating a costimulatory signal in an immune cell, or to modulate inhibition by modulating an inhibitory signal in an immune cell, e.g., by engaging a natural receptor on an immune cell. When an activating form of the PD-1 ligand binds to a costimulatory receptor, a costimulatory signal is generated in the immune cell. When an activating form of the PD-1 ligand binds to an inhibitory receptor, an inhibitory signal is generated in the immune cell.

Modulation of a costimulatory signal results in modulation of effector function of an immune cell. Thus, the term "PD-1 ligand activity" includes the ability of a PD-1 ligand polypeptide to bind its natural receptor(s), the ability to modulate immune cell costimulatory or inhibitory signals, and the ability to modulate the immune response.

With respect to PD-1, the term "activity" includes the ability of a PD-1 polypeptide to modulate an inhibitory signal in an immune cell, e.g., by engaging a natural ligand on an antigen presenting cell. PD-1 transmits an inhibitory signal to an immune cell in a manner similar to CTLA4. Modulation of an inhibitory signal in an immune cell results in modulation of proliferation of and/or cytokine secretion by an immune cell. PD-1 can also modulate a costimulatory signal by competing with a costimulatory receptor for binding of a B7 molecule. Thus, the term "PD-1 activity" includes the ability of a PD-1 polypeptide to bind its natural ligand(s), the ability to modulate immune cell costimulatory or inhibitory signals, and the ability to modulate the immune response.

PD-1 inhibitors useful according to the invention include but are not limited to soluble monovalent form of PD-1, soluble monovalent form of a PD-1 ligand (for example PD-L1 or PD-L2), antibodies capable of binding to any one of PD-1, PD-L1 or PD-L2, PD-1, PD-L1 or PD-L2, antisense or siRNA nucleic acid molecules directed to a nucleic acid encoding any one of PD-1, PD-L1 or PD-L2, triplex oligonucleotides, a ribozyme, or a recombinant vector for expression of a PD-1 ligand or PD-1 protein, peptide nucleic acids (PNAs) of PD-1 or PD-1 ligands, isolated PD-1 ligand or a biologically active portion thereof, PD-1 or PD-1 ligand fusion or chimeric proteins, mutant or altered forms of PD-1 or PD-1 ligands that function as mimetics or antagonists of the respective proteins, and peptidomimetics of PD-1 or PD-1 ligands (reviewed in U.S. 2003/0232323, U.S. 2003/0044768 and U.S. 2006/0034826, incorporated by reference herein in their entirety).

VII. Anti-HIV Disease Therapy

Antiretroviral or anti-HIV disease therapy can include, but is not limited to, highly active antiretroviral therapy (HAART), protease inhibitors, fusion inhibitors, integrase inhibitors, co-receptor specific agents, 3TC, AZT, nevirapine, non-nucleoside analogue reverse transcriptase inhibitors and nucleoside analogue reverse transcriptase inhibitors. HAART can be three or more antiretroviral drugs in combination, including at least one protease inhibitor, or at least a reverse transcriptase inhibitor and a protease inhibitor; or at least two reverse transcriptase inhibitors with at least one protease inhibitor.

Typical reverse transcriptase inhibitors include nucleoside analogs, e.g., AZT (Zidovudine), ddi (didanosine), ddc (zalcitabine), D4T (stavudine), 3TC (lamivudine), Ziagen (abacavir), combivir (mix of AZT and 3TC), and non-nucleoside analogs, e.g., viramune (nevirapine), rescriptor (delavirdine), sustiva (efavirenz). Protease inhibitors include invirase (saquinavir), norvir (ritonavir), crixivan (indinavir), viracept (nelfinavir), agenerase (amprenivir), kaletra (lopinavir and ritonavir) and fortovase (saquinavir in a soft gelatin form). Thus, HAART can also be "triple cocktail" therapy. That is, a three drug regimen is used to combat HIV wherein one of the three drugs is usually a protease inhibitor (and the other two are usually reverse transcriptase inhibitors).

VIII. Agents

The invention provides for agents that modulate (increase or decrease) BATF expression or activity.

As used herein, the term "activity" with respect to a BATF binding protein or binding protein, for example JUN or other AP-1 family members or BATF protein includes activities which are inherent in the structure of a BATF binding protein or BATF protein.

With respect to BATF, the term "activity" includes the ability of a BATF polypeptide to reduce the expression of AP-1 target genes Also encompassed in the present invention is the use of gene expression profiles to screen for therapeutic agents, for example, agents that modulate (increase or decrease) BATF expression or activity.

In one embodiment, the present invention is directed to a method of screening for a therapeutic agent for an individual with HIV disease, comprising isolating a gene expression product from at least one informative gene from one or more cells of the individual with HIV disease; identifying a therapeutic agent by determining a gene expression profile of at least one informative gene before and after administration of the agent, wherein if the gene expression profile from the individual after administration of the agent is correlated with effective treatment of HIV disease, then the agent is identified as a therapeutic agent. In another embodiment, the cells are T-cells. Alternatively, the above method can utilize a cell line derived from an individual with HIV disease.

The invention also provides methods (also referred to herein as "screening assays") for identifying agents or compounds (e.g., fusion proteins, polypeptides, peptidomimetics, prodrugs, receptors, binding agents, antibodies, small molecules or other drugs, nucleic acids. or ribozymes) that alter or modulate (e.g., increase or decrease) the activity of the gene expression products of the informative genes (e.g., polypeptides encoded by the informative genes) as described herein, the expression of informative genes or that otherwise interact with the informative genes and/or polypeptides described herein. Such compounds can be compounds or agents that bind to informative gene expression products described herein (e.g., the polypeptides encoded by the informative genes in FIG. 11), and that have a stimulatory or inhibitory effect on, for example, activity of the polypeptide encoded by an informative gene described herein; or that change (e.g., enhance or inhibit) the ability of a polypeptide encoded by an informative gene to interact with compounds or agents that bind such an informative gene polypeptide; or that alter post-translational processing of such a polypeptide (e.g., agents that alter proteolytic processing to direct the polypeptide from where it is normally synthesized to another location in the cell, such as the cell surface or the nucleus; or agents that alter proteolytic processing such that more polypeptide is released from the cell, etc.). The modulation can be an increase or a decrease in the occurrence, severity, or progression of HIV disease. In addition, an agent that modulates HIV disease includes an agent that binds to a polypeptide that is upstream (earlier) or downstream (later) of the cell signaling events mediated by a polypeptide encoded by an informative gene of the present invention, and thereby modulates the overall activity of the signaling pathway; in turn, the HIV disease state is modulated.

The candidate compound can cause an alteration in the activity of a polypeptide encoded by an informative gene of the present invention. For example, the activity of the polypeptide can be altered (increased or decreased) by at least 1.5-fold to 2-fold, at least 3-fold, or, at least 5-fold, relative to the control. Alternatively, the polypeptide activity can be altered, for example, by at least 10%, at least 20%, 40%, 50%, or 75%, or by at least 90%, relative to the control.

In one embodiment, the invention provides assays for screening candidate compounds or test agents to identify compounds that bind to or modulate the activity of a polypeptide encoded by an informative gene described herein (or biologically active portion(s) thereof), as well as agents identifiable by the assays. As used herein, a "candidate compound" or "test agent" is a chemical molecule, be it naturally-occurring or artificially-derived, and includes, for example, peptides, proteins, synthesized molecules, for example, synthetic organic molecules, naturally-occurring molecule, for example, naturally occurring organic molecules, nucleic acid molecules, and components thereof.

In general, candidate compounds for use in the present invention may be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. For example, candidate compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, Anticancer Drug Des., 12: 145 (1997)). Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activities should be employed whenever possible.

When a crude extract is found to modulate (i.e., stimulate or inhibit) the expression and/or activity of the informative genes and/or their encoded polypeptides, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits nucleic acid expression, polypeptide expression, or polypeptide biological activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases in which it is desirable to alter the activity or expression of the nucleic acids or polypeptides of the present invention.

In one embodiment, to identify candidate compounds that alter the biological activity of a polypeptide encoded by an informative gene as described herein, a cell, tissue, cell lysate, tissue lysate, or solution containing or expressing a polypeptide encoded by the informative gene (e.g., a polypeptide encoded by a gene in FIG. 11), or a fragment or derivative thereof, can be contacted with a candidate compound to be tested under conditions suitable for biological activity of the polypeptide. Alternatively, the polypeptide can be contacted directly with the candidate compound to be tested. The level (amount) of polypeptide biological activity is assessed/measured, either directly or indirectly, and is compared with the level of biological activity in a control (i.e., the level of activity of the polypeptide or active fragment or derivative thereof in the absence of the candidate compound to be tested, or in the presence of the candidate compound vehicle only). If the level of the biological activity in the presence of the candidate compound differs, by an amount that is statistically significant, from the level of the biological activity in the absence of the candidate compound, or in the presence of the candidate compound vehicle only, then the candidate compound is a compound that alters the biological activity of the polypeptide encoded by an informative gene of the invention. For example, an increase in the level of polypeptide biological activity relative to a control, indicates that the candidate compound is a compound that enhances (is an agonist of) the polypeptide biological activity. Similarly, a decrease in the polypeptide biological activity relative to a control, indicates that the candidate compound is a compound that inhibits (is an antagonist of) the polypeptide biological activity.

In another embodiment, the level of biological activity of a polypeptide encoded by an informative gene, or a derivative or fragment thereof in the presence of the candidate compound to be tested, is compared with a control level that has previously been established. A level of polypeptide biological activity in the presence of the candidate compound that differs from (i.e., increases or decreases) the control level by an amount that is statistically significant indicates that the compound alters the biological activity of the polypeptide.

The present invention also relates to an assay for identifying compounds (e.g., antisense nucleic acids, fusion proteins, polypeptides, peptidomimetics, prodrugs, receptors, binding agents, antibodies, small molecules or other drugs, or ribozymes) that alter (e.g., increase or decrease) expression (e.g., transcription or translation) of an informative gene or that otherwise interact with an informative gene described herein, as well as compounds identifiable by the assays. For example, a solution containing an informative gene can be contacted with a candidate compound to be tested. The solution can comprise, for example, cells containing the informative gene or cell lysate containing the informative gene; alternatively, the solution can be another solution that comprises elements necessary for transcription/translation of the informative gene. Cells not suspended in solution can also be employed, if desired. The level and/or pattern of informative gene expression (e.g., the level and/or pattern of mRNA or protein expressed) is assessed, and is compared with the level and/or pattern of expression in a control (i.e., the level and/or pattern of the informative gene expressed in the absence of the candidate compound, or in the presence of the candidate compound vehicle only). If the expression level and/or pattern in the presence of the candidate compound differs by an amount or in a manner that is statistically significant from the level and/or pattern in the absence of the candidate compound, or in the presence of the candidate compound vehicle only, then the candidate compound is a compound that alters the expression of an informative gene. Enhancement of informative gene expression indicates that the candidate compound is an agonist of informative gene polypeptide activity. Similarly, inhibition of informative gene expression indicates that the candidate compound is an antagonist of informative gene polypeptide activity.

In another embodiment, the level and/or pattern of an informative gene in the presence of the candidate compound to be tested, is compared with a control level and/or pattern that has previously been established. A level and/or pattern of informative gene expression in the presence of the candidate compound that differs from the control level and/or pattern by an amount or in a manner that is statistically significant indicates that the candidate compound alters informative gene expression.

In another embodiment of the invention, compounds that alter the expression of an informative gene, or that otherwise interact with an informative gene described herein, can be identified using a cell, cell lysate, or solution containing a nucleic acid encoding the promoter region of the informative gene operably linked to a reporter gene. As used herein by "promoter" means a minimal nucleotide sequence sufficient to direct transcription, and by "operably linked" means that a gene and one or more regulatory sequences are connected in such a way as to permit gene expression when the appropriate molecules (e.g., transcriptional activator proteins) are bound to the regulatory sequences. Examples of reporter genes and methods for operably linking a reporter gene to a promoter are known in the art. After contact with a candidate compound to be tested, the level of expression of the reporter gene (e.g., the level of mRNA or of protein expressed) is assessed, and is compared with the level of expression in a control (i.e., the level of expression of the reporter gene in the absence of the candidate compound, or in the presence of the candidate compound vehicle only). If the level of expression in the presence of the candidate compound differs by an amount or in a manner that is statistically significant from the level in the absence of the candidate compound, or in the presence of the candidate compound vehicle only, then the candidate compound is a compound that alters the expression of the informative gene, as indicated by its ability to alter expression of the reporter gene that is operably linked to the informative gene promoter. Enhancement of the expression of the reporter gene indicates that the compound is an agonist of the informative gene polypeptide activity. Similarly, inhibition of the expression of the reporter gene indicates that the compound is an antagonist of the informative gene polypeptide activity.

In another embodiment, the level of expression of the reporter in the presence of the candidate compound to be tested, is compared with a control level that has been established previously. A level in the presence of the candidate compound that differs from the control level by an amount or in a manner that is statistically significant indicates that the candidate compound alters informative gene expression.

The present invention also features methods of detecting and/or identifying a compound that alters the interaction between a polypeptide encoded by an informative gene and a polypeptide (or other molecule) with which the polypeptide normally interacts with (e.g., in a cell or under physiological conditions). In one example, a cell or tissue that expresses or contains a compound (e.g., a polypeptide or other molecule) that interacts with a polypeptide encoded by an informative gene (such a molecule is referred to herein as a "polypeptide substrate") is contacted with the informative gene polypeptide in the presence of a candidate compound, and the ability of the candidate compound to alter the interaction between the polypeptide encoded by the informative gene and the polypeptide substrate is determined, for example, by assaying activity of the polypeptide. Alternatively, a cell lysate or a solution containing the informative gene polypeptide, the polypeptide substrate, and the candidate compound can be used. A compound that binds to the informative gene polypeptide or to the polypeptide substrate can alter the interaction between the informative gene polypeptide and the polypeptide substrate by interfering with (inhibiting), or enhancing the ability of the informative gene polypeptide to bind to, associate with, or otherwise interact with the polypeptide substrate.

In one embodiment, the polypeptide of interest is BATF and the second interacting polypeptide is JUN or other AP-1 family members.

Determining the ability of the candidate compound to bind to the informative gene polypeptide or a polypeptide substrate can be accomplished, for example, by coupling the candidate compound with a radioisotope or enzymatic label such that binding of the candidate compound to the informative gene polypeptide or polypeptide substrate can be determined by directly or indirectly detecting the candidate compound labeled with $^{125}I$, $^{35}S$, $^{14}C$, or $^{3}H$, and then detecting the radioisotope (e.g., by direct counting of radioemission or by scintillation counting). Alternatively, the candidate compound can be enzymatically labeled with, for example, horseradish peroxidase, alkaline phosphatase, or luciferase, and the enzymatic label is then detected by determination of conversion of an appropriate substrate to product. In another alternative, one of the other components of the screening assay (e.g., the polypeptide substrate or the informative gene polypeptide) can be labeled, and alterations in the interaction between the informative gene polypeptide and the polypeptide substrate can be detected. In these methods, labeled unbound components can be removed (e.g., by washing) after the interaction step in order to accurately detect the effect of the candidate compound on the interaction between the informative gene polypeptide and the polypeptide substrate.

It is also within the scope of this invention to determine the ability of a candidate compound to interact with the informative gene polypeptide or polypeptide substrate without the labeling of any of the interactants. For example, a microphysiometer can be used to detect the interaction of a candidate compound with a polypeptide encoded by an informative gene or a polypeptide substrate without the labeling of either the candidate compound, the polypeptide encoded by the informative gene, or the polypeptide substrate (McConnell et al., Science 257: 1906-1912 (1992)). As used herein, a "microphysiometer" (e.g., CYTOSENSOR™) is an analytical instrument that measures the rate at which a cell acidifies its environment using a light-addressable potentiometric sensor (LAPS). Changes in this acidification rate can be used as an indicator of the interaction between ligand and polypeptide.

In another embodiment of the invention, assays can be used to identify polypeptides that interact with one or more polypeptides encoded by an informative gene. For example, a yeast two-hybrid system such as that described by Fields and Song (Fields and Song, Nature 340: 245-246 (1989)) can be used to identify polypeptides that interact with one or more polypeptides encoded by an informative gene. In such a yeast two-hybrid system, vectors are constructed based on the flexibility of a transcription factor that has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used that includes a nucleic acid encoding a DNA binding domain and a polypeptide encoded by an informative gene, or fragment or derivative thereof, and a second vector is used that includes a nucleic acid encoding a transcription activation domain and a nucleic acid encoding a polypeptide that potentially may interact with the informative gene polypeptide, or fragment or derivative thereof. Incubation of yeast containing the first vector and the second vector under appropriate conditions (e.g., mating conditions such as used in the MATCHMAKER™ system from Clontech) allows identification of colonies that express the markers of the polypeptide(s). These colonies can be examined to identify the polypeptide(s) that interact with the polypeptide encoded by the informative gene or a fragment or derivative thereof. Such polypeptides may be useful as compounds that alter the activity or expression of an informative gene polypeptide.

In more than one embodiment of the above assay methods of the present invention, it may be desirable to immobilize a polypeptide encoded by an informative gene, or a polypeptide substrate, or other components of the assay on a solid support, in order to facilitate separation of complexed from uncomplexed forms of one or both of the polypeptides, as well as to accommodate automation of the assay. Binding of a candidate compound to the polypeptide, or interaction of the polypeptide with a polypeptide substrate in the presence and absence of a candidate compound, can be accomplished in any vessel suitable for containing the reactants. Examples of such vessels include microtitre plates, test tubes, and micro-centrifuge tubes. In one embodiment, a fusion protein (e.g., a glutathione-S-transferase fusion protein) can be provided that adds a domain that allows the informative gene polypeptide, or the polypeptide substrate to be bound to a matrix or other solid support.

This invention further pertains to novel compounds identified by the above-described screening assays. Accordingly, it is within the scope of this invention to further use a compound identified as described herein in an appropriate animal model. For example, a compound identified as described herein can be used in an animal model to determine the efficacy, toxicity, or side effects of treatment with such a compound. Alternatively, a compound identified as described herein can be used in an animal model to determine the mechanism of action of such a compound. Furthermore, this invention pertains to uses of novel compounds identified by the above-described screening assays for treatments as described herein. In addition, a compound identified as described herein can be used to alter activity of a polypeptide encoded by an informative gene, or to alter expression of the informative gene, by contacting the polypeptide or the nucleic acid molecule (or contacting a cell comprising the polypeptide or the nucleic acid molecule) with the compound identified as described herein.

The present invention encompasses a method of treating HIV disease, comprising the administration of an agent which modulates the expression level or activity of an informative gene product, for example. BATF. A therapeutic agent may increase or decrease the level or activity of the gene product. Other suitable therapeutic targets for drug development include genes described herein in FIG. 11.

The present invention further relates to antibodies that specifically bind a polypeptide, preferably an epitope, of an informative gene of the present invention (as determined, for example, by immunoassays, a technique well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, for example, anti-Id antibodies to antibodies of the invention), and epitope-binding fragments of any of the above.

The term "antibody," as used herein, refers to immunoglobulin molecules and immunologically active portions of immunoglobulin molecules, and more specifically, molecules that contain an antigen binding site that specifically binds an antigen. The immunoglobulin molecules of the invention can be of any type (for example, IgG, IgE, IgM, IgD, IgA and IgY), and of any class (for example, IgG1, IgG2, IgG3, IgG4, IgA1 and IgA2) or subclass of an immunoglobulin molecule.

In one embodiment, the antibodies are antigen-binding antibody fragments and include, without limitation, Fab, Fab' and F(ab)$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of one or more of the following: hinge region, CH1, CH2, and CH3 domains. Also included in the invention are antigen-binding fragments also comprising any combination of variable region(s) with a hinge region, CH1, CH2, and/or CH3 domains.

The antibodies of the invention may be from any animal origin including birds and mammals. Preferably, the antibodies are human, murine, donkey, sheep, rabbit, goat, guinea pig, hamster, horse, or chicken.

As used herein, "human" antibodies include antibodies having the amino acid sequence of a human immunoglobulin and include antibodies produced by human B cells, or isolated from human sera, human immunoglobulin libraries or from animals transgenic for one or more human immunoglobulins and that do not express endogenous immunoglobulins, as described in U.S. Pat. No. 5,939,598 by Kucherlapati et al., for example.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material.

Antibodies of the present invention may be described or specified in terms of the epitope(s) or portion(s) of a polypeptide of the present invention that they recognize or specifically bind. The epitope(s) or polypeptide portion(s) may be specified, for example, by N-terminal and/or C-terminal positions, or by size in contiguous amino acid residues. Antibodies that specifically bind any epitope or polypeptide encoded by an informative gene of the present invention may also be excluded. Therefore, the present invention includes antibodies that specifically bind a polypeptide encoded by an informative gene of the present invention, and allows for the exclusion of the same.

The term "epitope," as used herein, refers to a portion of a polypeptide which contacts an antigen-binding site(s) of an antibody or T cell receptor. Specific binding of an antibody to an antigen having one or more epitopes excludes non-specific binding to unrelated antigens, but does not necessarily exclude cross-reactivity with other antigens with similar epitopes.

Antibodies of the present invention may also be described or specified in terms of their cross-reactivity. Antibodies of the present invention may not display any cross-reactivity, such that they do not bind any other analog, ortholog, or homolog of a polypeptide of the present invention. Alternatively, antibodies of the invention can bind polypeptides with at least about 95%, 90%, 85%, 80%, 75%, 70%, 65%, 60%, 55%, or 50% identity (as calculated using methods known in the art) to a polypeptide encoded by an informative gene of the present invention. Further included in the present invention are antibodies that bind polypeptides encoded by informative genes that hybridize to an informative gene of the present invention under stringent hybridization conditions, as will be appreciated by one of skill in the art.

Antibodies of the present invention can also be described or specified in terms of their binding affinity to a polypeptide of the invention. Preferred binding affinities include those with a dissociation constant or Kd less than $5 \times 10^{-6}$ M, $10^{-6}$ M, $10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

The invention also provides antibodies that competitively inhibit binding of an antibody to an epitope of a polypeptide of the invention, as determined by any method known in the art for determining competitive binding, for example, using immunoassays. In particular embodiments, the antibody competitively inhibits binding to the epitope by at least about 90%, 80%, 70%, 60%, or 50%.

Antibodies of the present invention can act as agonists or antagonists of polypeptides encoded by the informative genes of the present invention. For example, the present invention includes antibodies which disrupt interactions with the polypeptides encoded by the informative genes of the invention either partially or fully. The invention also includes antibodies that do not prevent binding, but prevent activation or activity of the polypeptide. Activation or activity (for example, signaling) may be determined by techniques known in the art. Also included are antibodies that prevent both binding to and activity of a polypeptide encoded by an informative gene. Likewise included are neutralizing antibodies.

Antibodies of the present invention may be used, for example, and without limitation, to purify, detect, and target the polypeptides encoded by the informative genes described herein, including both in vitro and in vivo diagnostic and therapeutic methods. For example, the antibodies have use in immunoassays for qualitatively and quantitatively measuring levels of the polypeptides in biological samples. See, for example, Harlow et al., Antibodies: A Laboratory Manual (Cold Spring Harbor Laboratory Press, 2nd ed. 1988).

As discussed in more detail below, the antibodies of the present invention may be used either alone or in combination with other compositions. The antibodies may further be recombinantly fused to a heterologous polypeptide at the N- and/or C-terminus or chemically conjugated (including covalent and non-covalent conjugations) to polypeptides or other compositions. For example, antibodies of the present invention may be recombinantly fused or conjugated to molecules useful as labels in detection assays, or effector molecules such as heterologous polypeptides, drugs, or toxins.

The antibodies of the invention include derivatives that are modified, for example, by the covalent attachment of any type of molecule to the antibody such that covalent attachment does not prevent the antibody from recognizing its epitope. For example, but not by way of limitation, the antibody derivatives include antibodies that have been modified, for example, by glycosylation, acetylation, pegylation, phosphorylation, amidation, derivatization by known protecting/blocking groups, proteolytic cleavage, or linkage to a cellular ligand or other protein. Any of numerous chemical modifications can be carried out by known techniques, including, but not limited to, specific chemical cleavage, acetylation, formylation, and metabolic synthesis of tunicamycin. Additionally, the derivative can contain one or more non-classical amino acids.

The antibodies of the present invention can be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, or the like, to induce the production of sera containing polyclonal antibodies specific for the antigen. Various adjuvants can be used to increase the immunological response, depending on the host species, and include, but are not limited to, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *corynebacterium parvum*. Such adjuvants are well known in the art.

Monoclonal antibodies can be prepared using a wide variety of techniques also known in the art, including hybridoma cell culture, recombinant, and phage display technologies, or a combination thereof. For example, monoclonal antibodies can be produced using hybridoma techniques as is known in the art and taught, for example, in Harlow et al., Antibodies: A Laboratory Manual (Cold Spring Harbor Laboratory Press, 2nd ed. 1988). The term "monoclonal antibody" as used herein is not necessarily limited to antibodies produced through hybridoma technology, but also refers to an antibody that is derived from a single clone, including any eukaryotic, prokaryotic, or phage clone.

Human antibodies are desirable for therapeutic treatment of human patients. These antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes. The transgenic mice are immunized with a selected antigen, for example, all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For a detailed discussion of this technology for producing human antibodies and human monoclonal antibodies and protocols for producing such antibodies, see, for example, PCT publications WO 98/24893; WO 96/34096; WO 96/33735; and U.S. Pat. Nos. 5,413,923; 5,625,126; 5,633,425; 5,569,825; 5,661,016; 5,545,806; 5,814,318; and 5,939,598.

In another embodiment, antibodies to the polypeptides encoded by the informative genes as described herein can, in turn, be utilized to generate anti-idiotype antibodies that "mimic" polypeptides of the invention using techniques well known to those skilled in the art. (See, for example, Greenspan & Bona, FASEB J. 7(5):437-444 (1989) and Nissinoff, J. Immunol. 147(8):2429-2438 (1991)). For example, antibodies that bind to and competitively inhibit polypeptide multimerization and/or binding of a polypeptide to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide encoded by an informative gene and/or to bind its ligands, and thereby block its biological activity.

The antibodies or fragments thereof of the present invention can be fused to marker sequences, such as a peptide to facilitate their purification. In one embodiment, the marker amino acid sequence is a hexa-histidine peptide, an HA tag, or a FLAG tag, as will be readily appreciated by one of skill in the art.

The present invention further encompasses antibodies or fragments thereof conjugated to a diagnostic or therapeutic agent. The antibodies can be used diagnostically, for example, to monitor the development or progression of a tumor as part of a clinical testing procedure to determine the efficacy of a given treatment regimen. Detection can be facilitated by coupling the antibody to a detectable substance. Examples of detectable substances include enzymes (such as, horseradish peroxidase, alkaline phosphatase, beta-galactosidase, or acetylcholinesterase), prosthetic group (such as streptavidin/biotin and avidin/biotin), fluorescent materials (such as umbelliferone, fluorescein, fluorescein isothiocyanate, rhodamine, dichlorotriazinylamine fluorescein, dansyl chloride or phycoerythrin), luminescent materials (such as luminol), bioluminescent materials (such as luciferase, luciferin, and aequorin), radioactive materials (such as, $^{125}$I, $^{131}$I, $^{111}$In or $^{99}$Tc), and positron emitting metals using various positron emission tomographies, and nonradioactive paramagnetic metal ions.

In an additional embodiment, an antibody or fragment thereof can be conjugated to a therapeutic moiety such as a cytotoxin, for example, a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (for example, daunorubicin (formerly daunomycin) and doxorubicin), antibiotics (for example, actinomycin, bleomycin, mithramycin, and anthramycin (AMC)), and anti-mitotic agents (for example, vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .α.-interferon, .β.-interferon, nerve growth factor, platelet derived growth factor, tissue plasminogen activator, a thrombotic agent or an anti-angiogenic agent, for example, angiostatin or endostatin; or, biological response modifiers such as, for example, lymphokines, interleukins, granulocyte macrophase colony stimulating factor ("GM-CSF"), granulocyte colony stimulating factor ("G-CSF"), or other growth factors.

Antibodies of the invention can also be attached to solid supports. These are particularly useful for immunoassays or purification of the target antigen. Such solid supports include, but are not limited to, glass, cellulose, silicon, polyacrylamide, nylon, polystyrene, polyvinyl chloride or polypropylene. Techniques for conjugating such therapeutic moiety to antibodies are well known in the art, see, for example, Amon et al., "Monoclonal Antibodies For Immunotargeting Of Drugs In Cancer Therapy", in Monoclonal Antibodies And Cancer Therapy, Reisfeld et al. eds., pp. 243-56 (Alan R. Liss, Inc. 1985).

Alternatively, an antibody can be conjugated to a second antibody to form an antibody heteroconjugate as described by Segal in U.S. Pat. No. 4,676,980.

An antibody of the invention, with or without conjugation to a therapeutic moiety, administered alone or in combination with cytotoxic factor(s) and/or cytokine(s), can be used as a therapeutic.

Antisense antagonists of the informative genes of the present invention are also included. Antisense technology can be used to control gene expression through antisense DNA or RNA, or through triple-helix formation. Antisense techniques are discussed for example, in Okano, J., Neurochem. 56:560 (1991). The methods are based on binding of a polynucleotide to a complementary DNA or RNA. In one embodiment, an antisense sequence is generated internally by the organism, in another embodiment, the antisense sequence is separately administered (see, for example, O'Connor, J., Neurochem. 56:560 (1991)).

In one embodiment, the 5' coding portion of an informative gene can be used to design an antisense RNA oligonucleotide from about 10 to 40 base pairs in length. Generally, a DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid of the invention. Such a vector contains the sequence encoding the antisense nucleic acid. The vector can remain episomal or become chromosomally integrated, as long as it can be transcribed to produce the desired antisense RNA. Vectors can be constructed by recombinant DNA technology and can be plasmid, viral, or otherwise, as is known to one of skill in the art.

Expression can be controlled by any promoter known in the art to act in the target cells, such as vertebrate cells, and preferably human cells. Such promoters can be inducible or constitutive and include, without limitation, the SV40 early promoter region (Bernoist and Chambon, Nature 29:304-310 (1981), the promoter contained in the 3' long terminal repeat of Rous sarcoma virus (Yamamoto et al., Cell 22:787-797 (1980)), the herpes thymidine promoter (Wagner et al., Proc. Natl. Acad. Sci. U.S.A. 78:1441-1445 (1981)), and the regulatory sequences of the metallothionein gene (Brinster et al., Nature 296:39-42 (1982)).

The antisense nucleic acids of the invention comprise a sequence complementary to at least a portion of an RNA transcript of an informative gene. Absolute complementarity, although preferred, is not required. A sequence "complementary to at least a portion of an RNA," referred to herein, means a sequence having sufficient complementarity to be able to hybridize with the RNA, forming a stable duplex. The ability to hybridize will depend on both the degree of complementarity and the length of the antisense nucleic acid. Generally, the larger the hybridizing nucleic acid, the more base mismatches with the RNA it may contain and still form a stable duplex. One skilled in the art can ascertain a tolerable degree of mismatch by use of standard procedures to determine the melting point of the hybridized complex.

Oligonucleotides that are complementary to the 5' end of the RNA, for example, the 5' untranslated sequence up to and including the AUG initiation codon, are generally regarded to work most efficiently at inhibiting translation. However, sequences complementary to the 3' untranslated sequences of mRNAs have been shown to be effective at inhibiting translation of mRNAs as well. Thus, oligonucleotides complementary to either the 5'- or 3'-non-translated, non-coding regions of a nucleotide sequence can be used in an antisense approach to inhibit mRNA translation. Oligonucleotides complementary to the 5' untranslated region of the mRNA can include the complement of the AUG start codon. Antisense oligonucleotides complementary to mRNA coding regions can also be used in accordance with the invention. In one embodiment, the antisense nucleic acids are at least six nucleotides in length, and are preferably oligonucleotides ranging from about 6 to about 50 nucleotides in length. In other embodiments, the oligonucleotide is at least about 10, 17, 25 or 50 nucleotides in length.

The antisense oligonucleotides of the invention can be DNA or RNA, or chimeric mixtures, or derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide can include other appended groups such as peptides (for example, to target host cell receptors in vivo), or agents that facilitate transport across the cell membrane, or the blood-brain barrier, or intercalating agents.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, a-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an .α-anomeric oligonucleotide. An .α-anomeric oligonucleotide forms specific double-stranded hybrids with complementary RNA in which, contrary to the usual .β-units, the strands run parallel to each other (Gautier et al., Nucl. Acids Res. 15:6625-6641 (1987)). The oligonucleotide is a 2'-O-methylribonucleotide (Inoue et al., Nucl. Acids Res. 15:613-16148 (1987)), or a chimeric RNA-DNA analog (Inoue et al., FEBS Lett. 215:327-330 (1987)).

Antisense oligonucleotides of the invention may be synthesized by standard methods known in the art, for example, by use of an automated DNA synthesizer.

Potential antagonists of informative genes of the present invention also include catalytic RNA, or a ribozyme. Hammerhead ribozymes cleave mRNAs at locations dictated by flanking regions that form complementary base pairs with the target mRNA. The target mRNA has the following sequence of two bases: 5'-UG-3'. The construction and production of hammerhead ribozymes is well known in the art and is described more fully in Haseloff and Gerlach (Nature 334: 585-591 (1988)). Preferably, the ribozyme is engineered so that the cleavage recognition site is located near the 5' end of the mRNA in order to increase efficiency and minimize the intracellular accumulation of non-functional mRNA transcripts.

Ribozymes of the invention can be composed of modified oligonucleotides (for example for improved stability, targeting, and the like). DNA constructs encoding the ribozyme can be under the control of a strong constitutive promoter, such as, for example, pol III or pol II promoter, so that a transfected cell will produce sufficient quantities of the ribozyme to destroy endogenous target mRNA and inhibit translation. Since ribozymes, unlike antisense molecules, are catalytic, a lower intracellular concentration is generally required for efficiency.

Antagonists of the informative genes of the present invention that function via gene silencing mechanisms are also included.

The phrase "gene silencing" refers to a process by which the expression of a specific gene product is lessened or attenuated. Gene silencing can take place by a variety of pathways. Unless specified otherwise, as used herein, gene silencing refers to decreases in gene product expression that results from RNA interference (RNAi), a defined, though partially characterized pathway whereby small inhibitory RNA (siRNA) act in concert with host proteins (e.g., the RNA induced silencing complex, RISC) to degrade messenger RNA (mRNA) in a sequence-dependent fashion.

RNA interference ("RNAi") is a method of post-transcriptional gene regulation that is conserved throughout many eukaryotic organisms. RNAi is induced by short (i.e., <30 nucleotide) double stranded RNA ("dsRNA") molecules which are present in the cell (Fire A et al. (1998), Nature 391: 806-811). These short dsRNA molecules, called "short interfering RNA" or "siRNA," cause the destruction of messenger RNAs ("mRNAs") which share sequence homology with the siRNA to within one nucleotide resolution (Elbashir S M et al. (2001), Genes Dev, 15: 188-200). It is believed that the siRNA and the targeted mRNA bind to an RNA-induced silencing complex ("RISC"), which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi is therefore more effective than other currently available technologies for inhibiting expression of a target gene.

RNA interference (RNAi) is a phenomenon wherein double-stranded RNA, when present in a cell, inhibits expression of a gene that has an identical or nearly identical sequence. Inhibition is caused by degradation of the messenger RNA (mRNA) transcribed from the target gene. The double-stranded RNA responsible for inducing RNAi is termed interfering RNA. The mechanism and cellular machinery through which dsRNA mediates RNAi has been investigated using both genetic and biochemical approaches. Biochemical analyses suggest that dsRNA introduced into the cytoplasm of a cell is first processed into RNA fragments 21 25 nucleotides long. It has been shown in in vitro studies that these dsRNAs, termed small interfering RNAs (siRNA) are generated at least in part by the RNAse III-like enzyme Dicer. These siRNAs likely act as guides for mRNA cleavage, as the target mRNA is cleaved at a position in the center of the region covered by a particular siRNA. Biochemical evidence suggests that the siRNA is part of a multicomponent nuclease complex termed the RNA-induced silencing complex (RISC). One of the proteins of this complex, Argonaute2, has been identified as a product of the argonaute gene family. This gene family, which also contains the *C. elegans* homolog rde-1 and related genes, the *N. crassa* homolog qde-2, and the *Arabidopsis* homolog arg-1, has been shown to be required for RNAi through genetic studies. Genetic screens in *C. elegans* have also identified the mut-7 gene as essential for RNAi. This gene bears resemblance to RNAse D, suggesting that its gene product acts in the mRNA degradation step of the reaction.

Elbashir S M et al. (2001), has shown that synthetic siRNA of 21 and 22 nucleotides in length, and which have short 3' overhangs, can induce RNAi of target mRNA in a *Drosophila* cell lysate. Cultured mammalian cells also exhibit RNAi with synthetic siRNA (Elbashir S M et al. (2001) Nature, 411: 494-498), and RNAi induced by synthetic siRNA has recently been shown in living mice (McCaffrey A P et al. (2002), Nature, 418: 38-39; Xia H et al. (2002), Nat. Biotech. 20: 1006-1010). The therapeutic potential of siRNA-mediated RNAi has been demonstrated by several recent in vitro studies, including the siRNA-directed inhibition of HIV-1 infection (Novina C D et al. (2002), Nat. Med. 8: 681-686) and reduction of neurotoxic polyglutamine disease protein expression (Xia H et al. (2002)). Therapeutic RNAi has also been demonstrated in human cancer cells by Alan Gewirtz, as described in published U.S. patent application US 2002/0173478.

The level of gene silencing can be measured by a variety of means, including, but not limited to, measurement of transcript levels by Northern Blot Analysis, B-DNA techniques, transcription-sensitive reporter constructs, expression profiling (e.g., DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g., fluorescent properties (e.g., GFP) or enzymatic activity (e.g., alkaline phosphatases), or several other procedures.

The term "miRNA" refers to microRNA.

The term "siRNA" refers to small inhibitory RNA duplexes that induce the RNA interference (RNAi) pathway. These molecules can vary in length (generally 18-35 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

siRNA may be divided into five (5) groups (non-functional, semi-functional, functional, highly functional, and hyperfunctional) based on the level or degree of silencing that they induce in cultured cell lines. As used herein, these definitions are based on a set of conditions where the siRNA is transfected into said cell line at a concentration of 100 nM and the level of silencing is tested at a time of roughly 24 hours after transfection, and not exceeding 72 hours after transfection. In this context, "non-functional siRNA" are defined as those siRNA that induce less than 50% (<50%) target silencing. "Semi-functional siRNA" induce 50-79% target silencing. "Functional siRNA" are molecules that induce 80-95% gene silencing. "Highly-functional siRNA" are molecules that induce greater than 95% gene silencing. "Hyperfunctional siRNA" are a special class of molecules. For purposes of this document, hyperfunctional siRNA are defined as those molecules that: (1) induce greater than 95% silencing of a specific target when they are transfected at subnanomolar concentrations (i.e., less than one nanomolar); and/or (2) induce functional (or better) levels of silencing for greater than 96 hours. These relative functionalities (though not intended to be absolutes) may be used to compare siRNAs to a particular target for applications such as functional genomics, target identification and therapeutics.

The siRNA contains sequence that is identical or nearly identical to a portion of a gene. RNA may be polymerized in vitro, recombinant RNA, contain chimeric sequences, or derivatives of these groups. The siRNA may contain ribonucleotides, deoxyribonucleotides, synthetic nucleotides, or any suitable combination such that expression of the target gene is inhibited. The RNA is preferably double stranded, but may be single, triple, or quadruple stranded.

A delivered siRNA can stay within the cytoplasm or nucleus. The siRNA can be delivered to a cell to inhibit expression of an endogenous or exogenous nucleotide sequence or to affect a specific physiological characteristic not naturally associated with the cell.

A siRNA can be delivered to a cell in order to produce a cellular change that is therapeutic. The delivery of siRNA or other genetic material for therapeutic purposes (the art of improving health in an animal including treatment or prevention of disease) is called gene therapy. The siRNA can be delivered either directly to the organism in situ or indirectly by transfer to a cell ex vivo that is then transplanted into the organism. Entry into the cell is required for the siRNA to block the production of a protein or to decrease the amount of a RNA. Delivery of siRNA would block production of the dominant protein thereby lessening HIV disease.

By "double stranded RNA" or "dsRNA" is meant a double stranded RNA that matches a predetermined gene sequence that is capable of activating cellular enzymes that degrade the corresponding messenger RNA transcripts of the gene. These dsRNAs are referred to as short intervening RNA (siRNA) and can be used to inhibit gene expression (see for example Elbashir et al., 2001, Nature, 411, 494 498; and Bass, 2001, Nature, 411, 428 429). The term "double stranded RNA" or "dsRNA" as used herein refers to a double stranded RNA molecule capable of RNA interference "RNAi", including short interfering RNA "siRNA" see for example Bass, 2001, Nature, 411, 428 429; Elbashir et al., 2001, Nature, 411, 494 498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.

Drug discovery could also be facilitated by siRNA technology. The siRNA approach for target validation will provide a quicker and less expensive approach to screen potential drug targets. Information for drug targeting will be gained not only by inhibiting a potential drug target but also by determining whether an inhibited protein, and therefore the pathway, has significant phenotypic effects. Expression arrays can be used to determine the responsive effect of inhibition on the expression of genes other than the targeted gene or pathway. It will place the gene product within functional pathways and networks (interacting pathways).

Peptidomimetics (Fauchere, J. (1986) Adv. Drug Res. 15:29; Veber and Freidinger (1985) TINS p. 392; and Evans et al. (1987) J. Med. Chem. 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as human BATF or a BATF binding protein, but have one or more peptide linkages optionally replaced by a linkage selected from the group consisting of: —CH2NH—, —CH2S—, —CH2-CH2-, —CH.dbd.CH— (cis and trans), —COCH2-, —CH(OH)CH2-, and —CH2SO—, by methods known in the art and further described in the following references: Spatola, A. F. in "Chemistry and Biochemistry of Amino Acids, Peptides, and Proteins" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) Trends Pharm. Sci. pp. 463-468 (general review); Hudson, D. et al. (1979) Int. J. Pept. Prot. Res. 14:177-185 (—CH2NH—, CH2CH2-); Spatola, A. F. et al. (1986) Life Sci. 38:1243-1249 (—CH2-S); Hann, M. M. (1982) J. Chem. Soc. Perkin Trans. I. 307-314 (—CH═CH—, cis and trans); Almquist, R. G. et al. (190) J. Med. Chem. 23:1392-1398 (—COCH2-); Jennings-White, C. et al.

(1982) Tetrahedron Lett. 23:2533 (—COCH2-); Szelke, M. et al. European Appln. EP 45665 (1982) CA: 97:39405 (1982) (—CH(OH)CH2-); Holladay, M. W. et al. (1983) Tetrahedron Lett. (1983) 24:4401-4404 (—C(OH)CH2-); and Hruby, V. J. (1982) Life Sci. (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Also encompassed by the present invention are small molecules. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner USP '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. USA 87:6378-6382); (Felici (1991) J. Mol. Biol. 222:301-310); (Ladner supra.). Compounds can be screened in cell based or non-cell based assays. Compounds can be screened in pools (e.g. multiple compounds in each testing sample) or as individual compounds.

IX. Assays

Cytokine production and secretion is measured in the supernatant of cultured cells according to methods known in the art and including but not limited to using the respective Quantikine Immunoassays according to manufacturer's direction (R&D Systems, Minneapolis, Minn.).

T-cell proliferation can be measured as follows.

Primary human CD4-positive or CD8-positive T-cells from the peripheral blood of healthy volunteers are isolated via magnetic selection using the CD4 or CD8 isolation kit according to the manufacturer's instructions (Miltenyi Biotec, Auburn Calif.). Cells are labeled with CFSE according to manufacturer's instructions (Molecular Probes/Invitrogen) and proliferation detected by loss of CSFE fluorescence after 4-6 days in culture.

BATF Expression can be detected by any of the methods of detecting DNA, RNA or protein expression described herein, for Example in Example 4.

IX. Methods of Treatment

As used herein, "treating" HIV refers to preventing the onset of HIV disease and/or reducing, delaying, or eliminating HIV disease symptoms such as decreased CD4 positive cell count and increased HIV viral load.

Alternatively, "treating" means arresting or otherwise ameliorating symptoms of HIV disease as defined herein.

According to the methods of the invention, HIV disease is treated, as defined herein by administering to an HIV infected subject an agent that modulates BATF expression or activity.

The efficacy of treatment according to a method of the invention can be assessed by monitoring the appearance or severity of HIV disease symptoms, for example, HIV viral load or the number of CD4 positive T cells.

Treatment according to the invention is measured by determining viral load, T-cell function, for example IL-2 secretion, T-cell proliferation, T-cell survival, BATF expression or activity or by evaluation of the expression profile of the subject being treated.

X. Pharmaceutical Compositions and Formulations

The invention provides for compositions and formulations comprising an agent that modulates or inhibits BATF expression activity, admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art.

The invention also provides for pharmaceutical compositions. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the subject.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. . . . Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition with information including amount, frequency and method of administration.

The compositions of the present invention include any agent that modulates BATF expression or activity, for example, soluble form of BATF, soluble form of a BATF ligand, antibodies capable of binding to BATF, antisense or siRNA nucleic acid molecules directed to a nucleic acid encoding BATF, triplex oligonucleotides, a ribozyme, or a recombinant vector for expression of a BATF ligand or BATF protein, peptide nucleic acids (PNAs) of BATF or BATF ligands, isolated BATF ligand or a biologically active portion thereof, BATF or BATF ligand fusion or chimeric proteins, mutant or altered forms of BATF or BATF ligands that function as mimetics or antagonists of the respective proteins, and peptidomimetics of BATF or BATF ligands.

The pharmaceutical composition may be formulated from a range of preferred doses, as necessitated by the condition of the patient being treated.

The actual dosage employed may be varied depending upon the requirements of the patient and the severity of the condition being treated. Determination of the proper dosage for a given condition is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

The pharmaceutical compositions of the invention may be formulated as sustained release or extended release formulations.

VII. Dosage and Mode of Administration

An agent that modulates BATF expression or activity, may be administered systemically or locally in a dosage wherein administration results in treatment of HIV disease. Systemic administration of the composition according to the invention may be performed by methods of whole-body drug delivery that are well known in the art. These include, but are not limited to, administration orally as well as by intravenous, intramuscular, or subcutaneous routes. In some cases it may be desirable to administer the composition directly to the airways in the form of an aerosol. Localized administration of a therapeutic compound according to the invention is preferably by a drip device, drug pump, or drug-saturated solid matrix from which the composition can diffuse once implanted at the target site. Examples of solid carriers include starch, lactose, dicalcium phosphate, microcrystalline cellulose, sucrose and kaolin, while examples of liquid carriers include sterile water, polyethylene glycols, non-ionic surfactants and edible oils such as corn, peanut and sesame oils, as are appropriate to the nature of the active ingredient and the particular form of administration desired. Advantageously, adjuvants routinely used in the preparation of pharmaceutical compositions may be included, including flavoring agents, coloring agents, preserving agents, and antioxidants, for example, vitamin E, ascorbic acid, BHT and BHA.

An agent that modulates BATF expression or activity of the invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form is advantageously sterile and fluid to the extent that easy syringability exists. Advantageously, the form is stable under the conditions of manufacture and storage and is preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

By way of example, a patient suffering from or susceptible to HIV disease, as described herein can be treated as follows. An agent that modulates BATF expression or activity, can be administered to the patient, preferably in a biologically compatible solution or a pharmaceutically acceptable delivery vehicle, by ingestion, injection, inhalation, or any number of other methods. The dosages administered will vary from patient to patient; a "therapeutically effective dose" can be determined, for example, by monitoring the viral load of the patient and/or the number of CD4-positive cells. A therapeutically effective dose refers to a dose wherein the compound has an effect on the treatment of HIV disease.

In the treatment of HIV disease, a therapeutically effective dosage regimen should be used. By "therapeutically effective" or "effective amount", one refers to a treatment regimen sufficient to decrease the viral load of a subject and/or increase the number of CD4-positive cells. Alternatively, a "therapeutically effective regimen" may be sufficient to arrest or otherwise ameliorate symptoms of HIV disease. Generally, in the treatment of HIV disease, an effective dosage regimen requires providing the medication over a period of time to achieve noticeable therapeutic effects.

It is contemplated that global administration of a therapeutic composition to an animal is not needed in order to achieve a highly localized effect. Localized administration of a therapeutic composition according to the invention is preferably oral, by injection, catheter or by means of a drip device, drug pump or drug-saturated solid matrix from which the composition can diffuse implanted at the target site. When a tissue that is the target of treatment according to the invention is on a surface of an organism, topical administration of a pharmaceutical composition is possible. For example, antibiotics are commonly applied directly to surface wounds as an alternative to oral or intravenous administration, which methods necessitate a much higher absolute dosage in order to counter the effect of systemic dilution, resulting both in possible side-effects in otherwise unaffected tissues and in increased cost.

Compositions comprising a therapeutic composition which are suitable for topical administration can take one of several physical forms, as summarized below:

(i) A liquid, such as a tincture or lotion, which may be applied by pouring, dropping or "painting" (i.e. spreading manually or with a brush or other applicator such as a spatula) or injection.

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the target tissue or, alternatively, applied as a nebulized spray.

(iv) A liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of a therapeutic composition.

Note that in some cases, the surface in question is internal; in such a case, topical application would comprise taking the therapeutic composition via an oral route, whether in liquid, gel or solid form.

Systemic administration of a therapeutic composition according to the invention may be performed by methods of whole-body drug delivery well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device. Note that injection may be performed either by conventional means (i.e. using a hypodermic needle) or by hypospray (see Clarke and Woodland, 1975, *Rheumatol. Rehabil.*, 14: 47-49).

Systemic administration is advantageous when a pharmaceutical composition must be delivered to a target tissue that is widely-dispersed, inaccessible to direct contact or, while accessible to topical or other localized application, is resident in an environment (such as the digestive tract) wherein the native activity of the nucleic acid or other agent might be compromised, e.g. by digestive enzymes or extremes of pH.

A therapeutic composition of use in the invention can be given in a single- or multiple dose. A multiple dose schedule is one in which a primary course of administration can include 1-10 separate doses, followed by other doses given at subsequent time intervals when it is desirable to maintain and or reinforce the level of the therapeutic agent. Such intervals are dependent on the continued need of the recipient for the therapeutic agent, and/or the half-life of a therapeutic agent. The efficacy of administration may be assayed by monitoring the reduction in the levels of a symptom indicative or associated with HIV disease which it is designed to inhibit. The assays can be performed as described herein or according to methods known to one skilled in the art.

A therapeutically effective regimen may be sufficient to arrest or otherwise ameliorate symptoms of a disease. An effective dosage regimen requires providing the regulatory drug over a period of time to achieve noticeable therapeutic effects wherein symptoms are reduced to a clinically acceptable standard or ameliorated. The symptoms are specific for the disease in question. For example, for HIV disease, the claimed invention is successful when HIV viral load is decreased, as defined herein, or when CD4-positive cell number is increased, as defined herein.

VIII. Kits or Pharmaceutical Systems

The present compositions may be assembled into kits or pharmaceutical systems for use in any one of monitoring the efficacy of anti-HIV therapy, monitoring HIV disease progression, detecting an increase in HIV viral load, detecting a change in the number of CD4+ cells, and treatment of HIV disease. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the agents of the invention, for example an agent that treats HIV.

IX. Use

The present invention is directed to expression profiles of HIV-specific T-cells and their methods of use, including but not limited to increasing HIV specific T-cell function in HIV infected subjects, increasing the survival of HIV specific T-cells in HIV infected subjects, monitoring the efficacy of an anti HIV therapy in an HIV infected subject, monitoring HIV disease progression, and identifying HIV infected subjects that are controllers or chronic progressor. The present invention is also directed to agents useful for treatment of HIV.

Having now generally described the invention, the same will be more readily understood through reference to the following Examples which are provided by way of illustration, and are not intended to be limiting of the present invention, unless specified.

The following examples are put forth so as to provide those of ordinary skill in the art with a complete disclosure and description of how to make and use the methods of the invention, and are not intended to limit the scope of what the inventors regard as their invention.

EXAMPLES

The present invention is described by reference to the following Examples, which are offered by way of illustration and are not intended to limit the invention in any manner. Standard techniques well known in the art or the techniques specifically described below were utilized.

Example 1

Identification of an Evolutionarily Conserved Transcriptional Signature of Exhausted Antigen-Specific CD8+ T Cells Gene expression profiles were generated from populations of tetramer-sorted HIV Gag-specific CD8 T cells from 42 patients; 18 from chronic progressors and 24 from controllers. All patients were off therapy and had detectable HIV-specific CD8+ T cells in the peripheral blood (See Table 1), allowing a median of 21,500 HIV Gag tetramer+ T cells (range 3,000-85,000 cells) to be isolated for microarray analysis from each patient (FIG. 7 a-d). There was a two-log difference in mean viral load between the two cohorts (FIG. 1a). The distribution of HLA-types (Table 1) and the frequency, memory phenotype, and sorted number tetramer+ cells were not significantly different between the groups (FIGS. 7d and e).

The gene expression profiles of Gag-specific CD8+ T cells from chronic progressors showed marked differences to those from controllers (n=518, moderated t-statistic <−2.0, FIG. 1b and Table 1). These tetramer+ gene expression profiles were validated in two ways. First, inspection of the list of genes differentially expressed in either direction revealed genes with known roles in functional or dysfunctional T cell responses. For instance, IL-7R and CD28 were expressed at higher levels in controllers, whereas the inhibitory receptors CD244 and LAG3 were increased in expression in chronic progressors (See Table 1). Second, we found significant similarity at the whole-genome level between dysfunctional CD8+ Gag-specific T cells from progressors and exhausted CD8+ T cells in the mouse model of chronic LCMV infection. We identified the similarity between human and mouse gene expression datasets using an analytical approach called gene set enrichment analysis[14]. In brief, enrichment analysis asks whether a set of genes of interest (in this case genes upregulated in HIV chronic progressors compared to controllers) tends to occur towards the top (or bottom) of a second list of genes rank ordered based on class distinction (in this case the LCMV exhausted vs. memory signatures). Using this approach we found that the HIV chronic progressor signature was significantly enriched in the LCMV exhausted profiles compared with those of functional LCMV memory T cells (FIG. 1c, P=4.8e-005). Thus the transcriptional program associated with T cell exhaustion is evolutionarily conserved between mice and humans.

TABLE 1

Patient characteristics and distribution of class I HLA alleles associated with disease progression

| | HIV Controllers | Chronic Progressors |
|---|---|---|
| Number of subjects | 24 | 18 |
| Gender Male (%) | 22 (92) | 15 (83) |
| Female (%) | 2 (8) | 3 (17) |
| Race (%) White | 19 (79) | 10 (56) |
| Black | 3 (13) | 1 (6) |
| Other/Unknown | 2 (8) | 7 (38) |
| Plasma HIV RNA, copies/ml median (IQR) | Below detection (49-100)[A] | 11,784 (5,035-29,915) |
| CD4+ cell count, cells/mm³ median (IQR) | 792 (666-945)[A] | 468 (358-582) |
| Duration of HIV diagnosis, years median (IQR) | 14 (7-20) | 4 (2-10) |
| HLA B*57 (%) | 8 (33) | 6 (33) |
| HLA B*27 (%) | 7 (29) | 0 (0) |
| All protective HLA alleles[B] | 20 (83) | 8 (44) |

[A]HIV controllers compared to chronic progressors
*P < 0.0001 (non-parametric Mann Whitney test)
[B]Includes HLA B*57, 27, 13, 14, 1503, 51 and 5801

Example 2

PD-1 Ligation Alters Gene Expression in T Cells

Figure 2:
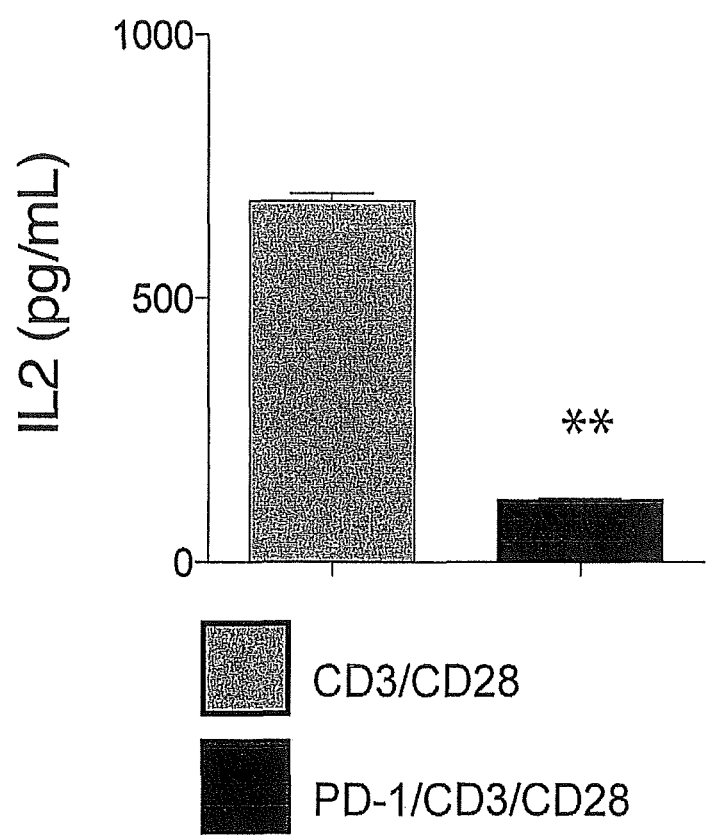
FIG. 2 presents identification of PD-1-induced signature genes. (a) IL-2 secretion from PD-1 expressing Jurkat cells cultured with inhibitory PD-1/CD3/CD28 beads (black bar) or control CD3/CD28 beads (grey bar) measured by ELISA (**P=0.007). (b) Differentially expressed genes in PD-1 Jurkat cells cultured as in a. Top 100 differentially expressed genes from either condition shown. Each column represents an individual replicate sample and each row an individual gene, and colored to indicate normalized expression. (c) Dose-dependent induction of the PD-1 signature genes in primary human CD4$^+$ T cells cultured either with CD3/CD28 beads (grey columns) or PDL1/CD3/CD28 beads with a 2-fold decreasing amounts of bead-bound PD-L1-Ig in replicates of five (black columns). (d) Correlation between inhibition of proliferation and upregulated of PD-1 signature genes presented in c. PD-1 signature gene expression summarized by average Z score (x-axis) and extent of proliferation by primary T cells over a four day period of stimulation with the relevant beads (y-axis, $R^2$=0.98).
Figure 2:
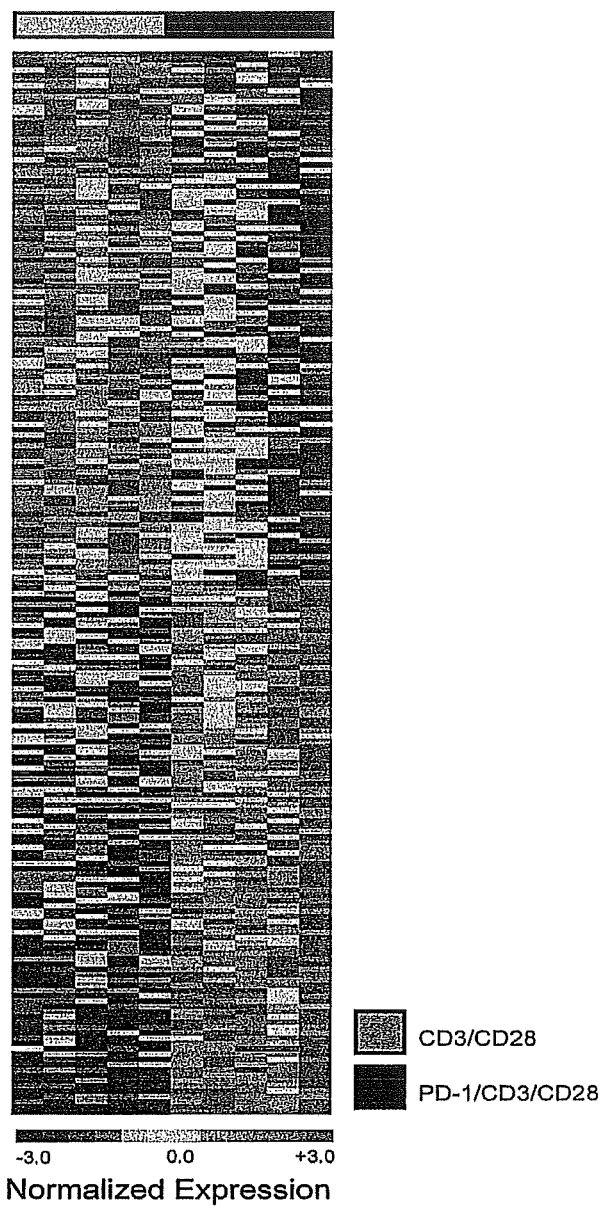
Figure 2:
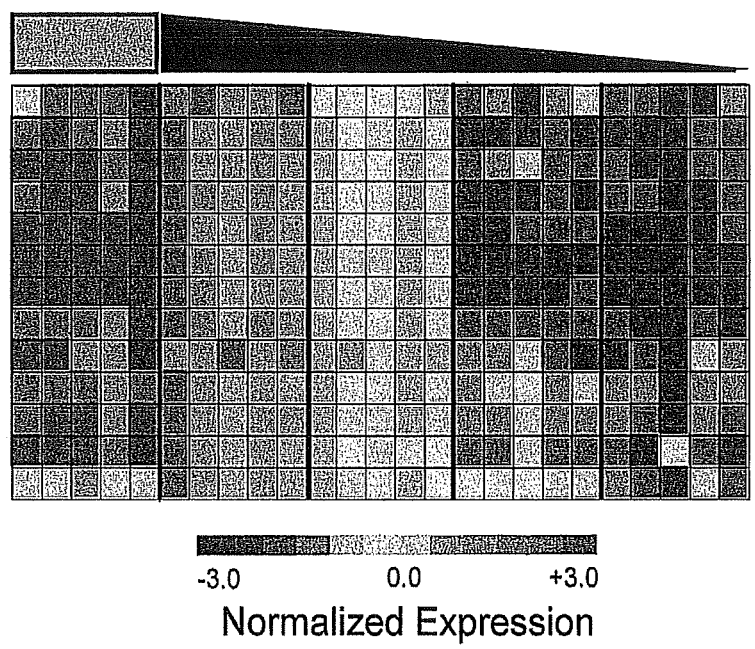
Figure 2:
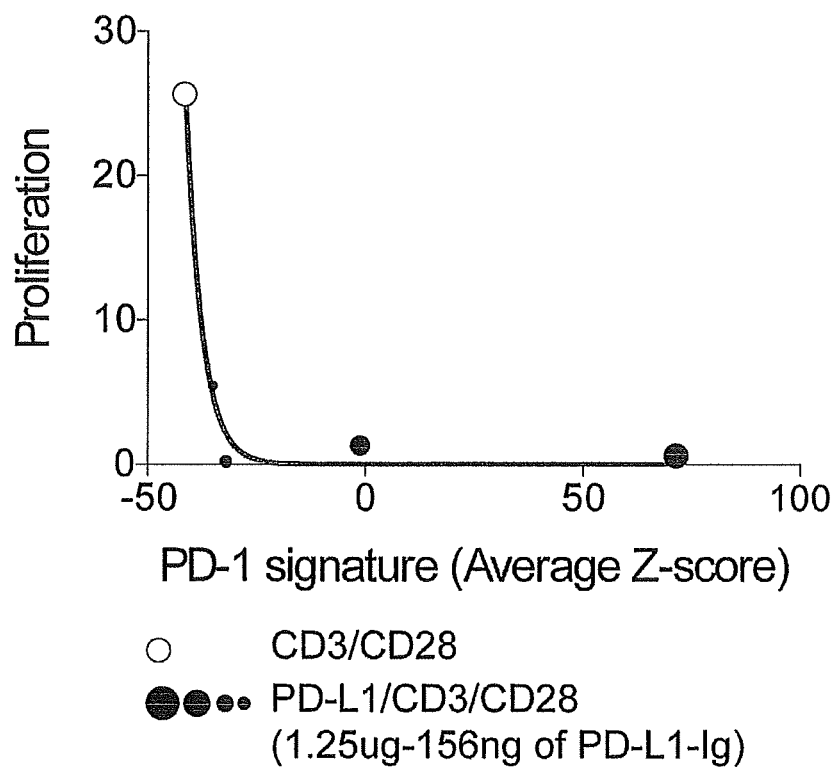

To determine whether the exhausted signature described in Example 1 was influenced by PD-1 ligation, the genes upregulated by PD-1 ligation were identified by using a PD-1 expressing cell-line that provided a tractable in vitro system. PD-1 expressing Jurkat cells were incubated with beads coated with a cross-linking antibody to PD-1 together with antibodies to CD3 and CD28 (PD-1/CD3/CD28 beads); or with beads coated with equivalent amounts of control antibody together with CD3 and CD28 (CD3/CD28 beads). The inclusion of CD3/CD28 induced concomitant TCR signaling and allowed the functional inhibition mediated by PD-1 ligation to be detected. Consistent with previous reports, incubation with PD-1/CD3/CD28 beads significantly decreased production of IL-2 as compared to cells incubated with CD3/CD28 beads (P=0.007, FIG. 2a)[9,15]. Comparison of microarray data from cells cultured in either condition identified over one thousand genes that were significantly upregulated in cells functionally inhibited by PD-1 (n=1179, t>2.0, FIG. 2b and FIG. 14). A similar number of genes was reduced in expression following PD-1 ligation (n=1361, t<2.0, FIG. 2b and FIG. 14).

This pattern of gene expression was validated under more physiologic conditions, by using beads coated with the natural ligand of PD-1, PDL1, as an Ig-fusion protein. Primary human CD4+ T cells were studied to provide a more representative cell type using a quantitative multiplex RT-PCR reaction described previously[16,17]. 13 representative genes were selected for validation based on their differential expression in PD-1-ligated Jurkat cells. Incubation of human T cells with PDL1-Ig/CD3/CD28 beads led to the coordinate upregulation of these representative PD-1 signature genes in a PDL1-Ig dose-dependent manner (FIG. 2c) compared to resting (not shown) or CD3/CD28 stimulated T cells. Induction of the PD-1 signature correlated with the extent of inhibition of proliferation in the primary T cells (FIG. 2d). Thus ligation of PD-1 in CD3/CD28 stimulated cells induces a specific transcriptional program in both Jurkat cells and primary human T cells.

Example 3

Figure 3:
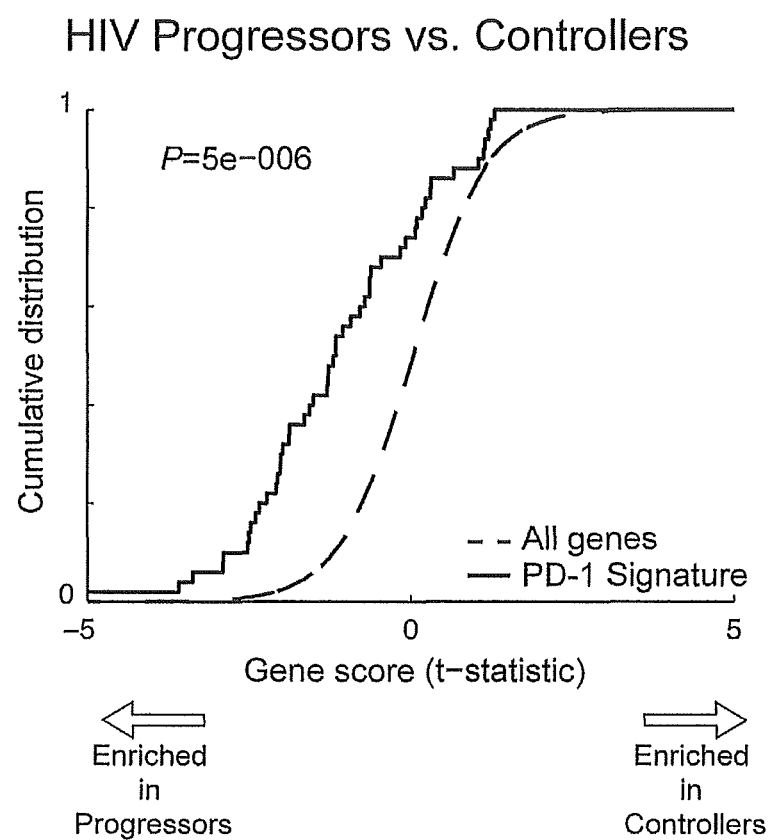
FIG. 3 presents demonstrates that PD-1-induced genes are coordinately upregulated in exhausted HIV-specific and LCMV-specific CD8$^+$ T cells. (a) Enrichment analysis of PD-1 signature genes in HIV progressors. The top 200 genes in the Jurkat-derived PD-1 signature were tested for enrichment in the rank-ordered list of genes differentially expressed in progressors. (b) Enrichment analysis of the PD-1 signature in exhausted CD8$^+$ T cells from the Clone 13 LCMV mouse model compared with functional LCMV-specific memory CD8$^+$ T cells. (c) Unsupervised hierarchical clustering of samples from controllers (grey bars) or progressors (black bars) samples in the space of the 200 gene PD-1 signature. The two major clusters are arbitrarily colored blue and red to help visualize unequal distribution of controller and progressor samples. (d) Confusion matrix quantifying the accuracy of a gene-expression predictor based on Baysian model averaging of Probit models.
Figure 3:
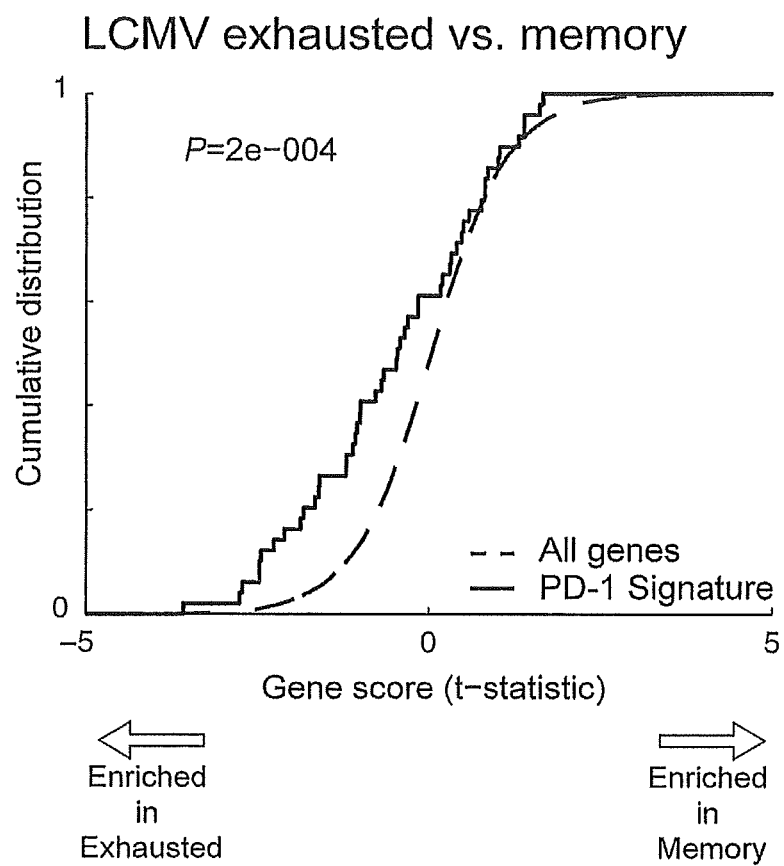
Figure 3:
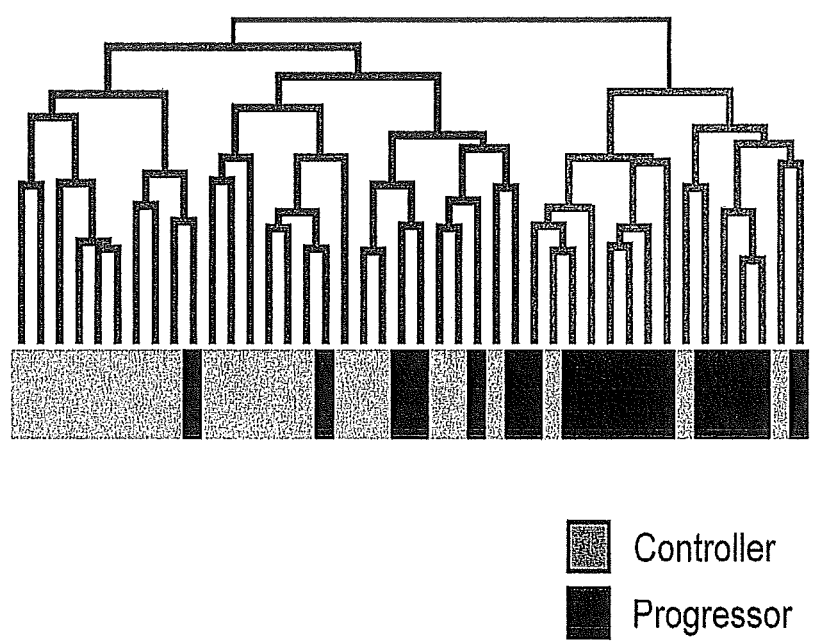

PD-1-Induced Genes are Coordinately Upregulated in Exhausted T Cells from Humans and Mice To determine whether the transcriptional program induced by PD-1 signaling defined in vitro could be detected in gene expression profiles from exhausted HIV-specific and LCMV-specific T cells ex vivo it was determined whether PD-1 induced genes were coordinately upregulated in Gag-specific T cells from HIV chronic Progressors, the T cell population in which PD-1-mediated inhibition would be expected to be more pronounced. The top 100 genes that were most upregulated by PD-1 ligation in Jurkat cells were selected. Using enrichment analysis, it was found that this signature of genes was significantly upregulated in the HIV chronic progressors compared with controls (FIG. 3a, P=5e-006). Similar results were obtained for PD-1-induced gene sets of 50 and 200 genes (data not shown). Interestingly, this difference was in contrast to the expression of PD-1 itself, which was equivalent as measured by microarray analysis between the two cohorts (Supplementary FIG. 2). These data demonstrate that coordinate upregulation of a signature of genes induced by PD-1 ligation occurs in exhausted HIV-specific T cells, even when upregulation of individual genes associated with T cell exhaustion is not be detected for biological or technical reasons.

To determine whether this finding could be generalized to other populations of exhausted T cells enrichment analysis was used. Using enrichment analysis, it was found that PD-1 signature genes were significantly upregulated in exhausted LCMV-specific CD8+ T cells compared with their functional memory counterparts (FIG. 3b, P=2e-004). Thus upregulation of PD-1 induced genes may be a hallmark of T cell exhaustion in humans and mice.

Expression of PD-1 signature genes was sufficiently dissimilar between chronic progressors and controllers that the signature could effectively distinguish between the two classes of antigen-specific CD8+ T cells. The ability of PD-1 signature genes to differentiate HIV-specific T cells from chronic progressors and controllers was tested using two analytic methods. First, hierarchical clustering in the space of the PD-1 signature genes was performed (FIG. 3c). In this unsupervised approach, two main clusters of samples were apparent (colored blue and red, FIG. 3c) which contained either predominantly controller samples (blue cluster) or chronic progressor samples (red cluster). Second, the accuracy with which PD-1 signature genes distinguished each class of tetramer+ samples was quantified. Classification models were applied to the data, and the model with the best performance was a Bayesian model averaging of linear models[42]. This gene expression classifier correctly identified samples from chronic progressors and controllers with an accuracy of 81% (FIG. 3d). Alteration of PD-1 signature genes is therefore a distinguishing feature of T cell dysfunction in HIV.

Example 4

Figure 4:
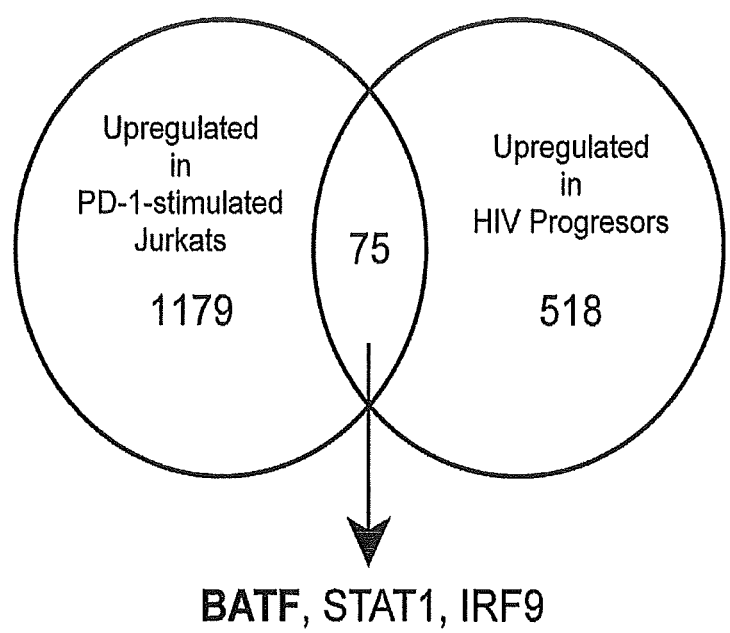
FIG. 4 demonstrates that expression of BATF is upregulated by PD-1 and increased in exhausted T cells. (a) Venn diagram representation of the three transcription factors upregulated in Gag-specific T cells from HIV progressors and Jurkat cells after PD-1 ligation (t>2.0). (b) Mean fold-change in BATF expression measured by real-time quantitative PCR in primary human CD4 (left bars) and CD8 (right bars) T cells cultured with CD3/CD28 beads (grey bars) or PDL1/CD3/CD28 beads (black bars) for 4 days. Data represents independent experiments with three normal donors (*P<0.0001 for CD4 and P<0.001 for CD8 T cells). (c) Relative BATF expression in arbitrary expression units from Affymetrix analysis of sorted naïve (white bars) or HIV gag-specific CD8 T cell populations from controllers (grey bar) and progressors (black bar) (*P<0.05 and **P<0.001). (d) Relative BATF expression measured by real-time quantitative PCR in LCMV-specific CD8 T cells from mice infected with LCMV Armstrong infected mice (grey bar), or LCMV Clone 13 infected mice sorted on the basis of PD-1 expression (black and white bars) (*P<0.05).
Figure 4:
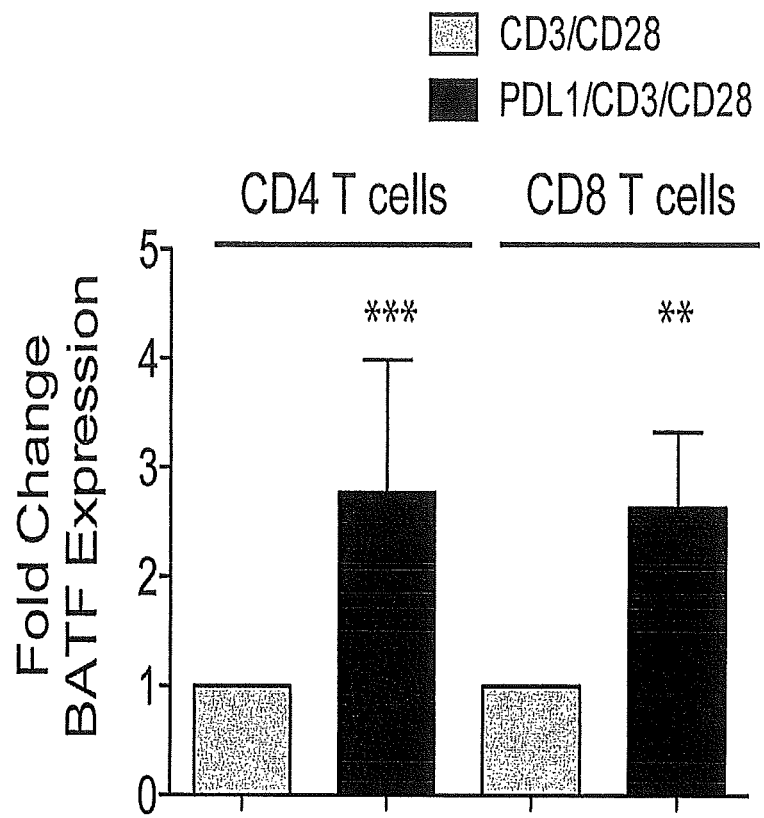
Figure 4:
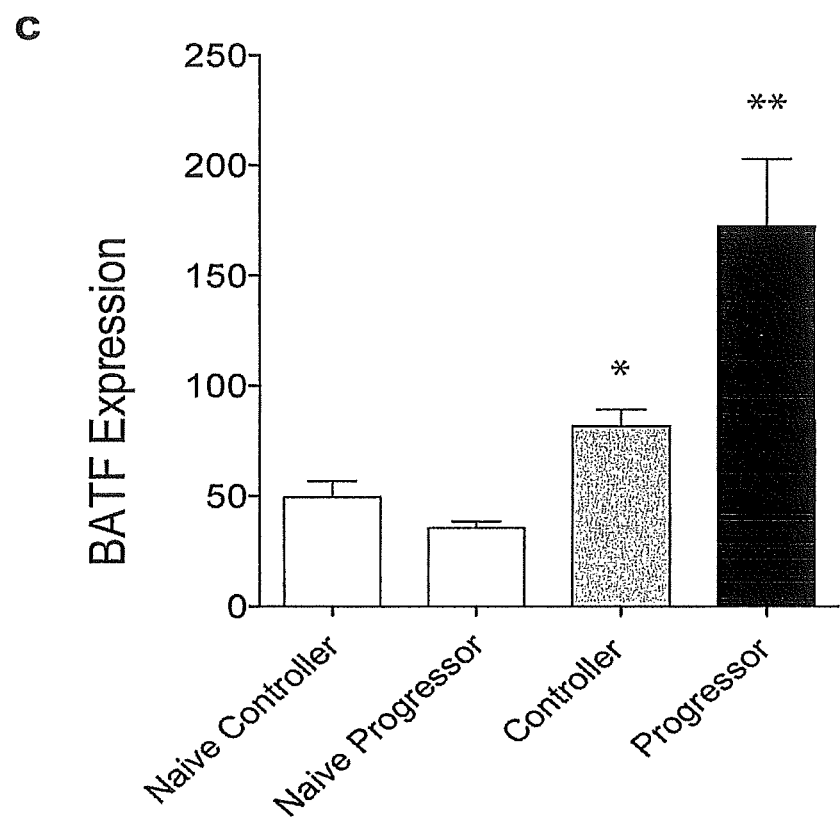
Figure 4:
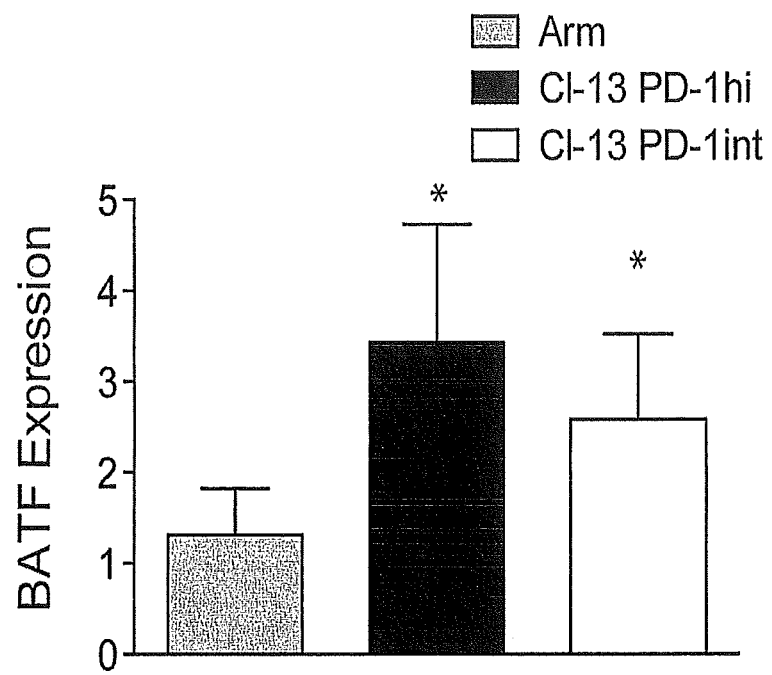

BATF is Induced by PD-1 Ligation and is Increased in Expression in Exhausted T Cells from Humans and Mice To determine if genes upregulated by PD-1 in exhausted cells might include those involved in the inhibition of T cell function, genes that were both upregulated by PD-1 ligation in Jurkat cells and increased in HIV chronic progressors compared with controllers (t<2.0 and t<−2.0, respectively, FIG. 4a and Supplementary Table 15) were identified. Because of their broad effect on cellular function transcription factors were the focus of these studies. Of the 75 genes common to both gene sets, only three were transcription factors: BATF, STAT1 and IRF9 (FIG. 4a and Supplementary List 3). BATF was selected for further analysis because it has been observed to be upregulated during CD8+ memory differentiation in humans and mice[16], and because it has been shown to function as a negative regulator of AP-1 activity[20,21]. Quantitative RT-PCR was used to confirm that PD-1 ligation induced BATF expression in primary human T cells. BATF expression showed a 3-4 fold increase in expression after incubation PDL1/CD3/CD28 beads compared with CD3/CD28 beads, indicating that BATF expression is increased by PD-1 ligation (P<0.0001 and P<0.001, respectively, FIG. 4b).

High BATF levels were seen in antigen-specific T cells with the greatest degree of dysfunction. As we have previously described[22], BATF expression was lowest in naïve human CD8 T cells and was not significantly different in naïve CD8 T cells from controllers or chronic progressors (P=NS, FIG. 4c). However, BATF expression was significantly higher in exhausted Gag-specific CD8 T cells from chronic progressors than in HIV-specific T cells from controllers (P=0.003, FIG. 4c).

CD8+ T cells from the LCMV model of acute and chronic viral infection were evaluated. In chronic infection, PD-1 surface expression defines two subpopulations of exhausted LCMV-specific T cells: $PD^{hi}$ and $PD-1^{int}$. Of the two, $PD-1^{hi}$ T cells are more terminally differentiated and cannot be rescued by PD-1 pathway blockade[23]. Consistent with this, BATF levels were significantly higher in the $PD-1^{hi}$ subset than in the $PD-1^{int}$ subset (P=0.026, FIG. 4d). BATF expression was greater in either exhausted subset than in functional memory CD8+ T cells from acute infection (P=0.018). Thus in humans and mice, BATF levels are highest in antigen-specific T cells with poorest function.

Genes that are known to anti-correlate with BATF[22] were identified. This allowed for establishment of a set of genes that would include putative targets of BATF repression in an independent microarray dataset of human T cells. The top 200 genes whose expression was most anti-correlated with BATF were selected. Using enrichment analysis, it was found that BATF anti-correlated genes were significantly increased in HIV controllers compared with chronic progressors (Supplementary FIG. 3, P=4e-006), consistent with the idea that BATF functions as a transcriptional repressor in HIV-specific T cells from chronic progressors.

Example 5

Overexpression of BATF in Primary Human T Cells Recapitulates PD-1-Mediated T Cell Exhaustion Previous data have demonstrated a role for BATF in inhibiting murine thymocyte proliferation[24]. BATF was overexpressed in primary human CD4+ and CD8+ T cells using lentiviral transduction to determine whether BATF inhibited T cell function. T cells transduced with this method consistently showed a 3-5 fold increase in BATF expression over endogenous levels (FIG. 10). This extent of overexpression was in the physiologic range because it is similar to the difference seen in BATF levels between exhausted T cells and functional T cells in humans and mice, as well as to that induced by PD-1 ligation in vitro, (FIG. 4b-d). Overexpression of BATF in primary human T cells markedly reduced proliferation in response to CD3/CD28 (P=0.002, FIGS. 5a and b). Apoptosis was also slightly increased in BATF overexpressing cells following stimulation, consistent with the previous defined role of PD-1 signaling in reducing cell survival[25] (P=0.013, FIGS. 5a and b). Overexpression of BATF also significantly reduced IL-2 secretion following CD3/CD28 stimulation, (P=4.5e-005 FIG. 5c). However, BATF overexpression was not overtly toxic to T cells because IFN-γ secretion was not significantly reduced compared with vector controls. Thus increased expression of BATF reduces proliferation and IL2 secretion but not IFN-γ secretion, recapitulating features of exhausted T cells.

Example 6

Reducing BATF Expression Partially Rescues PD-1 Mediated T Cell Dysfunction

Figure 5:
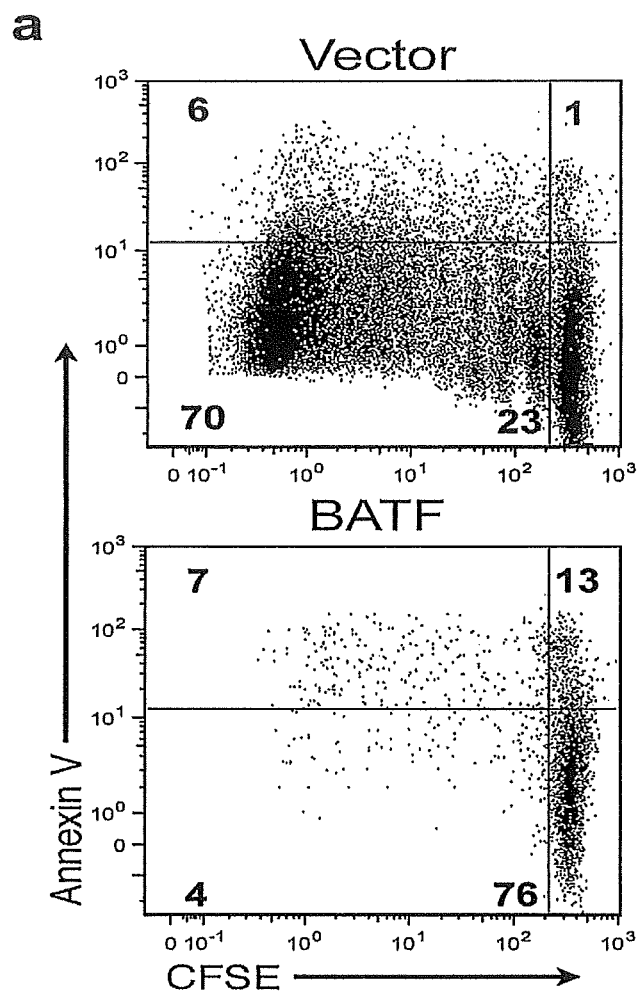
FIG. 5 demonstrates that BATF inhibits T cell function and is required for PD-1-mediated inhibition. (a) CFSE-labeled primary human CD4 or CD8 T cells from healthy volunteers transduced with a lentivirus expressing BATF (lower plot) or with control vector (upper plot) and cultured for 4 days with CD3/CD28 beads. (b) Summary data of proliferation (percent CFSE$^{dim}$Annexin$^-$, upper plot), and cell death (percent Annexin V$^+$, lower plot) in primary human CD4 or CD8 T cells (n=14) transduced as in (a) and cultured for 4 days with CD3/CD28 beads. (c) IL-2 (left bars, P=4.5e-05) and IFN-γ (right bars, P=NS) secretion by primary human CD4 T cells (n=10) transduced as in (a) and cultured with CD3/CD28 beads. Data is shown normalized to the empty vector condition. (d) BATF expression in PD-1 expressing Jurkat cells lentivirally transduced with shGFP (control) or two separate shBATF sequences measured by western blot (upper panel) or quantitative PCR (lower panel). (e) IL-2 secretion by PD-1 Jurkat cells transduced with shGFP (white and black bar) or shBATF (grey bars) cultured with either CD3/CD28 beads (white bar) or PD-1/CD3/CD28 beads (black and grey bars) for 18 hours. Data shows average absolute IL-2 production (+/− standard deviation) and is representative of three independent experiments (*P<0.03 for all experiments). (f) Correlation between rescue of IL-2 secretion in PD-1 expressing Jurkats cultured with PD-1/CD3/D28 beads and BATF expression in cells transduced with shGFP (white symbol) or five different shBATF sequences (black symbols). (g) Proliferation of CD8$^+$ T cells from healthy volunteers (n=4) transduced with shGFP (white and black bar) or shBATF (grey bars) cultured with either CD3/CD28 beads (white bar) or PDL1-Ig/CD3/CD28 beads (black and grey bars) for four days (*P=0.047).
Figure 5:
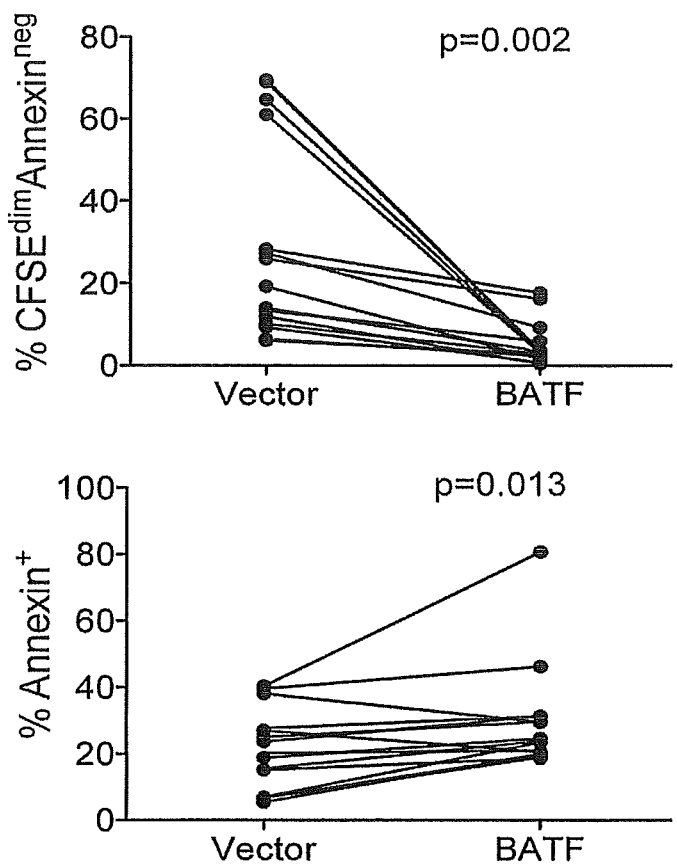
Figure 5:
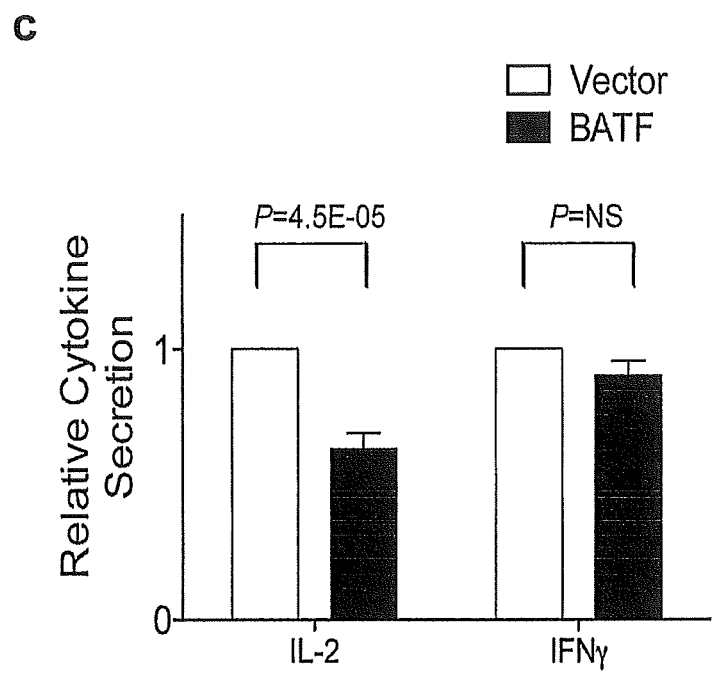
Figure 5:
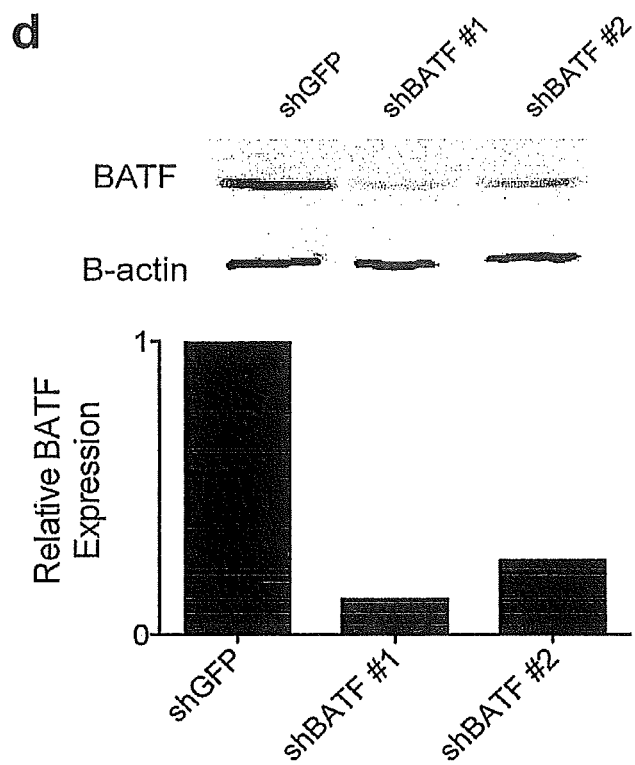
Figure 5:
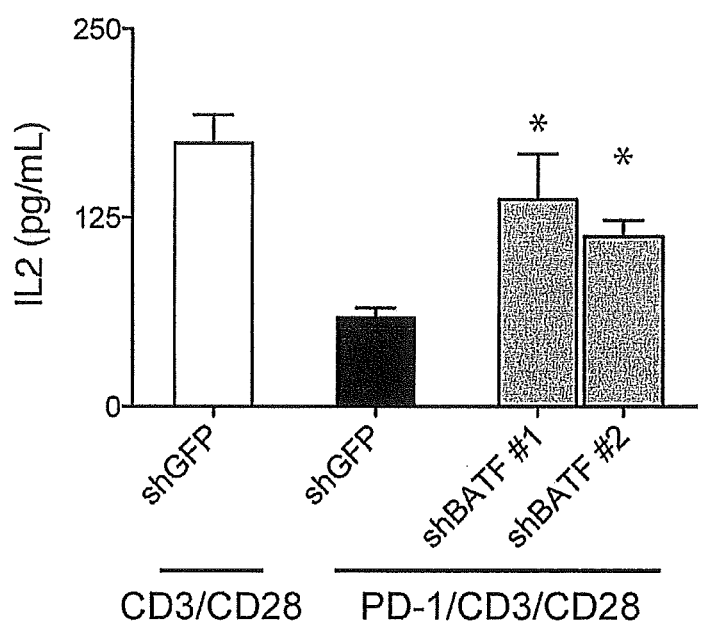
Figure 5:
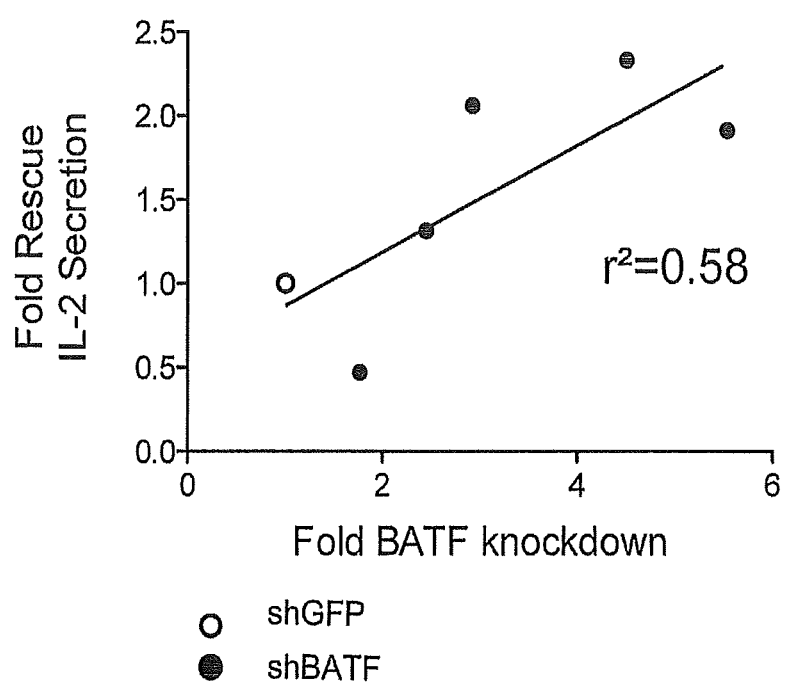
Figure 5:
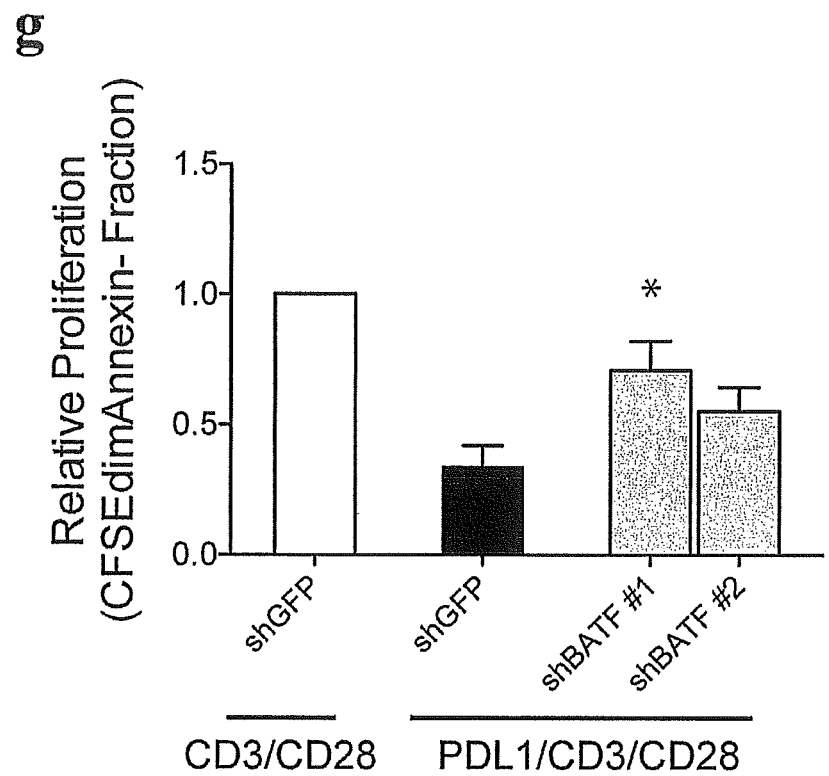

To determine whether BATF is required for PD-1-mediated inhibition of T cell function, PD-1-expressing Jurkat cells were transduced with shRNA sequences directed at BATF, effectively reducing levels of BATF transcript and protein to −10-20% of endogenous levels (FIG. 5d). Compared with control hairpins, depletion of BATF in Jurkats with two different hairpins markedly increased IL2 secretion in PD-1/CD3/CD28 treated cells (P=0.03, FIG. 5e), reversing inhibition almost to levels seen in CD3/CD28 stimulated cells. Moreover, when the analysis was extended to additional hairpins with less efficient knockdown of BATF, it was found that the extent of BATF depletion correlated with the degree of rescue of PD-1 mediated inhibition in Jurkat cells (FIG. 5f). The ability of BATF depletion to rescue inhibition mediated by PD-L1 in primary T cells was determined. shRNA-mediated reduction of BATF in primary CD8+ T cells from healthy donors significantly increased proliferation in PD-L1-inhibited cells almost to levels seen in CD3/CD28 stimulated cells. Thus BATF depletion rescues PD-1 mediated inhibition of IL2 secretion and proliferation in cell lines and primary CD8+ T cells.

Example 7

Silencing BATF Improves HIV-Specific T Cell Function

Figure 6:
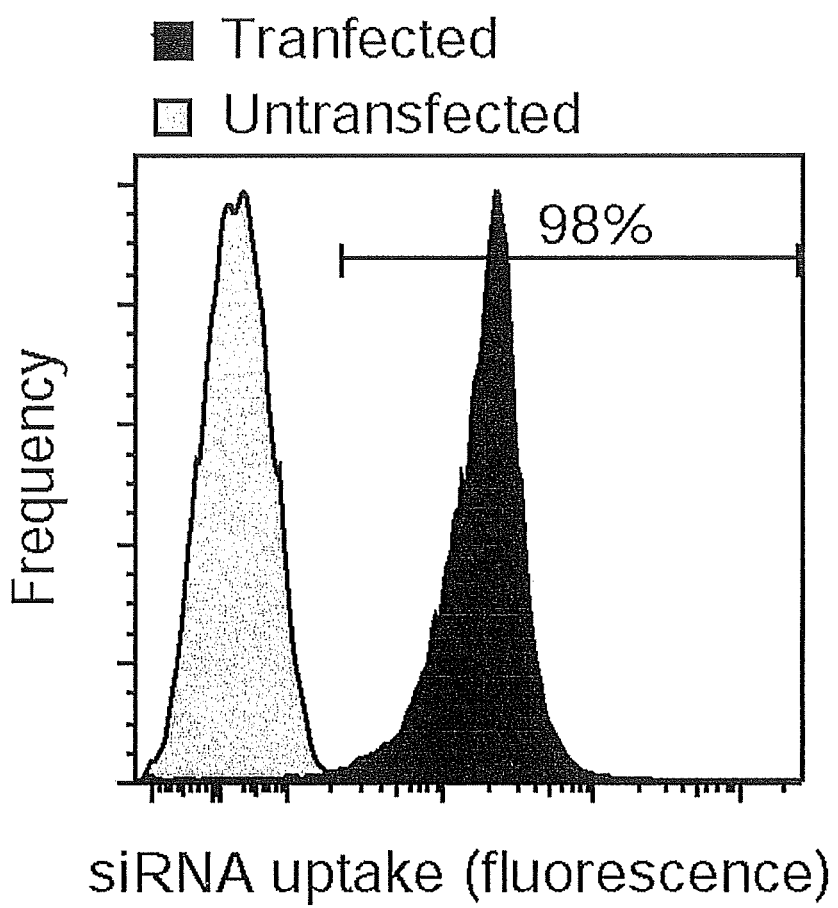
FIG. 6 demonstrates the ability of BATF knockdown to improve antigen-specific T cell function in HIV patients.
Figure 6:
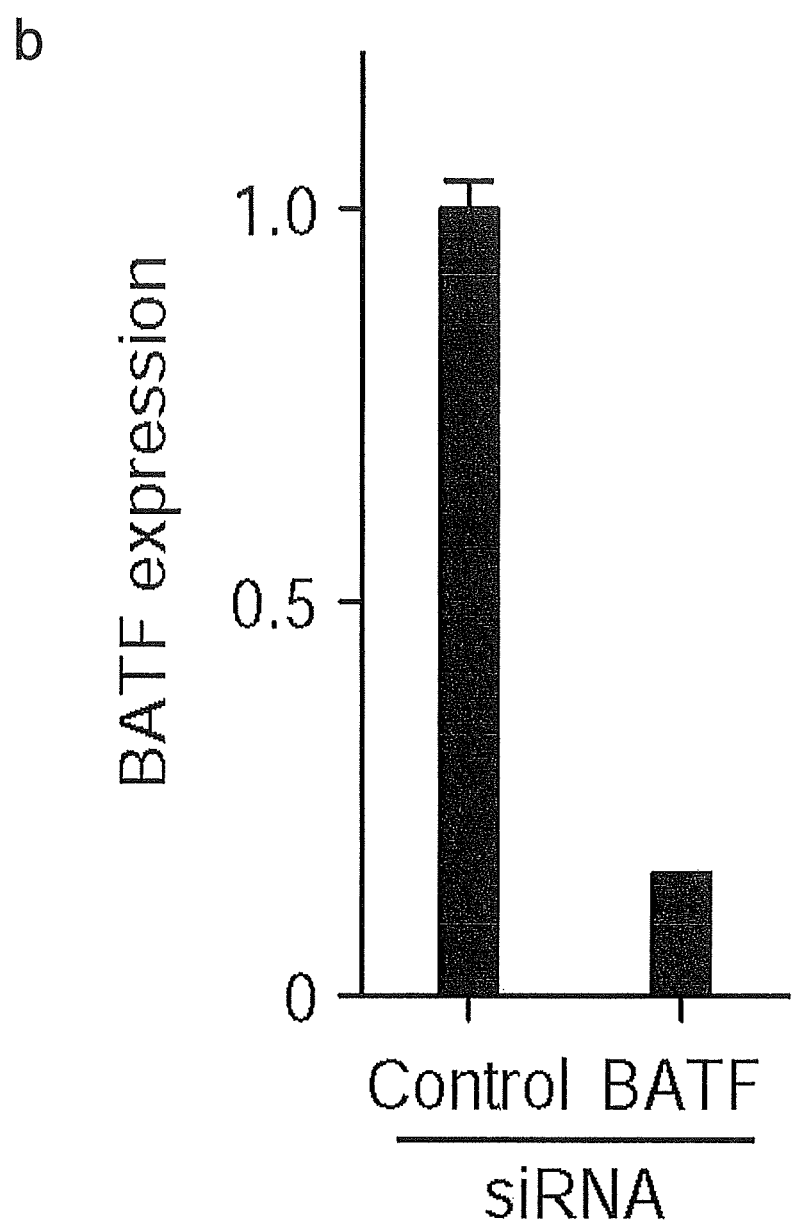
Figure 6:
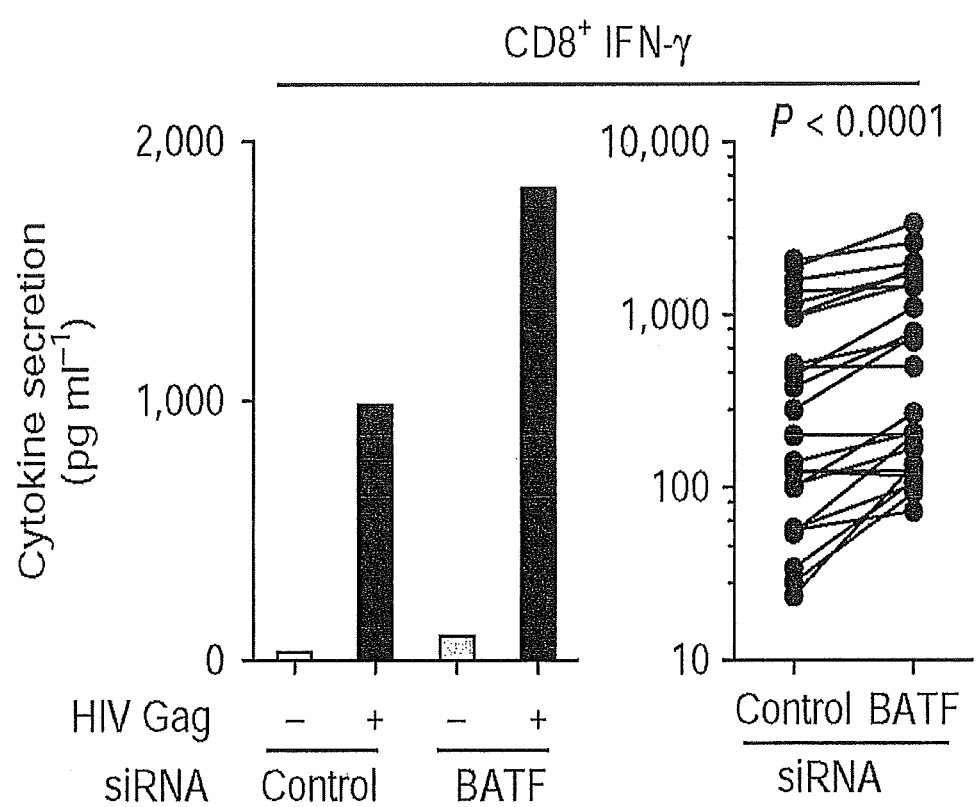
Figure 6:
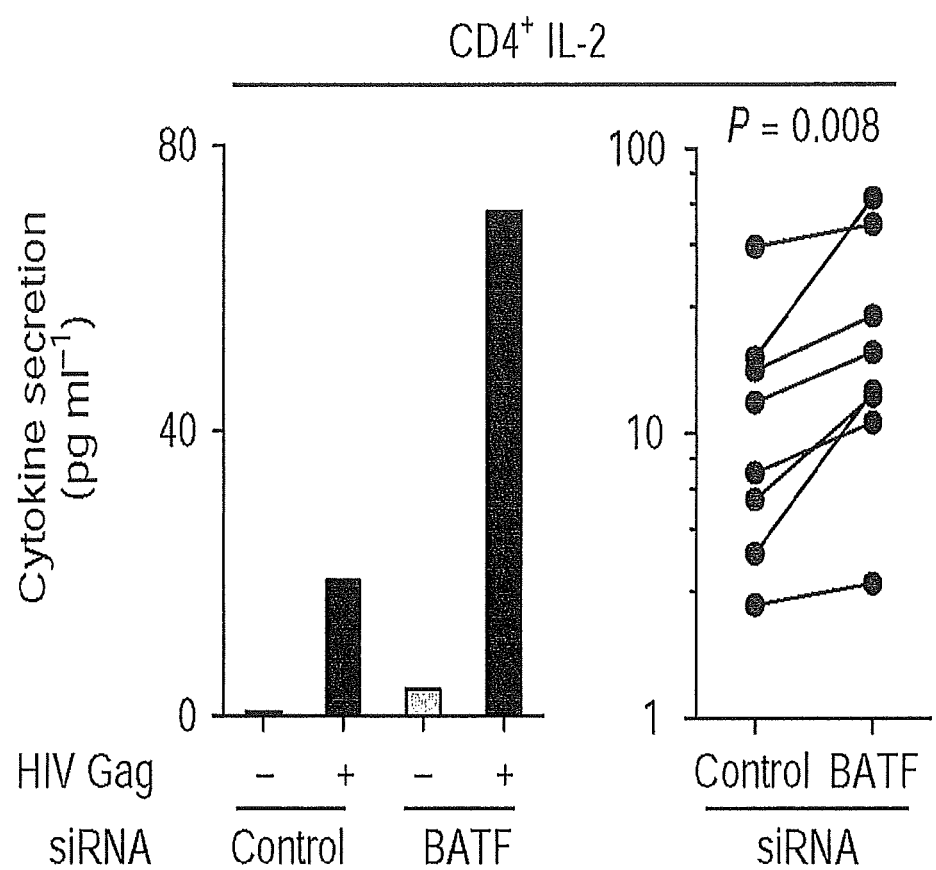
Figure 6:
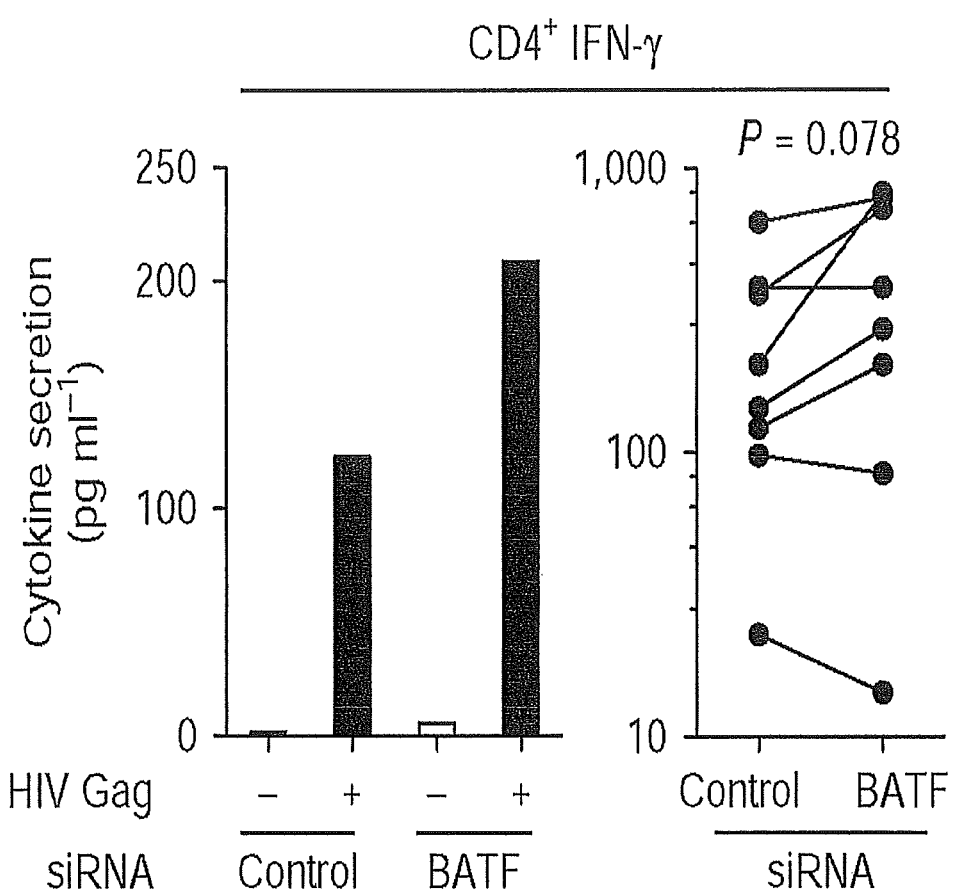
Figure 6:
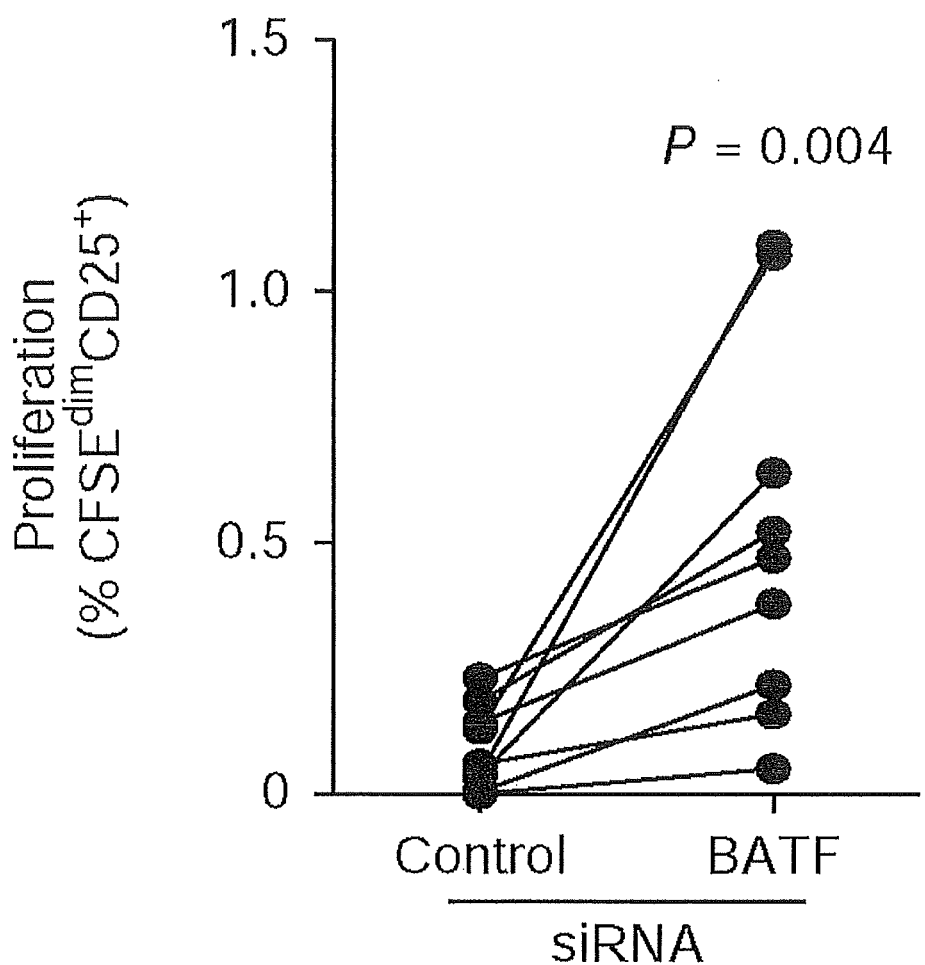

Whether silencing BATF would improve the function of HIV-specific T cells was tested. HIV-specific T cell function after BATF knockdown (FIGS. 6A and 6B) was assessed by measuring cytokine secretion or proliferation in response to Gag peptides. BATF knockdown caused a significant increase in CD8+ Gag-specific IFN-γ secretion (FIG. 6C) compared to a control siRNA pool. BATF knockdown increased IFN-γ secretion an average of 60% (P<0.0001). Similar results were seen in HIV-specific CD4+ T cells where silencing BATF caused a two-fold increase in Gag-specific IL-2 secretion (P=0.008, FIG. 6D) and a trend towards increase IFN-γ secretion (P=0.078, FIG. 6E). HIV-specific CD8+ T cell proliferation was also increased by BATF knockdown, with a 5-fold increase in proliferating cells incubated with optimal Gag peptides (P=0.004, FIG. 6F). These data demonstrate that reducing BATF expression therefore increases the function of exhausted HIV-specific T cells.

Example 8

Exhausted CD8+ T Cells Display Increased Upregulation of PD-1 Signature Genes Compared to Human Virus-Specific CD8+ Cells Associated with Functional T Cell Responses The upregulation of PD-1 signature genes in exhausted CD8+ T cells contrasted with that seen in profiles of human virus-specific CD8+ T cells associated with functional T cell responses. Using single-sample GSEA, we found that the PD-1 signature was significantly more enriched in HIV-specific CD8+ T cells than in antigen-specific CD8+ T cells specific for CMV (P<0.01), EBV (P<0.001), or influenza virus (P<0.001) from healthy HIV-uninfected donors (FIG. 17). Notably, the PD-1 signature was significantly more enriched in HIV-specific T cells than in EBV-specific T cells, despite the fact EBV-specific T cells express PD-1.

Example 9

BATF Expression Kinetics Temporally Correlates with Upregulation of PD-1

In order to define the kinetics of BATF expression following infection with a persistent virus, BATF expression in murine virus-specific CD8+ T cells was compared during acute and chronic infection (FIG. 18A). As early as day 8 post-infection, DbGP33-specific CD8+ T cells in Cl13 infection expressed significantly higher levels of BATF than in Arm infection (P=0.02). BATF expression was maintained at higher levels in virus-specific cells in Cl13 infection at day 15 and by day 30 was −7 fold higher than in DbGP33-specific CD8+ T cells generated during LCMV Arm infection (P=0.02). The increased expression of BATF during acute and chronic infection was coincident with the upregulation of PD-1 as GP33-specific T cells showed increased levels of both PD-1 and BATF by day 8 (FIGS. 18A and 18B). Increased BATF expression is therefore an early and persistent feature of exhausted CD8+ T cells in the setting of chronic viral infection in vivo and correlates, at least temporarily, with upregulation of PD-1.

Example 10

Silencing of BATF Increases IL-2 Expression in PD-1 Jurkat Cells

Whether depletion of BATF enhances T cell function was examined using shRNA-mediated gene-silencing (FIGS. 19A and 19B). Compared with control hairpins, depletion of BATF in Jurkat cells with two different shRNA sequences (FIG. 19A) significantly increased IL-2 expression in cells cultured with PD-1/CD3/CD28 (P<0.01, FIG. 19A). Particularly, inhibition was reversed to levels seen in CD3/CD28 stimulated cells. Testing additional hairpin sequences showed that there was a strong correlation between the extent of knockdown and degree of increase in IL-2 secretion, confirming the on-target specificity of BATF silencing (RS −0.82, P=0.056; FIG. 19B).

BATF silencing also increased IL-2 expression in cells stimulated with CD3/CD28 without exogenous PD-1 cross-linking (P<0.01, FIG. 19A), indicating that pathways in addition to PD-1 could inhibit cell activation via BATF. Consistent with this, the expression of BATF across 42 samples of HIV-specific CD8+ T cells correlated significantly with expression levels of several receptors with known or putative inhibitory function.

Materials and Methods

Subjects and Samples

Subjects were recruited from outpatient clinics at local Boston hospitals, and referred from providers throughout the US, following institutional review board approval and written informed consent. HIV controllers included elite controllers (n=20) with HIV RNA below the level of detection in the absence of antiviral therapy (ARV) for the respective available ultrasensitive assay (e.g., <75 copies per ml by bDNA or <50 copies per ml by ultrasensitive PCR); and viremic controllers (n=4) with HIV RNA levels without ARVs <2000 copies per ml. Chronic progressors were defined as having HIV RNA levels without ARVs above 2,000 copies (Table 1). To qualify as an HIV controller, each subject had to have a minimum of 3 determinations within the respective range of HIV plasma RNA spanning at least a 12-month period.

Flow Cytometry and Sorting

PBMC were isolated via density centrifugation and were stained with a cocktail of antibodies chosen to exclude irrelevant lineages and dead cells, anti-CD8 and MHC Class I HIV-Gag-specific tetramers to identify the antigen-specific populations, and antibodies against CD62L and CD45RA to characterize the memory phenotype populations of the tetramer+ fraction. CD8+tetramer+ cells were sorted using a FACSAria Cell Sorter (BD Biosciences). Following sorting, cells were pelleted and resuspended in TRIzol reagent (Invitrogen, Carlsbad, Calif.). Experiments with Annexin V staining were carried out according to the manufacturer's instructions (BD Biosciences). All experiments examining proliferation via CFSE dilution were collected on a FC500 flow cytometer (Beckman Coulter, Fullerton, Calif.). Analysis of flow cytometry data was carried out using FlowJo software (version 8.8.6, Tree Star)

Cell Culture

PD-1 expressing Jurkat cells were generated by transduction with a lentivirus expressing full-length PD-1, and maintained in RPMI 1640 (MediaTech, Manassas, Va.) supplemented with 10% Fetal Bovine Serum (Hyclone, Logan, Utah), 1% of both pen/strep and L-glutamine, 16.6 ug/ml gentamicin (Gibco/Invitrogen) and 10 ug/ml blasticidin (InvivoGen, San Diego, Calif.).

Primary human CD4 or CD8 T cells from the peripheral blood of healthy volunteers were isolated via magnetic selection using the CD4 or CD8 isolation kit according to the manufacturer's instructions (Miltenyi Biotec, Auburn, Calif.). In most cases, cells were labeled with CFSE according to manufacturer's instructions (Molecular Probes/Invitrogen).

293FT cells used to generate lentivirus particles were maintained in DMEM (MediaTech) supplemented with 10% Fetal Bovine Serum (Hyclone), 1% of both pen/strep and L-glutamine and 16.6 ug/ml gentamicin (Gibco/Invitrogen).

Microarray Data Acquisition and Analysis

Tetramer-sorted human CD8 T cells, Jurkat cells following 18 h of stimulation were resuspended in TRIzol. RNA extraction was performed using the RNAdvance Tissue Isolation kit (Agencourt). Concentrations of total RNA were determined using a Nanodrop spectrophotometer (Wilmington, Del.) or via the Ribogreen RNA quantitation kit (Molecular Probes/Invitrogen). RNA purity was determined by Bioanlyzer 2100 traces (Agilent Technologies, Santa Clara, Calif.). Total RNA was amplified using the WT-Ovation Pico RNA Amplification system (NuGEN, San Carlos, Calif.) according to the manufacturer's instructions. Following fragmentation and biotinylation, cDNA was hybridized to Affymetrix HT HG-U133A or HG-U133A2.0 microarrays.

Prior to analysis, microarray data was pre-processed and normalized using robust multi-chip averaging, as previously described[22]. Differentially expressed genes between classes were ranked using Smyth's variance-moderated t-test[40]. Unsupervised hierarchical clustering was performed using GenePattern[41]. Gene set enrichment analysis was performed as previously described using the Zhang statistic as implemented in the program RenderCat[14]. For the classification of chronic progressor vs. controller samples using PD-1 signature genes, we tested various classification models including support vector machine and Bayesian model averaging of linear models, probit models or logistic models as we have previously described[42]. Linear models provided the superior classification performance, and predictor accuracy was tested using leave-one-out cross validation.

Quantitative PCR

Expression of BATF following in vitro stimulation of primary human T cells, shRNA and overexpression experiments was determined by real-time quantitative PCR. Briefly, RNA was isolated from cells resuspended in TRIzol and cDNA was generated from a reverse transcription reaction using the ImProm-II Reverse Transcription System (Promega, Madison, Wis.) according to the manufacturer's directions. Normalized BATF expression was then determined in a real-time PCR reaction using Taqman gene expression assays for BATF (assay #Hs00232390_m1) and β-actin (Hs00357333_g1) which served as a loading control.

Quantitative multiplex RT-PCR via ligation-mediated amplification was carried out as previously described[16]. PD-1 signature genes were selected for the multiplex validation panel based using criteria previously established[16] and sequences for primer sets are available upon request.

Lentiviral Vectors and Transduction

Lentiviral vectors encoding shRNA hairpin sequences targeting BATF or GFP as control as well as a puromycin resistance cassette in the pLKO.1 backbone were obtained from The RNAi Consortium (TRC, http://broadinstitute.org/rnai/trc) of the Broad Institute (Cambridge, Mass.). The lentiviral vector used to overexpress BATF was generated by gateway cloning of full-length human BATF cDNA (Open Biosystems, Huntsville, Ala.) into the pLenti6.2/V5-DEST vector that includes a blasticidin resistance cassette (Invitrogen). Lentivirus-containing supernatant was generated according to TRC protocols (http://www.broadinstitute.org/rnai/trc/lib) via a lipid-based delivery system using TransIT-LT1 transfection reagent (Mirus Bio, Madison, Wis.) and 293FT cells provided by the TRC.

For lentiviral transduction of primary human T cells, following isolation and CFSE labeling, cells were placed at a concentration of $2\times10^6$ cells/well in 24 well plates previously coated with 2.5 ug/ml of anti-CD3 (OKT3 clone, eBiosciences, San Diego, Calif.) and anti-CD28 (CD28.2 clone, BD Biosciences) antibodies in media comprised of RPMI 1640 supplemented with 10% FBS, 1% of pen/strep, L-glutamine and HEPES and 16.6 ug/ml gentamicin (Gibco/Invitrogen), in the presence of 20 U/ml recombinant human IL-2 (Roche Diagnostics, Basel, Switzerland). Following 2 days of stimulation, cells were counted and placed in wells of a 96 well U-bottom plate at a concentration of $2\times10^5$ cells per well in media supplemented with 8 μg/ml of polybrene (Sigma, St. Louis, Mo.) and 20 U/ml rhIL-2 together with lentivirus-containing supernatant at an MOI of 1. Transduction occurred via a 90 min spin infection at 2250 rpm at 37° C., after which the lentivirus-containing supernatant was removed and replaced with fresh media supplemented with 20 U/ml rhIL-2. At day 2 following transduction, media containing selection reagents, (puromycin for shRNA vectors and blasticidin for overexpression vectors), as well as IL-2 was added and selection was allowed to occur for a total of 5 days. All subsequent experiments with lentivirus-transduced T cells were conducted in the absence of IL-2.

Bead Preparation

Beads used for cell stimulation were generated by conjugation of anti-CD3 (64 ng, clone UCHT1) and anti-CD28 (80 ng, clone CD28.2) as well as either control IgG1 (1.25 ug clone MOPC-31C) (all from BD Biosciences) for positive CD3/CD28 beads or either an anti-human PD-1 antibody (1.25 ug, clone EH12) or PDL1-Ig fusion protein (1.25 ug, both gifts from G. Freeman) for PD1/CD3/CD28 or PDL1/CD3/CD28 beads, respectively, to CELLection Pan Mouse IgG beads (Invitrogen/Dynal, Oslo, Norway). For PDL1-Ig titration experiments, the amount of PDL1-Ig conjugated to the beads was decreased in 2-fold increments while IgG1 was added to maintain equivalent amounts of total protein on the beads (1.394 ug total protein). Conjugation occurred over a 90 minute incubation period at 4° C. with constant end-over-end rotation in PBS supplemented with 0.1% FBS. Following incubation, beads were washed twice to remove unbound antibody and stored at 4° C. in the 0.1% FBS-containing PBS prior to use.

Cytokine Measurement Using Enzyme-Linked Immunosorbent Assay (ELISA)

IL-2 and IFN-γ production was measured in the supernatant of cultured primary human T cells or Jurkat cells using the respective Quantikine Immunoassays according to manufacturer's direction (R&D Systems, Minneapolis, Minn.).

BATF siRNA Knockdown in PBMC and HIV-Specific CD4 T Cell Responses

Freshly isolated PBMC from untreated, chronically HIV-infected individuals were depleted of CD8$^+$ T cells during density gradient centrifugation (Ficoll-Histopaque, Sigma Aldrich) using RosetteSep CD8 depletion reagents (StemCell). Inhibition of BATF expression was achieved through siRNA transfection by electroporation on a Gene Pulser XCell (BioRad). Fifteen million cells were resuspended in 300 ml of Opti-MEM in a 2-mm cuvette and pulsed with 1 nmol of siRNA (ON-TARGET Non-targeting pool and BATF ON-TARGETplus SMARTpool, Dharmacon). The pulse conditions were designed to maximize electroporation efficiency in T cells (a unique square wave with a pulse of 360V and a duration of 5 ms), and routinely achieved approximately 80% electroporation efficiency. After electroporation, cells were rested overnight in RPMI 1640 medium (Invitrogen) supplemented with 10% human AB serum (Gemini Bioproducts) at 37° C., 5% $CO_2$ before being stimulated with an HIV Gag peptide pool (1 mg/ml/peptide) or left unstimulated. Input cell numbers were normalized at 1 million cells/mL of culture medium per condition. After a 96-hour incubation, IFN-γ and IL-2 levels were measured in the collected supernatants with the Milliplex High sensitivity Kit (Millipore) using the Bio-Plex 200 system (BioRad) according to the manufacturer's instructions.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying DsiRNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

REFERENCES

1. Shin, H. & Wherry, E. J., E. J. CD8 T cell dysfunction during chronic viral infection. *Current Opinion in Immunology* 19, 408-415 (2007).
2. Wherry, E. J., E. J., Blattman, J. N., Murali-Krishna, K., van der Most, R. & Ahmed, R. Viral persistence alters CD8 T-cell immunodominance and tissue distribution and results in distinct stages of functional impairment. *J Virol* 77, 4911-4927 (2003).
3. Zajac, A. J., et al. Viral immune evasion due to persistence of activated T cells without effector function. *J Exp Med* 188, 2205-2213 (1998).
4. Wherry, E. J., E. J., et al. Molecular signature of CD8+ T cell exhaustion during chronic viral infection. *Immunity* 27, 670-684 (2007).
5. Barber, D. L., et al. Restoring function in exhausted CD8 T cells during chronic viral infection. *Nature* 439, 682-687 (2005).
6. Velu, V., et al. Enhancing SIV-specific immunity in vivo by PD-1 blockade. *Nature* 458, 206-210 (2009).
7. Riley, J. L. PD-1 signaling in primary T cells. *Immunol Rev* 229, 114-125 (2009).
8. Sheppard, K. A., et al. PD-1 inhibits T-cell receptor induced phosphorylation of the ZAP70/CD3zeta signalosome and downstream signaling to PKCtheta. *FEBS LETTERS* 574, 37-41 (2004).
9. Parry, R. V., et al. CTLA-4 and PD-1 receptors inhibit T-cell activation by distinct mechanisms. *Mol Cell Biol* 25, 9543-9553 (2005).
10. Chemnitz, J. M., Parry, R. V., Nichols, K. E., June, C. H. & Riley, J. L. SHP-1 and SHP-2 associate with immunoreceptor tyrosine-based switch motif of programmed death 1 upon primary human T cell stimulation, but only receptor ligation prevents T cell activation. *J Immunol* 173, 945-954 (2004).
11. Pereyra, F., et al. Genetic and immunologic heterogeneity among persons who control HIV infection in the absence of therapy. *J Infect Dis* 197, 563-571 (2008).
12. Betts, M. R., M. R., et al. HIV nonprogressors preferentially maintain highly functional HIV-specific CD8+ T-cells. *Blood* (2006).
13. Migueles, S. A., et al. HIV-specific CD8+ T cell proliferation is coupled to perforin expression and is maintained in nonprogressors. *Nat. Immunol.* 3, 1061-1068 (2002).
14. Nilsson, B., Hakansson, P., Johansson, M., Nelander, S. & Fioretos, T. Threshold-free high-power methods for the ontological analysis of genome-wide gene-expression studies. *Genome Biol* 8, R74 (2007).
15. Chemnitz, J. M., et al. RNA fingerprints provide direct evidence for the inhibitory role of TGFbeta and PD-1 on CD4+ T cells in Hodgkin lymphoma. *Blood* 110, 3226-3233 (2007).
16. Haining, W. N., et al. High-throughput gene expression profiling of memory differentiation in primary human T cells. *BMC Immunol* 9, 44 (2008).
17. Peck, D., et al. A method for high-throughput gene expression signature analysis. *Genome Biol* 7, R61 (2006).
18. Day, C. L., et al. PD-1 expression on HIV-specific T cells is associated with T-cell exhaustion and disease progression. *Nature* 443, 350-354 (2006).
19. Trautmann, L., et al. Upregulation of PD-1 expression on HIV-specific CD8+ T cells leads to reversible immune dysfunction. *Nat. Med.* 12, 1198-1202 (2006).
20. Echlin, D. R., Tae, H. J., Mitin, N. & Taparowsky, E. J. B-ATF functions as a negative regulator of AP-1 mediated transcription and blocks cellular transformation by Ras and Fos. *Oncogene* 19, 1752-1763 (2000).
21. Williams, K. L., et al. Characterization of murine BATF: a negative regulator of activator protein-1 activity in the thymus. *European Journal of Immunology* 31, 1620-1627 (2001).
22. Haining, W. N., et al. Identification of an evolutionarily conserved transcriptional signature of CD8 memory differentiation that is shared by T and B cells. *J Immunol* 181, 1859-1868 (2008).
23. Blackburn, S. D., Shin, H., Freeman, G. J. & Wherry, E. J., E. J. Selective expansion of a subset of exhausted CD8 T cells by {alpha}PD-L1 blockade. *Proceedings of the National Academy of Sciences of the United States of America* (2008).
24. Thornton, T. M., Zullo, A. J., Williams, K. L. & Taparowsky, E. J. Direct manipulation of activator protein-1 controls thymocyte proliferation in vitro. *European Journal of Immunology* 36, 160-169 (2006).
25. Petrovas, C., et al. PD-1 is a regulator of virus-specific CD8+ T cell survival in HIV infection. *J. Exp. Med.* 203, 2281-2292 (2006).
26. Riley, J. L. & June, C. H. The road to recovery: translating PD-1 biology into clinical benefit. *Trends Immunol* 28, 48-50 (2007).
27. Kaufmann, D. E. & Walker, B. D. PD-1 and CTLA-4 Inhibitory Cosignaling Pathways in HIV Infection and the Potential for Therapeutic Intervention. *The Journal of Immunology* 182, 5891 (2009).
28. Berger, R., et al. Phase I Safety and Pharmacokinetic Study of CT-011, a Humanized Antibody Interacting with PD-1, in Patients with Advanced Hematologic Malignancies. *Clinical Cancer Research* 14, 3044 (2008).
29. Suntharalingam, G., et al. Cytokine storm in a phase 1 trial of the anti-CD28 monoclonal antibody TGN1412. *N Engl J Med* 355, 1018-1028 (2006).

30. Foletta, V. C., Segal, D. H. & Cohen, D. R. Transcriptional regulation in the immune system: all roads lead to AP-1. *Journal of Leukocyte Biology* 63, 139-152 (1998).
31. Dorsey, M. J., et al. B-ATF: a novel human bZIP protein that associates with members of the AP-1 transcription factor family. *Oncogene* 11, 2255-2265 (1995).
32. Harari, A., Petitpierre, S., Vallelian, F. & Pantaleo, G. Skewed representation of functionally distinct populations of virus-specific CD4 T cells in HIV-1-infected subjects with progressive disease: changes after antiretroviral therapy. *Blood* 103, 966-972 (2004).
33. Schraml, B. U., et al. The AP-1 transcription factor Batf controls T(H) 17 differentiation. *Nature* (2009).
34. Wu, J. Q., et al. Transcriptional profiles in CD8+ T cells from HIV+ progressors on HAART are characterized by coordinated up-regulation of oxidative phosphorylation enzymes and interferon responses. *Virology* 380, 124-135 (2008).
35. Kaufmann, D. E., et al. Upregulation of CTLA-4 by HIV-specific CD4(+) T cells correlates with disease progression and defines a reversible immune dysfunction. *Nature Immunology* 8, 1246-1254 (2007).
36. Blackburn, S. D., et al. Coregulation of CD8+ T cell exhaustion by multiple inhibitory receptors during chronic viral infection. *Nat. Immunol.* 10, 29-37 (2009).
37. van't Veer, L. J. & Bernards, R. Enabling personalized cancer medicine through analysis of gene-expression patterns. *Nature* 452, 564-570 (2008).
38. Querec, T. D., et al. Systems biology approach predicts immunogenicity of the yellow fever vaccine in humans. *Nat. Immunol. aop* (2008).
39. Chaussabel, D., et al. A modular analysis framework for blood genomics studies: application to systemic lupus erythematosus. *Immunity* 29, 150-164 (2008).
40. Smyth, G. K. Linear models and empirical bayes methods for assessing differential expression in microarray experiments. *Statistical applications in genetics and molecular biology* 3, Article 3 (2004).
41. Kuehn, H., Liberzon, A., Reich, M. & Mesirov, J. P. Using GenePattern for gene expression analysis. *Current protocols in bioinformatics/editorial board, Andreas D Baxevanis [et al] Chapter* 7, Unit 7.12 (2008).
42. Jesneck, J. L., et al. Do serum biomarkers really measure breast cancer? *BMC Cancer* 9, 164 (2009).

What is claimed:

1. A method of classifying an immune response in an individual infected with HIV comprising:
   obtaining a biological sample from an individual infected with HIV;
   determining an expression profile of HIV specific T-cells from said HIV-infected individual by determining hybridization of a nucleic acid in said sample to a probe on a microarray, wherein said expression profile comprises an expression level of at least two genes selected from those presented in FIG. 11;
   comparing said expression profile to at least one of:
   a. the expression profile of T-cells from a subject that is not infected with HIV;
   b. the expression profile of HIV-specific T-cells that are controllers; and
   c. the expression profile of HIV-specific T-cells that are chronic progressors; and
   determining if said individual is a controller or a chronic progressor, thereby classifying-an immune response.

2. The method of claim 1, wherein said expression profile comprises an expression level of interferon regulatory factor 9 (IRF9), basic leucine zipper transcription factor ATF-like (BATF), and signal transducers and activators of transcription 1 (STAT1).

3. The method of claim 1, wherein an expression profile of said individual infected with HIV that is substantially similar to the expression profile of HIV-specific T-cells that are controllers classifies said immune response of said individual as that of a controller.

4. The method of claim 3, wherein said individual infected with HIV exhibits a decrease in HIV viral load after the individual is infected with HIV, and maintains the decreased HIV viral load over time.

5. The method of claim 3, wherein said individual infected with HIV remains asymptomatic with normal CD4 positive T-cell counts and low or undetectable plasma viral loads in the absence of antiretroviral therapy.

6. The method of claim 3, wherein said individual infected with HIV exhibits plasma HIV RNA levels fewer than 2,000 copies/mL.

7. The method of claim 3, wherein said individual infected with HIV has an expression profile that is substantially similar to that presented in FIG. 1b.

8. The method of claim 1, wherein an expression profile of an individual infected with HIV that is substantially similar to the expression profile of HIV-specific T-cells that are chronic progressors classifies said immune response of said individual as that of a chronic progressor.

9. The method of claim 8, wherein said individual infected with HIV exhibits an increase in viral load over time following initial HIV infection.

10. The method of claim 8, wherein said individual infected with HIV exhibits plasma HIV RNA levels greater than 10,000 copies/mL.

11. The method of claim 8, wherein said individual infected with HIV has an expression profile that is substantially similar to that presented in FIG. 1b.

12. The method of claim 1, wherein said expression profile comprises an expression level of at least three genes selected from those presented in FIG. 11.

13. The method of claim 1, wherein said expression profile comprises an expression level of each of the genes presented in FIG. 11.

* * * * *